US008012997B2

(12) United States Patent
Robarge et al.

(10) Patent No.: US 8,012,997 B2
(45) Date of Patent: *Sep. 6, 2011

(54) ISOINDOLE-IMIDE COMPOUNDS, COMPOSITIONS, AND USES THEREOF

(75) Inventors: Michael J. Robarge, North Plainfield, NJ (US); Roger Shen-Chu Chen, Edison, NJ (US); George W. Muller, Bridgewater, NJ (US); Hon-Wah Man, Princeton, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/508,483

(22) Filed: Jul. 23, 2009

(65) Prior Publication Data

US 2009/0286986 A1 Nov. 19, 2009

Related U.S. Application Data

(60) Continuation of application No. 11/230,448, filed on Sep. 21, 2005, now Pat. No. 7,576,104, which is a division of application No. 10/032,286, filed on Dec. 21, 2001, now Pat. No. 7,091,353, which is a continuation-in-part of application No. 09/972,487, filed on Oct. 5, 2001, now abandoned.

(60) Provisional application No. 60/258,372, filed on Dec. 27, 2000.

(51) Int. Cl.
*A61K 31/454* (2006.01)
*C07D 403/02* (2006.01)

(52) U.S. Cl. ......... 514/323; 546/199; 546/200; 546/201

(58) Field of Classification Search .................. 514/323; 546/193, 200, 201
See application file for complete search history.

(56) References Cited

U.S. PATENT DOCUMENTS

| 3,992,189 | A | 11/1976 | Goddard |
| 5,045,108 | A | 9/1991 | Elbe et al. |
| 5,198,402 | A | 3/1993 | Kaji et al. |
| 5,326,800 | A | 7/1994 | Horn et al. |
| 5,385,901 | A | 1/1995 | Kaplan et al. |
| 5,605,914 | A | 2/1997 | Muller |
| 5,635,517 | A | 6/1997 | Muller et al. |
| 5,658,940 | A | 8/1997 | Muller et al. |
| 5,698,579 | A | 12/1997 | Muller |
| 5,703,098 | A | 12/1997 | Muller et al. |
| 5,728,845 | A | 3/1998 | Muller et al. |
| 5,736,570 | A | 4/1998 | Muller et al. |
| 5,798,368 | A | 8/1998 | Muller et al. |
| 5,801,195 | A | 9/1998 | Muller et al. |
| 5,874,448 | A | 2/1999 | Muller et al. |
| 5,877,200 | A | 3/1999 | Muller |
| 5,929,117 | A | 7/1999 | Muller et al. |
| 5,955,476 | A | 9/1999 | Muller et al. |
| 5,968,945 | A | 10/1999 | Muller et al. |
| 6,011,050 | A | 1/2000 | Muller et al. |
| 6,020,358 | A | 2/2000 | Muller et al. |
| 6,046,221 | A | 4/2000 | Muller et al. |
| 6,075,041 | A | 6/2000 | Muller |
| 6,130,226 | A | 10/2000 | Muller et al. |
| 6,180,644 | B1 | 1/2001 | Muller et al. |
| 6,200,987 | B1 | 3/2001 | Muller |
| 6,214,857 | B1 | 4/2001 | Muller et al. |
| 6,316,471 | B1 | 11/2001 | Muller et al. |
| 6,335,349 | B1 | 1/2002 | Muller et al. |
| 6,395,754 | B1 | 5/2002 | Muller et al. |
| 6,476,052 | B1 | 11/2002 | Muller et al. |
| 7,041,680 | B2 | 5/2006 | Muller et al. |
| 7,091,353 | B2 * | 8/2006 | Robarge et al. ............... 546/200 |
| 7,119,106 | B2 | 10/2006 | Muller et al. |
| 7,189,740 | B2 | 3/2007 | Zeldis |
| 7,576,104 | B2 * | 8/2009 | Robarge et al. ............... 514/323 |

FOREIGN PATENT DOCUMENTS

| EP | 0 797 437 | 7/1996 |
| EP | 1 004 572 | 5/2000 |
| EP | 1 004 580 | 5/2000 |
| EP | 1 004 581 | 5/2000 |
| WO | WO 92/18496 | 10/1992 |
| WO | WO 95/01348 | 1/1995 |
| WO | WO 96/20705 | 7/1996 |
| WO | WO 96/20926 | 7/1996 |
| WO | WO 97/08143 | 3/1997 |
| WO | WO 97/12859 | 4/1997 |
| WO | WO 97/23457 | 7/1997 |
| WO | WO 97/37988 | 10/1997 |
| WO | WO 97/45117 | 12/1997 |
| WO | WO 98/03502 | 1/1998 |
| WO | WO 98/06692 | 2/1998 |

(Continued)

OTHER PUBLICATIONS

Seddon "Pseudomorph . . . " Crystal growth & design 4(6) 1087 (2004) (two pages from internet).*
Braga et al. "making crystal . . . " roy. soc. chem. Chem. Commun. p. 3635-3645 (2005).*
Corral et al., 1999, "Differential cytokine modulation and T cell activation by two distinct classes of thalidomide analogues that are potent inhibitors of INF-α," J. Immunol. 163:380-86.
He et al., 1993, "Synthesis of thalidomide analogs and their biological potential for treatment of graft versus host disease," Abstracts of Papers, 206th ACS National Meeting, Abstract No. 216.

(Continued)

*Primary Examiner* — Celia Chang
(74) *Attorney, Agent, or Firm* — Jones Day

(57) ABSTRACT

The invention relates to isoindole-imide compounds and pharmaceutically acceptable salts, hydrates, solvates, clathrates, enantiomers, diastereomers, racemates, or mixtures of stereoisomers thereof, pharmaceutical compositions comprising these isoindole-imide compounds, and methods for reducing the level of cytokines and their precursors in mammals. In particular, the invention pertains to isoindole-imide compounds that are potent inhibitors of the production of TNF-α in mammals. The isoindole-imides described herein are useful for treating or preventing diseases or disorders in mammals, for example, cancers, such as solid tumors and blood-born tumors; heart disease, such as congestive heart failure; osteoporosis; and genetic, inflammatory; allergic; and autoimmune diseases.

8 Claims, No Drawings

FOREIGN PATENT DOCUMENTS

| | | |
|---|---|---|
| WO | WO 98/24763 | 6/1998 |
| WO | WO 98/41525 | 9/1998 |
| WO | WO 98/54170 | 12/1998 |
| WO | WO 99/06041 | 2/1999 |
| WO | WO 99/46258 | 9/1999 |
| WO | WO 99/47512 | 9/1999 |
| WO | WO 00/25777 | 5/2000 |
| WO | WO 00/38521 | 7/2000 |
| WO | WO 00/55134 | 9/2000 |

OTHER PUBLICATIONS

Muller et al., 1996, "Structural modifications of thalidomide produce analogs with enhanced tumor necrosis factor inhibitory activity," J. Med. Chem. 39:3238-40.

Muller et al., 1998, "Thalidomide analogs and PDE4 inhibition," Bioorg. Med. Chem. Lett. 8:2669-74.

Muller et al., 1999, "Amino-substituted thalidomide analogs: potent inhibitors of TNF-α production," Bioorg. Med. Chem. Lett. 9:1625-30.

Bundgaard, 1986, "Design of prodrugs," Elsevier, Amsterdam—New York —Oxford, pp. 27-43.

Corral et al., 1996, "Selection of novel analogs of thalidomide with enhanced tumor necrosis factor alpha inhibitory activity," Mol. Med. Jul;2(4):506-15.

Database Caplus on STN (Columbus, OH, USA), No. 118:131893, "The hydrolysis of azidoprofen esters: a model for a soft anti-inflammatory drug for topical application," Int. J. Phar. 89:65-74 (1993), abstract.

Database Caplus on STN (Columbus, OH, USA), No. 128:140615, "Substituted 2-(2,6-dioxo-3- piperidinyl)phthalimides and 1-oxoisoindolines and method of reducing TNF-alpha levels," WO98/03502, abstract and registry No. 191732-76-0, 202271-87-2, 202271-88-3, 202271-89-4, 202271-90-7.

Database Caplus on STN (Columbus, OH, USA), No. 130:38290, "Substituted 2-(2,6-dioxo-3-piperidinyl)phthalimides and 1-oxoisoindolines and method of reducing TNF-alpha levels," WO98/54170, abstract and registry No. 202271-88-3, 216669-27-1, 191732-72-6.

Database Caplus on STN (Columbus, OH, USA), No. 131:214197, "Preparation of 2-(2,6-dioxo-3-fluoropiperidin-3—yl) isoindolines for reducing inflammatory cytokine levels," U.S. 5,955,476, abstract and registry No. 220460-56-0, 220460-57-1, 220460-62-8, 220460-64-0.

Marriott et al., 2001, "Immunotherapeutic and antitumor potential of thalidomide analogue," Exp. Opin. Biol. Ther. Jul; 1(4):675-82. Review.

Miyachi et al., 1998, "Tumor necrosis factor-alpha production enhancing activity of substituted 3'-methylthalidomide: influence of substituents at the phthaloyl moiety on the activity and stereoselectivity," Chem. Pharm. Bull. (Tokyo). Jul;46(7):1165-68.

Price et al., 2002, "5'-OH-thalidomide, a metabolite of thalidomide, inhibits angiogenesis," Ther. Drug Monit. Feb;24(1):104-10.

Foster, "The Functions of Cytokines . . . ," CA 136:230735 (2001).

Joseph et al., "Macrophage Role in the Anti-Prostate Cancer Response to One Class of Antiangiogenic Agents," J. National Can. Inst. 90:1648-1653 (1998).

Naik et al., "the Hydrolysis of Azidoprofen Esters: A Model for a Soft Anti-Inflammatory Drug for Topical Application," International Journal of Pharmaceutics, 89:65-74 (1993).

Schmahl et al., "The Enantiomers of the Teratogenic Thalidomide Analog EM 12: 1. Chiral Inversion and Plasma Pharmakokinetics in the Marmoset Monkey" CA 110:822 (1989).

Vecchiarelli, "Cytokines and costimulatory . . . ," CA 135:286931 (2000).

Webster Medical Dictionary "Prodrug" (2009) (from internet).

\* cited by examiner

ISOINDOLE-IMIDE COMPOUNDS, COMPOSITIONS, AND USES THEREOF

This application is a continuation of U.S. application Ser. No. 11/230,448, filed Sep. 21, 2005, now U.S. Pat. No. 7,576,104, which is a divisional of U.S. application Ser. No. 10/032,286, filed Dec. 21, 2001, now U.S. Pat. No. 7,091,353, which is a continuation-in-part of U.S. application Ser. No. 09/972,487, filed Oct. 5, 2001, now abandoned, which claims the benefit of U.S. Provisional Application No. 60/258,372, filed Dec. 27, 2000, all of which are hereby expressly incorporated by reference herein.

1. FIELD OF THE INVENTION

The invention encompasses novel compounds including compounds having an isoindole-imide moiety, pharmaceutically acceptable salts, hydrates, solvates, clathrates, enantiomers, diastereomers, racemates, or mixtures of stereoisomers thereof, pharmaceutical compositions of these compounds, and methods of using these compounds and compositions in mammals for treatment or prevention of diseases.

2. INTRODUCTION

The present invention relates to isoindole-imide compounds and pharmaceutically acceptable salts, hydrates, solvate, clathrate, enantiomer, diastereomer, racemate, or mixture of stereoisomers thereof; pharmaceutical compositions comprising these isoindole-imide compounds; and methods for reducing the level of cytokines and their precursors in mammals. In particular, the invention includes isoindole-imide compounds that have one or more of the following activities: modulation of the production of TNF-α; modulation of the production of IL-1β; stimulation of the production of IL-10; or stimulation of the production T-cells.

The isoindole-imides described herein are useful for treating or preventing diseases or disorders in mammals, for example, cancers, such as solid tumors and blood-born tumors. Specific examples of cancers treatable or preventable by compounds of the invention include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are particularly useful for treating cancers of the blood and bone marrow, such as multiple myeloma and acute and chronic leukemias, for example, lymphoblastic, myelogenous, lymphocytic, and myelocytic leukemias.

The compounds of the invention are also useful to treat or prevent heart disease, such as congestive heart failure, cardiomyopathy, pulmonary edema, endotoxin-mediated septic shock, acute viral myocarditis, cardiac allograft rejection, and myocardial infarction.

The compounds of the invention can also be used to treat or prevent viral, genetic, inflammatory, allergic, and autoimmune diseases. For example, the compounds are useful to treat or prevent diseases including, but not limited to, HIV; hepatitis; adult respiratory distress syndrome; bone-resorption diseases; chronic pulmonary inflammatory diseases; dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft rejection including graft versus host disease; auto-immune disease; rheumatoid spondylitis; arthritic conditions, such as rheumatoid arthritis and osteoarthritis; osteoporosis; Crohn's disease; ulcerative colitis; inflammatory-bowel disease; multiple sclerosis; systemic lupus erythrematosus; ENL in leprosy; radiation damage; asthma; and hyperoxic alveolar injury.

The compounds of the invention are also useful for treating or preventing bacterial infections or the symptoms of bacterial infections including, but not limited to, malaria, mycobacterial infection, and opportunistic infections resulting from HIV.

3. BACKGROUND OF THE INVENTION

Tumor necrosis factor alpha, (TNF-α) is a cytokine that is released primarily by mono-nuclear phagocytes in response to immunostimulators. TNF-α is capable of enhancing most cellular processes, such as differentiation, recruitment, proliferation, and proteolytic degradation. At low levels, TNF-α confers protection against infective agents, tumors, and tissue damage. But TNF-α also has role in many disease processes. When administered to mammals or humans, TNF-α causes or aggravates inflammation, fever, cardiovascular effects, hemorrhage, coagulation, and acute phase responses similar to those seen during acute infections and shock states. Enhanced or unregulated TNF-α production has been implicated in a number of diseases and medical conditions, for example, cancers, such as solid tumors and blood-born tumors; heart disease, such as congestive heart failure; and viral, genetic, inflammatory, allergic, and autoimmune diseases.

The interleukins are a subclass of the cytokine family and possess a wide spectrum of biological activities including involvement in cell activation, cell differentiation, cell proliferation, and cell-to-cell interactions. Interleukin 1 beta (IL-1β) and interleukin 10 (IL-10), in combination with other cytokines, play a central role in mediating inflammatory processes and IL-1β has been implicated as both a growth factor and growth suppressor in certain tumor cells.

T-cells are a class of white blood cells that play an important role in the immune response, and help protect the body from viral and bacterial infections. Diminished T-cell levels strongly contribute to the inability of HIV patients to combat infections, and abnormally low T-cell levels are prominent in a number of other immune deficiency syndromes, including DiGeorge Syndrome, and in certain forms of cancer, such as T-cell lymphoma.

Cancer is a particularly devastating disease, and increase in blood TNF-α levels are implicated in the risk of and the spreading of cancer. Normally, in healthy subjects, cancer cells fail to survive in the circulatory system, one of the reasons being that the lining of blood vessels acts as a barrier to tumor-cell extravasation. But increased levels of cytokines, have been shown to substantially increase the adhesion of cancer cells to endothelium in vitro. One explanation is that cytokines, such as TNF-α stimulate the biosynthesis and expression of a cell surface receptors called ELAM-1 (endothelial leukocyte adhesion molecule). ELAM-1 is a member of a family of calcium-dependent cell adhesion receptors, known as LEC-CAMs, which includes LECAM-1 and GMP-140. During an inflammatory response, ELAM-1 on endothelial cells functions as a "homing receptor" for leukocytes. Recently, ELAM-1 on endothelial cells was shown to mediate the increased adhesion of colon cancer cells to endothelium treated with cytokines (Rice et al., 1989, *Science* 246:1303-1306). It has been suggested that an uncontrolled synthesis of IL-1β in leukemia blast cells is thought to result in the production of factors which promote proliferation of these malignant cells (Hestdal et al., 1992, *Blood* 80: 2486-94). In addition to this, IL-1β, in combination with other cytokines, appears to stimulate the growth of human gastric and thyroid carcinoma cells (Ito et. al., 1993, *Cancer Research* 53: 4102-6).

Inflammatory diseases such as arthritis, related arthritic conditions (e.g. osteoarthritis and rheumatoid arthritis), inflammatory bowel disease, sepsis, psoriasis, and chronic inflammatory pulmonary diseases are also prevalent and problematic ailments. Both TNF-α and IL-1β play central roles in the inflammatory response and the administration of their antagonists block chronic and acute responses in animal models of inflammatory disease. Conversely, IL-10 is an anti-inflammatory cytokine and is responsible for down-regulating inflammatory responses and as such possesses anti-inflammatory ability, including the suppression of production of proinflammatory cytokines such as TNF-α and IL-1β.

Heart disease has caused wide-spread death and debilitation. TNF-α has been implicated in a broad variety of cardiac pathophysiological conditions, such as septic shock, acute viral myocarditis, cardiac allograft rejection, myocardial infarction, and congestive heart failure (see e.g., Steadman et al., 1988, *IEEE Trans. Biomed. Eng.* 35:264-272; Tracey et al., 1986, *Science Wash. DC* 234:470-474; for a review see Ferrari, 1998, *Cardiovascular Research* 37:554-559). In one study, it was found that protective TNF-α binding proteins are downregulated in the hearts of patients with advanced congestive heart failure. During the study it was found that a large percentage of the diseased hearts analyzed had elevated TNF-α levels. The authors noted that the results support the proposition that the heart itself is a target of TNF-α and that myocardial TNF-α production may be a maladaptive mechanism that contributes to progressive heart failure (Torre-Amione et al., 1996, *Circulation* 93:704-711). In other studies, it has been demonstrated in-vitro and in-vivo (feline) that TNF-α is produced in the myocardium portion of the heart upon endotoxin stimulation. These studies provide compelling evidence indicating that a pathogenic level of biologically active TNF-α may be produced in the heart during endotoxin-mediated septic shock. And that such local concentrations of TNF-α may be the primary instigator of myocardial-function depression during systemic sepsis (Kapadia et al., 1995, *J. Clin. Invest.* 96:1042-1052). Thus, inhibitors of TNF-α activity may prevent its deleterious effects on the heart. For example, it has been demonstrated that soluble TNF-binding proteins modulate the negative inotropic effects of TNF-α in vitro in isolated contracting cardiac myocytes (Kapadia et al., 1995, *Am. J. Physiol.* 268:H517-H525).

Enhanced or unregulated TNF-α production has been implicated in viral, genetic, inflammatory, allergic, and autoimmune diseases, for example, HIV; hepatitis; adult respiratory distress syndrome; bone-resorption diseases; chronic pulmonary inflammatory diseases; dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft rejection; auto-immune disease; rheumatoid spondylitis; arthritic conditions, such as rheumatoid arthritis and osteoarthritis; osteoporosis, Crohn's disease; ulcerative colitis; inflammatory-bowel disease; multiple sclerosis; systemic lupus erythrematosus; ENL in leprosy; radiation damage; asthma; and hyperoxic alveolar injury. For discussions see Tracey et al., 1987, *Nature* 330:662-664 and Hinshaw et al., 1990, *Circ. Shock* 30:279-292 (endotoxic shock); Dezube et al., 1990, *Lancet*, 335:662 (cachexia); Millar et al., 1989, *Lancet* 2:712-714 and Ferrai-Baliviera et al., 1989, *Arch. Surg.* 124:1400-1405 (adult respiratory distress syndrome); Bertolini et al., 1986, *Nature* 319:516-518, Johnson et al., 1989, *Endocrinology* 124:1424-1427, Holler et al., 1990, *Blood* 75:1011-1016, and Grau et al., 1989, *N. Engl. J. Med.* 320:1586-1591 (bone resorption diseases); Pignet et al., 1990, *Nature*, 344:245-247, Bissonnette et al., 1989, *Inflammation* 13:329-339 and Baughman et al., 1990, *J. Lab. Clin. Med.* 115:36-42 (chronic pulmonary inflammatory diseases); Elliot et al., 1995, *Int. J. Pharmac.* 17:141-145 (rheumatoid arthritis); von Dullemen et al., 1995, *Gastroenterology*, 109:129-135 (Crohn's disease); Duh et al., 1989, *Proc. Nat. Acad. Sci.* 86:5974-5978, Poll et al., 1990, *Proc. Nat. Acad. Sci.* 87:782-785, Monto et al., 1990, *Blood* 79:2670, Clouse et al., 1989, *J. Immunol* 142, 431-438, Poll et al., 1992, *AIDS Res. Hum. Retrovirus*, 191-197, Poll et al. 1990, *Proc. Natl. Acad. Sci.* 87:782-784, Folks et al., 1989, *PNAS* 86:2365-2368 (HIV and opportunistic infections resulting from HIV).

Pharmaceutical compounds that can block the activity or inhibit the production of certain cytokines, including TNF-α and IL-1β, may be beneficial therapeutics. Many small-molecule inhibitors have demonstrated an ability to treat or prevent inflammatory diseases implicated by TNF-α (for a review see Lowe, 1998 *Exp. Opin. Ther. Patents* 8:1309-1332). In addition, pharmaceutical compounds that can stimulate the activity or increase the production of certain cytokines, including IL-10, and immune response factors such as T-cells, may be beneficial therapeutics.

Thalidomide is an emerging immunotherapeutic agent and, in addition to utility in treating a variety of inflammatory disorders, it is projected to be useful in treating cancers (see e.g., Marriott et al., 1999, *Immunology Today* 20:537-540). Thalidomide has been shown to inhibit production of both TNF-α and IL-1β while simultaneously increasing the production of IL-10 and T-cells, and has been tested against a variety of autoimmune and inflammatory diseases, see e.g., Gutierrez-Rodriguez, 1984, *Arth. and Rheum* 27:1118; *The Physician's Desk Reference*, 54th edition, 911-916, Medical Economics Company (2000). Thalidomide's teratogenic properties, however, have limited its use and driven efforts to discover analogs or derivatives with reduced toxicity and improved therapeutic activity. The design of thalidomide analogs and derivatives attempts to maintain/enhance activity while subverting toxicity (for a discussion of some recent advances in TNF-α inhibitors structurally related to thalidomide see Marriott, 1997, *Exp. Opin. Invest. Drugs* 6:1105-1108). For example, the following references have disclosed alternatives to thalidomide as inhibitors of TNF-α production: U.S. Pat. Nos. 5,385,901; 5,635,517; and 5,798,368 and PCT International Application WO 98/54170. Despite these disclosures, there remains a need for non-toxic and high-potency compounds that treat or prevent cancer, inflammatory disorders, and autoimmune diseases.

Citation or identification of any reference in Section 3 of this application is not an admission that such reference is available as prior art to the present invention.

4. SUMMARY OF THE INVENTION

The invention encompasses novel isoindole-imide compounds and compositions thereof that are useful to treat or prevent diseases in mammals, including humans. The invention further encompasses the use of these compounds for treating or preventing diseases or disorders including, but not limited to, cancer; viral, genetic, inflammatory, allergic, and autoimmune diseases; and bacterial infections. The compounds of the invention are particularly useful to treat or prevent diseases caused or aggravated by excessive or unregulated levels of TNF-α, or IL-1β; or diminished or unregulated levels of IL-10 or T-cells.

In one embodiment, the invention relates to compounds encompassed by Formula I:

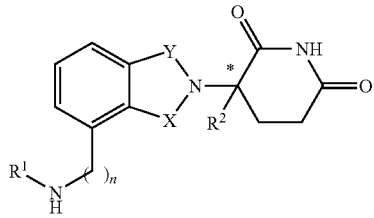

wherein:
one of X and Y is C=O and the other is CH$_2$ or C=O;
R$^1$ is H, (C$_1$-C$_8$)alkyl, (C$_3$-C$_7$)cycloalkyl, (C$_2$-C$_8$)alkenyl, (C$_{2\text{-}8}$)alkynyl, benzyl, aryl, (C$_0$-C$_4$)alkyl-C$_1$-C$_6$)heterocycloalkyl, (C$_0$-C$_4$)alkyl-C$_2$-C$_5$)heteroaryl, C(O)R$^3$, C(S)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^4$, C(O)NHR$^3$, C(S)NHR$^3$, C(O)NR$^3$R$^{3'}$, C(S)NR$^3$R$^{3'}$ or (C$_1$-C$_8$)alkyl-O(CO)R$^5$;
R$^2$ is H, F, benzyl, (C$_1$-C$_8$)alkyl, (C$_2$-C$_8$)alkenyl, or (C$_2$-C$_8$)alkynyl;
R$^3$ and R$^{3'}$ are independently (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-C$_1$-C$_6$)heterocycloalkyl, (C$_0$-C$_4$) alkyl-(C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$;
R$^4$ is (C$_1$-C$_8$)alkyl, (C$_2$-C$_8$)alkenyl, (C$_2$-C$_8$)alkynyl, (C$_1$-C$_4$)alkyl-OR$^5$, benzyl, aryl, (C$_0$-C$_4$)alkyl)-C$_1$-C$_6$)heterocycloalkyl, or (C$_0$-C$_4$)alkyl-C$_2$-C$_5$)heteroaryl;
R$^5$ is (C$_1$-C$_8$)alkyl, (C$_2$-C$_8$)alkenyl, (C$_2$-C$_8$)alkynyl, benzyl, aryl, or (C$_2$-C$_5$)heteroaryl;
each occurrence of R$^6$ is independently H, (C$_1$-C$_8$)alkyl, (C$_2$-C$_8$)alkenyl, (C$_2$-C$_8$)alkynyl, benzyl, aryl, (C$_2$-C$_8$)heteroaryl, or (C$_0$-C$_8$)alkyl-C(O)OR$^5$ or the R$^6$ groups can join to form a heterocycloalkyl group;
n is 0 or 1; and
\* represents, in formula I and in the following formulas of the invention, a chiral-carbon center; with the proviso that when n is 0 then R$^1$ is not H.

In a separate embodiment, the compounds of the invention include compounds of formula I, wherein when n is 0 then R$^1$ is (C$_3$-C$_7$)cycloalkyl, (C$_2$-C$_8$)alkenyl, (C$_2$-C$_8$)alkynyl, benzyl, aryl, (C$_0$-C$_4$)alkyl-C$_1$-C$_6$)heterocycloalkyl, (C$_0$-C$_4$)alkyl-C$_2$-C$_5$)heteroaryl, C(O)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, C(S)NHR$^3$, or (C$_{1\text{-}8}$)alkyl-O(CO)R$^5$;
R$^2$ is H or (C$_1$-C$_8$)alkyl; and
R$^3$ is (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-C$_1$-C$_6$)heterocycloalkyl, (C$_1$-C$_4$)alkyl-C$_{2\text{-}5}$)heteroaryl, (C$_5$-C$_8$)alkyl-N(R$^6$)$_2$; (C$_0$-C$_8$)alkyl-NH—C(O)C—R$^5$; (C$_1$-C$_8$)alkyl R$^5$, (C$_1$-C$_8$)alkyl-C(O)OR$^5$, (C$_1$-C$_8$)alkyl-O(CO)R$^5$, or C(O)OR$^5$; and the other variables are as described above.

In another embodiment of the compounds of formula I, R$^2$ is H or (C$_1$-C$_4$)alkyl.

In still another embodiment of the compounds of formula I, R$^1$ is (C$_1$-C$_8$)alkyl or benzyl.

In yet another embodiment of the compounds of formula I, R$^1$ is H, (C$_1$-C$_8$)alkyl, benzyl, CH$_2$OCH$_3$, CH$_2$CH$_2$OCH$_3$, or

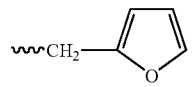

In another embodiment of the compounds of formula I, R$^1$ is

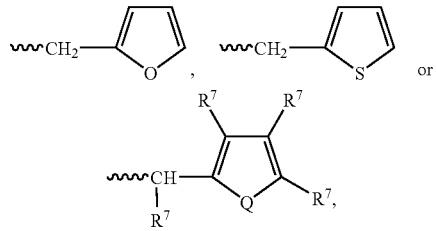

wherein Q is O or S, and each occurrence of R$^7$ is independently H, (C$_1$-C$_8$)alkyl, (C$_3$-C$_7$)cycloalkyl, (C$_2$-C$_8$)alkenyl, (C$_2$-C$_8$)alkynyl, benzyl, aryl, halogen, (C$_0$-C$_4$)alkyl-(C$_1$-C$_6$)heterocycloalkyl, (C$_0$-C$_4$)alkyl-C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$, or adjacent occurrences of R$^7$ can be taken together to form a bicyclic alkyl or aryl ring.

In still another embodiment of the compounds of formula I, R$^1$ is C(O)R$^3$ or C(O)OR$^4$.

In another embodiment of the compounds of formula I, R$^3$ is (C$_0$-C$_4$)alkyl(C$_2$-C$_5$)heteroaryl, (C$_1$-C$_9$)alkyl, aryl, or (C$_0$-C$_4$)alkyl-OR$^5$.

In yet another embodiment of the compounds of formula I, heteroaryl is pyridyl, furyl, or thienyl.

In another embodiment of the compounds of formula I, the H of C(O)NHC(O) can be replaced with (C$_1$-C$_4$)alkyl, aryl, or benzyl.

In another embodiment, the invention encompasess compounds of Formula II:

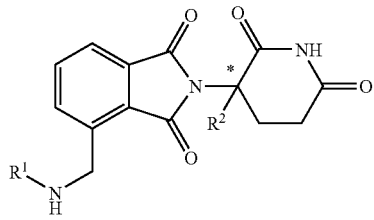

wherein:
R$^1$ is H, (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(S)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, C(O)NHR$^3$, C(S)NHR$^3$, C(O)NR$^3$R$^{3'}$, C(S)NR$^3$R$^{3'}$ or (C$_1$-C$_8$)alkyl-O(CO)R$^5$;
R$^2$ is H or (C$_1$-C$_8$)alkyl;
R$^3$ and R$^{3'}$ are independently (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-C$_1$-C$_6$)heterocycloalkyl, (C$_0$-C$_4$)alkyl)-C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$;
R$^4$ is (C$_1$-C$_8$)alkyl, (C$_2$-C$_8$)alkenyl, (C$_2$-C$_8$)alkynyl, (C$_1$-C$_4$)alkyl-OR$^5$, benzyl, aryl, (C$_0$-C$_4$)alkyl-C$_1$-C$_6$)heterocycloalkyl, or (C$_0$-C$_4$)alkyl-C$_2$-C$_5$)heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-C(O)(O)—$R^5$ or the $R^6$ groups can join to form a heterocycloalkyl group; and the * represents a chiral-carbon center.

In another embodiment of the compounds of formula II, $R^1$ is H, $(C_1-C_4)$alkyl, $CH_2OCH_3$, $CH_2CH_2OCH_3$, or

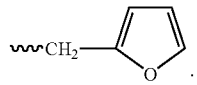

In yet another embodiment of the compounds of formula II, $R^1$ is

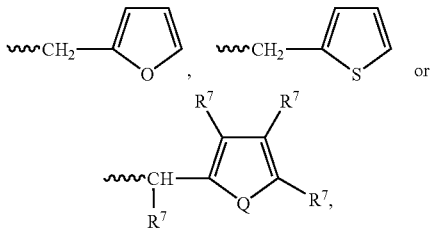

wherein Q is O or S, and each occurrence of $R^7$ is independently H, $(C_1-C_8)$alkyl, $(C_3-C_7)$cycloalkyl, $(C_2-C_8)$alkenyl, $(C_2-C_8)$alkynyl, benzyl, aryl, halogen, $(C_0-C_4)$alkyl-$(C_1-C_6)$heterocycloalkyl, $(C_0-C_4)$alkyl)-$C_2-C_5$)heteroaryl, $(C_0-C_8)$alkyl-N$(R^6)_2$, $(C_1-C_8)$alkyl-OR$^5$, $(C_1-C_8)$alkyl-C(O)OR$^5$, $(C_1-C_8)$alkyl (CO)R$^5$, or C(O)OR$^5$, or adjacent occurrences of $R^7$ can be taken together to form a bicyclic alkyl or aryl ring.

In still another embodiment of the compounds of formula II, $R^1$ is C(O)R$^3$ or C(O)OR$^4$.

In a further embodiment, the invention encompasses compounds of Formula III:

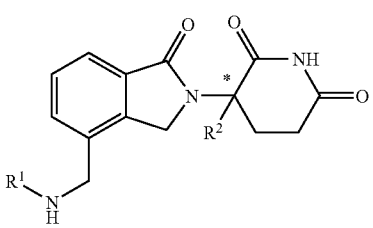

III wherein:
$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_{1-6})$heterocycloalkyl, $(C_0-C_4)$alkyl)-$C_2-C_5$)heteroaryl, C(O)R$^3$, C(S)R$^3$, C(O)OR$^4$, $(C_1-C_8)$alkyl-N$(R^6)_2$, $(C_1-C_8)$alkyl-OR$^5$, $(C_1-C_8)$alkyl-C(O)OR$^5$, C(O)NHR$^3$, C(S)NHR$^3$, C(O)NR$^3$R$^3$, C(S)NR$^3$R$^3$' or $(C_1-C_8)$alkyl-O(CO)R$^5$;

$R^2$ is H or $(C_1-C_8)$alkyl;

$R^3$ and $R^{3'}$ are independently is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$C_1-C_6$)heterocycloalkyl, $(C_0-C_4)$alkyl-$C_2-C_5$)heteroaryl, $(C_0-C_8)$alkyl-N$(R^6)_2$, $(C_1-C_8)$alkyl-OR$^5$, $(C_1-C_8)$alkyl-C(O)OR$^5$, $(C_1-C_8)$alkyl-O(CO)R$^5$, or C(O)OR$^5$;

$R^4$ is $(C_1-C_8)$alkyl, $(C_2-C_8)$alkenyl, $(C_2-C_8)$alkynyl, $(C_1-C_4)$alkyl-OR$^5$, benzyl, aryl, $(C_0-C_4)$alkyl-$(C_1-C_6)$heterocycloalkyl, or $(C_0-C_4)$alkyl-$(C_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-C(O)O—$R^5$ or the $R^6$ groups can join to form a heterocycloalkyl group; and the * represents a chiral-carbon center.

In yet another embodiment of the compounds of formula III, $R^1$ is H, $(C_1-C_4)$alkyl, $CH_2OCH_3$, $CH_2CH_2OCH_3$, or

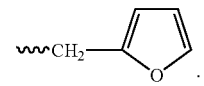

In another embodiment of the compounds of formula III, $R^1$ is

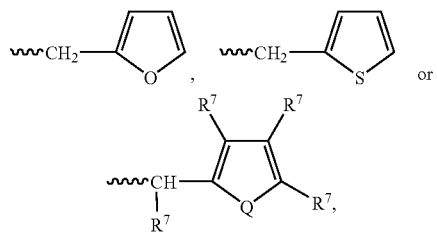

wherein Q is O or S, and each occurrence of $R^7$ is independently H, $(C_1-C_8)$alkyl, $(C_3-C_7)$cycloalkyl, $(C_2-C_8)$alkenyl, $(C_2-C_8)$alkynyl, benzyl, aryl, halogen, $(C_0-C_4)$alkyl)-$C_1-C_6$ heterocycloalkyl, $(C_0-C_4)$alkyl $C_2-C_5$)heteroaryl, $(C_0-C_8)$alkyl-N$(R^6)_2$, $(C_1-C_8)$alkyl-OR$^5$, $(C_1-C_8)$alkyl-C(O)OR$^5$, $(C_{1-8})$alkyl-O(CO)R$^5$, or C(O)OR$^5$, or adjacent occurrences of $R^7$ can be taken together to form a bicyclic alkyl or aryl ring.

In still another embodiment of the compounds of formula III, $R^1$ is C(O)R$^3$ or C(O)OR$^4$.

In a further embodiment still, the invention encompasses compounds of Formula IV:

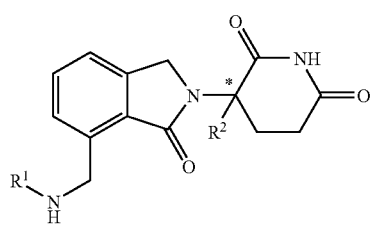

IV wherein:
$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$C_2-C_5$)heteroaryl, C(O)R$^3$, C(S)R$^3$, C(O)OR$^4$, $(C_1-C_8)$alkyl-N$(R^6)_2$, $(C_1-C_8)$alkyl-OR$^5$, $(C_1-C_8)$alkyl-C(O)OR$^5$, C(O)NHR$^3$, C(S)NHR$^3$, C(O)NR$^3$R$^{3''}$, C(S)NR$^3$R$^3$ or $(C_1-C_8)$alkyl-O(CO)R$^5$;

$R^2$ is H or $(C_1-C_8)$alkyl;

R$^3$ and R$^{3'}$ are independently (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-C$_1$-C$_6$)heterocycloalkyl, (C$_0$-C$_4$)alkyl-C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$;

R$^4$ is (C$_1$-C$_8$)alkyl, (C$_2$-C$_8$)alkenyl, (C$_2$-C$_8$)alkynyl, (C$_1$-C$_4$)alkyl-OR$^5$, benzyl, aryl, (C$_0$-C$_4$)alkyl(C$_1$-C$_6$)heterocycloalkyl, or (C$_0$-C$_4$)alkyl-(C$_2$-C$_5$)heteroaryl;

R$^5$ is (C$_{1-8}$)alkyl, (C$_2$-C$_8$)alkenyl, (C$_{2-8}$)alkynyl, benzyl, aryl, or (C$_2$-C$_5$)heteroaryl;

each occurrence of R$^6$ is independently H, (C$_1$-C$_8$)alkyl, (C$_2$-C$_8$)alkenyl, (C$_2$-C$_8$)alkynyl, benzyl, aryl, (C$_2$-C$_5$)heteroaryl, or (C$_0$-C$_8$)alkyl-C(O)O—R$^5$ or the R$^6$ groups can join to form a heterocycloalkyl group; and the * represents a chiral-carbon center.

In another embodiment of the compounds of formula IV, R$^1$ is H, (C$_1$-C$_4$)alkyl, CH$_2$OCH$_3$, CH$_2$CH$_2$OCH$_3$, or

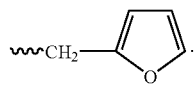

In yet another embodiment of the compounds of formula IV, R$^1$ is

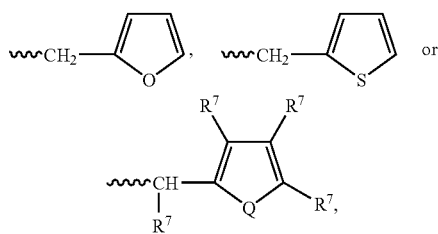

wherein Q is O or S, and each occurrence of R$^7$ is independently H, (C$_1$-C$_8$)alkyl, (C$_3$-C$_7$)cycloalkyl, (C$_2$-C$_8$)alkenyl, (C$_2$-C$_8$)alkynyl, benzyl, aryl, halogen, (C$_0$-C$_4$)alkyl(C$_1$-C$_6$)heterocycloalkyl, (C$_0$-C$_4$)alkyl-(C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$, or adjacent occurrences of R$^7$ can be taken together to form a bicyclic alkyl or aryl ring.

In still another embodiment of the compounds of formula IV, R$^1$ is C(O)R$^3$ or C(O)OR$^4$.

In yet another embodiment, the invention encompasses compounds of Formula V:

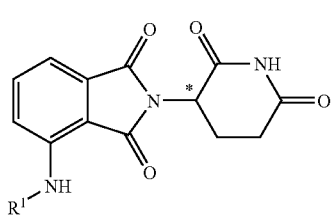

wherein:
R$^1$ is H, (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl)-C$_1$-C$_6$)heterocycloalkyl, (C$_0$-C$_4$)alkyl-C$_2$-C$_5$)heteroaryl, C(O)R$^3$, C(S)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, C(O)NHR$^3$, C(S)NHR$^3$, C(O)NR$^3$R$^3$, C(S)NR$^3$R$^3$ or (C$_3$-C$_8$)alkyl-O(CO)R$^5$;

R$^3$ and R$^{3'}$ are independently (C$_1$-C$_8$)alkyl, (C$_3$-C$_7$)cycloalkyl, (C$_7$-C$_8$)alkenyl, (C$_2$-C$_8$)alkynyl, benzyl, aryl, (C$_0$-C$_4$)alkyl-C$_1$-C$_6$)heterocycloalkyl, (C$_0$-C$_4$)alkyl-(C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl —C(O)OR$^5$, (C$_1$-C$_8$)alkyl-O(CO)R$^5$, or C(O)OR$^5$;

R$^4$ is (C$_1$-C$_8$)alkyl, (C$_2$-C$_8$)alkenyl, (C$_2$-C$_8$)alkynyl, (C$_1$-C$_4$)alkyl-OR$^5$, benzyl, aryl, (C$_0$-C$_4$)alkyl-(C$_1$-C$_6$)heterocycloalkyl, or (C$_0$-C$_4$)alkyl-C$_2$-C$_5$)heteroaryl;

R$^5$ is (C$_1$-C$_8$)alkyl, (C$_2$-C$_8$)alkenyl, (C$_2$-C$_8$)alkynyl, benzyl, aryl, or (C$_{2-5}$)heteroaryl;

each occurrence of R$^6$ is independently H, (C$_1$-C$_8$)alkyl, (C$_2$-C$_8$)alkenyl, (C$_2$-C$_8$)alkynyl, benzyl, aryl, (C$_2$-C$_5$)heteroaryl, or (C$_0$-C$_8$)alkyl-C(O)O—R$^5$ or the R$^6$ groups can join to form a heterocycloalkyl group; and the * represents a chiral-carbon center.

In a separate embodiment of compounds of formula V, R$^1$ is (C$_3$-C$_7$)cycloalkyl, (C$_2$-C$_8$)alkenyl, (C$_2$-C$_8$)alkynyl, benzyl, aryl, (C$_0$-C$_4$)alkyl-C$_1$-C$_6$)heterocycloalkyl, (C$_0$-C$_4$)alkyl-C$_2$-C$_5$)heteroaryl, C(O)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, or (C$_1$-C$_8$)alkyl-O(CO)R$^5$; and R$^3$ is (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-C$_1$-C$_6$)heterocycloalkyl, (C$_0$-C$_4$)alkyl)-C$_2$-C$_5$)heteroaryl, (C$_5$-C$_8$)alkyl-N(R$^6$)$_2$; (C$_0$-C$_8$)alkyl-NH—C(O)O—R$^5$; (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$; and the other variables have the definitions above.

In another embodiment of the compounds of formula V, R$^1$ is (C$_1$-C$_8$)alkyl or benzyl, CH$_2$OCH$_3$, CH$_2$CH$_2$OCH$_3$, or

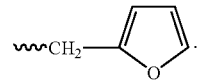

In another embodiment of the compounds of formula V, R$^1$ is

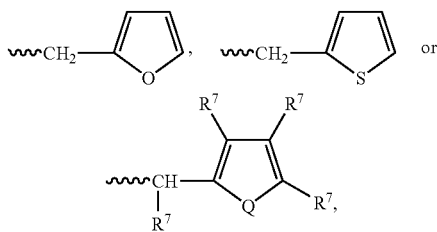

wherein Q is O or S, and each occurrence of R$^7$ is independently H, (C$_1$-C$_8$)alkyl, (C$_3$-C$_7$)cycloalkyl, (C$_2$-C$_8$)alkenyl, (C$_2$-C$_8$)alkynyl, benzyl, aryl, halogen, (C$_0$-C$_4$)alkyl)-C$_1$-C$_6$)heterocycloalkyl, (C$_0$-C$_4$)alkyl)-C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(O)OR$^5$, or adjacent occurrences of R$^7$ can be taken together to form a bicyclic alkyl or aryl ring.

In still another embodiment of the compounds of formula V, R$^1$ is C(O)R$^3$ or C(O)OR$^4$.

In another embodiment of the compounds of formula V, R$^3$ is (C$_0$-C$_4$)alkyl)-C$_2$-C$_5$)heteroaryl, (C$_1$-C$_8$)alkyl, aryl, or (C$_0$-C$_4$)alkyl-OR$^5$.

In yet another embodiment of the compounds of formula V, heteroaryl is pyridyl, furyl, or thienyl.

In another embodiment, the invention further provides compounds of Formula VI:

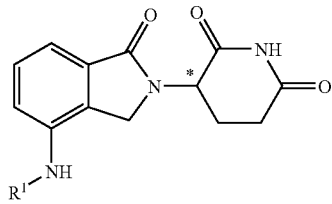

VI wherein:
$R^1$ is $(C_1-C_8)$alkyl, $(C_3-C_7)$cycloalkyl, $(C_2-C_8)$alkenyl, $(C_2-C_8)$alkynyl; benzyl, aryl, $(C_0-C_4)$alkyl)-$(C_1-C_6)$heterocycloalkyl, $(C_0-C_4)$alkyl-$C_2-C_5)$heteroaryl, $C(O)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(S)NHR^3$, or $(C_1-C_8)$alkyl-$O(CO)R^5$;
$R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$C_1-C_6)$heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;
$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$C_1-C_6)$heterocycloalkyl, or $(C_0-C_4)$alkyl-$(C_2-C_5)$heteroaryl;
$R^5$ is $(C_1-C_8)$alkyl, $(C_2-C_8)$alkenyl, $(C_2-C_8)$alkynyl, benzyl, aryl, or $(C_2-C_5)$heteroaryl;
each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-$C(O)O$—$R^5$ or the $R^6$ groups can join to form a heterocycloalkyl group; and
the * represents a chiral-carbon center.

In a separate embodiment of compounds of formula VI, $R^1$ is $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$,$C(S)NHR^3$, or $(C_1-C_8)$alkyl-$O(CO)R^5$; and
$R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$C_1-C_6)$heterocycloalkyl, $(C_0-C_4)$alkyl-$C_2-C_5)$heteroaryl, $(C_5-C_8)$alkyl-$N(R^6)_2$; $(C_0-C_8)$alkyl-$NH$—$C(O)O$—$R^5$; $(C_1-C_8)$alkyl-$OR^5$, $(C_1-C_8)$alkyl-$C(O)OR^5$, $(C_1-C_8)$alkyl-$O(CO)R^5$, or $C(O)OR^5$; and the other variables are defined as above.

In another embodiment of the compounds of formula VI, $R^1$ is $(C_1-C_8)$alkyl, benzyl, $CH_2OCH_3$, $CH_2CH_2OCH_3$, or

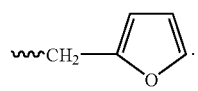

In another embodiment of the compounds of formula VI, $R^1$ is

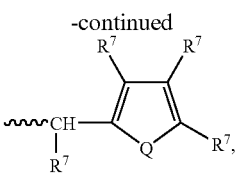

wherein Q is O or S, and each occurrence of $R^7$ is independently H, $(C_1-C_8)$alkyl, $(C_3-C_7)$cycloalkyl, $(C_2-C_8)$alkenyl, $(C_{2-8})$alkynyl, benzyl, aryl, halogen, $(C_0-C_4)$alkyl-$(C_1-C_6)$heterocycloalkyl, $(C_0-C_4)$alkyl-$C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$, or adjacent occurrences of $R^7$ can be taken together to form a bicyclic alkyl or aryl ring.

In still another embodiment of the compounds of formula VI, $R^1$ is $C(O)R^3$ or $C(O)OR^4$.

In another embodiment of the compounds of formula VI, $R^3$ is $(C_0-C_4)$alkyl-$C_2-C_5)$heteroaryl, $(C_1-C_8)$alkyl, aryl, or $(C_0-C_4)$alkyl-$OR^5$.

In yet another embodiment of the compounds of formula VI, heteroaryl is pyridyl, furyl, or thienyl. In another embodiment of the compounds of formula VI, the H of $C(O)NHC(O)$ can be replaced with $(C_1-C_4)$alkyl, aryl, or benzyl.

In still another embodiment, the invention encompasses compounds of Formula VII:

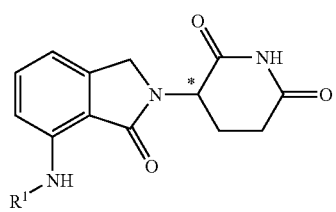

VII wherein:
$R^1$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$C_1-C_6)$heterocycloalkyl, $(C_0-C_4)$alkyl-$(C_2-C_5)$heteroaryl, $C(O)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(S)NHR^3$, or $(C_1-C_8)$alkyl-$O(CO)R^5$;
$R^3$ is $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$C_1-C_6)$heterocycloalkyl, $(C_0-C_4)$alkyl)-$C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;
$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$(C_1-C_6)$heterocycloalkyl, or $(C_0-C_4)$alkyl-$C_2-C_5)$heteroaryl;
$R^5$ is $(C_1-C_8)$alkyl, $(C_2-C_8)$alkenyl, $(C_2-C_8)$alkynyl, benzyl, aryl, or $(C_2-C_5)$heteroaryl;
each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-$C(O)O$—$R^5$ or the $R^6$ groups can join to form a heterocycloalkyl group; and
the * represents a chiral-carbon center.

In a separate embodiment of compounds of formula VII, $R^1$ is $(C_3-C_7)$cycloalkyl, $(C_2-C_8)$alkenyl, $(C_2-C_8)$alkynyl, benzyl, aryl, $(C_0-C_4)$alkyl-$C_1-C_6)$heterocycloalkyl, $(C_0-C_4)$alkyl-$(C_2-C_5)$heteroaryl, $C(O)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(S)NHR^3$, or $(C_1-C_8)$alkyl-$O(CO)R^5$; and $R^3$ is $(C_1$-$C_8)$alkyl, $(C_3$-$C_7)$cycloalkyl, $(C_2$-$C_8)$alkenyl, $(C_2$-$C_8)$alkynyl, benzyl, aryl, $(C_0$-$C_4)$alkyl-$C_1$-$C_6)$heterocycloalkyl, $(C_0$-$C_4)$alkyl)-$C_2$-$C_5)$heteroaryl, $(C_5$-$C_8)$alkyl-N $(R^6)_2$; $(C_0$-$C_8)$alkyl-NH—C(O)O—$R^5$; $(C_1$-$C_8)$alkyl-$OR^5$, $(C_1$-$C_8)$alkyl-C(O)$OR^5$, $(C_1$-$C_8)$alkyl-O(CO)$R^5$, or C(O)$OR^5$; and the other variables are as defined above.

In another embodiment of the compounds of formula VII $R^1$ is $(C_1$-$C_8)$alkyl, benzyl, $CH_2OCH_3$, $CH_2CH_2OCH_3$, or

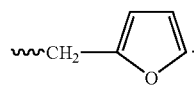

In another embodiment of the compounds of formula VII, $R^1$ is

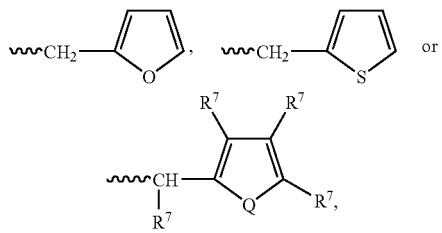

wherein Q is O or S, and each occurrence of $R^7$ is independently H, $(C_1$-$C_8)$alkyl, $(C_3$-$C_7)$cycloalkyl, $(C_2$-$C_8)$alkenyl, $(C_2$-$C_8)$alkynyl, benzyl, aryl, halogen, $(C_0$-$C_4)$alkyl-$C_1$-$C_6)$ heterocycloalkyl, $(C_0$-$C_4)$alkyl-$(C_2$-$C_5)$heteroaryl, $(C_0$-$C_8)$ alkyl-$N(R^6)_2$, $(C_1$-$C_8)$alkyl-$OR^5$, $(C_1$-$C_8)$alkyl-C(O)$OR^5$, $(C_1$-$C_8)$alkyl-O(CO)$R^5$, or C(O)$OR^5$, or adjacent occurrences of $R^7$ can be taken together to form a bicyclic alkyl or aryl ring.

In still another embodiment of the compounds of formula VII, $R^1$ is C(O)$R^3$ or C(O)$OR^4$.

In another embodiment of the compounds of formula VII, $R^3$ is $(C_0$-$C_4)$alkyl-$C_2$-$C_5)$heteroaryl, $(C_1$-$C_8)$alkyl, aryl, or $(C_0$-$C_4)$alkyl-$OR^5$. In yet another embodiment of the compounds of formula VII, heteroaryl is pyridyl, furyl, or thienyl.

As used herein, the phrase "compounds of the invention" means, collectively, compounds falling within Formulas I, II, III, IV, V, VI, and VII and include pharmaceutically acceptable salts, hydrates, solvates, and clathrates thereof.

The compounds of the invention generally exist in solid form and can be recrystallized according to well-known methods affording high-purity crystals, preferably, in greater than 95% purity, more preferably, in greater than 98% purity. Narrow melting-point range is an indication of purity, thus, compounds of the invention generally have a melting point within a range of 3° C. to 4° C., more preferably, within a range of 2° C.

The compounds of the invention can contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding enantiomers and stereoisomers, that is, both the stereomerically pure form (e.g., geometrically pure, enantiomerically pure, or diastereomerically pure) and enantiomeric and stereoisomeric mixtures, e.g., racemates.

A compound of the invention is considered optically active or enantiomerically pure (i.e., substantially the R-form or substantially the S-form) with respect to a chiral center when the compound is about 90% ee (enantiomeric excess) or greater, preferably, equal to or greater than 95% ee with respect to a particular chiral center. A compound of the invention is considered to be in enantiomerically enriched form when the compound has an enantiomeric excess of greater than about 1% ee, preferably greater than about 5% ee, more preferably, greater than about 10% ee with respect to a particular chiral center. As used herein, a racemic mixture means about 50% of one enantiomer and about 50% of is corresponding enantiomer relative to all chiral centers in the molecule. Thus, the invention encompasses all enantiomerically pure, enantiomerically enriched, and racemic mixtures of compounds of Formulas I through VII.

Enantiomeric and stereoisomeric mixtures of compounds of the invention can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The invention further encompasses prodrugs of compounds falling within Formulas I, II, III, IV, V, VI, and VII. The term "prodrug" refers to a compound that, following administration in a mammal, converts, via a biotransformation, into a compound falling within Formulas I, II, III, IV, V, VI, and VII in vivo. Prodrugs of compounds falling within Formulas I, II, III, IV, V, VI, and VII can be synthesized using well-known methods, such as those described by Burger's Medicinal Chemistry and Drug Chemistry, Fifth Ed., Vol. 1, pp. 172-178, 949-982 (1995).

The compounds of the invention are defined herein by their chemical structures and/or chemical names. Where a compound is referred to by both a chemical structure and a chemical name, and the chemical structure and chemical name conflict, the chemical structure is determinative of the compound's identity.

In another embodiment, the present invention further provides pharmaceutical compositions comprising a therapeutically effective or a prophylactically effective amount of one or more compounds of the invention and a pharmaceutically acceptable vehicle or carrier. A pharmaceutically acceptable vehicle or carrier can comprise an excipient, diluent, or a mixture thereof. The term "therapeutically effective amount" means the amount of a compound of the invention that will elicit the biological or medical response in a mammal that is being that is being treated by the veterinarian or clinician. The term "prophylactically effective" means the amount of a compound of the invention that will prevent or inhibit affliction or mitigate affliction of a mammal with a medical condition that a veterinarian or clinician is trying to prevent, inhibit, or mitigate.

In another embodiment, the invention concerns a method of modulating the production or lowering the levels of TNF-α in a mammal comprising administering to said mammal an effective amount of a compound of the invention.

In yet another embodiment, the invention concerns a method of modulating the production or lowering the levels of IL-1 β in a mammal comprising administering to said mammal an effective amount of a compound of the invention.

In a further embodiment, the invention concerns a method of modulating the production or increasing the levels of IL-10 in a mammal comprising administering to said mammal an effective amount of a compound of the invention.

In still another embodiment, the invention concerns a method of modulating the production or increasing the levels of T-cells in a mammal comprising administering to said mammal an effective amount of a compound of the invention.

In still another embodiment, the invention concerns a method of treating or preventing cancer in a mammal, comprising administering to said mammal a therapeutically effective amount of a compound of the invention. The compounds of the invention can be used to treat or prevent any cancer, for example, solid tumors and blood-born tumors. Specific examples of cancers treatable or preventable by compounds of the invention include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are particularly useful for treating cancers of the blood and bone marrow, such as multiple myeloma and acute and chronic leukemias, for example, lymphoblastic, myclogenous, lymphocytic, and myelocytic leukemias. The compounds of the invention can be used for treating or preventing either primary or metastatic tumors.

In yet one more embodiment, the invention provides methods of treating or preventing cancer in a mammal, comprising administering to a mammal in need thereof, a therapeutically effective amount of a compound of the invention and another cancer chemotherapeutic agent.

In yet another embodiment, the invention concerns a method of treating or preventing inflammatory disorders in a mammal, comprising administering to said mammal a therapeutically effective amount of a compound of the invention. The compounds of the invention are especially effective to treat or prevent inflammatory diseases related to the up-regulation of TNF-α including, but not limited to, arthritic conditions, such as, rheumatoid arthritis, and osteoarthritis; rheumatoid spondylitis; psoriasis; post ischemic perfusion injury; inflammatory bowel disease; and chronic inflammatory pulmonary disease.

In one more embodiment still, the invention provides methods of treating or preventing inflammatory disorders in a mammal, comprising administering to a mammal in need thereof, a therapeutically effective amount of a compound of the invention and another anti-inflammatory agent.

In a further embodiment, the invention concerns a method of treating or preventing heart disease in a mammal comprising administering to said mammal a therapeutically effective amount of a compound of the invention. For example, the compounds of the invention can be used to treat or prevent congestive heart failure, cardiomyopathy, pulmonary edema, endotoxin-mediated septic shock, acute viral myocarditis, cardiac allograft rejection, and myocardial infarction.

In an additional embodiment, the invention concerns a method of treating or preventing osteoporosis in a mammal comprising administering to said mammal a therapeutically effective amount of a compound of the invention.

In a further embodiment, the invention relates to a method of treating or preventing viral, genetic, inflammatory, allergic, and autoimmune diseases. For example, the compounds are useful to treat or prevent diseases including, but not limited to, HIV, hepatitis, adult respiratory distress syndrome, bone resorption diseases, chronic pulmonary inflammatory diseases, dermatitis, cystic fibrosis, septic shock, sepsis, endotoxic shock, hemodynamic shock, sepsis syndrome, post ischemic reperfusion injury, meningitis, psoriasis, fibrotic disease, cachexia, graft rejection, auto-immune disease, rheumatoid spondylitis, Crohn's disease, ulcerative colitis, inflammatory-bowel disease, multiple sclerosis, systemic lupus erythrematosus, ENL in leprosy, radiation damage, asthma, or hyperoxic alveolar injury in a mammal comprising administering to said mammal a therapeutically effective amount of a compound of the invention.

In still another embodiment, the invention concerns a method of treating or preventing malaria, mycobacterial infection, or an opportunistic infection resulting from HIV in a mammal, comprising administering to said mammal a therapeutically effective amount of a compound of the invention.

In still one more embodiment, the invention relates to treating or preventing mammals having more than one of the conditions treatable by a compound of the invention.

In the above embodiments, it is preferable that the mammal be in need of the treatment or prevention, that is, the mammal is actually suffering from a medical condition or at risk of a medical condition for which a compound of the invention can provide treatment or prevention. However, the compounds of the invention can also be administered to test animals that do not necessarily require such treatment or prevention.

In a further embodiment, the invention encompasses a method of modulating the production or lowering the levels of TNF-α in a mammalian cell or tissue comprising contacting an effective amount of a compound of the invention with said mammalian cell or tissue.

In yet another embodiment, the invention encompasses a method of modulating the production or lowering the levels of IL-1β in a mammalian cell or tissue comprising contacting an effective amount of a compound of the invention with said mammalian cell or tissue.

In still another embodiment, the invention encompasses a method of modulating the production or lowering the levels of IL-10 in a mammalian cell or tissue comprising contacting an effective amount of a compound of the invention with said mammalian cell or tissue.

In still another embodiment, the invention encompasses a method of modulating the production or lowering the levels of T-cells in a mammalian cell or tissue comprising contacting an effective amount of a compound of the invention with said mammalian cell or tissue.

In these embodiments, the term "effective amount" means the amount of the compound that will induce the biological response sought by the researcher, veterinarian, physician, or clinician. It should be understood that the cell can be in a cell culture or a tissue culture (in vitro) or in an organism (in vivo) including a human.

The present invention may be understood by reference to the detailed description and examples that are intended to exemplify non-limiting embodiments of the invention.

5. DEFINITIONS

The phrase "pharmaceutically acceptable salt(s)," as used herein includes, but is not limited to, salts of acidic or basic groups that may be present in the compounds of the invention. Compounds of the invention that are basic in nature are capable of forming a wide variety of salts with various inorganic and organic acids. The acids that may be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate (i.e., 1,1'-methylene-bis-(2-hydroxy-3-naphthoate)). Compounds of the invention that include an amino moiety also can form pharmaceutically acceptable salts with various amino acids, in addition to the acids mentioned above. Compounds of the invention that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

As used herein, the term "solvate" means a compound of the invention or a salt thereof, that further includes a stoichiometric or non-stoichiometric amount of a solvent bound by non-covalent intermolecular forces. Preferred solvents are volatile, non-toxic, and/or acceptable for administration to humans in trace amounts.

As used herein, the term "hydrate" means a compound of the invention or a salt thereof, that further includes a stoichiometric or non-stoichiometric amount of water bound by non-covalent intermolecular forces.

The term "clathrate" means a compound of the invention or a salt thereof in the form of a crystal lattice that contains spaces (e.g., channels) that have a guest molecule (e.g., a solvent or water) trapped within.

As used herein, the term "alkyl group" means a saturated, monovalent, unbranched or branched hydrocarbon chain. Examples of alkyl groups include, but are not limited to, $(C_1-C_8)$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, heptyl, and octyl. An alkyl group can be unsubstituted or substituted with one or two suitable substituents.

An "alkenyl group" means a monovalent, unbranched or branched hydrocarbon chain having one or more double bonds therein. The double bond of an alkenyl group can be unconjugated or conjugated to another unsaturated group. Suitable alkenyl groups include, but are not limited to $(C_2-C_8)$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

An "alkynyl group" means monovalent, unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_8)$alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

An "aryl group" means a monocyclic or polycyclic-aromatic group comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more suitable substituents. Preferably, the aryl group is a monocyclic ring, wherein the ring comprises 6 carbon atoms, referred to herein as "$(C_6)$ aryl.".

A "heteroaryl group" means a monocyclic or polycyclic aromatic ring comprising carbon atoms and one or more heteroatoms, preferably, 1 to 3 heteroatoms, independently selected from nitrogen, oxygen, and sulfur. Preferred heteroaryl-ring systems include 5 to 6 membered monocyclic, 8 to 11 membered bicyclic, and 11 to 15 membered tricyclic ring systems. As well known to those skilled in the art, heteroaryl rings have less aromatic character than their all-carbon counter parts. Thus, for the purposes of the invention, a heteroaryl group need only have some degree of aromatic character. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, phenyl, isoxazolyl, and oxazolyl. A heteroaryl group can be unsubstituted or substituted with one or two suitable substituents. Preferably, a heteroaryl group is a 5 or 6 membered monocyclic ring, wherein the ring comprises 2 to 5 carbon atoms and 1 to 3 heteroatoms, referred to herein as "$(C_2-C_5)$heteroaryl", which optionally can be fused to one or more other aryl, cycloalkyl, heteroaryl, or heterocyclic ring systems to form 7 to 10 membered bicyclic or 10 to 15 membered tricyclic ring systems.

A "cycloalkyl group" means a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, $(C_3-C_8)$cycloalkyl groups, such as cyclopropyl, cyclobutyl, cyclopentyl, cyclohexyl, and cycloheptyl, and saturated cyclic and bicyclic terpenes and $(C_3-C_8)$cycloalkenyl groups, such as cyclopropenyl, cyclobutenyl, cyclopentenyl, cyclohexenyl, and cycloheptenyl, and unsaturated cyclic and bicyclic terpenes. A cycloalkyl group can be unsubstituted or substituted by one or two suitable substituents. Preferably, the cycloalkyl group is a monocyclic ring or bicyclic ring.

A "heterocycloalkyl group" means a non-aromatic monocyclic or polycyclic ring comprising carbon atoms and at least one heteroatom, preferably, 1 to 4 heteroatoms independently selected from nitrogen, oxygen, and sulfur. Preferred heterocyclic-ring systems include 3 to 8 membered monocyclic, 8 to 11 membered bicyclic, and 11 to 15 membered tricyclic ring systems. A heterocycloalkyl group can have one or more carbon-carbon double bonds or carbon-heteroatom double bonds in the ring as long as the ring is not rendered aromatic by their presence. Examples of heterocycloalkyl groups include aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl. A heterocycloalkyl group can be unsubstituted or substituted with one or more suitable substituents. Preferably, the heterocycloalkyl group is a monocyclic or bicyclic ring, more preferably, a 3-7 membered monocyclic ring, wherein the ring comprises from 1 to 6 carbon atoms and from 1 to 3 heteroatoms, referred to herein as "($C_1$-$C_6$)heterocycloalkyl", which optionally can be fused to one or more other aryl, cycloalkyl, heteroaryl, or heterocyclic ring systems to form 7 to 10 membered bicyclic or 10 to 15 membered tricyclic ring systems.

The term "alkoxy group" means an —O-alkyl group, wherein alkyl is as defined above. An alkoxy group can be unsubstituted or substituted with one or two suitable substituents. Preferably, the alkyl chain of an alkyloxy group is from 1 to 8 carbon atoms in length, referred to herein as "($C_1$-$C_8$) alkoxy".

The term "aryloxy group" means an O-aryl group, wherein aryl is as defined above. An aryloxy group can be unsubstituted or substituted with one or two suitable substituents.

Preferably, the aryl ring of an aryloxy group is a monocyclic ring, wherein the ring comprises 6 carbon atoms, referred to herein as "($C_6$)aryloxy".

The term "benzyl" means $CH_2$-phenyl. A benzyl group can be unsubstituted or substituted with one or more suitable substituents.

The term "phenyl" means $C_6H_5$. A phenyl group can be unsubstituted or substituted with one or more suitable substituents.

A "carbonyl" group is a divalent group of the formula —C(O)—.

An "alkoxycarbonyl" group means a monovalent group of the formula C(O)-alkoxy. Preferably, the hydrocarbon chain of an alkoxycarbonyl group is from 1 to 8 carbon atoms in length, referred to herein as a "lower alkoxycarbonyl" group.

As used herein, "halogen" means fluorine, chlorine, bromine, or iodine. Correspondingly, the meaning of the term "halo" encompass fluoro, chloro, bromo, and iodo.

As used herein, a "suitable substituent" means a group that does not nullify the synthetic or pharmaceutical utility of the compounds of the invention or the intermediates useful for preparing them. Examples of suitable substituents include, but are not limited to: ($C_1$-$C_8$)alkyl; ($C_1$-$C_8$)alkenyl; ($C_1$-$C_8$) alkynyl; aryl; ($C_2$-$C_5$)heteroaryl; ($C_1$-$C_6$)heterocycloalkyl; ($C_3$-$C_7$)cycloalkyl; O—($C_1$-$C_8$)alkyl; O—($C_1$-$C_8$)alkenyl; O—($C_1$-$C_8$)alkynyl; O-aryl; CN; OH; oxo; halo, C(O)OH; COhalo; O(CO)halo; $CF_3$, $N_3$; $NO_2$, $NH_2$; NH(($C_{1-8}$)alkyl); N(($C_{1-8}$)alkyl)$_2$; NH(aryl); N(aryl)$_2$; (CO)$NH_2$, (CO)NH (($C_1$-$C_8$)alkyl); (CO)N(($C_1$-$C_8$)alkyl)$_2$; (CO)NH(aryl); (CO) N(aryl)$_2$; O(CO)$NH_2$; NHOH; NOH(($C_1$-$C_8$)alkyl); NOH (aryl); O(CO)NH(($C_1$-$C_8$)alkyl); O(CO)N(($C_1$-$C_8$)alkyl)$_2$; O(CO)NH(aryl); O(CO)N(aryl)$_2$; CHO; CO(($C_1$-$C_8$)alkyl); CO(aryl); C(O)O(($C_1$-$C_8$)alkyl); C(O)O(aryl); O(CO)(($C_1$-$C_8$)alkyl); O(CO)(aryl); O(CO)O(($C_1$-$C_8$)alkyl); O(CO)O (aryl); S—($C_1$-$C_8$)alkyl; S—($C_1$-$C_8$)alkenyl; S—($C_1$-$C_8$) alkynyl; and S-aryl. One of skill in art can readily choose a suitable substituent based on the stability and pharmacological and synthetic activity of the compound of the invention.

6. DETAILED DESCRIPTION OF THE INVENTION

In one embodiment, the invention encompasses compounds of the formula:

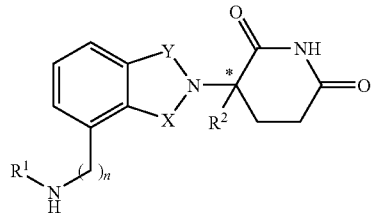

or a pharmaceutically acceptable salt, hydrate, solvate, clathrate, enantiomer, diastereomer, racemate, or mixture of stereoisomers thereof, wherein:

one of X and Y is C═O and the other is $CH_2$ or C═O;

$R^1$ is H, ($C_1$-$C_8$)alkyl, ($C_3$-$C_7$)cycloalkyl, ($C_2$-$C_8$)alkenyl, ($C_2$-$C_8$)alkynyl, benzyl, aryl, ($C_0$-$C_4$)alkyl)-$C_1$-$C_6$)heterocycloalkyl, ($C_0$-$C_4$)alkyl)-$C_2$-$C_5$)heteroaryl, C(O)$R^3$, C(S) $R^3$, C(O)O$R^4$, ($C_1$-$C_8$)alkyl-N($R^6$)$_2$, ($C_1$-$C_8$)alkyl-O$R^5$, ($C_1$-$C_8$)alkyl-C(O)O$R^5$, C(O)NH$R^3$, C(S)NH$R^3$, C(O) N$R^3R^3$, C(S)N$R^3R^{3'}$ or ($C_3$-$C_8$)alkyl-O(CO)$R^5$;

$R^2$ is H, F, benzyl, ($C_1$-$C_8$)alkyl, ($C_2$-$C_8$)alkenyl, or ($C_2$-$C_8$) alkynyl;

$R^3$ and $R^{3'}$ are independently ($C_1$-$C_8$)alkyl, ($C_3$-$C_7$)cycloalkyl, ($C_2$-$C_8$)alkenyl, ($C_2$-$C_8$)alkynyl, benzyl, aryl, ($C_0$-$C_4$)alkyl-($C_1$-$C_6$)heterocycloalkyl, ($C_0$-$C_4$)alkyl-$C_2$-$C_5$)heteroaryl, ($C_0$-$C_8$)alkyl-N($R^6$)$_2$, ($C_1$-$C_8$)alkyl-O$R^5$, ($C_1$-$C_8$)alkyl-C(O)O$R^5$, ($C_1$-$C_8$)alkyl-O(CO)$R^5$, or C(O) O$R^5$;

$R^4$ is ($C_1$-$C_8$)alkyl, ($C_{2-8}$)alkenyl, ($C_2$-$C_8$)alkynyl, ($C_1$-$C_4$) alkyl-O$R^5$, benzyl, aryl, ($C_0$-$C_4$)alkyl)-$C_1$-$C_6$)heterocycloalkyl, or ($C_0$-$C_4$)alkyl-$C_2$-$C_5$)heteroaryl;

$R^5$ is ($C_1$-$C_8$)alkyl, ($C_2$-$C_8$)alkenyl, ($C_2$-$C_8$)alkynyl, benzyl, aryl, or ($C_2$-$C_5$)heteroaryl;

each occurrence of $R^6$ is independently H, ($C_1$-$C_8$)alkyl, ($C_2$-$C_8$)alkenyl, ($C_2$-$C_8$)alkynyl, benzyl, aryl, ($C_2$-$C_5$)heteroaryl, or ($C_0$-$C_8$)alkyl-C(O)O—$R^5$ or the $R^6$ groups can join to form a heterocycloalkyl group;

n is 0 or 1; and the * represents a chiral-carbon center;

with the proviso that when n is 0 then $R^1$ is not H.

In a separate embodiment of compounds of formula I, when n is 0 then $R^1$ is ($C_3$-$C_7$)cycloalkyl, ($C_2$-$C_8$)alkenyl, ($C_2$-$C_8$)alkynyl, benzyl, aryl, ($C_0$-$C_4$)alkyl-$C_1$-$C_6$)heterocycloalkyl, ($C_{0-4}$)alkyl-$C_2$-$C_5$)heteroaryl, C(O)$R^3$, C(O)$R^4$, ($C_1$-$C_8$)alkyl-N($R^6$)$_2$, ($C_1$-$C_8$)alkyl-O$R^5$, ($C_{1-8}$)alkyl-C(O) O$R^5$, or ($C_1$-$C_8$)alkyl-O(CO)$R^5$;

$R^2$ is H or ($C_1$-$C_8$)alkyl; and $R^3$ is ($C_1$-$C_8$)alkyl, ($C_3$-$C_7$)cycloalkyl, ($C_2$-$C_8$)alkenyl, ($C_2$-$C_8$)alkynyl, benzyl, aryl, ($C_0$-$C_4$)alkyl($C_1$-$C_6$)heterocycloalkyl, ($C_0$-$C_4$)alkyl)-$C_2$-$C_5$)heteroaryl, ($C_{5-8}$)alkyl-N ($R^6$)$_2$; ($C_0$-$C_8$)alkyl-NH—(O)O—$R^5$; ($C_1$-$C_8$)alkyl-O$R^5$, ($C_1$-$C_8$)alkyl-C(O)O$R^5$, ($C_1$-$C_8$)alkyl-O(CO)$R^5$, or C(O) O$R^5$; and the other variables have the same definitions. Further, the compounds encompassed by Formulas II, III, IV, V, VI, and VII as described above are also included within the invention.

A few examples of compounds of the invention which are illustrative and non-limiting are depicted in Table 1 below.

TABLE 1

Examples of Compounds of the Invention

| Structure | Name |
|---|---|
| I-1 | [2-(2,6-Dioxo-piperidin-3-yl)-1,3-dioxo-2,3-dihydro-1H-isoindol-4-yl-methyl]-carbamic acid tert-butyl ester |
| I-2 | 4-(Aminomethyl)-2-(2,6-dioxo(3-piperidiyl))-isoindoline-1,3-dione |
| I-3 | N-[2-(2,6-Dioxo-piperidin-3-yl)-1,3-dioxo-2,3-dihydro-1H-isoindol-4-yl-methyl]-acetamide |
| I-4 | N-{[2-(2,6-Dioxo(3-piperidyl)-1,3-dioxoisoindolin-4-yl]methyl}cyclopropyl-carboxamide |
| I-5 | [2-(2,6-Dioxo-piperidin-3-yl)-1,3-dioxo-2,3-dihydro-1H-isoindol-4-ylmethyl]-carbamic acid ethyl ester |
| I-6 | 2-(2,6-Dioxo-piperidin-3-yl)-1,3-dioxo-2,3-dihydro-1H-isoindol-4-ylmethyl]-carbamic acid benzyl ester |

TABLE 1-continued
Examples of Compounds of the Invention
| Structure | Name |
|---|---|
| 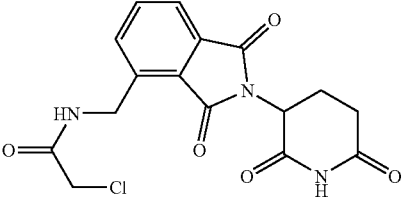 I-7 | 2-Chloro-N-{[2-(2,6-dioxo(3-piperidyl))-1,3-dioxoisoindolin-4-yl]methyl}acetamide |
| 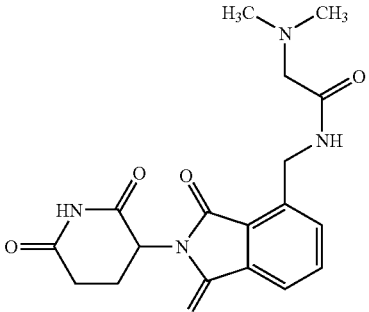 I-8 | 2-(Dimethylamino)-N-{[2-(2,6-dioxo(3-piperidyl))-1,3-dioxoisoindolin-4-yl]methyl}-acetamide |
| 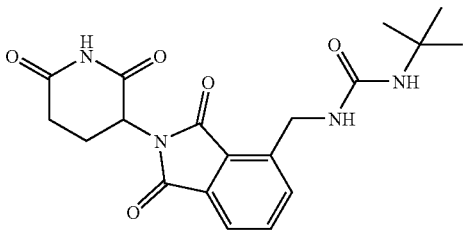 I-9 | 1-tert-Butyl-3-[2-(2,6-dioxo-piperidin-3-yl)-1,3-dioxo-2,3-dihydro-1H-isoindol-4-ylmethyl]-urea |
| 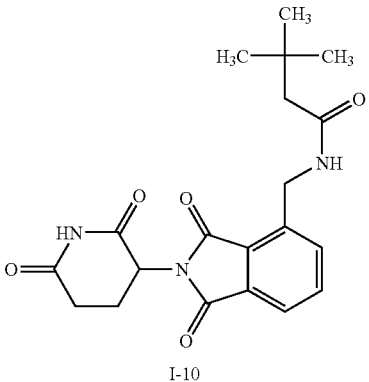 I-10 | N-{[2-(2,6-Dioxo(3-piperidyl))-1,3-dioxoisoindolin-4-yl]methyl}-3,3-dimethylbutanamide |

TABLE 1-continued

Examples of Compounds of the Invention

| Structure | Name |
|---|---|
| I-11 | N-[2-(2,6-Dioxo(3-piperidyl))-1,3-dioxoisoindolin-4-yl]-3-pyridylcarboxamide |
| I-12 | 3-{1-Oxo-4-[benzylamino]isoindolin-2-yl}piperidine-2,6-dione |
| I-13 | 2-(2,6-Dioxo(3-piperidyl))-4-[benzylamino]isoindoline-1,3-dione |
| I-14 | N-{[2-(2,6-Dioxo(3-piperidyl))-1,3-dioxoisoindolin-4-yl]methyl}propanamide |
| I-15 | N-{[2-(2,6-Dioxo(3-piperidyl))-1,3-dioxoisoindolin-4-yl]methyl}-3-pyridylcarboxamide |

TABLE 1-continued

Examples of Compounds of the Invention

| Structure | Name |
| --- | --- |
| I-16 | N-{[2-(2,6-Dioxo(3-piperidyl))-1,3-dioxoisoindolin-4-yl]methyl}heptanamide |
| I-17 | N-{[2-(2,6-Dioxo(3-piperidyl))-1,3-dioxoisoindolin-4-yl]methyl}-2-furylcarboxamide |
| I-18 | 2-Azido-N-[2-(2,6-dioxo-piperidin-3-yl)-1,3-dioxo-2,3-dihydro-1H-isoindol-4-ylmethyl]-acetamide |
| I-19 | 2-Amino-N-{[2-(2,6-dioxo(3-piperidyl))-1,3-dioxoisoindolin-4-yl]methyl}acetamide |
| I-20 | Ethyl 6-(N-{[2-(2,6-dioxo(3-piperidyl))-1,3-dioxoisoindolin-4-yl]methyl}carbamoyl)hexanoate |

TABLE 1-continued

Examples of Compounds of the Invention

| Structure | Name |
| --- | --- |
| I-21 | 3-[(tert-Butoxy)carbonylamino]-N-{[2-(2,6-dioxo(3-piperidyl))-1,3-dioxoisoindolin-4-yl]methyl}propanamide |
| I-22 | 3-Amino-N-{[2-(2,6-dioxo(3-piperidyl))-1,3-dioxoisoindolin-4-yl]methyl}propanamide |
| I-23 | N-{[2-(2,6-Dioxo(3-piperidyl))-1,3-dioxoisoindolin-4-yl]methyl}-2-thienylcarboxamide |
| I-24 | N-{[2-(2,6-Dioxo(3-piperidyl))-1,3-dioxoisoindolin-4-yl]methyl}-2-methoxyacetamide |
| I-25 | (N-{[2-(2,6-Dioxo(3-piperidyl))-1,3-dioxoisoindolin-4-yl]methyl}carbamoyl)methyl acetate |

TABLE 1-continued

Examples of Compounds of the Invention

| Structure | Name |
|---|---|
| 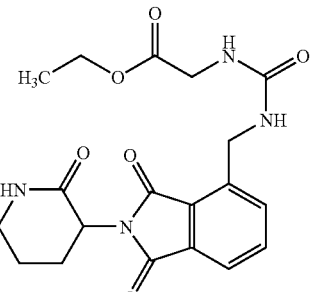<br>I-26 | Ethyl 2-[(N-{[2-(2,6-dioxo(3-piperidyl))-1,3-dioxoisoindolin-4-yl]methyl}carbamoyl)amino]acetate |
| 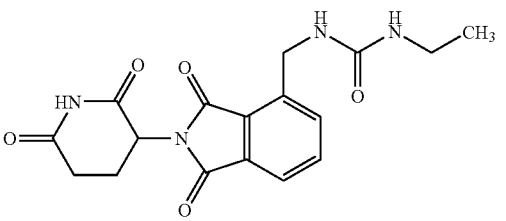<br>I-27 | N-{[2-(2,6-Dioxo(3-piperidyl))-1,3-dioxoisoindolin-4-yl]methyl}(ethylamino)carboxamide |
| 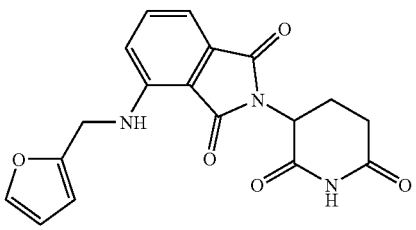<br>I-28 | 2-(2,6-Dioxo(3-piperidyl))-4-[(2-furylmethyl)amino]isoindoline-1,3-dione |
| 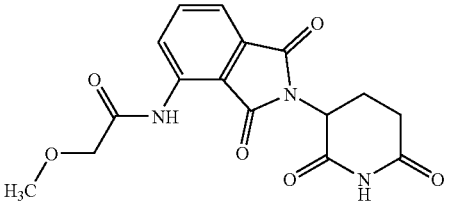<br>I-29 | N-[2-(2,6-dioxo(3-piperidyl))-1,3-dioxoisoindolin-4-yl]-2-methoxyacetamide |
| 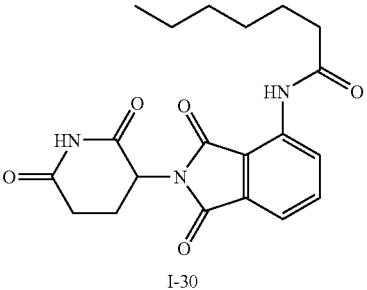<br>I-30 | N-[2-(2,6-dioxo(3-piperidyl))-1,3-dioxoisoindolin-4-yl]heptanamide |

TABLE 1-continued

Examples of Compounds of the Invention

| Structure | Name |
|---|---|
| 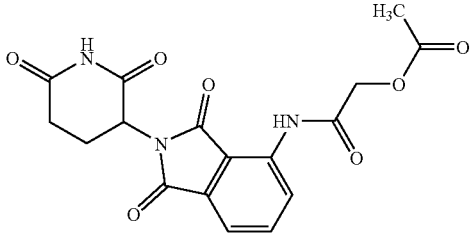<br>I-31 | {N-[2-(2,6-dioxo(3-piperidyl))-1,3-dioxoisoindolin-4-yl]carbamoyl}methyl acetate |
| 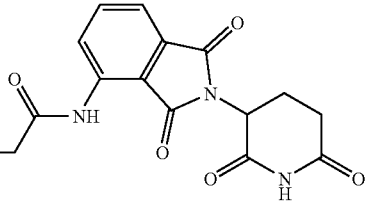<br>I-32 | N-[2-(2,6-dioxo(3-piperidyl))-1,3-dioxoisoindolin-4-yl]pentamide |
| 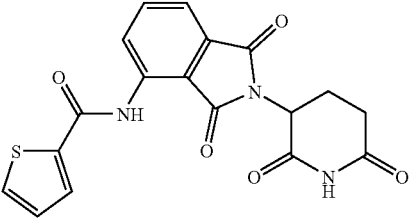<br>I-33 | N-[2-(2,6-dioxo(3-piperidyl))-1,3-dioxoisoindolin-4-yl]-2-thienylcarboxamide |
| 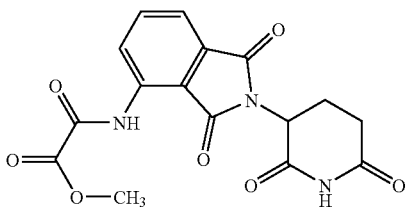<br>I-34 | Methyl {N-[2-(2,6-dioxo(3-piperidyl))-1,3-dioxoisoindolin-4-yl]carbamoyl}formate |
| 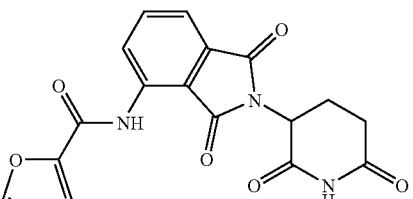<br>I-35 | N-[2-(2,6-dioxo(3-piperidyl))-1,3-dioxoisoindolin-4-yl]-2-furylcarboxamide |

TABLE 1-continued

Examples of Compounds of the Invention

| Structure | Name |
| --- | --- |
| I-36 | N-[2-(2,6-dioxo(3-piperidyl))-1,3-dioxoisoindolin-4-yl]benzamide |
| I-37 | N-[2-(2,6-dioxo(3-piperidyl))-1,3-dioxoisoindolin-4-yl]propanamide |
| I-38 | Methyl 3-{N-[2-(2,6-dioxo(3-piperidyl))-1,3-dioxoisoindolin-4-yl]carbamoyl}propanoate |
| I-39 | N-[2-(2,6-dioxo(3-piperidyl))-1,3-dioxoisoindolin-4-yl]-2-phenylacetamide |
| I-40 | N-[2-(2,6-dioxo(3-piperidyl))-1,3-dioxoisoindolin-4-yl]-2-pyridylcarboxam |

TABLE 1-continued

Examples of Compounds of the Invention

| Structure | Name |
|---|---|
| 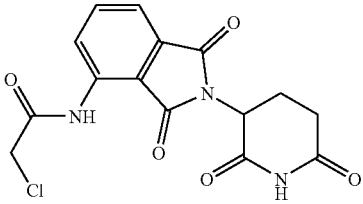 I-41 | N-[2-(2,6-dioxo(3-piperidyl))-1,3-dioxoisoindolin-4-yl]-2-chloroacetamide |
| 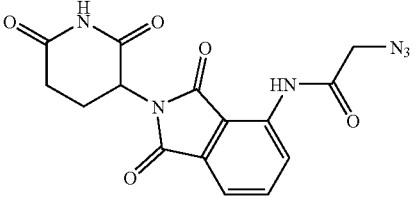 I-42 | 2-azido-N-[2-(2,6-dioxo(3-piperidyl))-1,3-dioxoisoindolin-4-yl]acetamide |
| 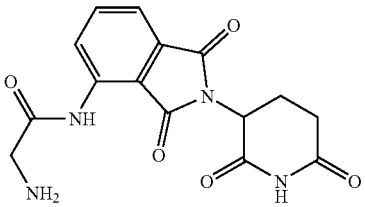 I-43 | 2-Amino-N-[2-(2,6-dioxo(3-piperidyl))-1,3-dioxoisoindolin-4-yl]acetamide |
| 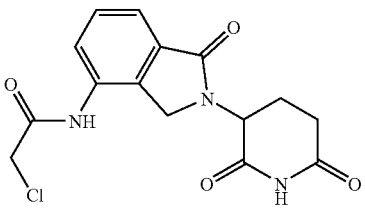 I-44 | N-[2-(2,6-dioxo(3-piperidyl))-1-oxoisoindolin-4-yl]-2-chloroacetamide |
| 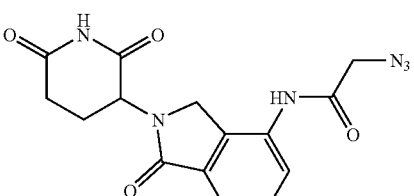 I-45 | 2-azido-N-[2-(2,6-dioxo(3-piperidyl))-1-oxoisoindolin-4-yl]acetamide |
| 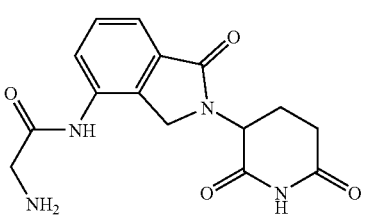 I-46 | 2-Amino-N-[2-(2,6-dioxo(3-piperidyl))-1-oxoisoindolin-4-yl]acetamide |

TABLE 1-continued

Examples of Compounds of the Invention

| Structure | Name |
|---|---|
| I-47 | 3-{4-[(2-Furylmethyl)amino]-1-oxoisoindolin-2-yl}piperidine-2,6-dione |
| I-48 | 3-[1-Oxo-4-(pentylamino)isoindolin-2-yl]piperidine-2,6-dione |
| I-49 | 2-(2,6-Dioxo-piperidin-3-yl)-4-(2-methoxy-ethylamino)-isoindole-1,3-dione |
| I-50 | 2-Benzyloxy-N-[2-(2,6-dioxo-piperidin-3-yl)-1,3-dioxo-2,3-dihydro-1H-isoindol-4-yl]-acetamide |
| I-51 | 2-(2,6-Dioxo-piperidin-3-yl)-4-pentylamino-isoindole-1,3-dione |

TABLE 1-continued

Examples of Compounds of the Invention

| Structure | Name |
|---|---|
| 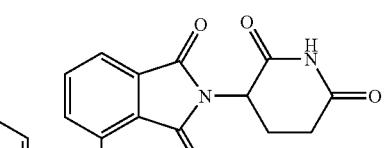 I-52 | 3-Chloro-N-[2-(2,6-dioxo-piperidin-3-yl)-1,3-dioxo-2,3-dihydro-1H-isoindol-4-yl]-benzamide |
| 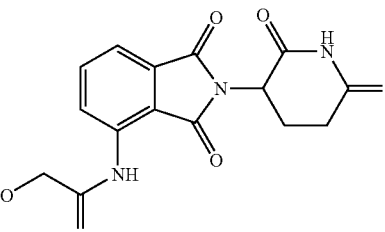 I-53 | N-[2-(2,6-Dioxo-piperidin-3-yl)-1,3-dioxo-2,3-dihydro-1H-isoindol-4-yl]-2-phenoxy-acetamide |
| 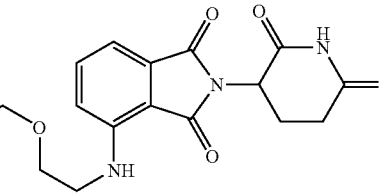 I-54 | 4-(2-Benzyloxy-ethylamino)-2-(2,6-dioxo-piperidin-3-yl)-isoindole-1,3-dione |
| 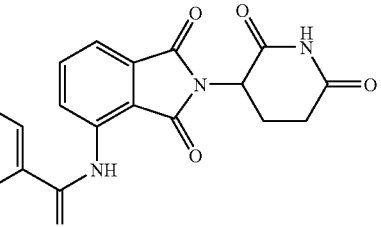 I-55 | N-[2-(2,6-Dioxo-piperidin-3-yl)-1,3-dioxo-2,3-dihydro-1H-isoindol-4-yl]-3-fluoro-benzamide |
| 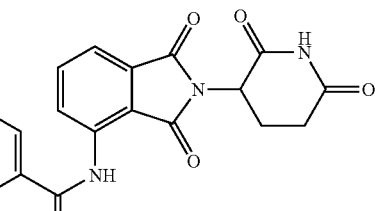 I-56 | N-[2-(2,6-Dioxo-piperidin-3-yl)-1,3-dioxo-2,3-dihydro-1H-isoindol-4-yl]-3-methyl-benz |

TABLE 1-continued

Examples of Compounds of the Invention

| Structure | Name |
|---|---|
| 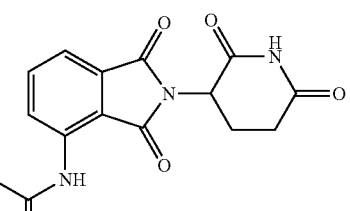 I-57 | N-[2-(2,6-Dioxo-piperidin-3-yl)-1,3-dioxo-2,3-dihydro-1H-isoindol-4-yl]-3-methoxy-benzamide |
| 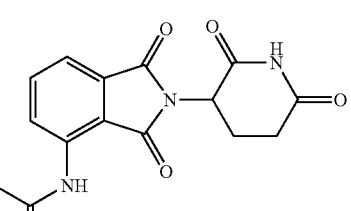 I-58 | N-[2-(2,6-Dioxo-piperidin-3-yl)-1,3-dioxo-2,3-dihydro-1H-isoindol-4-yl]-3-trifluoromethyl-benzamide |
| 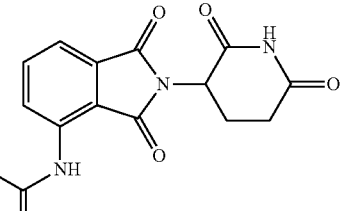 I-59 | N-[2-(2,6-Dioxo-piperidin-3-yl)-1,3-dioxo-2,3-dihydro-1H-isoindol-4-yl]-3-nitro-benzamide |
| 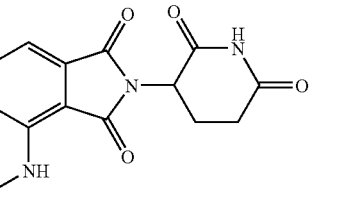 I-60 | N-[2-(2,6-Dioxo-piperidin-3-yl)-1,3-dioxo-2,3-dihydro-1H-isoindol-4-yl]-butyramide |
| 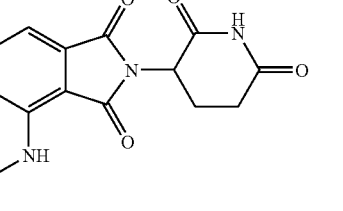 I-61 | N-[2-(2,6-Dioxo-piperidin-3-yl)-1,3-dioxo-2,3-dihydro-1H-isoindol-4-yl]-2-methylamino-acetamide |

TABLE 1-continued

Examples of Compounds of the Invention

| Structure | Name |
|---|---|
| 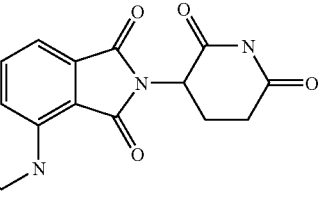 I-62 | 2-(2,6-Dioxo-piperidin-3-yl)-4-heptylamino-isoindole-1,3-dione |
| 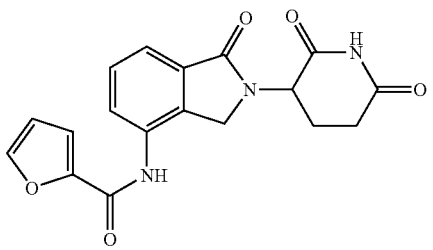 I-63 | 4-Chloro-N-[2-(2,6-dioxo-piperidin-3-yl)-1,3-dioxo-2,3-dihydro-1H-isoindol-4-yl]-benzamide |
| 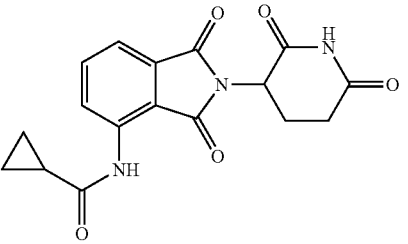 I-64 | Cyclopropanecarboxylic acid [2-(2,6-dioxo-piperidin-3-yl)-1,3-dioxo-2,3-dihydro-1H-isoindol-4-yl]-amide |
| 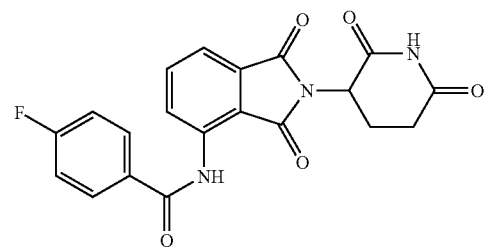 I-65 | N-[2-(2,6-Dioxo-piperidin-3-yl)-1,3-dioxo-2,3-dihydro-1H-isoindol-4-yl]-4-fluoro-benzamide |
| 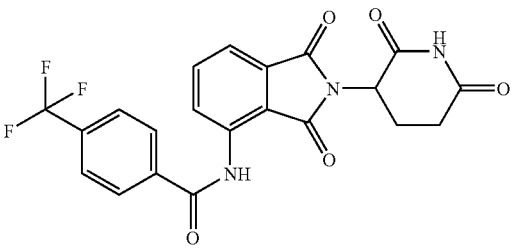 I-66 | N-[2-(2,6-Dioxo-piperidin-3-yl)-1,3-dioxo-2,3-dihydro-1H-isoindol-4-yl]-4-trifluoromethyl-benzamide |

TABLE 1-continued

Examples of Compounds of the Invention

| Structure | Name |
|---|---|
| I-67 | N-[2-(2,6-Dioxo-piperidin-3-yl)-1,3-dioxo-2,3-dihydro-1H-isoindol-4-yl]-4-methyl-benzamide |
| I-68 | N-[2-(2,6-Dioxo-piperidin-3-yl)-1,3-dioxo-2,3-dihydro-1H-isoindol-4-yl]-4-nitro-benzamide |
| I-69 | N-[2-(2,6-Dioxo-piperidin-3-yl)-1,3-dioxo-2,3-dihydro-1H-isoindol-4-yl]-2-ethoxy-acetamide |
| I-70 | N-[2-(2,6-Dioxo-piperidin-3-yl)-1,3-dioxo-2,3-dihydro-1H-isoindol-4-yl]-2-methylsulfanyl-acetamide |
| I-71 | N-[2-(2,6-Dioxo-piperidin-3-yl)-1,3-dioxo-2,3-dihydro-1H-isoindol-4-yl]-2-methoxy-benzam |

TABLE 1-continued

Examples of Compounds of the Invention

| Structure | Name |
|---|---|
| 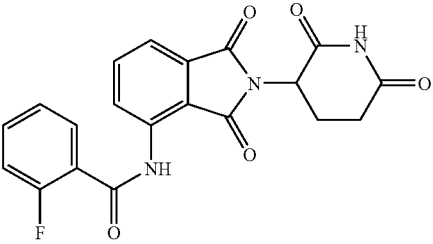 I-72 | N-[2-(2,6-Dioxo-piperidin-3-yl)-1,3-dioxo-2,3-dihydro-1H-isoindol-4-yl]-2-fluoro-benzamide |
| 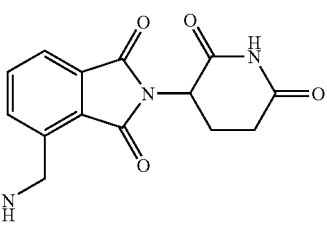 | 7-Amino-N-{[2-(2,6-dioxo(3-piperidyl))-1,3-dioxoisoindolin-4-yl]methyl}heptanamide |
| 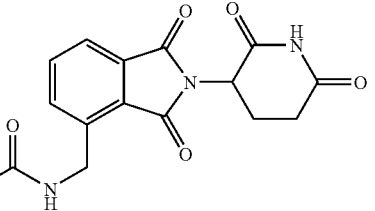 | N-{[2-(2,6-Dioxo(3-piperidyl))-1,3-dioxoisoindolin-4-yl]methyl}butanamide |
| 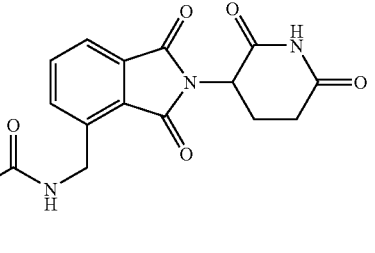 I-75 | N-{[2-(2,6-Dioxo(3-piperidyl))-1,3-dioxoisoindolin-4-yl]methyl}benzamide |
| 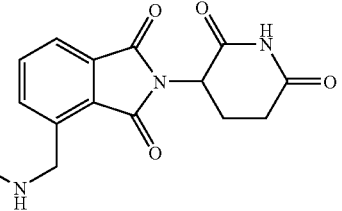 | N-{[2-(2,6-Dioxo(3-piperidyl))-1,3-dioxoisoindolin-4-yl]methyl}phenylacetamide |

TABLE 1-continued

Examples of Compounds of the Invention

| Structure | Name |
| --- | --- |
| I-77 | N-{[2-(2,6-Dioxo(3-piperidyl))-1,3-dioxoisoindolin-4-yl]methyl}-2-pyridylcarboxamide |
| I-78 | N-{[2-(2,6-Dioxo(3-piperidyl))-1,3-dioxoisoindolin-4-yl]methyl}undecamide |
| I-79 | N-{[2-(2,6-Dioxo(3-piperidyl))-1,3-dioxoisoindolin-4-yl]methyl}-2-methylpropanamide |
| I-80 | N-{[2-(2,6-Dioxo(3-piperidyl))-1,3-dioxoisoindolin-4-yl]methyl}cyclopentylcarboxamide |
| I-81 | N-{[2-(2,6-Dioxo(3-piperidyl))-1,3-dioxoisoindolin-4-yl]methyl}cyclohexylcarboxa |

TABLE 1-continued

Examples of Compounds of the Invention

| Structure | Name |
|---|---|
| 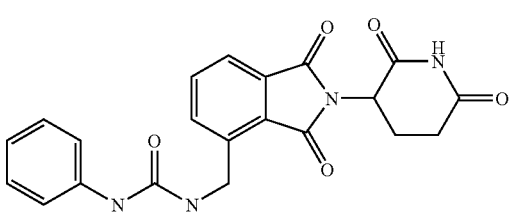<br>I-82 | N-{[2-(2,6-Dioxo(3-piperidyl))-1,3-dioxoisoindolin-4-yl]methyl}(phenylamino)carboxamide |
| 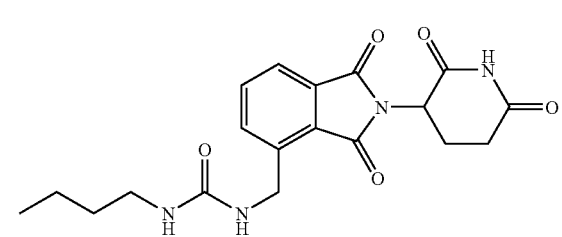<br>I-83 | N-{[2-(2,6-Dioxo(3-piperidyl))-1,3-dioxoisoindolin-4-yl]methyl}(butylamino)carboxamide |
| 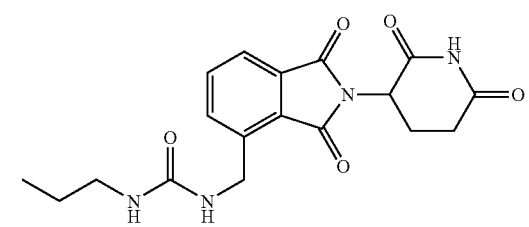<br>I-84 | N-{[2-(2,6-Dioxo(3-piperidyl))-1,3-dioxoisoindolin-4-yl]methyl}(propylamino)carboxamide |
| 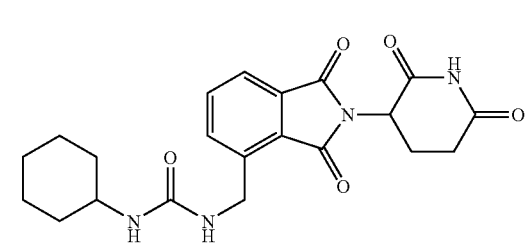<br>I-85 | N-{[2-(2,6-Dioxo(3-piperidyl))-1,3-dioxoisoindolin-4-yl]methyl}(cyclohexylamino)carboxamide |
| 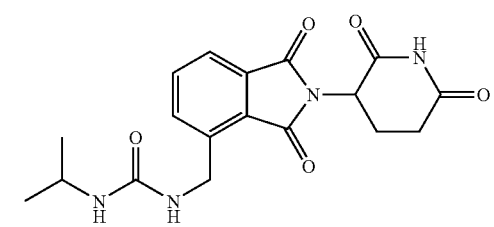<br>I-86 | N-{[2-(2,6-Dioxo(3-piperidyl))-1,3-dioxoisoindolin-4-yl]methyl}[(methylethylamino)]carboxamide |

TABLE 1-continued

Examples of Compounds of the Invention

| Structure | Name |
|---|---|
| I-87 | N-{[2-(2,6-Dioxo(3-piperidyl))-1,3-dioxoisoindolin-4-yl]methyl}(octylamino)carboxamide |
| I-88 | N-{[2-(2,6-Dioxo(3-piperidyl))-1,3-dioxoisoindolin-4-yl]methyl}(benzylamino)carboxamide |
| I-89 | N-{[2-(2,6-Dioxo(3-piperidyl))-1,3-dioxoisoindolin-4-yl]methyl}(cyclopropylamino)carboxamide |
| I-90 | 2-Chloro-N-[2-(2,6-dioxo-piperidin-3-yl)-1,3-dioxo-2,3-dihydro-1H-isoindol-4-yl]-benzamide |
| I-91 | [2-(2,6-Dioxo-piperidin-3-yl)-1,3-dioxo-2,3-dihydro-1H-isoindol-4-yl]-carbamic acid benzyl ester |

TABLE 1-continued

Examples of Compounds of the Invention

| Structure | Name |
|---|---|
| I-92 | N-[2-(2,6-Dioxo-piperidin-3-yl)-1,3-dioxo-2,3-dihydro-1H-isoindol-4-yl]-acetamide |
| I-93 | Pentanoic acid [2-(2,6-dioxo-piperidin-3-yl)-1-oxo-2,3-dihydro-1H-isoindol-4-yl]-amide |
| I-94 | N-[2-(2,6-Dioxo-piperidin-3-yl)-1-oxo-2,3-dihydro-1H-isoindol-4-yl]-propionamide |
| I-95 | N-[2-(2,6-Dioxo-piperidin-3-yl)-1-oxo-2,3-dihydro-1H-isoindol-4-yl]-nicotinamide |
| I-96 | 2-(2,6-Dioxo-piperidin-3-yl)-4-{[(furan-2-ylmethyl)-amino]-methyl} isoindole-1,3-dione |

TABLE 1-continued

Examples of Compounds of the Invention

| Structure | Name |
|---|---|
| I-97 | N-[2-(2,6-Dioxo-piperidin-3-yl)-1-oxo-2,3-dihydro-1H-isoindol-4-yl]-benzamide |
| I-98 | 2-Dimethylamino-N-[2-(2,6-dioxo-piperidin-3-yl)-1,3-dioxo-2,3-dihydro-1H-isoindol-4-yl]-acetamide |
| I-99 | N-[2-(2,6-Dioxo-piperidin-3-yl)-1,3-dioxo-2,3-dihydro-1H-isoindol-4-yl]-2-methyl-benzamide |
| I-100 | Heptanoic acid [2-(2,6-dioxo-piperidin-3-yl)-1-oxo-2,3-dihydro-1H-isoindol-4-yl]-amide |
| I-101 | N-[2-(2,6-Dioxo-piperidin-3-yl)-1,3-dioxo-2,3-dihydro-1H-isoindol-4-yl]-3,3-dimethyl-butyramide |

TABLE 1-continued

Examples of Compounds of the Invention

| Structure | Name |
| --- | --- |
| I-102 | N-[2-(2,6-Dioxo-piperidin-3-yl)-1,3-dioxo-2,3-dihydro-1H-isoindol-4-yl]-isobutyramide |
| I-103 | N-[2-(2,6-Dioxo-piperidin-3-yl)-1,3-dioxo-2,3-dihydro-1H-isoindol-4-yl]-3-phenyl-propionamide |
| I-104 | N-[2-(2,6-Dioxo-piperidin-3-yl)-1,3-dioxo-2,3-dihydro-1H-isoindol-4-yl]-4-methoxy-benzamide |
| I-105 | N-[2-(2,6-Dioxo-piperidin-3-yl)-1,3-dioxo-2,3-dihydro-1H-isoindol-4-yl]-2-trifluoromethyl-benzamide |
| I-106 | N-[2-(2,6-Dioxo-piperidin-3-yl)-1,3-dioxo-2,3-dihydro-1H-isoindol-4-yl]-malonamic acid methyl ester |

TABLE 1-continued

Examples of Compounds of the Invention

| Structure | Name |
| --- | --- |
| 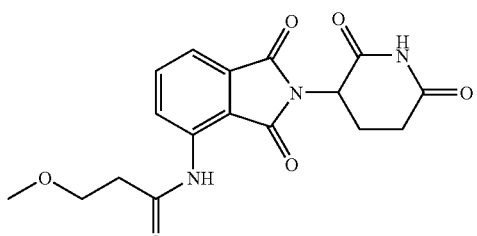 I-107 | N-[2-(2,6-Dioxo-piperidin-3-yl)-1,3-dioxo-2,3-dihydro-1H-isoindol-4-yl]-3-methoxy-propionamide |
| 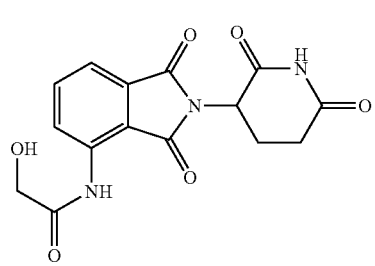 I-108 | N-[2-(2,6-Dioxo-piperidin-3-yl)-1,3-dioxo-2,3-dihydro-1H-isoindol-4-yl]-2-hydroxy-acetamide |
| 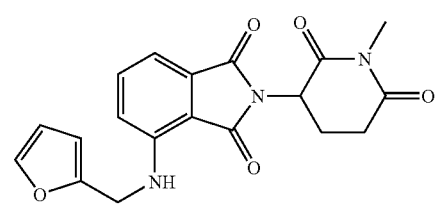 I-109 | 4-[(Furan-2-ylmethyl)-amino]-2-(1-methyl-2,6-dioxo-piperidin-3-yl)-isoindole-1,3-dione |
| 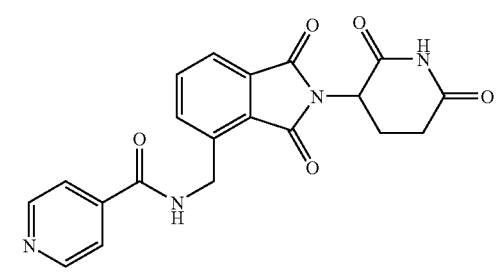 I-110 | N-[2-(2,6-Dioxo-piperidin-3-yl)-1,3-dioxo-2,3-dihydro-1H-isoindol-4-ylmethyl]-isonicotinamide |
| 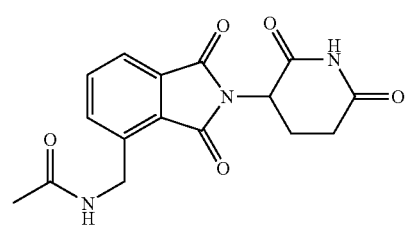 I-111 | N-[2-(2,6-Dioxo-piperidin-3-yl)-1,3-dioxo-2,3-dihydro-1H-isoindol-4-ylmethyl]-acetamide |

TABLE 1-continued

Examples of Compounds of the Invention

| Structure | Name |
|---|---|
| 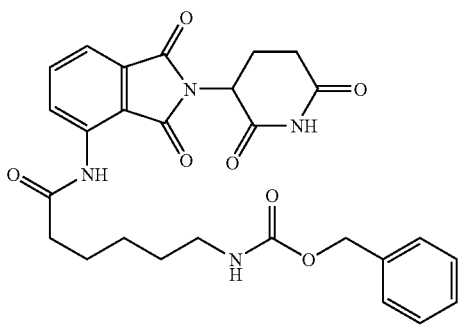 I-112 | {5-[2-(2,6-Dioxo-piperidin-3-yl)-1,3-dioxo-2,3-dihydro-1H-isoindol-4-ylcarbamoyl]-pentyl}-carbamic acid benzyl ester |
| 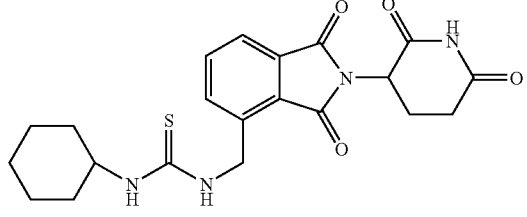 I-113 | 2-(2,6-Dioxo(3-piperidyl))-4-({[(cyclohexylamino)thioxomethyl]amino}methyl)isoindole-1,3-dione |
| 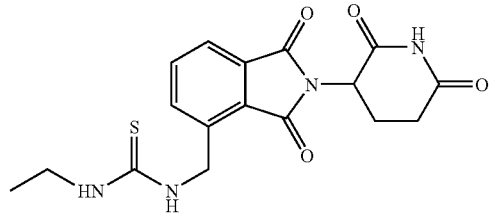 I-114 | 2-(2,6-Dioxo(3-piperidyl))-4-({[(ethylamino)thioxomethyl]amino}methyl)isoindole-1,3-dione |
| 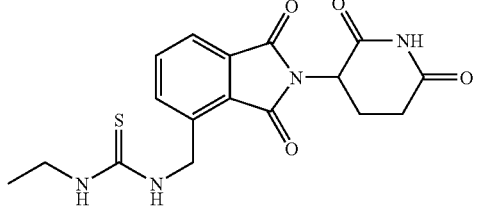 I-115 | 2-(2,6-Dioxo(3-piperidyl))-4-({[(propylamino)thioxomethyl]amino}methyl)isoindole-1,3-dione |
| 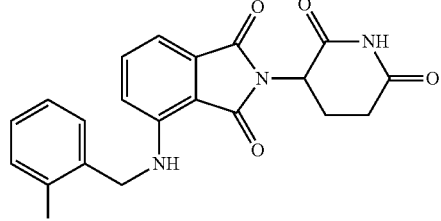 I-116 | N-[2-(2,6-dioxo(3-piperidyl))-1,3-dioxoisoindolin-4-yl]-2-chloro-benzylamine |

TABLE 1-continued

Examples of Compounds of the Invention

| Structure | Name |
|---|---|
| 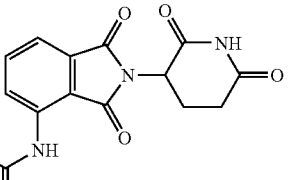 I-117 | {5-[2-(2,6-Dioxo-piperidin-3-yl)-1,3-dioxo-2,3-dihydro-1H-isoindol-4-ylcarbamoyl]-pentyl}-carbamic acid benzyl ester |
| 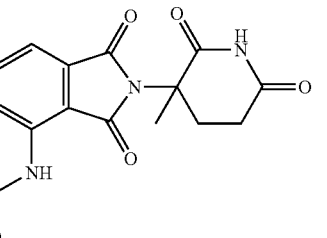 I-118 | 2-Methoxy-N-[2-(3-methyl-2,6-dioxo-piperidin-3-yl)-1,3-dioxo-2,3-dihydro-1H-isoindol-4-yl]-acetamide |
| 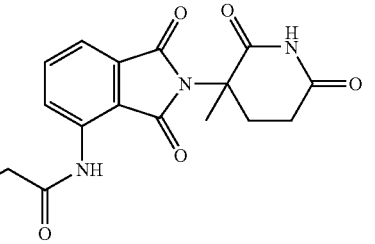 I-119 | Pentanoic acid [2-(3-methyl-2,6-dioxo-piperidin-3-yl)-1,3-dioxo-2,3-dihydro-1H-isoindol-4-yl]-amide |
| 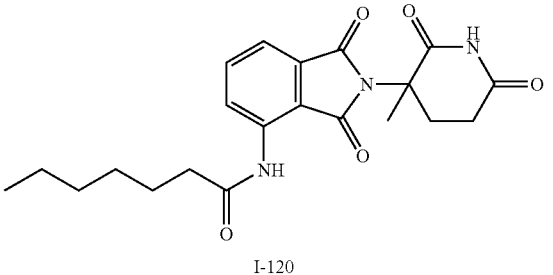 I-120 | Heptanoic acid [2-(3-methyl-2,6-dioxo-piperidin-3-yl)-1,3-dioxo-2,3-dihydro-1H-isoindol-4-yl]-amide |
| 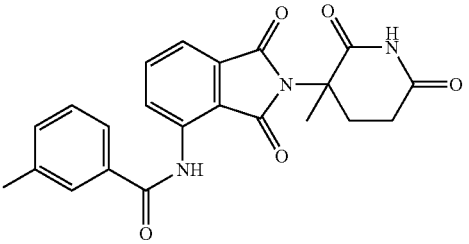 I-121 | 3-Chloro-N-[2-(3-methyl-2,6-dioxo-piperidin-3-yl)-1,3-dioxo-2,3-dihydro-1H-isoindol-4-yl]-benzamide |

TABLE 1-continued

Examples of Compounds of the Invention

| Structure | Name |
|---|---|
| I-122 | N-[2-(3-Methyl-2,6-dioxo-piperidin-3-yl)-1,3-dioxo-2,3-dihydro-1H-isoindol-4-yl]-propionamide |
| I-123 | Thiophene-2-carboxylic acid [2-(3-methyl-2,6-dioxo-piperidin-3-yl)-1,3-dioxo-2,3-dihydro-1H-isoindol-4-yl]-amide |
| I-124 | 2-(2,6-Dioxo-piperidin-3-yl)-4-[(5-methyl-furan-2-ylmethyl)-amino]-isoindole-1,3-dione |
| I-125 | 2-(2,6-Dioxo-piperidin-3-yl)-4-[(5-hydroxymethyl-furan-2-ylmethyl)-amino]-isoindole-1,3-dione |
| I-126 | 2-(2,6-Dioxo-piperidin-3-yl)-4-[(thiophen-2-ylmethyl)-amino]-isoindole-1,3-dione |

TABLE 1-continued

Examples of Compounds of the Invention

| Structure | Name |
|---|---|
| I-127 | 4-(3-Chloro-benzylamino)-2-(2,6-dioxo-piperidin-3-yl)-isoindole-1,3-dione |
| I-128 | 2-(2,6-Dioxo-piperidin-3-yl)-4-[(pyridin-3-ylmethyl)-amino]-isoindole-1,3-dione |
| I-129 | 5-{[2-(2,6-Dioxo-piperidin-3-yl)-1,3-dioxo-2,3-dihydro-1H-isoindol-4-ylamino]-methyl}-furan-2-carboxylic acid |
| I-130 | 4-[(4,5-Dimethyl-furan-2-ylmethyl)-amino]-2-(2,6-dioxo-piperidin-3-yl)-isoindole-1,3-dione |
| I-131 | 4-[(Benzofuran-2-ylmethyl)-amino]-2-(2,6-dioxo-piperidin-3-yl)-isoindole-1,3-dione |
| I-132 | 4-(3-Chloro-benzylamino)-2-(3-methyl-2,6-dioxo-piperidin-3-yl)-isoindole-1,3-dione |

TABLE 1-continued

Examples of Compounds of the Invention

| Structure | Name |
|---|---|
| 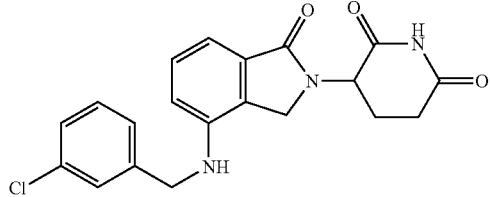 I-133 | 3-[4-(3-Chloro-benzylamino)-1-oxo-1,3-dihydro-isoindol-2-yl]-piperidine-2,6-dione |
| 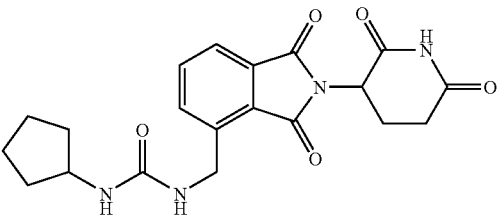 I-134 | N-{[2-(2,6-Dioxo(3-piperidyl))-1,3-dioxoisoindolin-4-yl]methyl}(cyclopentylamino)carboxamide |
| 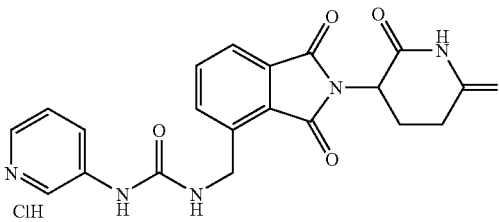 I-135 | N-{[2-(2,6-Dioxo(3-piperidyl))-1,3-dioxoisoindolin-4-yl]methyl}(3-pyridylamino)carboxamide Hydrochloride |
| 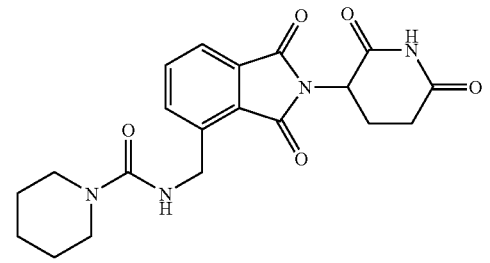 I-136 | N-{[2,(2,6-dioxo(3-piperidyl))-1,3-dioxoisoindolin-4-yl]methyl}piperidylcarboxamide |
| 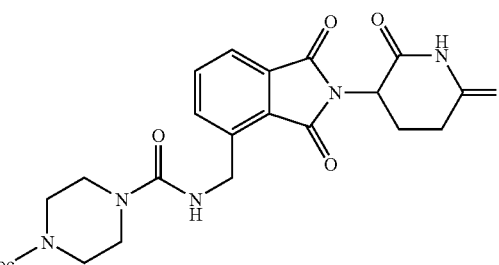 I-137 | Tert-Butyl 4-(N-{[2-(2,6-dioxo(3-piperidyl))-1,3-dioxoisoindolin-4-yl]methyl}(carbamoyl)piperazinecarboxylate |

TABLE 1-continued

Examples of Compounds of the Invention

| Structure | Name |
|---|---|
| 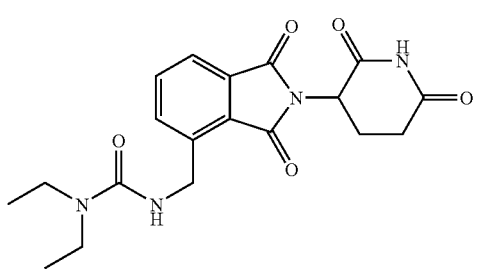 I-138 | N-{[2-(2,6-Dioxo(3-piperidyl))-1,3-dioxoisoindolin-4-yl]methyl}(diethylamino)carboxamide |
| 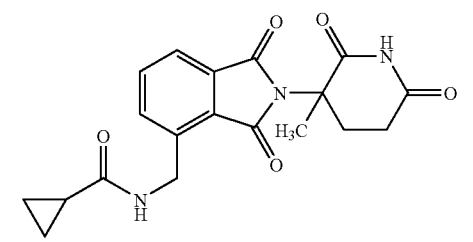 I-139 | Cyclopropyl-N-{[2-(3-methyl-2,6-dioxo(3-piperidyl))-1,3-dioxoisoindolin-4-yl]methyl}carboxamide |
| 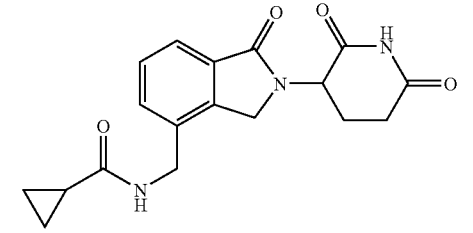 I-140 | N-{[2-(2,6-Dioxo(3-piperidyl))-1-oxoisoindolin-4-yl]methyl}cyclopropylcarboxamide |
| 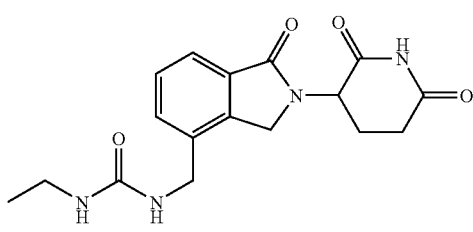 I-141 | N-{[2-(2,6-Dioxo(3-piperidyl))-1-oxoisoindolin-4-yl]methyl}(ethylamino)carboxamide |
| 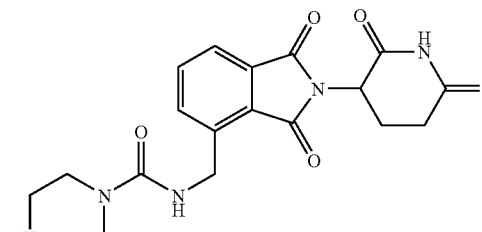 I-142 | Piperazine-1-carboxylic acid [2-(2,6-dioxo-piperidin-3-yl)-1,3-dioxo-2,3-dihydro-1H-isoindol-4-ylmethyl]-amide |

Selected compounds of Table 1 were tested using the in vitro assays described below and found to be active for modulating the production of TNF-α.

Examples of optically or enantiomerically pure stereoisomers of the invention are depicted in Table 2 below.

TABLE 2

Examples of Stereoisomers of the Invention

| No. | Structure |
|---|---|
| (R)-I-1 | 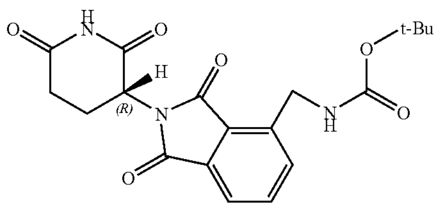 |
| (R)-I-3 | 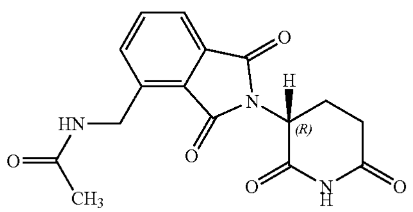 |
| (R)-I-4 | 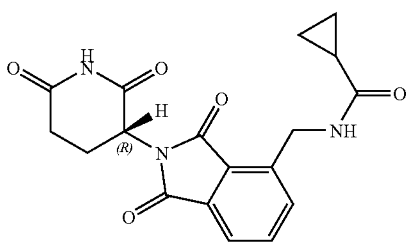 |
| (R)-I-9 | 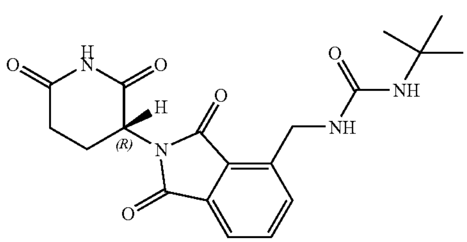 |
| (R)-I-13 | 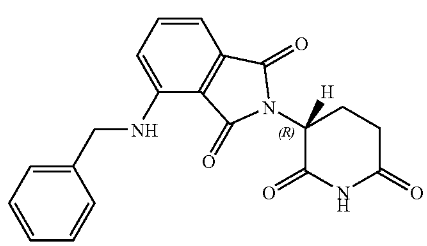 |
| (R)-I-27 | 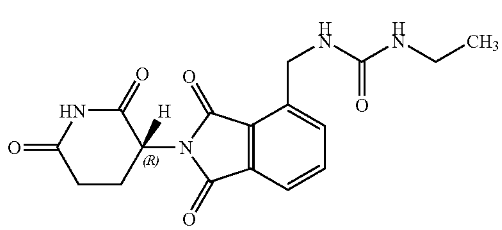 |
| (R)-I-28 | |
| (R)-I-29 | |
| (R)-I-30 | |
| (R)-I-47 | |
| (S)-I-1 | |
| (S)-I-3 | |

TABLE 2-continued

Examples of Stereoisomers of the Invention

| No. | Structure |
|---|---|
| (S)-I-4 | 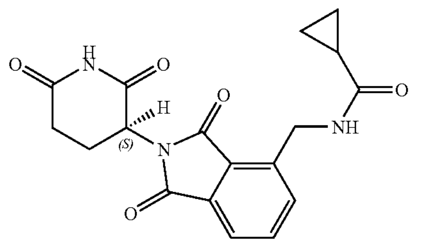 |
| (S)-I-9 | 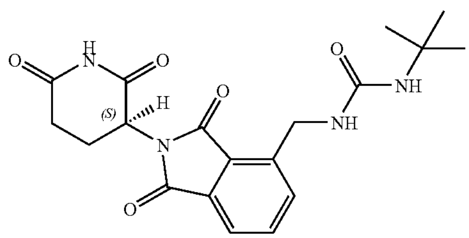 |
| (S)-I-13 | 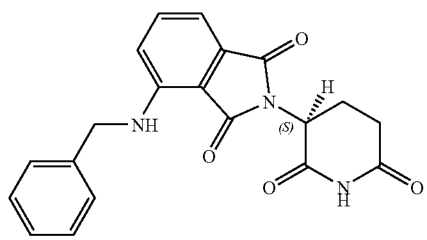 |
| (S)-I-27 | 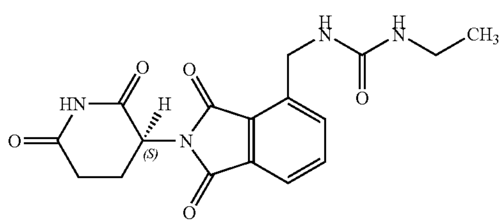 |
| (S)-I-28 | 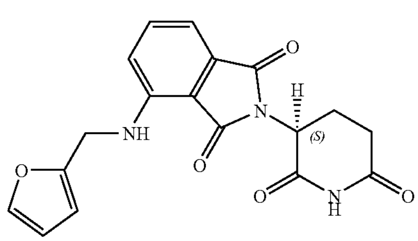 |
| (S)-I-29 | 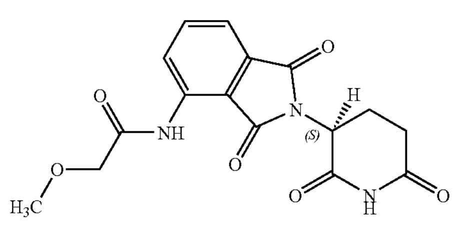 |
| (S)-I-30 | 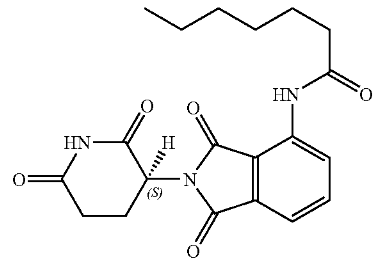 |
| (S)-I-47 | 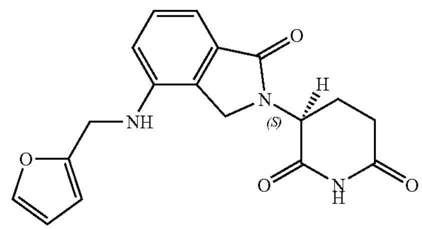 |

6.1 Synthesis of the Compounds of the Invention

The compounds of the invention can be obtained via standard, synthetic methodology. Some convenient methods are illustrated in Schemes 1-8. Starting materials useful for preparing the compounds of the invention and intermediates therefor, are commercially available or can be prepared from commercially available materials using known synthetic methods and reagents. Such starting materials include, but are not limited to, methyl-2-(methoxycarbonyl)-3-nitrobenzoate; methyl-3-aminomethyl-2-(methoxycarbonyl)benzoate; substituted and unsubstituted aminoglutarimide hydrochloride; di-t-butyl dicarbonate; and cyclopropylcarbonyl chloride.

Scheme 1: Synthesis of 4-(aminomethyl)-2-(2,6-dioxo(3-piperidyl))isoindoline-1,3-dione (Formula I, wherein $R^1$ is H and n is 1)

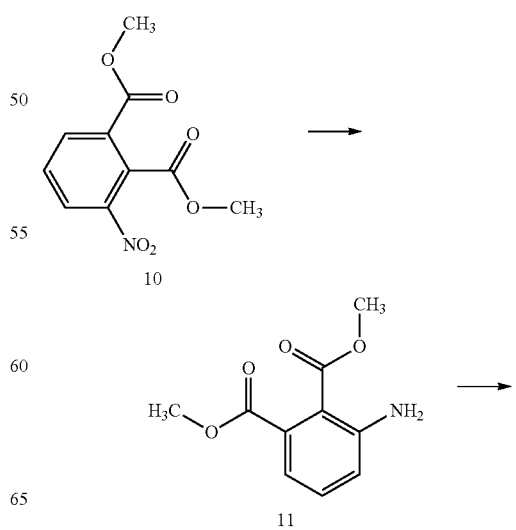

-continued

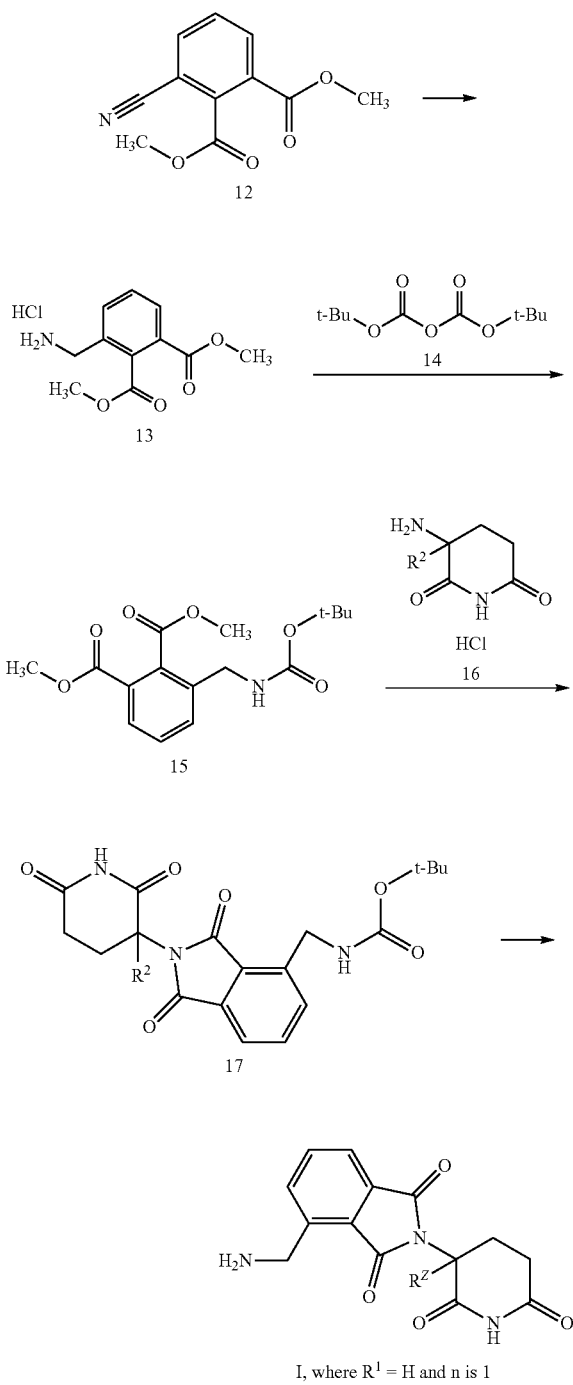

I, where R¹ = H and n is 1

Scheme 1 outlines one method to synthesize 4-(aminomethyl)-2-(2,6-dioxo(3-piperidyl))-isoindoline-1,3-dione (I, wherein R¹ is H and n is 1) from compound 10. In the first step, reduction of 10 (commercially available), for example, with palladium on charcoal and 50 psi of hydrogen, followed by standard isolation and purification gives arylamine 11. Arylamine 11 converts to nitrile 12 by diazonium salt formation effected by treatment with sodium nitrate then displacement of nitrogen with cyanide according to the classic Sandmeyer procedure. Reduction of nitrile 12, for example, with palladium on carbon in methanol/aqueous hydrochloric acid under an atmosphere of hydrogen, gives the hydrochloride salt of compound 13. Treatment of 13 with triethylamine liberates the free base, which in turn reacts with di-t-butyl dicarbonate (14) (commercially available, for example, from Aldrich Chemical Co. Milwaukee, Wis.) giving carbamate 15. Treatment of carbamate 15 with 16, where R² is as defined above, and a base, such as diisopropylethyl amine gives compound 17 that converts to I, wherein R¹ is H and n is 1 upon standard hydrolysis, for example, with aqueous hydrochloric acid/dioxane. Compounds 16 can be obtained by cyclizing the appropriately substituted, amino-protected glutamine by well-known methods (e.g., see WO 98/54170, incorporated herein by reference).

Scheme 2: Synthesis of 4-Amino-2-(2,6-dioxo-piperidin-3-yl)-isoindole-1,3-dione (Formula I, wherein R¹ is H and n is 0)

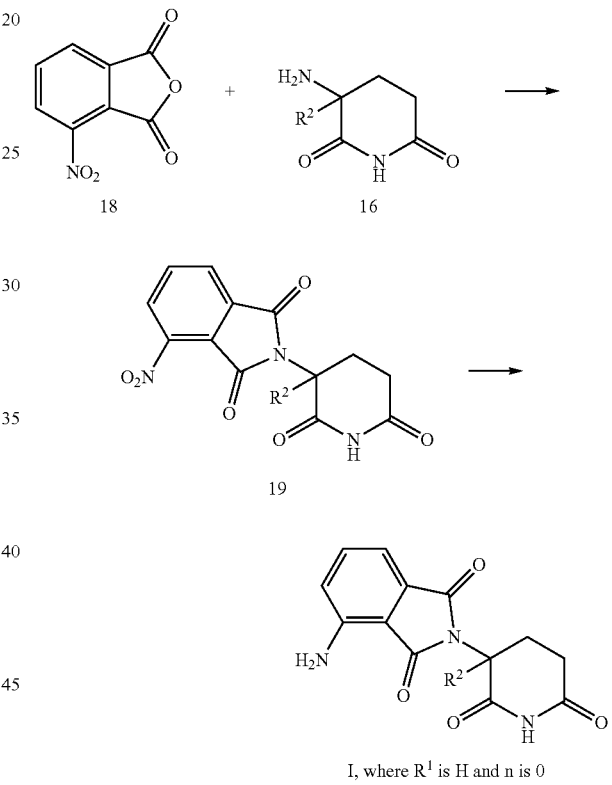

I, where R¹ is H and n is 0

Scheme 2 outlines a convenient method to synthesize 4-amino-2-(2,6-dioxo-piperidin-3-yl)-isoindole-1,3-dione (I, wherein R¹ is H and n is 0) from 4-nitrophthalic anhydride (18). In the first step, a mixture of 18 and 16 in an acidic medium (e.g., sodium acetate in glacial acetic acid) is heated at about 60° C. to about 150° C. for a time of about 1 hour to about 24 hours, until the reaction is substantially complete. After an aqueous workup, 19 is isolated and characterized according to standard methods (see e.g., U.S. Pat. No. 5,635,517, incorporated herein by reference). Alternately, the reaction may be carried out in other solvents, including pyridine. Conversion of 19 to I, wherein R¹ is H and n is 0, is accomplished by standard hydrogen reduction, for example, with palladium on carbon under about 50 psi to 200 psi of hydrogen at about room temperature to about 100° C. (see e.g., the procedure recited in U.S. Pat. No. 5,635,517).

Scheme 3: Synthesis of Compounds of Formula I, wherein $R^1$ is $C(O)R^3$ or $C(O)OR^4$

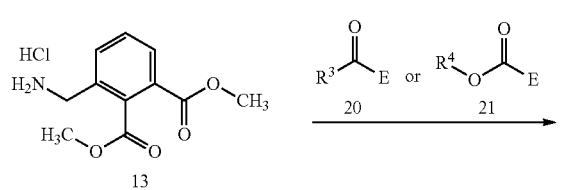

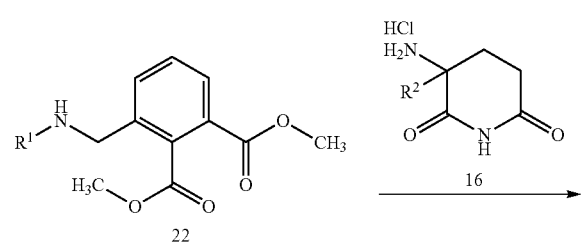

I, where n is 1

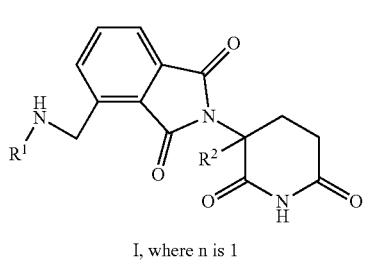

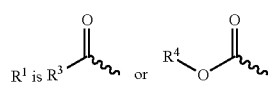

Scheme 3 outlines a convenient synthesis of compounds of Formula I, wherein $R^1$ is $C(O)R^3$ or $C(O)OR^4$. In the first step, compound 13, as prepared as in Scheme 1 above, reacts with a compounds 20 or 21, depending on whether $R^1$ of $C(O)R^3$ or $C(O)OR^4$ is desired, to give compounds 22. According to scheme 3, E is a suitable leaving group, for example, but not limited to halides, such as chloride, bromide, and iodide; azido (N3); arylsulfonyloxy or alkylsulfonyloxy (e.g., tosyloxy or mesyloxy); phenoxy; alkoxy; and oxycarbonyl groups. Preferably, E is a halide, more preferably, chloride. Preferably, compounds 20 are acid chlorides, such as acetyl chloride and cyclopropylcarbonyl chloride and compounds 21 are chloroformates, such as ethylchloroformate or benzylchloroformate. The reaction is carried out according to standard, well-known procedures, e.g. see March, J. *Advanced Organic Chemistry; Reactions Mechanisms, and Structure*, 4th ed., 1992, pp. 417-419, incorporated herein by reference. Treatment of 22 with 16 using the same procedure as outlined in Scheme 1 gives compounds of Formula I, wherein $R^1$ is $C(O)R^3$ or $C(O)OR^4$.

Scheme 4: Alternative Synthesis of Compounds of Formula I, wherein $R^1$ is $C(O)R^3$, OR $C(O)OR^4$

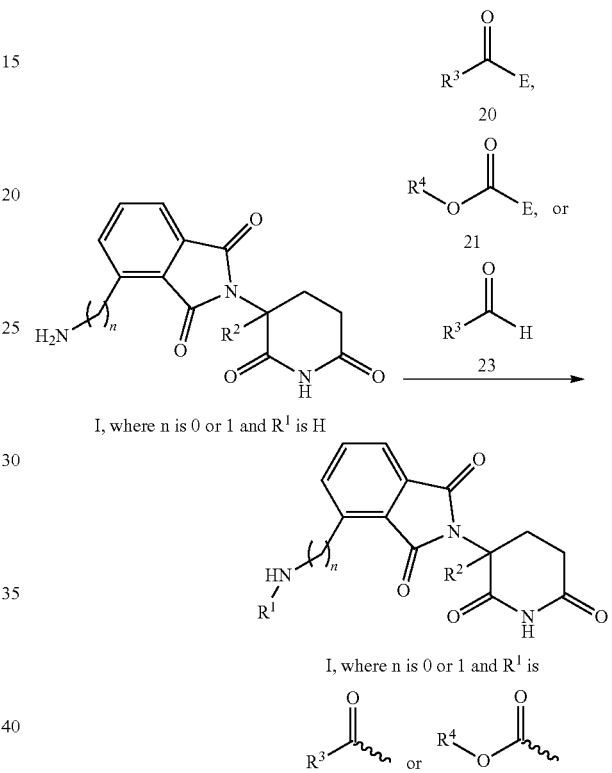

Scheme 4 outlines an alternative synthesis of compounds of Formula I, wherein $R^1$ is $C(O)R^3$ or $C(O)OR^4$ and a convenient synthesis of compounds of Formula I, wherein $R^1$ is $CH_2R^3$. In the first step, compounds I, wherein $R^1$ is H, as prepared as in Scheme I (n=1) or Scheme 2 (n=0) above, reacts with a compounds 20, 21, or 23 depending on whether $R^1$ of $C(O)R^3$, $C(O)OR^4$, or $CH_2R^3$ is desired, to give compounds I where $R^1$ is $C(O)R^3$, $C(O)OR^4$, or $CH_2R^3$. As defined above for Scheme 3, E is a suitable leaving group. Preferably, E is a halide, more preferably, chloride. Preferably, compounds 20 are acid chlorides, such as chloroacetyl chloride and t-butylacetyl chloride. Aldehydes 23 are readily available commercially or synthesized by well-known methods The reaction of 20 or 21 with I, where $R^1$ is H is carried out according to standard, well-known procedures for nucleophilic displacement, e.g. see March, J. *Advanced Organic Chemistry; Reactions Mechanisms, and Structure*, 4th ed., 1992, pp. 417-419. The reaction of 23 with I, where $R^1$ is H is accomplished according to the well-known reductive-amination procedure between an aldehyde and a primary amine, e.g. see March, J. *Advanced Organic Chemistry; Reactions Mechanisms, and Structure*, 4th ed., 1992, pp. 898-902, incorporated herein by reference.

Scheme 5: Synthesis of Compounds of Formula I, wherein R¹ is C(O)CH₂N(R⁶)₂

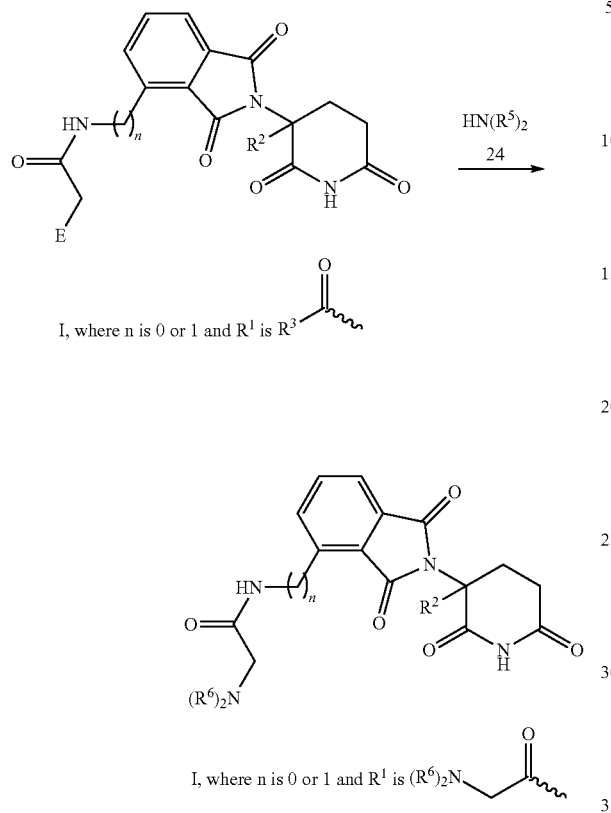

Scheme 5 outlines one method for the synthesis of compounds of Formula I, wherein R¹ is C(O)CH₂N(R⁶)₂. A compound of Formula I, wherein R¹ is C(O)R³ and R³ is (CH₂)E, where E is a suitable leaving group as defined for Scheme 3, reacts with amines 24 to give the desired Formula I compound, where R¹ is C(O)CH₂N(R⁶)₂. Preferably, E is chloro and R⁵ is (C₁-C₈)alkyl, such as methyl. The reaction is performed according to standard, well-known procedures, e.g. see March, J. *Advanced Organic Chemistry; Reactions Mechanisms, and Structure,* 4th ed., 1992, pp. 411-413, incorporated herein by reference.

Scheme 6: Synthesis of Compounds of Formula I, wherein R1 is C(O)NHR⁵

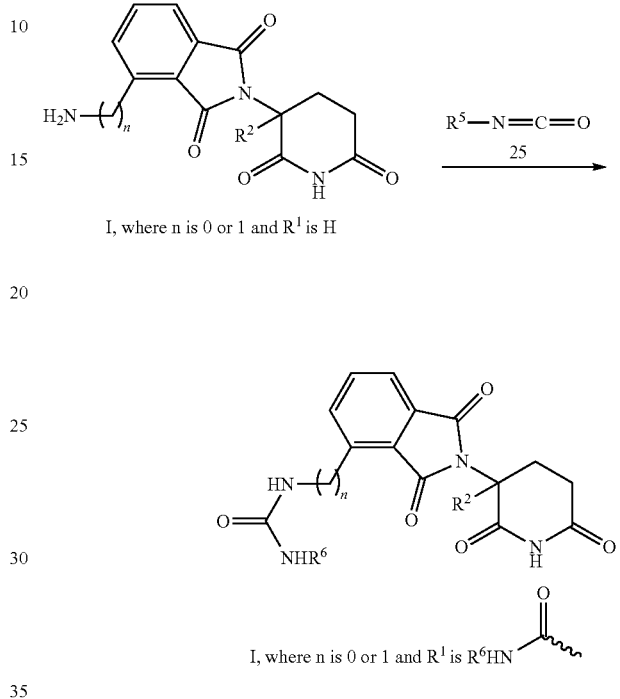

Scheme 6 shows one method to synthesize compounds of Formula I, wherein R¹ is C(O)NHR⁵. A compound of Formula I, where R¹ is H reacts with isocyanates 25 under routine conditions to give a compounds I, where R¹ is C(O)NHR⁵. The reaction is performed according to standard, well-known procedures, e.g. see March, J. *Advanced Organic Chemistry; Reactions Mechanisms, and Structure,* 4th ed., 1992, p. 903, incorporated herein by reference.

Scheme 7: Synthesis of Compounds of Formula I, wherein R² is F

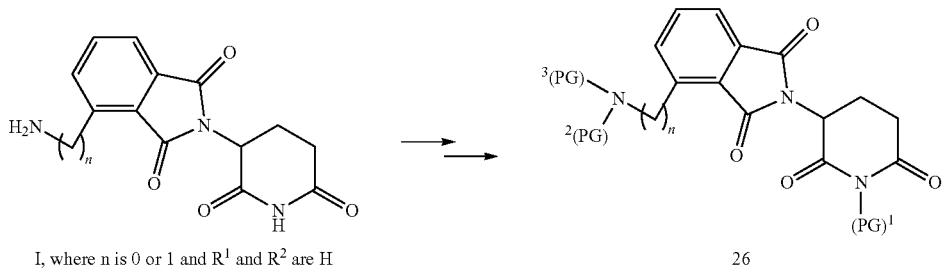

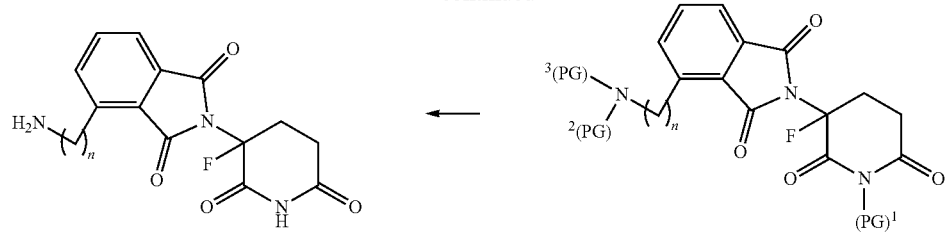

I, where n is 0 or 1, $R^1$ is H, and $R^2$ is F

27

Scheme 7 shows one method to synthesize compounds of Formula I, wherein $R^2$ is F. A similar method is described in U.S. Pat. No. 5,874,448, incorporated herein by reference. In the first step, compounds of Formula I, where $R^1$ and $R^2$ are H are first protected with suitable nitrogen-protecting groups ($PG^1$, $PG^2$, and $PG^3$) at the methyleneamino and glutarimide nitrogens, respectively, to give compounds 26. As used herein, a "nitrogen protecting group" means a group that is reversibly attached to the nitrogen that renders the nitrogen moiety unreactive during a subsequent reaction(s) and that can be selectively cleaved to regenerate the original nitrogen moiety once its protecting purpose has been served. Examples of suitable protecting groups are found in Greene, T. W., *Protective Groups in Organic Synthesis,* 3rd edition 494-654 (1999), incorporated herein by reference, and U.S. Pat. No. 5,874,448. Preferably, the nitrogen-protecting group is stable in a basic reaction medium but can be cleaved by acid. Preferably, all of $PG^1$, $PG^2$, and $PG^3$ protecting groups are tert-butyloxycarbonyl, attached by treatment of compounds of Formula I, where $R^1$ and $R^2$ are H with in excess of 3 equivalents of di-tert-butyl carbonate as described in U.S. Pat. No. 5,874,448. The fluorination-reaction procedure, to give compounds 27, is described in detail in U.S. Pat. No. 5,874,448 and can be effected by treating deprotonated 26 with a variety of reagents, such as N-fluorobenzenesulfonimide, perchloryl fluoride, or N-fluorobenzenedisulfonimide. Deprotonated 26 can be prepared by treatment of 26 with strong base, such as n-butyl lithium, sodium bis(trimethylsilyl)amide, sodium hydride, or lithium diisopropylamide. Deprotection of compounds 27 to give compounds I, where $R^1$ is H and $R^2$ is F is effected by standard procedures such as those described in Greene, T. W., *Protective Groups in Organic Synthesis,* 3rd edition 494-654 (1999) and U.S. Pat. No. 5,874,448.

Scheme 8: Synthesis of Compounds of Formula I, wherein one of one of X and Y is C=O and the other is $CH_2$

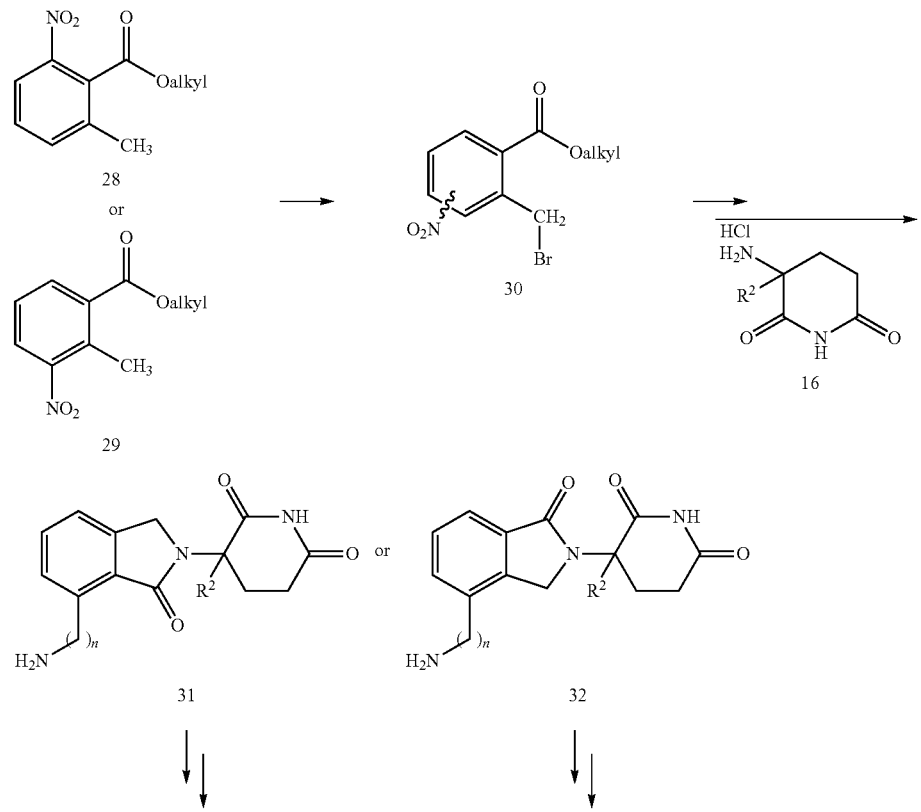

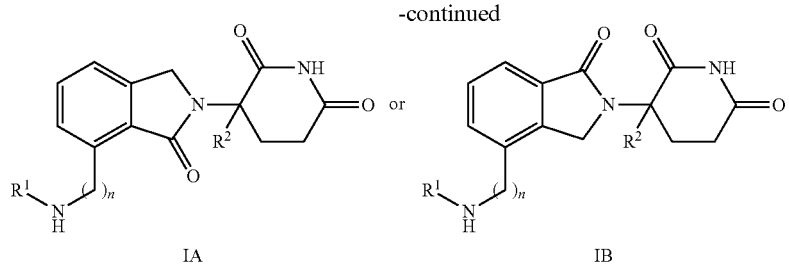

compounds I, where n is 0 or 1 and one of X and Y is C=O and the other is CH$_2$ Scheme 8 depicts convenient general synthetic methodology to prepare compounds of Formula I, wherein one of X and Y is C=O and the other is CH$_2$ (i.e., compounds IA and IB). In compounds IA, the isoindolin-ring carbonyl is cis with respect to the methyleneamino (n=1) or the amino (n=0) group, conversely, in compounds IB, the isoindolin-ring carbonyl is trans. In one convenient methods, compounds IA and IB can be prepared starting from compounds 28 or 29 respectively, for example, using the methodology described in WO 98/54170, incorporated herein by reference. Compounds 28 and compounds 29 are available commercially or readily available through well-known synthetic methodology. For example, methyl-2-methyl-3-nitrobenzoate (29, where alkyl is methyl) is commercially available from Aldrich Chemical Co., Milwaukee, Wis. Compounds 28 and 29 are first brominated at the activated benzylic position with a brominating agent such as N-bromosuccinimide under the influence of light or other radical initiator to yield methylbromo-compounds 30. Exemplary brominating procedures are reviewed in March, J. *Advanced Organic Chemistry, Reactions Mechanisms, and Structure*, 4th ed., 1992, pp. 694-697, incorporated herein by reference. Compounds 30 are then converted into compounds 31 or 32 and thereafter to IA or IB by adapting the synthetic methods presented in Schemes 1 to 5 above, including standard cyclization with compounds 16.

Scheme 9: Synthesis of Compounds of Formula I, wherein R$^1$ is C(S)NHR$^3$

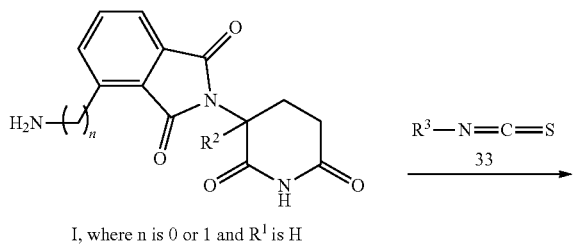

I, where n is 0 or 1 and R$^1$ is H

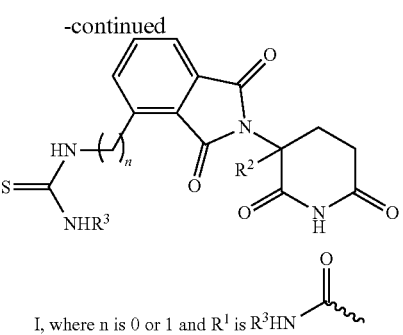

I, where n is 0 or 1 and R$^1$ is R$^3$HN

Scheme 9 shows one method to synthesize compounds of Formula I, wherein R$^1$ is C(S)NHR$^3$. A compound of Formula I, where R$^1$ is H reacts with isothiocyanates 28 under routine conditions to give a compounds I, where R$^1$ is C(O)NHR$^5$. The reaction is performed according to standard, well-known procedures, e.g. see March, J. *Advanced Organic Chemistry; Reactions Mechanisms, and Structure*, 4th ed., 1992, p. 903, incorporated herein by reference.

7. THERAPEUTIC USES OF COMPOUNDS OR COMPOSITIONS OF THE INVENTION

In accordance with the invention, a compound or composition of the invention is administered to a mammal, preferably, a human, with or at risk of a disease or medical condition, for example, cancer, such as solid tumors and blood-born tumors. Specific examples of cancers treatable or preventable by administering compounds of the invention include, but are not limited to, cancers of the skin, such as melanoma; lymph node; breast; cervix; uterus; gastrointestinal tract; lung; ovary; prostate; colon; rectal; mouth; brain; head and neck; throat; testes; kidney; pancreas; bone; spleen; liver; bladder; larynx; nasal passages; and AIDS-related cancers. The compounds are particularly useful for treating cancers of the blood and bone marrow, such as multiple myeloma and acute and chronic leukemias, for example, lymphoblastic, myelogenous, lymphocytic, and myelocytic leukemias.

The compounds of the invention are also useful to treat or prevent heart disease, such as congestive heart failure, cardiomyopathy, pulmonary edema, endotoxin-mediated septic shock, acute viral myocarditis, cardiac allograft rejection, and myocardial infarction.

The compounds of the invention can also be used to treat or prevent viral, genetic, inflammatory, allergic, and autoimmune diseases. For example, the compounds are useful to treat or prevent diseases including, but not limited to, HIV; hepatitis; adult respiratory distress syndrome; bone-resorption diseases; chronic pulmonary inflammatory diseases; dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft rejection; auto-immune disease; rheumatoid spondylitis; arthritic conditions, such as rheumatoid arthritis and osteoarthritis; osteoporosis, Crohn's disease; ulcerative colitis; inflammatory-bowel disease; multiple sclerosis; systemic lupus erythrematosus; ENL in leprosy; radiation damage; asthma; and hyperoxic alveolar injury.

The compounds of the invention are also useful for treating or preventing bacterial infections including, but not limited to, malaria, mycobacterial infection, and opportunistic infections resulting from HIV.

In one embodiment, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the mammal. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In certain embodiments, the compounds of the invention or the compositions of the invention are administered to a mammal, preferably, a human, as a prophylactic. As used herein, "prevention" or "preventing" refers to a reduction of the risk of acquiring a given disease or disorder. In a preferred mode of the embodiment, the compounds and compositions of the present invention are administered as a preventative measure to a mammal, preferably, a human, having a genetic or non-genetic predisposition to a medical condition, for example, cancers, such as solid tumors and blood-born tumors. Specific examples of cancers preventable by compounds of the invention include, but are not limited to, cancers of the skin, such as melanoma; lymph node; breast; cervix; uterus; gastrointestinal tract; lung; ovary; prostate; colon; rectal; mouth; brain; head and neck; throat; testes; kidney; pancreas; bone; spleen; liver; bladder; larynx; nasal passages; and AIDS-related cancers. The compounds are particularly useful for treating cancers of the blood and bone marrow, such as multiple myeloma and acute and chronic leukemias, for example, lymphoblastic, myelogenous, lymphocytic, and myelocytic leukemias.

The compounds of the invention are also useful for preventing heart disease, such as congestive heart failure, cardiomyopathy, pulmonary edema, endotoxin-mediated septic shock, acute viral myocarditis, cardiac allograft rejection, and myocardial infarction.

The compounds of the invention can also be used to prevent viral, genetic, inflammatory, allergic, and autoimmune diseases. For example, the compounds are useful to prevent diseases including, but not limited to, HIV; hepatitis; adult respiratory distress syndrome; bone-resorption diseases; chronic pulmonary inflammatory diseases; dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft rejection; auto-immune disease; rheumatoid spondylitis; arthritic conditions, such as rheumatoid arthritis and osteoarthritis; osteoporosis, Crohn's disease; ulcerative colitis; inflammatory-bowel disease; multiple sclerosis; systemic lupus erythrematosus; ENL in leprosy; radiation damage; asthma; and hyperoxic alveolar injury.

The compounds of the invention are also useful for preventing bacterial infections or symptoms including, but not limited to, malaria, mycobacterial infection, and opportunistic infections resulting from HIV.

8. THERAPEUTIC/PROPHYLACTIC ADMINISTRATION OF THE COMPOUNDS AND COMPOSITIONS OF THE INVENTION

Due to the activity of the compounds and compositions of the invention, they are useful in veterinary and human medicine. The invention provides methods of treatment and prevention by administration of a therapeutically effective amount of a compound or a composition of the invention to a mammal, preferably, a human. The term "mammal" as used herein, encompasses any mammal. Preferably a mammal is in need of such treatment or prevention. Examples of mammals include, but are not limited to, cows, horses, sheep, pigs, cats, dogs, mice, rats, rabbits, guinea pigs, monkeys, etc., more preferably, a human.

Administration of compounds of the invention can be systemic or local. In most instances, administration to a mammal will result in systemic release of the compounds of the invention (i.e., into the bloodstream). Methods of administration include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. Preferably, the compounds and compositions of the invention are administered orally. In specific embodiments, it may be desirable to administer one or more compounds of the invention locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The compounds of the invention can be administered via typical as well as non-standard delivery systems, e.g., encapsulation in liposomes, microparticles, microcapsules, capsules, etc. For example, the compounds and compositions of the invention can be delivered in a vesicle, in particular a liposome (see Langer, 1990, *Science* 249:1527-1533; Treat et al., in Liposomes in *Therapy of Infectious Disease and Cancer*, Lopez-Berestein and Fidler (eds.), Liss, New York, pp. 353-365 (1989); Lopez-Berestein, ibid., pp. 317-327; see generally ibid.). In another example, the compounds and compositions of the invention can be delivered in a controlled release system. In one embodiment, a pump may be used (see Langer, supra; Sefton, 1987, *CRC Crit. Ref. Biomed. Eng.* 14:201; Buchwald et al., 1980, *Surgery* 88:507 Saudek et al., 1989, *N. Engl. J. Med.* 321:574). In another example, polymeric materials can be used (see Medical Applications of Controlled Release, Langer and Wise (eds.), CRC Press., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In still another example, a controlled-release system can be placed in proximity of the target area to be treated, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, *Science* 249:1527-1533) can be used.

When administered as a composition, a compound of the invention will be formulated with a suitable amount of a pharmaceutically acceptable vehicle or carrier so as to provide the form for proper administration to the mammal. The term "pharmaceutically acceptable" means approved by a regulatory agency of the Federal or a state government or listed in the U.S. Pharmacopeia or other generally recognized pharmacopeia for use in mammals, and more particularly in humans. The term "vehicle" refers to a diluent, adjuvant, excipient, or carrier with which a compound of the invention is formulated for administration to a mammal. Such pharmaceutical vehicles can be liquids, such as water and oils, including those of petroleum, animal, vegetable or synthetic origins such as peanut oil, soybean oil, mineral oil, sesame oil and the like. The pharmaceutical vehicles can be saline, gum acacia, gelatin, starch paste, talc, keratin, colloidal silica, tirea, and the like. In addition, auxiliary stabilizing, thickening, lubricating and coloring agents may be used. Preferably, when administered to a mammal, the compounds and compositions of the invention and pharmaceutically acceptable vehicles, excipients, or diluents are sterile. An aqueous medium is a preferred vehicle when the compound of the invention is administered intravenously, such as water, saline solutions, and aqueous dextrose and glycerol solutions.

The present compounds and compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In a preferred embodiment, the compounds and compositions of the invention are formulated for administration in accordance with routine procedures as a pharmaceutical composition adapted for oral or intravenous administration to humans. In one embodiment, the pharmaceutically acceptable vehicle is a hard gelatin capsule. Examples of suitable pharmaceutical vehicles and methods for formulation thereof are described in *Remington: The Science and Practice of Pharmacy*, Alfonso R. Gennaro ed., Mack Publishing Co. Easton, Pa., 19th ed., 1995, Chapters 86, 87, 88, 91, and 92, incorporated herein by reference.

Compounds and compositions of the invention formulated for oral delivery, are preferably in the form of capsules, tablets, pills, or any compressed pharmaceutical form. Moreover, where in tablet or pill form, the compounds and compositions may be coated to delay disintegration and absorption in the gastrointestinal tract thereby providing a sustained action over an extended period of time. Selectively permeable membranes surrounding an osmotically active driving compound are also suitable for orally administered compounds and compositions of the invention. In these later platforms, fluid from the environment surrounding the capsule is imbibed by the driving compound that swells to displace the agent or agent composition through an aperture. These delivery platforms can provide an essentially zero order delivery profile as opposed to the spiked profiles of immediate releases-formulations. A time delay material such as glycerol monostearate or glycerol stearate may also be used. Oral compositions can include standard vehicles, excipients, and diluents, such as magnesium stearate, sodium saccharine, cellulose, magnesium carbonate, lactose, dextrose, sucrose, sorbitol, mannitol, starch, gum acacia, calcium silicate, microcrystalline cellulose, polyvinylpyrrolidinone, water, syrup, and methyl cellulose, the formulations can additionally include lubricating agents, such as talc, magnesium stearate, mineral oil, wetting agents, emulsifying and suspending agents, preserving agents such as methyl- and propylhydroxybenzoates. Such vehicles are preferably of pharmaceutical grade. Orally administered compounds and compositions of the invention can optionally include one or more sweetening agents, such as fructose, aspartame or saccharin; one or more flavoring agents such as peppermint, oil of wintergreen, or cherry; or one or more coloring agents to provide a pharmaceutically palatable preparation.

A therapeutically effective dosage regimen for the treatment of a particular disorder or condition will depend on its nature and severity, and can be determined by standard clinical techniques according to the judgment of a medical practitioner. In addition, in vitro or in vivo assays can be used to help identify optimal dosages. Of course, the amount of a compound of the invention that constitutes a therapeutically effective dose also depends on the administration route. In general, suitable dosage ranges for oral administration are about 0.001 milligrams to about 20 milligrams of a compound of the invention per kilogram body weight per day, preferably, about 0.7 milligrams to about 6 milligrams, more preferably, about 1.5 milligrams to about 4.5 milligrams. In a preferred embodiment, a mammal, preferably, a human is orally administered about 0.01 mg to about 1000 mg of a compound of the invention per day, more preferably, about 0.1 mg to about 300 mg per day, or about 1 mg to about 250 mg in single or divided doses. The dosage amounts described herein refer to total amounts administered; that is, if more than one compound of the invention is administered, the preferred dosages correspond to the total amount of the compounds of the invention administered. Oral compositions preferably contain 10% to 95% of a compound of the invention by weight. Preferred unit oral-dosage forms include pills, tablets, and capsules, more preferably capsules. Typically such unit-dosage forms will contain about 0.01 mg, 0.1 mg, 1 mg, 5 mg, 10 mg, 15 mg, 20 mg, 50 mg, 100 mg, 250 mg, or 500 mg of a compound of the invention, preferably, from about 5 mg to about 200 mg of compound per unit dosage.

In another embodiment, the compounds and compositions of the invention can be administered parenterally (e.g., by intramuscular, intrathecal, intravenous, and intraarterial routes), preferably, intravenously. Typically, compounds and compositions of the invention for intravenous administration are solutions in sterile isotonic aqueous vehicles, such as water, saline, Ringer's solution, or dextrose solution. Where necessary, the compositions may also include a solubilizing agent. Compositions for intravenous administration may optionally include a local anesthetic such as lignocaine to ease pain at the site of the injection. For intravenous administration, the compounds and compositions of the invention can be supplied as a sterile, dry lyophilized powder or water-free concentrate in a hermetically sealed container, such as an ampule or sachette, the container indicating the quantity of active agent. Such a powder or concentrate is then diluted with an appropriate aqueous medium prior to intravenous administration. An ampule of sterile water, saline solution, or other appropriate aqueous medium can be provided with the powder or concentrate for dilution prior to administration. Or the compositions can be supplied in pre-mixed form, ready for administration. Where a compound or composition of the invention is to be administered by intravenous infusion, it can be dispensed, for example, with an infusion bottle containing sterile pharmaceutical-grade water, saline, or other suitable medium.

Rectal administration can be effected through the use of suppositories formulated from conventional carriers such as cocoa butter, modified vegetable oils, and other fatty bases.

Suppositories can be formulated by well-known methods using well-known formulations, for example see *Remington: The Science and Practice of Pharmacy*, Alfonso R. Gennaro ed., Mack Publishing Co. Easton, Pa., 19th ed., 1995, pp. 1591-1597, incorporated herein by reference To formulate and administer topical dosage forms, well-known transdermal and intradermal delivery mediums such as lotions, creams, and ointments and transdermal delivery devices such as patches can be used (Ghosh, T. K.; Pfister, W. R.; Yum, S. I. *Transdermal and Topical Drug Delivery Systems*, Interpharm Press, Inc. p. 249-297, incorporated herein by reference). For example, a reservoir type patch design can comprise a backing film coated with an adhesive, and a reservoir compartment comprising a compound or composition of the invention, that is separated from the skin by a semipermeable membrane (e.g., U.S. Pat. No. 4,615,699, incorporated herein by reference). The adhesive coated backing layer extends around the reservoir's boundaries to provide a concentric seal with the skin and hold the reservoir adjacent to the skin.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In one embodiment, the kit contains more than one compound of the invention. In another embodiment, the kit comprises a compound of the invention and another biologically active agent.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred. The compounds and compositions of the invention may also be demonstrated to be effective and safe using animal model systems. Other methods will be known to the skilled artisan and are within the scope of the invention.

8.1 Combination Therapy

In certain embodiments, a compound of the invention is administered to a mammal, preferably, a human concurrently with one or more other biologically active agents, or with one or more other compounds of the invention, or with both. By "concurrently" it is meant that a compound of the invention and the other agent are administered to a mammal in a sequence and within a time interval such that the compound of the invention can act together with the other agent to provide an increased or synergistic benefit than if they were administered otherwise. For example, each component may be administered at the same time or sequentially in any order at different points in time; however, if not administered at the same time, they should be administered sufficiently closely in time so as to provide the desired treatment effect. Preferably, all components are administered at the same time, and if not administered at the same time, preferably, they are all administered from about 6 hours to about 12 hours apart from one another.

When used in combination with other therapeutic agents, the compounds of the invention and the therapeutic agent can act additively or, more preferably, synergistically. In one embodiment, a compound or a composition of the invention is administered concurrently with another therapeutic agent in the same pharmaceutical composition. In another embodiment, a compound or a composition of the invention is administered concurrently with another therapeutic agent in separate pharmaceutical compositions. In still another embodiment, a compound or a composition of the invention is administered prior or subsequent to administration of another therapeutic agent. As many of the disorders for which the compounds and compositions of the invention are useful in treating are chronic disorders, in one embodiment combination therapy involves alternating between administering a compound or a composition of the invention and a pharmaceutical composition comprising another therapeutic agent, e.g., to minimize the toxicity associated with a particular drug. In certain embodiments, when a composition of the invention is administered concurrently with another therapeutic agent that potentially produces adverse side effects including, but not limited to toxicity, the therapeutic agent can advantageously be administered at a dose that falls below the threshold that the adverse side effect is elicited.

The present compounds and compositions can be administered together with hormonal and steroidal anti-inflammatory agents, such as, estradiol, conjugated estrogens (e.g., PREMARIN, PREMPRO, AND PREMPHASE), 17 beta estradiol, calcitonin-salmon, levothyroxine, dexamethasone, medroxyprogesterone, prednisone, cortisone, flunisolide, and hydrocortisone; non-steroidal anti-inflammatory agents, such as tramadol, fentanyl, metamizole, ketoprofen, naproxen, nabumetone, ketoralac, tromethamine, loxoprofen, ibuprofen, aspirin, and acetaminophen; anti-TNF-α antibodies, such as infliximab (REMICADE™) and etanercept (ENBREL™); AIDS and AIDS-related therapies, such as lamivudine, zidovudine, indinavir sulfate, stavudine, and lamivudine; chemotherapeutics and cancer-related therapies, such as anti-angiogenesis agents, topoisomerase inhibitors, alkylating agents, nitrogen mustards, antibiotics such as doxorubicin, and paclitaxel, cisplatin, tamoxifen, docetaxel, irinotecan, temozolomide, thalidomide, amino-thalidomide, amino-EM-12, epirubicin, leuprolide, bicalutamide, goserelin implant, gemcitabine, sargramostim anti-cancer antibodies, such as Rituxan, and anti-cancer vaccines, such as Theratope and HSPPC-96; antibiotics, such as amoxicillin, ampicillin sodium, cefaclor, and ciprofloxacin; dermatological therapeutics, such as isotretinoin, clindamycin phosphate topical; antiarthritic therapies, such as diclofenac sodium, nabumetone, misoprostol, and rofecoxib; immunosuppressive therapies, such as cyclosporine, FK506, mycophenolate mofetil, and methylprednisolone; multiple sclerosis therapies, such as interferon beta-1a, interferon beta-1b, and glatiramer; osteoporosis therapies, such as vitamin $K_2$; cystic fibrosis therapies, such as domase alpha and tobramycin; and Alzheimer's disease therapies, such as dolasetron mesylate, and donepezil hydrochloride.

In one embodiment of the invention, the compounds of the invention can be used, not only to directly treat the disorder, but also to reduce the dose or toxicity of another chemotherapeutic. For example, the compounds of the invention can be administered to reduce gastrointestinal toxicity associated with a topoisomerase inhibitor, such as irinotecan.

8.2 Assays

The compounds of the invention can be assayed for their ability to modulate the production of TNF-α by well-known methods in the art, see e.g., Corral et al., 1999, *J. Immun.* 163:380-386 and Muller et al., 1996, *J. Med. Chem.* 39:3238 (assay for the inhibition of production of TNF-α) and Muller et al., 1998, Bioorg. Med. Chem. Lett. 8:2669, all three of which citations are incorporated herein by reference.

8.2.1 Assay for the Ability of a Compound of the Invention to Modulate the Production of TNF-α

PBMC cells—normal human donors—were obtained by Ficoll-Hypaque density centrifugation (Pharmacia Fine Chemicals, Piscataway, N.J.). The cells (about $2 \times 10^5$ to $10^6$ cells/ml) are cultured with RPMI (commercially available, e.g., from Gibco Laboratories, Grand Island, N.Y.) supplemented with 10AB+ serum (commercially available, e.g., from Biocell, Rancho Dominguez, Calif.), about 2 mM$_L$-glutamine, about 100 U/ml penicillin, and about 100 µg/ml streptomycin (Gibco). The test compounds are dissolved in DMSO at 20 mg/ml, further dilution can be done with culture medium. The final DMSO concentration in all samples including the controls should be about 0.25% by weight. Test compounds were added to cells 1 hour prior to the addition of LPS. The PBMC cells, in triplicate, are stimulated by 1 µg/ml LPS from *Salmonella Minnesota* R595 (List Biological Labs, Campbell, Calif.) and incubated for about 18 to about 20 hours at ~37° C. (5% $CO_2$) in 96-well flat-bottom polystyrene Costar tissue culture plates (Corning, Corning, N.Y.) for the induction of TNF-α. Cells are incubated with or without compounds of the invention (negative controls). The supernatants are collected for the determination of cytokine levels by ELISA (Endogen, Cambridge, Mass.). Percent inhibition can be determined as $100 \times [1-(\text{TNF-}\alpha\ \text{EXPERIMENTAL}/\text{TNF-}\alpha\ \text{CONTROL})]$. Assays are performed, in accordance with the assay kit's manufacturer, in 96-well plates (Nunc Immunoplates, Roskilde, Denmark) coated with the affinity-purified rabbit anti-TNF-α antibody (0.5 µg/ml; 12-16 hours; 4° C.) and blocked for 2 hours at room temperature with PBS/0.05% Tween 20 (Sigma Chemical Co., St. Louis, Mo.) containing 5 mg/ml BSA. After washing, 100 µl of TNF-α standards, samples and controls are applied to the wells, and the plates are incubated for 12-24 hours at 4° C. After the incubation, plates are washed and a second antibody, horseradish peroxidase (HRP)-conjugated mouse monoclonal anti-TNF-α, diluted 1:2,000 in PBS/BSA/Tween, is applied to the wells, after which they incubated for 2 hours at room temperature. The color reaction is developed with the OPD substrate (0.4 mg/ml o-phenylenediamine [Sigma Chemical Co.] in 24 mM citric acid, 51 mM sodium phosphate, pH 5.0 [phosphate-citrate buffer: Sigma Chemical Co.] containing 0.012% hydrogen peroxide [Fisher Scientific Co., Pittsburgh, Pa.]) and absorbance read at 492 nm in an automated ELISA reader (Dynatech Laboratories, Inc., Alexandria, Va.).

8.2.2 Assay For T-Cell Stimulation and IL-2 Stimulation: PMC Stimulation by Anti-CD3 Ab PBMC ($1 \times 10^6$ cells) are stimulated by cross-linking of the TCR by immobilized monoclonal mouse anti-human CD3 (Orthoclone OKT3) as described in Haslett et al., 1998, *J. Exp. Med.* 187:1885, incorporated herein by reference. The anti-CD3 Ab is diluted to 10 µg/ml in 100 µl PBS and coated onto 48-well flat-bottom polystyrene Falcon tissue culture plates (Becton Dickinson, Franklyn Lakes, N.J.) by overnight incubation at 4° C. Appropriate dilutions of compounds of the invention are added at the start of the cell culture. Supernatants are collected at 24, 43, and 72 hours and assayed for TNF-α levels. Cells are collected at 48 hours for evaluation of CD40 ligand (CD40L)[3] and CD3 surface expression by two-color flow cytometry (anti-CD40L, PharMingen, San Diego, Calif.; anti-CD3, Becton Dickinson, San Jose, Calif.).

8.2.3 Assay For the Modulation of Production of IL-1β and IL-10

This assay can be performed according to the procedure outlined in Muller et. al., 1999, *J. Immunol.* 176, 380, hereby expressly incorporated herein by reference. PMBC ($2 \times 10^5$ cells) incubated in 96-well flat-bottom polystyrene Costar tissue culture plates (Corning, Corning, N.Y.) were stimulated by 1 mg/ml LPS from *Salmonella minnesota* R595 (List Biological Labs, Campbell, Calif.) for the induction of IL-1β, and IL-10. Cells were incubated with or without thalidomide or analogues for 20 h, and culture supernatants were collected and frozen immediately at −70° C. until assayed in triplicate or duplicate. IL-1β and IL-10 levels were measured by ELISA (Endogen, Cambridge, Mass.) as described by the manufacturer.

9. EXAMPLES OF SYNTHESES OF COMPOUNDS OF THE INVENTION

The following Examples further illustrate methods for synthesizing compounds and intermediates of the invention. It is to be understood that the invention is not limited to the specific details of the Examples set forth below.

Methyl-3-amino-2-(methoxycarbonyl)benzoate

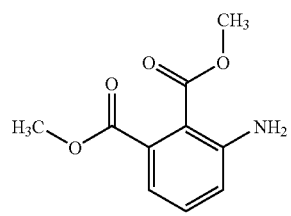

To a solution of methyl-2-(methoxycarbonyl)-3-nitrobenzoate (23.8 g, 99.51 mmol) in ethyl acetate (200 ml) was added 10% Pd/C (1.8 g). The mixture was hydrogenated under 50 psi of hydrogen for 3 hours in a Parr Type Shaker. The mixture was filtered through Celite and the filtrate was concentrated in vacuo to yield an oil. The crude product was purified by flash chromatography (dichloromethane/ethyl acetate 95 to 5) to afford 18.1 g (87%) of the product as a brown oil: $^1$H NMR (CDCl$_3$) δ 7.22 (t, J=7.6 Hz, 1H), 6.90 (d, J=7.2 Hz, 1H), 6.79 (d, J=8.7 Hz), 5.07 (b, 2H), 3.85 (s, 3H), 3.83 (s, 3H).

Methyl-3-cyano-2-(methoxycarbonyl)benzoate

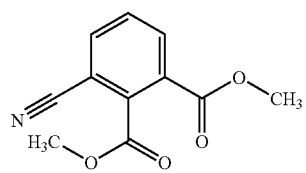

To a stirred suspension of methyl-3-amino-2-(methoxycarbonyl)benzoate (17.0 g, 81 mmol) in a mixture of concentrated HCl (44 ml) and water (440 ml) at 4° C. was added a solution of NaNO₂ (6.73 g, 97 mmol) in water (25 ml) dropwise at 4-5° C. Stirring was continued for 30 min at 4° C. The mixture was then carefully neutralized with sat. sodium carbonate to pH 6. A stirred solution of CuCN (9.46 g, 105 mmol) and KCN (6.38 g, 105 mmol) in water (150 ml) was warned to 6° C. The cold neutralized diazonium solution was then added in small portions at a time with vigorous stirring. The mixture was stirred at 60° C. for 1 hour and then cooled to room temperature. The mixture was extracted with dichloromethane (4×150 ml) and the combined dichloromethane extracts were washed with water (2×100 ml), brine (100 ml) and dried. The solvent was removed in vacuo and the product was purified by chromatography (dichloromethane) to afford 12.36 g (65%) of the product as a light yellow solid: 1 H NMR (CDCl₃) δ 8.19 (d, J=7.9 Hz, 1H), 7.8.9 (d, J=7.4 Hz, 1H), 7.64 (t, J=8.0 Hz, 1H), 4.03 (s, 3H), 3.94 (s, 3H).

Methyl-3-aminomethyl-2-(methoxycarbonyl)benzoate hydrochloride

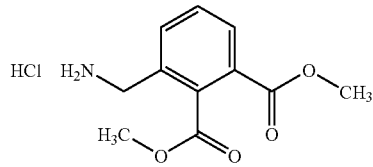

To a solution of methyl-3-cyano-2-(methoxycarbonyl) benzoate (12.3 g, 57 mmol) in methanol (250 ml) and 4N HCl (40 ml) was added 10% Pd/C (1.2 g). The mixture was hydrogenated under 50 psi of hydrogen in a Parr Type Shaker for 17 hours. The mixture was filtered through Celite and the filtrate was concentrated in vacuo. The residue was further evaporated with ethanol (2×25 ml) and toluene (25 ml) and dried under vacuum. The resulting solid was slurried in ether (50 ml) for 1 hour. The slurry was then filtered and dried to give 13.46 g (90%) of the product as a white solid: ¹H NMR (DMSO-d₆) δ 8.79 (b, 2H), 7.94 (d, J=7.8 Hz, 1H), 7.88 (d, J=7.7 Hz, 1H), 7.72 (t, J=7.7 Hz, 1H), 4.03 (s, 2H), 3.86 (s, 3H), 3.85 (s, 3H); ¹³C NMR (DMSO-d₆) δ 167.58, 166.12, 133.41, 133.18, 132.28, 130.62, 129.49, 52.99, 52.92, 39.25.

Methyl-3-[(t-butoxycarbonylamino)methyl]-2-(methoxycarbonyl)benzoate

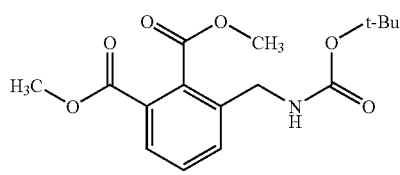

Triethylamine (3.89 g, 38 mmol) was added dropwise to a stirred suspension of methyl-3-aminomethyl-2-(methoxycarbonyl)benzoate hydrochloride (4.0 g, 15 mmol) in dichloromethane (100 ml). The mixture was cooled in an ice bath to 8° C. A solution of di-t-butyl dicarbonate (3.7 g, 16 mmol) in dichloromethane (20 ml) was added dropwise at 8° C. After the addition was complete, the cooled mixture was stirred for an additional 30 minutes, and then warmed to room temperature for 1 hour. The mixture was washed with water (2×40 ml), brine (40 ml) and dried. Solvent was removed in vacuo and the product was purified by chromatography (hexane/ethyl acetate 7 to 3) to afford 4.66 g (93%) of the product as an oil: ¹H NMR (CDCl₃) δ 7.87 (d, J=7.4 Hz, 1H), 7.62 (d, J=7.4, Hz, 1H), 7.46 (t, J=7.8 Hz, 1H), 5.16 (b, 1H), 4.30 (d, J=6.1 Hz, 2H), 3.93 (s, 3H), 3.89 (s, 3H), 1.42 (s, 9H); ¹³C NMR (CDCl₃) δ 169.41, 166,18, 155.57, 137.09, 134.04, 133.32, 129.76, 128.95, 128.64, 79.52, 52.72, 52.50, 42.23.

[2-(2,6-Dioxo-piperidin-3-yl)-1,3-dioxo-2,3-dihydro-1H-isoindol-4-ylmethyl]-carbamic acid tert-butyl ester I-1

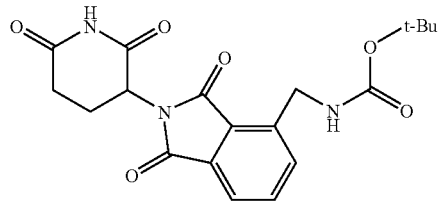

Diisopropylethylamine (3.20 g, 25 mmol) was added to a stirred suspension of methyl-3-[(t-butoxycarbonylamino)methyl]-2-(methoxycarbonyl)benzoate (8.00 g, 25 mmol) and aminoglutarimide hydrochloride (4.07 g, 25 mmol) in DMF (60 ml). The mixture was heated to 120° C. for 24 hours and then cooled to room temperature. The mixture was poured into cold water (300 ml) and extracted with ethyl acetate (4×100 ml each). The combined ethyl acetate extracts were washed with water (2×50 ml), brine (50 ml) and dried. Solvent was removed in vacuo and the product purified by flash chromatography (dichloromethane/ethyl acetate 8 to 2) to yield 4.66 g of recovered starting material and 3.31 g (82%) of the product as a white solid: mp 180-182° C.; ¹H NMR (CDCl₃) δ 8.51 (s, 1H), 7.81-7.67 (m, 3H), 5.54 (b, 1H), 5.03-4.96 (dd, J=5.2 and 11.2 Hz, 1H), 4.66 (d, J=6.3 Hz, 2H), 2.95-2.74 (m, 3H), 2.18-2.14 (m, 1H), 1.43 (s, 9H); ¹³C NMR (CDCl₃) δ 170.99, 168.08, 167.95, 167.07, 155.86, 139.17, 135.00, 134.61, 132,15, 128.22, 122.82, 79.81, 49.21, 40.53, 31.33, 28.32, 22.58; Anal. Calcd for C₁₉H₂₁N₃O₆: C, 58.91; H, 5.46; N, 10.85. Found: C, 59.08; H, 5.51; N, 10.69.

4-(Aminomethyl)-2-(2,6-dioxo(3-piperidyl))isoindoline-1,3-dione I-2, hydrochloride

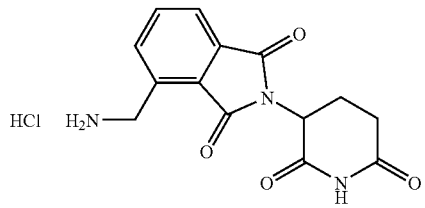

A solution of 4 N HCl in dioxane (10 ml) was added to a stirred solution of (t-butoxy)-N-{[2-(2,6-dioxo(3-piperidyl))-1,3-dioxoisoindolin-4-yl]methyl}carboxamide (3.3 g, 8.5 mmol) in dichloromethane (50 ml). The mixture was stirred at room temperature overnight. The resulting slurry was filtered and dried to afford 2.4 g (87%) of the product as a white solid: mp 291-293° C.; ¹H NMR (DMSO-d₆) δ 11.18

(s, 1H), 8.77 (b, 2H), 8.06-7.93 (m, 3H), 5.22-5.15 (dd, J=5.1 and 12.6 Hz, 1H), 4.49 (s, 2H), 2.97-2.85 (m, 1H), 2.65-2.51 (m, 2H), 2.08-2.04 (m, 1H); $^{13}$C NMR (DMSO-d$_6$) δ 172.86, 169.76, 167.35, 166.71, 135.62, 134.98, 132.80, 131.46, 128.62, 123.57, 49.00, 37.00, 30.95, 22.07; Anal. Calcd for $C_{14}H_{14}N_3O_4Cl$+0.22 water: C, 51.31; H. 4.44; N, 12.82; Cl, 10.82. Found: C, 51.08; H, 4.36; N, 12.47; Cl, 10.61.

3-(Acetylamino-methyl)-phthalic acid dimethyl ester

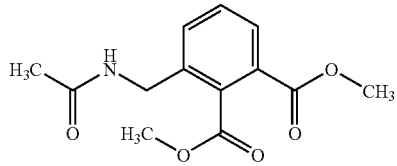

Triethylamine (1.87 g, 18 mmol) was added slowly to a stirred suspension of methyl-3-(aminomethyl)-2-(methoxycarbonyl)benzoate hydrochloride (2.0 g, 8 mmol) in dichloromethane (30 ml). The resulting mixture was cooled in an ice bath to 4° C. Acetyl chloride (0.73 g, 9 mmol) was added dropwise at a rate such that the temperature stayed between 4-7° C. After addition was complete, the mixture was stirred in the ice bath for an additional 30 minutes and then allowed to warm to room temperature and maintained for 2 hours. The reaction mixture was washed with water (2×30 ml), brine (30 ml) and dried. Solvent was removed in vacuo and the product was purified by chromatography (dichloromethane/ethyl acetate 6 to 4) to afford 1.65 g (80%) of the product as an oil: $^1$H NMR (CDCl$_3$) δ 7.86 (d, J=7.7 Hz, 1H), 7.62 (d, J=7.6 Hz); 7.46 (t, J=7.7 Hz); 6.29 (b, 1H), 4.39 (d, J=6.1 Hz, 2H), 3.93 (s, 3H), 3.90 (s, 3H), 1.96 (s, 3H).

N-[2-(2,6-Dioxo-piperidin-3-yl)-1,3-dioxo-2,3-dihydro-1H-isoindol-4-ylmethyl]-acetamide I-3

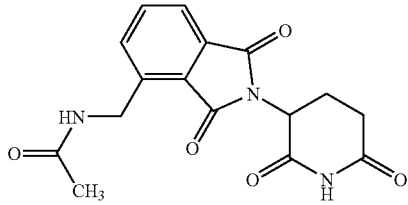

1,8-Diazabicyclo[5,4,0]undec-7-ene (0.93 g, 6 mmol) was added dropwise to a stirred suspension of 3-(acetylaminomethyl)-phthalic acid dimethyl ester (1.61 g, 6.0 mmol) and aminoglutarimide hydrochloride (1.0 g, 6.0 mmol) in DMF (15 ml). The mixture was then heated to 120° C. for 24 hours. The cooled mixture was concentrated in vacuo and the residue was stirred with water (25 ml) and dichloromethane (20 ml). The resulting slurry was filtered to give 0.45 g (22%) of the product as a gray solid. Recrystallization from methanol gave a white solid: mp 177-179° C.; $^1$H NMR (DMSO-d$_6$) δ (11.02 (s, 1H), 8.36 (t, J=5.8 Hz, 1H), 7.74-7.55 (m, 3H), 5.05-4.98 (dd, J=5.3 and 12.5 Hz, 1H), 4.57 9D, j=5.9 Hz, 2H), 2.84-2.70 (m, 1H), 2.51-2.34 (m, 2H), 1.95-1.91 (m, 1H), 1.79 (s, 3H); $^{13}$C NMR (DMSO-d$_6$) δ (172.85, 169.89, 169.81, 167.56, 167.05, 139.37, 134.83, 133.35, 131.58, 127.14, 121.94, 48.91, 37,84, 30.98, 22.54, 22.05; Anal. Calcd. For $C_{16}H_{15}N_3O_5$+0.96 water: C, 55.45; H, 4.92; N, 12.12. Found: C, 55.27; H, 4.82; N, 12.00.

Methyl-3-[(cyclopropylcarbonylamino)methyl]-2-(methoxycarbonyl)benzoate

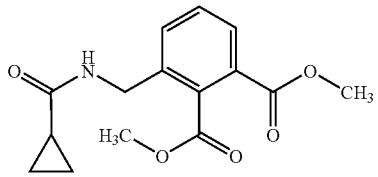

Triethylamine (1.87 g, 18 mmol) was added dropwise to a stirred suspension of methyl-3-(aminomethyl)-2-(methoxycarbonyl)benzoate hydrochloride (2.0 g, 7 mmol) in dichloromethane (40 ml). The mixture was cooled in an ice bath to 4° C. Cyclopropylcarbonyl chloride (0.99 g, 9 mmol) was added slowly at 4-8° C. After addition, the mixture was stirred in ice bath for 30 min and then warmed to room temperature for 2 hours. The mixture was washed with water (2×30 ml), brine (30 ml) and dried. Solvent was removed in vacuo and the product was purified by flash chromatography (dichloromethane/ethyl acetate 9 to 1) to give 2.1 g (93%) of the product as a white solid: $^1$H NMR (CDCl$_3$) (7.87 (d, J=7.8 Hz, 1H), 7.63 (d, J=7.7 Hz, 1H), 7.46 (t, J=7.77 Hz, 1H), 6.31 (m, 1H), 4.43 (d, J=6.0 Hz, 2H), 3.95 (s, 3H), 3.90 (s, 3H), 1.36-1.29 (m, 1H), 0.99-0.93 (m, 2H), 0.76-0.69 (m, 2H).

N-{[2-(2,6-Dioxo(3-piperidyl)-1,3-dioxoisoindolin-4-yl]methyl}cyclopropyl-carboxamide I-4

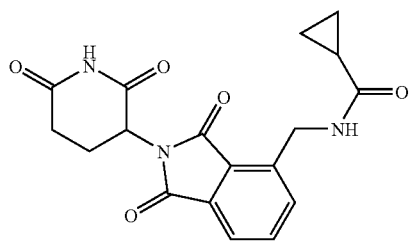

Diisopropylethylamine (0.92 g, 7 mmol) was added to a stirred suspension of methyl-3-[(cyclopropylcarbonylamino) methyl]-2-(methoxycarbonyl)benzoate (2.08 g, 7 mmol) and aminoglutarimide hydrochloride (1.17 g, 7 mmol) in DMF (15 ml). The mixture was heated to 120° C. for 24 hours. The mixture was concentrated in vacuo and the residue was stirred with water (40 ml) and ethyl acetate (15 ml). The resulting slurry was filtered to give 0.7 g (27%) of the product as a gray solid. Recrystallization for methanol gave a white solid: mp 240-242° C.; $^1$H NMR (DMSO-d$_6$) δ 11.06 (s, 1H), 8.62 (t, J=5.8 Hz, 1H), 7.79-7.70 (m, 2H), 7.60 (d, J=7.2 Hz, 1H), 5.09-5.02 (dd, J=5.3 and 12.5 Hz, 1H), 4.65 (d, J=5.8 Hz, 2H), 2.83-2.73 (m, 1H), 2.54-2.41 (m, 2H), 1.99-1.94 (m, 1H), 1.57 (m, 1H), 0.62-0.60 (m, 4H); $^{13}$C NMR (DMSO-d$_6$) δ 173.21, 172.85, 169.90, 167.52, 167.01, 139.44, 134.85, 133.37, 131.57, 127.13, 121.94, 48.89, 37.82, 30.97, 22.03, 13.58, 6.52; Anal. Calcd. For $C_{18}H_{17}N_3O_5$: C, 60.84; H, 4.82; N, 11.82. Found: C, 60.46; H, 4.84; N, 11.65.

Methyl-3-[(Ethoxycarbonylamino)methyl]-2-(methoxycarbonyl)benzoate

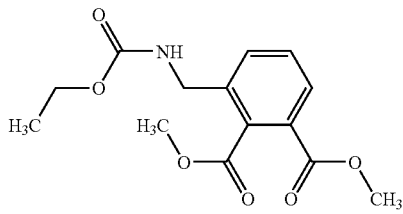

Triethylamine (1.57 g, 18.5 mmol) was added to a stirred suspension of methyl-3-(aminomethyl)-2-(methoxycarbonyl)benzoate hydrochloride (2.0 g, 8 mmol) in dichloromethane (30 ml). The mixture was cooled in an ice bath to 4° C. Ethyl chloroformate (1.0 g, 9 mmol) was added slowly keeping the mixture at 4-6° C. After addition was complete, the mixture was stirred in an ice bath for 30 minutes and then warmed to room temperature for 2 hours. The mixture was washed with water (2×30 ml), brine (30 ml) and dried. Solvent was removed in vacuo and the residue was purified by flash chromatography (dichloromethane/ethyl acetate 95 to 5) to give 1.59 g (70%) of the product as an oil: $^1$H NMR (CDCl$_3$) δ 7.87 (d, J=7.8 Hz, 1H), 7.36 (d, J=7.6 Hz, 1H), 7.46 (t, J=7.7 Hz, 1H), 5.30 (b, 1H), 4.32 (d, J=6.3 Hz, 2H), 4.12 (q, J=7.0 Hz, 2H), 3.93 (s, 3H), 3.89 (s, 3H), 1.22 (t, J=7.2 Hz, 3H).

[2-(2,6-Dioxo-piperidin-3-yl)-1,3-dioxo-2,3-dihydro-1H-isoindol-4-ylmethyl]-carbamic acid ethyl ester I-5

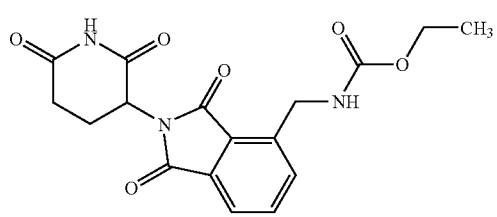

1,8-Diazabicyclo[5,4,0]undec-7-ene (0.8 g, 5 mmol) was added to a stirred suspension of methyl-3-[(ethoxycarbonylamino)methyl]-2-(methoxycarbonyl)benzoate (1.54 g, 5 mmol) and aminoglutarimide hydrochloride (0.86 g, 5 mmol) in DMF (15 ml). The mixture was heated to 120° C. for 24 hours. The mixture was cooled to room temperature and poured into water (150 ml). The mixture was extracted with ethyl acetate (3×30 ml) and the ethyl acetate solution was washed with water (30 ml), brine (30 ml) and dried. Solvent was removed and the residue was purified by flash chromatography (dichloromethane/ethyl acetate 7 to 3) to give 0.84 g (45%) of the product as a white solid: mp 187-189° C.; $^1$H NMR (DMSO-d$_6$) δ 11.03 (s, 1H), 7.76-7.58 (m, 4H), 5.06-4.99 (dd, J=5.4 and 12.6 Hz, 1H), 4.52 (d, J=5.9 Hz, 2H), 3.91 (q, J=7.0 Hz, 2H), 2.79-2.70 (m, 1H), 2.51-2.38 (m, 2H), 1.96-1.86 (m, 1H), 1.06 (t, J=7.0 Hz, 3H); $^{13}$C NMR (DMSO-d$_6$) δ 172.89, 169.93, 167.55, 167.05, 156.72, 139.69, 134.91, 132.90, 131.58, 127.04, 121.97, 60.15, 48.90, 39.34, 30.98, 22.04, 14.69; Anal. Calcd. For $C_{17}H_{11}N_3O_6$: C, 56.82; H, 4.77; N, 11.69. Found: C, 56.94; H, 4.81; N, 11.37.

Methyl-3-[(benzyloxcarbonylamino)methyl]-2-(methoxycarbonyl)benzoate

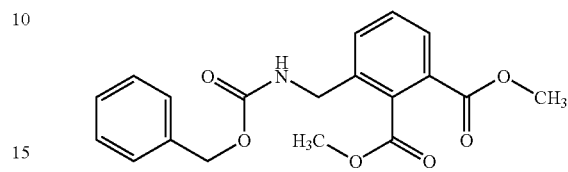

Triethylamine (1.87 g, 18.5 mmol) was added to a stirred suspension of methyl-3-(aminomethyl)-2-(methoxycarbonyl)benzoate hydrochloride (2.0 g, 8 mmol) in dichloromethane (30 ml). The mixture was cooled in an ice bath to 4° C. Benzyl chloroformate (1.66 g, 10 μmol) was added slowly keeping the temperature between 4-7° C. After the addition was complete, the cooled mixture was stirred an additional 30 minutes and then warmed to room temperature for 4 hours. The mixture was washed with water (2×30 ml), brine (30 ml) and dried. Solvent was removed and the residue was purified by chromatography (dichloromethane/ethyl acetate 95 to 5) to give 2.1 g (76%) of the product as a solid; $^1$H NMR (CDCl$_3$) δ 7.87 (d, J=7.8 Hz, 1H), 7.63 (d, J=7.6 Hz, 1H), 7.46 (t, J=7.7 Hz, 1H), 7.36-7.26 (m, 5H), 5.41 (b, 1H), 5.09 (s, 2H), 4.36 (d, J=6.3 Hz, 2H), 3.91 (s, 3H), 3.88 (s, 3H).

[2-(2,6-Dioxo-piperidin-3-yl)-1,3-dioxo-2,3-dihydro-1H-isoindol-4-ylmethyl]-carbamic acid benzyl ester I-6

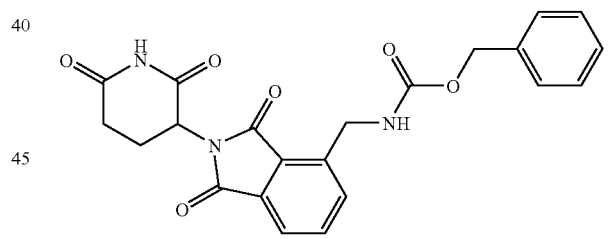

1,8-diazabicyclo[5,4,0]undec-7-ene (0.88 g, 6 mmol) was added to a stirred suspension of methyl-3-[(benzyloxycarbonylamino)methyl]-2-(methoxycarbonyl)benzoate (2.07 g, 6 mmol) and aminoglutarimide hydrochloride (0.95 g, 6 mmol) in DMF (15 ml). The mixture was heated to 120° C. for 24 hours. The mixture was cooled to room temperature and poured into water (150 ml). The mixture was extracted with ethyl acetate (3×30 ml) and the combined ethyl acetate extracts were washed with water (2×30 ml), brine (30 ml) and dried. Solvent was removed in vacuo and the residue was purified by chromatography (dichloromethane/ethyl acetate 8 to 2) to give 0.58 g (24%) of the product as a white solid: mp 166-168° C.; $^1$H NMR (DMSO-d$_6$) δ 11.15 (s, 1H), 7.99-7.71 (m, 4H), 7.37 (m, 5H), 5.19-5.12 (dd, J=5.1 and 17.4 Hz, 1H), 5.07 (s, 2H), 4.70 (d, J=5.7 Hz, 2H), 2.97-2.83 (m, 1H), 2.64-2.51 (m, 2H), 2.08-2.04 (m, 1H); $^{13}$C NMR (DMSO-d$_6$) δ 172.85, 169.89, 167.51, 167.01, 156.55, 139.46, 137.02, 134.87, 132.89, 131.57, 128.44, 127.92, 127.83, 127.06, 121.99, 65.69, 48.89, 30.97, 22.02; Anal. Calcd. For C$_{22}$H$_{19}$N$_3$O$_6$: C, 62.70; H, 4.54; N, 9.97. Found: C, 62.53; H, 4.57; N, 9.89.

2-Chloro-N-{[2-(2,6-dioxo(3-piperidyl))-1,3-dioxoisoindolin-4-yl]methyl}acetamide I-7

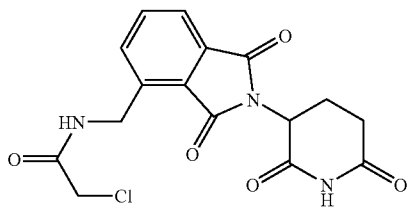

Triethylamine (0.6 g, 6 mmol) was added to a stirred suspension of 4-(aminomethyl)-2-(2,6-dioxo(3-piperidyl))isoindoline-1,3-dione hydrochloride (0.8 g, 2.5 mmol) in THF (70 ml). After stirring for 5 min, chloroacetyl chloride (0.34 g, 3 mmol) was added and the resulting mixture was heated at reflux for 3 hours. The solvent was removed in vacuo and the residue was dissolved in dichloromethane (70 ml), washed with water (20 ml), 2N HCl (30 ml), water (2×30 ml), brine (30 ml) and dried. Solvent was removed in vacuo and the resulting solid was slurried in dichloromethane (10 ml) and ether (10 ml) and filtered to give 0.76 g (84%) of the product: $^1$H NMR (DMSO-d$_6$) δ 11.15 (s, 1H), 8.87 (t, J=5.9 Hz, 1H), 7.88-7.68 (m, 3H), 5.19-5.12 (dd, J=5.3 and 12.6 Hz, 1H), 4.77 (d, J=5.9 Hz, 2H), 4.19 (s, 2H), 2.96-2.83 (m, 1H), 2.65-2.51 (m, 2H), 2.11-2.04 (m, 1H); $^{13}$C NMR (DMSO-d$_6$) δ 172.88, 169.90, 167.53, 167.01, 166,67, 138.46, 134.90, 133.22, 131.63, 127.26, 122.14, 48.94, 42.61, 38.27, 30.99, 22.05.

2-(Dimethylamino)-N-{[2-(2,6-dioxo(3-piperidyl))-1,3-dioxoisoindolin-4-yl]methyl}-acetamide I-8, hydrochloride

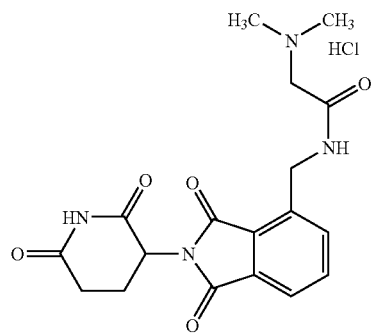

Dimethylamine (2M in THF, 5 ml, 10 mmol) was added to a stirred suspension of 2-chloro-N-{[2-(2,6-dioxo(3-piperidyl))-1,3-dioxoisoindolin-4-yl]methyl}acetamide (1.2 g, 3.3 mmol) in acetonitrile (120 ml). The mixture was stirred at room temperature overnight. Solvent was removed in vacuo and the residue was dissolved in dichloromethane (75 ml); washed with water (30 ml), brine (30 ml) and dried. Solvent was removed in vacuo and the residue was purified by flash chromatography (dichloromethane/methanol 95 to 5) to give 0.96 g (78%) of the free base. The free base was dissolved in ethyl acetate (20 ml) and treated with 1N HCl (5 ml) to afford 0.9 g (86%) of the hydrochloride salt: mp 185-187° C.; $^1$H NMR (DMSO-d$_6$) δ 11.15 (s, 1H), 10.05 (b. 1H), 9.40 (s, 1H), 7.84 (m, 3H), 5.14 (m, 1H), 4.81 (s, 2H), 4.07 (s, 2H), 2.84 (s, 6H), 2.65-2.52 (m, 3H), 2.09 (m, 1H); $^{13}$C NMR (DMSO-d$_6$) δ 172.81, 169.82, 167.40, 166.89, 164.77, 137.91, 134.88, 133.53, 131.55, 127.25, 122.23, 57.21, 48.88, 43.20, 37.91, 30.93, 21.89; Anal. Calcd. For C$_{18}$H$_{21}$N$_4$O$_5$Cl+0.65 water: C, 51.41; H, 5.34; N, 13.32; Cl, 8.43. Found: C, 51.12; H, 5.20; N, 12.67; Cl, 8.45.

1-tert-Butyl-3-[2-(2,6-dioxo-piperidin-3-yl)-1,3-dioxo-2,3-dihydro-1H-isoindol-4-ylmethyl]-urea I-9

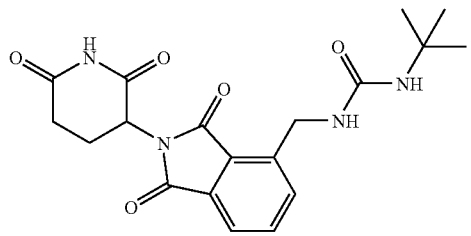

1,8-Diazabicyclo[5,4,0]undec-7-ene (0.28 g, 1.9 mmol) was added to stirred suspension of 4-(aminomethyl)-2-(2,6-dioxo(3-piperidyl))isoindoline-1,3-dione hydrochloride (0.6 g, 1.9 mmol) in acetonitrile (50 ml). After stirring for 1 hour, t-butylisocyanate (0.21 g, 2 mmol) was added. The mixture was stirred at room temperature for 17 hours. The solvent was removed in vacuo and the residue was dissolved in dichloromethane (70 ml) and washed with 0.1 N HCl (20 ml), water (20 ml), brine (20 ml) and dried. The solvent was removed in vacuo and the resulting solid was recrystallized from ethanol/isopropyl ether to give 0.36 g (51%) of the product: mp 186-188° C.; $^1$H NMR (DMSO-d$_6$) δ 11.04 (s, 1H), 7.77-7.59 (m, 3H), 6.17 (t, J=6.2 Hz, 1H), 5.86 (s, 1H), 5.08-5.01 (dd, J=5.4 and 12.4 Hz, 1H), 4.49 (d, J=6.0 Hz, 2H), 2.82-2.73 (m, 1H), 2.54-2.40 (m, 2H), 1.98-1.94 (m, 1H), 1.12 (s, 9H); $^{13}$C NMR (DMSO-d$_6$) δ 172.33, 169.39, 167.11, 166.59, 156.85, 140.72, 134.20, 132.99, 131.06, 126.54, 121.20, 48.69, 48.37, 37.89, 30.46, 28.88, 21.53; Anal. Calcd. For C$_{19}$H$_{22}$N$_4$O$_5$+0.2 water: C, 58.51; H, 5.79; N, 14.37. Found: C, 58.86; H, 6.15; N, 14.24.

N-{[2-(2,6-Dioxo(3-piperidyl))-1,3-dioxoisoindolin-4-yl]methyl}-3,3-dimethylbutanamide I-10

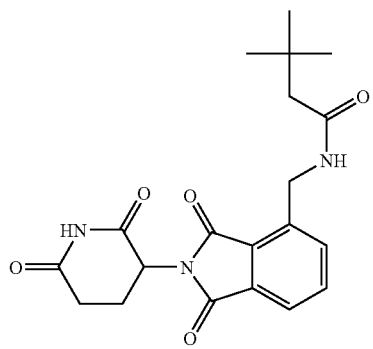

1,8-Diazabicyclo[5,4,0]undec-7-ene (0.62 g, 4 mmol) was added to a stirred suspension of 4-(aminomethyl)-2-(2,6-dioxo(3-piperidyl))isoindoline-1,3-dione hydrochloride (0.6 g, 1.9 mmol) in acetonitrile (50 ml). After stirring for 20 min, t-butylacetyl chloride (0.25 g, 1.9 mmol) was added. The mixture was stirred at room temperature for 17 hours. Solvent was removed in vacuo and the residue was dissolved in dichloromethane (90 ml) and washed with 0.1N HCl (30 ml), water (30 ml), brine (30 ml) and then dried. Solvent was removed in vacuo and the solid residue was slurried in ethanol (10 ml) to give after filtration 0.55 g (77%) of the product: mp 145-147° C.; $^1$H NMR (DMSO-d$_6$) δ 11.14 (s, $^1$H), 8.39 (t, J=5.7 Hz, 1H), 7.87-7.69 (m, 3H), 5.19-5.12 (dd, J=5.3 and 12.4 Hz, 1H), 4.72 (d, J=5.8 Hz, 2H), 2.92-2.83 (m, 1H), 2.63-2.51 (m, 2H), 2.08 (s, 2H), 2.08-2.04 (m, 1H), 0.97 (s, 9H); $^{13}$C NMR (DMSO-d$_6$) δ 172.69, 171.35, 169.74, 167.51, 166.96, 139.61, 134.69, 133.41, 131.52, 127.11, 121.87, 48.86, 48.62, 37.53, 30.93, 30.52, 29.71, 22.00; Anal. Calcd. For $C_{20}H_{23}N_3O_5$+0.28 water: C, 61.52; H, 6.08; N, 10.76. Found: C, 61.23; H, 6.18; N, 10.57.

N-[2-(2,6-Dioxo(3-piperidyl))-1,3-dioxoisoindolin-4-yl]-3-pyridylcarboxamide I-11

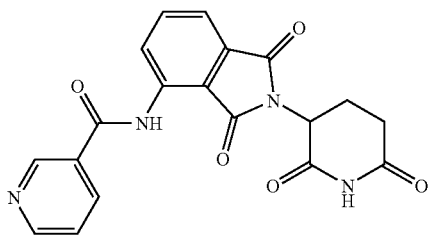

A stirred mixture of 4-amino-2-(2,6-dioxo(3-piperidyl)) isoindoline-1,3-dione (1.09 g, 4.0 mmol) and nicotinoyl chloride hydrochloride (1.42 g, 8.0 mmol) in tetrahydrofuran (60 ml) was heated to reflux for 22 h. The suspension was filtered and washed with tetrahydrofuran (20 ml) and ether (10 ml) to yield a white solid. The solid was slurried in pH 7 buffer (40 ml) and ether (30 ml) for 1 h. The suspension was filtered and washed with water (20 ml) and ether (20 ml) to N-[2-(2,6-dioxo(3-piperidyl))-1,3-dioxoisoindolin-4-yl]-3-pyridylcarboxamide as a white solid (1.2 g, 79% yield): mp, 176-178° C.; $^1$H NMR (DMSO-d$_6$) δ 2.06-2.10 (m, 1H, CHH), 2.49-2.65 (m, 2H, CH$_2$), 2.83-2.97 (m, 1H, CHH), 5.18 (dd, J=5.3, 12.5 Hz, 1H, NCH), 7.64 (dd, J=4.9, 7.9 Hz, 1H, Ar), 7.71 (d, J=7.3 Hz, 1H, Ar), 7.92 (t, J=7.8 Hz, 1H, Ar), 8.29-8.34 (m, 1H, Ar), 8.45 (d, J=8.2 Hz, 1H, Ar), 8.83 (dd, J=1.2, 4.8 Hz, 1H, Ar), 9.15 (d, J=1.7 Hz, 1H, Ar), 10.55 (s, 1H, NH), 11.17 (s, 1H, NH); $^{13}$C NMR (DMSO-d$_6$) δ 21.99, 30.93, 49.00, 119.06, 119.34, 123.91, 127.36, 129.17, 131.55, 135.24, 135.94, 136.20, 148.47, 152.95, 163.85, 166.59, 167.54, 169.69, 172.72; Anal Calcd for $C_{19}H_{14}N_4O_5$±0.13H$_2$O: C, 59.95; H, 3.78; N, 14.72; H$_2$O, 0.62. Found: C, 59.83; H, 3.66; N, 14.68; H$_2$O, 0.64.

3-{1-Oxo-4-[benzylamino]isoindolin-2-yl}piperidine-2,6-dione I-12

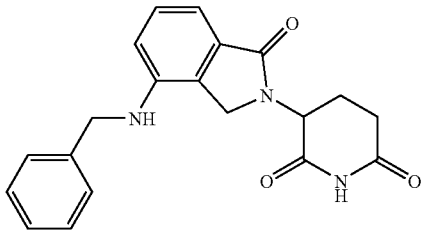

A stirred mixture of 3-(4-amino-1-oxoisoindolin-2-yl)piperidine-2,6-dione (518 mg, 2.0 mmol) and benzaldehyde (0.21 ml, 2.0 mmol) in methanol (20 ml) was heated to reflux for 5 h. The solvent was removed in vacuo to give a solid. The solid was re-dissolved in acetic acid (20 ml). The stirred solution was heated to reflux for 1 h, and was then allowed to cool to room temperature. To the stirred solution was added sodium borohydride (90 mg, 2.3 mmol) and stirring continued at room temperature for 18 h. The resulting suspension was filtered and washed with acetic acid (10 ml) and ether (20 ml) to give 3-{1-oxo-4-[benzylamino]isoindolin-2-yl}piperidine-2,6-dione as an off-white solid (420 mg, 60% yield): mp, 257-259° C.; $^1$H NMR (DMSO-d$_6$) δ 2.01-2.07 (m, 1H, CHH), 2.23-2.30 (m, 1H, CHH), 2.49-2.65 (m, 1H, CHH), 2.85-3.00 (m, 1H, CHH), 4.19 (d, J=17 Hz, 1H, CHH), 4.31 (d, J=17 Hz, 1H, CHH), 4.39 (d, J=5.7 Hz, 2H, CH$_2$), 5.12 (dd, J=5.1, 13 Hz, 1H, NCH), 6.37 (t, J=5.9 Hz, 1H, NH), 6.62 (d, J=8.0 Hz, 1H, Ar), 6.91 (d, J=7.3 Hz, 1H, Ar), 7.19-7.40 (m, 6H, Ar), 11.02 (s, 1H, NH); $^{13}$C NMR (DMSO-d$_6$) δ 22.79, 31.25, 45.79, 46.09, 51.56, 110.32, 112.34, 126.72, 127.05, 128.32, 129.07, 132.08, 139.72, 143.33, 168.82, 171.22, 172.90; Anal Calcd for $C_{20}H_{19}N_3O_3$: C, 68.75; H, 5.48; N, 12.03. Found C, 68.73; H, 5.41; N, 12.04.

2-(2,6-Dioxo(3-piperidyl))-4-[benzylamino]isoindoline-1,3-dione I-13

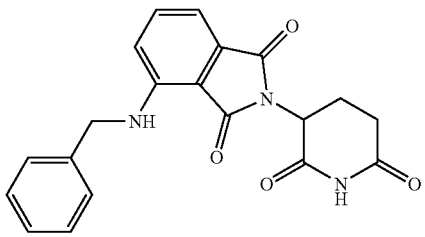

A mixture of 4-amino-2-(2,6-dioxo(3-piperidyl))isoindoline-1,3-dione (1.0 g, 3.7 mmol) and benzaldehyde (0.4 ml, 3.9 mmol) in acetic acid (20 ml) was stirred at room temperature for 17 h, then was heated to reflux for 3 h. The mixture was cooled to room temperature. To the stirred mixture was added sodium borohydride (140 mg, 3.7 mmol) and kept at room temperature for 18 h. The mixture was then heated to reflux for 2 h. To the mixture was added additional benzaldehyde (0.4 ml, 3.9 mmol) during reflux. After 30 min of reflux the reaction was allowed to cool to room temperature. To the mixture was added sodium borohydride (180 mg, 4.8 mmol) and the mixture stirred at room temperature for 3 days. The solvent was removed in vacuo to yield an oil. The oil was diluted with ethyl acetate (90 ml) and aqueous sodium hydrogen carbonate (sat, 100 ml). The organic layer was separated and was washed with aqueous sodium hydrogen carbonate (sat, 2×100 ml), brine (100 ml) and dried over MgSO$_4$. The solvent was removed in vacuo to give a solid. The solid was purified by column chromatography (Silca Gel, 50% EtOAc: CH$_2$Cl$_2$) to give a yellow solid. The solid was further purified by column chromatography (KP-C18-HS, 35:65 CH$_3$CN: 0.1% CF$_3$COOH in water) to give 2-(2,6-dioxo(3-piperidyl))-4-[benzylamino]isoindoline-1,3-dione as a yellow solid (210 mg, 16% yield): mp, 209-211° C.; $^1$H NMR (DMSO-d$_6$) δ 2.02-2.08 (m, 1H, CHH), 2.46-2.63 (m, 2H, CH$_2$), 2.82-2.97 (m, 1H, CHH), 4.56 (d, J=6 Hz, 2H, CH$_2$), 5.07 (dd, J=5.3, 12.4 Hz, 1H, NCH), 6.96 (d, J=8.6 Hz, 1H, Ar), 7.02 (d, J=7.0 Hz, 1H, Ar), 7.19-7.40 (m, 6H, Ar, NH), 7.51 (dd, J =7.5, 8.4 Hz, 1H, Ar), 11.11 (s, 1H, NH); $^{13}$C NMR (DMSO-d$_6$) δ 22.15, 30.99, 45.44, 48.59, 109.58, 110.74, 117.63, 126.95, 126.99, 128.53, 132.21, 136.09, 138.95, 146.09, 167.27, 168.78, 170.07, 172.79; Anal Calcd for C$_{20}$H$_{17}$N$_3$O$_4$: C, 66.11; H, 4.72; N, 11.56. Found: C, 65.96; H, 4.60; N, 11.49.

N-{[2-(2,6-Dioxo(3-piperidyl-1,3-dioxoisoindolin-4-yl]methyl}propanamide I-14

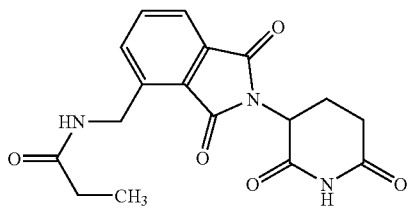

1,8-Diazabicyclo[5,4,0]undec-7-ene (0.65 g, 4.25 mmol) was added to a stirred suspension of 4-(aminomethyl)-2-(2,6-dioxo(3-piperidyl))isoindoline-1,3-dione hydrochloride (0.6 g, 1.85 mmol) in CH$_3$CN (50 ml). After stirring for 20 min, propionyl chloride (0.2 g, 2.13 mmol) was added. The mixture was stirred at room temperature for 17 hours. Solvent was removed in vacuo and the residue was dissolved in CH$_2$Cl$_2$ (60 ml) and washed with 1N HCl (30 ml), H$_2$O (30 ml), brine (30 ml) and dried (MgSO$_4$). The solvent was removed and the resulting solid was slurried in hot C$_2$H$_5$OH (10 ml) to give after filtration N-{[2-(2,6-dioxo(3-piperidyl))-1,3-dioxoisoindolin-4-yl]methyl}propanamide (0.41 g, 64%) as a white solid: mp 219-221° C.; $^1$H NMR (DMSO-d$_6$) δ d 11.15 (s, 1H), 8.42 (t, J=5.8 Hz, 1H), 7.87-7.67 (m, 3H), 5.19-5.12 (dd, J=5.3 and 12.5 Hz, 1H), 4.72 (d, J=5.8 Hz, 2H), 2.98-2.84 (m, 1H), 2.65-2.48 (m, 2H), 2.26-2.17 (m, 2H), 2.09-2.04 (m, 1H), 1.05 (t, J=7.8 Hz, 3H); $^{13}$C NMR (DMSO-d$_6$) δ d 173.52, 172.81, 169,79, 167.53, 167.01, 139.52, 134.79, 133.20, 131.55, 127.10, 121.86, 48.89, 37.69, 30.95, 28.43, 22.03, 9.90; Anal. Calcd. For C$_{17}$H$_{17}$N$_3$O$_5$+0.19H$_2$O: C, 58.88; H, 5.05; N, 12.12. Found: C, 58.77; H, 4.97; N, 12.12.

N-{[2-(2,6-Dioxo(3-piperidyl))-1,3-dioxoisoindolin-4-yl]methyl}-3-pyridylcarboxamide I-15

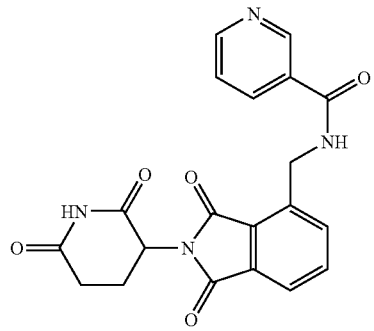

1,8-Diazabicyclo[5,4,0]undec-7-ene (0.98 g, 6.48 mmol) was added to stirred suspension of 4-(aminomethyl)-2-(2,6-dioxo(3-piperidyl))isoindoline-1,3-dione hydrochloride (0.6 g, 1.85 mmol) in CH$_3$CN (50 ml). After stirring for 20 min, nicotinoyl chloride (0.41 g, 2.22 mmol) was added. The mixture was stirred at room temperature for 17 hours. The solvent was removed in vacuo and the residue was dissolved in CH$_2$Cl$_2$ (70 ml). The CH$_2$Cl$_2$ solution was washed with H$_2$O (30 ml), brine (30 ml) and dried (MgSO$_4$). The solvent was removed in vacuo and the residue was purified by flash chromatography (SiO$_2$, CH$_2$Cl$_2$: CH$_3$OH 97.5:2.5) to give N-{[2-(2,6-dioxo(3-piperidyl))-1,3-dioxoisoindolin-4-yl]methyl}-3-pyridylcarboxamide (0.47 g, 64%) as a white solid: mp 148-151° C.; $^1$H NMR (DMSO-d$_6$) δ d 11.16 (s, 1H), 9.36 (t, J=5.6 Hz, 1H), 9.09 (d, J=1.25 Hz, 1H), 8.75-8.73 (m, 1H), 8.25 (d, J=8.0 Hz, 1H), 7.84-7.76 (m, 3H), 7.57-7.52 (m, 1H), 5.22-5.15 (dd, J=5.4 and 12.7 Hz, 1H), 4.96 (d, J=5.6 Hz, 2H), 2.92-2.85 (m, 1H), 2.65-2.50 (m, 2H), 2.11-2.06 (m, 1H); $^{13}$C NMR (DMSO-d$_6$) δ d 172.72, 169.80, 167.51, 166.94, 165.23, 152.02, 148.44, 138.86, 135.10, 134.83, 133.20, 131.55, 129.48, 127.20, 123.49, 121.95, 48.89, 38.33, 30.93, 21.98; Anal. Calcd. For C$_{20}$H$_{16}$N$_4$O$_5$+0.28H$_2$O: C, 60.45; H, 4.20; N, 14.10. Found: C, 60.29; H, 4.28; N, 13.82.

N-{[2-(2,6-Dioxo(3-piperidyl))-1,3-dioxoisoindolin-4-yl]methyl}heptanamide I-16

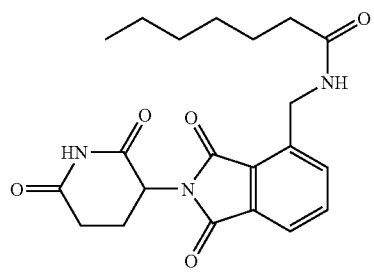

1,8-Diazabicyclo[5,4,0]undec-7-ene (0.65 g, 2.22 mmol) was added to a stirred suspension of 4-(aminomethyl)-2-(2,6-dioxo(3-piperidyl))isoindoline-1,3-dione hydrochloride (0.6 g, 1.85 mmol) in CH$_3$CN (50 ml). After stirring for 20 min, heptanoyl chloride (0.33 g, 2.22 mmol) was added. The mixture was stirred at room temperature for 17 hours. The solvent was removed in vacuo and the residue was dissolved in $CH_2Cl_2$ (70 ml). The $CH_2Cl_2$ solution was washed with 1N HCl (30 ml), $H_2O$ (30 ml), brine (30 ml) and dried ($MgSO_4$). The solvent was removed in vacuo and the residue was purified by chromatography ($SiO_2$, $CH_2Cl_2$: EtOAc 7:3) to give N-{[2-(2,6-dioxo(3-piperidyl))-1,3-dioxoisoindolin-4-yl]methyl}heptanamide (0.49 g, 66%) as a white solid: mp 130-132° C.; $^1$H NMR (DMSO-$d_6$) δ d 11.14 (s, 1H), 8.44 (t, J=5.7 Hz, 1H), 7.86-7.78 (m, 2H), 7.71-7.65 (m, 1H), 5.19-5.12 (dd, J=5.2 and 12.4 Hz, 1H), 4.69 (d, J=5.7 Hz, 2H), 2.98-2.83 (m, 1H), 2.64-2.50 (m, 2H), 2.18 (t, J=7.3 Hz, 2H), 2.08-2.04 (m, 1H), 1.53 (t, J=6.0 Hz, 2H), 1.25 (s, 6H), 0.85 (t, J=5.9 Hz, 3H); $^{13}$C NMR (DMSO-$d_6$) δ d 172.73, 172.66, 169.79, 167.47, 166.93, 139.54, 134.66, 133.13, 131.50, 127.06, 121.80, 54.86, 48.85, 37.57, 35.23, 30.96, 28.31, 25.16, 21.97, 13.87; Anal. Calcd. For $C_{21}H_{25}N_3O_5+0.3H_2O$: C, 62.30; H, 6.37; N, 10.38. Found: C, 62.07; H, 6.29; N, 10.23.

N-{[2-(2,6-Dioxo(3-piperidyl))-1,3-dioxoisoindolin-4-yl]methyl}-2-furylcarboxamide I-17

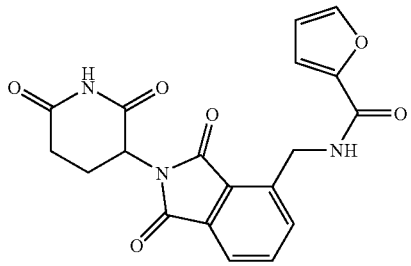

1,8-Diazabicyclo[5,4,0]undec-7-ene (0.650 g, 2.22 mmol) was added to a stirred suspension of 4-(aminomethyl)-2-(2,6-dioxo(3-piperidyl))isoindoline-1,3-dione hydrochloride (0.600 g, 1.85 mmol) in $CH_3CN$ (50 ml). After, stirring for 20 min, 2-furoyl chloride (0.290 g, 2.22 mmol) was added and the mixture was stirred at room temperature for 17 hours. The solvent was removed in vacuo and the residue was dissolved in $CH_2Cl_2$ (70 ml). The $CH_2Cl_2$ solution was washed 1N HCl (30 ml), $H_2O$ (30 ml), brine (30 ml) and dried ($MgSO_4$). The solvent was removed in vacuo and the residue was purified by chromatography ($SiO_2$, $CH_2Cl_2$: EtOAc 1:1) to give N-{[2-(2,6-diox (3-piperidyl))-1,3-dioxoisoindolin-4-yl]methyl}-2-furylcarboxamide (0.51 g, 73%) as a white solid: mp 121-123° C.; $^1$H NMR (DMSO-$d_6$) δ d 11.13 (s, 1H), 9.01 (t, J=5.7 Hz, 1H), 7.88-7.68 (m, 4H), 7.18 (d, J=3.3 Hz, 1H), 6.66 (m, 1H), 5.20-5.13 (dd, J=5.4 and 12.5 Hz, 1H), 4.90 (d, J=5.6 Hz, 2H), 2.97-2.84 (m, 1H), 2.65-2.49 (m. 2H), 2.10-1.98 (m, 1H); $^{13}$C NMR (DMSO-$d_6$) δ 172.73, 169.80, 167.52, 166.94, 158.09, 147.49, 145.27, 139.06, 134.80, 132.98, 131.52, 127.09, 121.88, 113.86, 111.91, 48.86, 37.64, 30.92, 21.97; Anal. Calcd. For $C_{19}H_{15}N_3O_6+0.18H_2O$: C, 59.34; H, 4.03; N, 10.93. Found: C, 59.47; H, 4.16; N, 10.49.

2-Azido-N-[2-(2,6-dioxo-piperidin-3-yl)-1,3-dioxo-2,3-dihydro-1H-isoindol-4-ylmethyl]-acetamide I-18

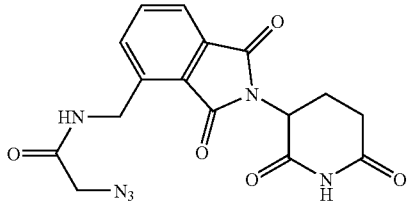

A mixture of 2-chloro-N-{[2-(2,6-dioxo(3-piperidyl))-1,3-dioxoisoindolin-4-yl]methyl}acetamide (1.3 g, 3.57 mmol), sodium azide (0.3 g, 4.65 mmol) and sodium iodide (0.54 g, 3.57 mmol) in acetone (50 ml) was refluxed for 17 hours. The solvent was removed in vacuo and the residue was dissolved in EtOAc (60 ml). The EtOAc solution was washed with $H_2O$ (30 ml), brine (30 ml), and dried ($MgSO_4$). The solvent was removed in vacuo to give 2-azido-N-{[2-(2,6-dioxo(3-piperidyl))-1,3-dioxoisoindolin-4-yl]methyl}acetamide (1.2 g, 90%) as a white solid: $^1$H NMR (CDCl$_3$) δ d 8.48 (s, 1H), 7.84-7.68 (m, 31), 7.51 (t, J=6.3 Hz, 1H), 5.04-4.97 (dd, J=4.7 and 11.8 Hz, 1H), 4.80 (d, J=6.5 Hz, 2H), 3.97 (s, 2H), 2.95-2.74 (m, 3H) 2.20-2.15 (m, 1H).

2-Amino-N{[2-(2,6-dioxo(3-piperidyl))-1,3-dioxoisoindolin-4-yl]methyl}acetamide I-19, hydrochloride

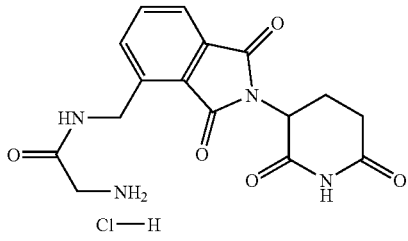

A mixture of 2-azido-N-{[2-(2,6-dioxo(3-piperidyl))-1,3-dioxoisoindolin-4-yl]methyl}acetamide (1.2 g, 3.24 mmol), and 10% Pd/C (0.15 g) in 4N HCl (20 ml) and $CH_3OH$ (50 ml) was hydrogenated in Parr shake apparatus, under 50 psi of hydrogen for 3 hours. The mixture was then filtered through celite and the filtrate was concentrated to a solid residue. The solid was slurried in ethanol (20 ml) and the suspension filtered to give 2-amino-N-{[2-(2,6-dioxo(3-piperidyl)) 1,3-dioxoisoindolin-4-yl]methyl}acetamide hydrochloride (0.86 g, 84%) as a white solid: mp 270-272° C.; $^1$H NMR (DMSO-$d_6$) δ d 11.16 (s, 1H), 9.28 (t, J=5.7 Hz, 1H), 8.33 (s, 3H), 7.83 (s, 3H), 5.20-5.13 (dd, J=5.3 and 12.5 Hz, 1H), 4.81 (d, J=5.7 Hz, 2H), 3.69 (s, 2H), 2.92-2.87 (m, 1H), 2.65-2.51 (m, 2H), 2.09-2.05 (m, 1H); $^{13}$C NMR (DMSO-$d_6$) δ d 172.76, 169.80, 167.44, 166.91, 166.52, 138.24, 134.74, 133.53, 131.51, 127.17, 122.08, 48.89, 37.89, 30.94, 21.99; Anal. Calcd. For $C_{16}H_{17}N_4O_5Cl$: C, 50.47; H, 4.50; N, 14.71; Cl, 9.31. Found: C, 50.39; H, 4.61; N, 14.42; Cl, 9.25.

Ethyl 6-(N-{[2-(2,6-dioxo(3-piperidyl))-1,3-dioxoisoindolin-4-yl]methyl}carbamoyl) hexanoate I-20

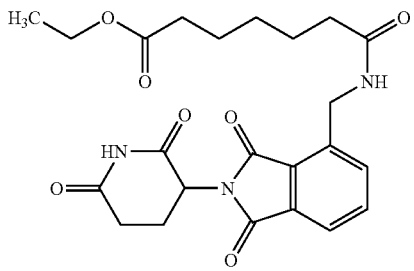

1,8-Diazabicyclo[5,4,0]undec-7-ene (0.65 g, 4.26 mmol) was added to a stirred suspension of 4-(aminomethyl)-2-(2,6-dioxo(3-piperidyl))isoindoline-1,3-dione hydrochloride (0.6 g, 1.85 mmol) in CH$_3$CN (50 ml). After stirring for 20 min, 6-(chloroformyl)hexanoic acid ethyl ester (0.46 g, 2.22 mmol) was added. The mixture was stirred at room temperature for 17 hours. The solvent was removed in vacuo and the residue was dissolved in CH$_2$Cl$_2$ (70 ml). The CH$_2$Cl$_2$ solution was washed with 1N HCl (30 ml), H$_2$O (30 ml), brine (30 ml) and dried (MgSO$_4$). The solvent was removed in vacuo and the residue was purified by chromatography (SiO$_2$, CH$_2$Cl$_2$: EtOAc 1:1) to give ethyl 6-(N-{[2-(2,6-dioxo(3-piperidyl))-1,3-dioxoisoindolin-4-yl]methyl}carbamoyl) hexanoate (0.43 g, 50%) as a white solid: mp 82-84° C.; $^1$H NMR (DMSO-d$_6$) δ d 11.11 (s, 1H), 8.41 (t, J=5.6 Hz, 1H), 7.86-7.65 (m, 3H), 5.18-5.11 (dd, J=5.4 and 12.4 Hz, 1H), 4.72 (d, J=5.7 Hz, 2H), 4.05 (q, J=7.1 Ha, 2H), 2.97-2.83 (m, 1H), 2.64-2.48 (m, 2H), 2.30-2.15 (m, 4H), 2.08-2.04 (m, 1H), 1.56-1.47 (m, 4H), 1.32-1.23 (m, 2H), 1.17 (t, J=7.1 Hz, 3H); $^{13}$C NMR (DMSO-d$_6$) δ d 172.80, 172.71, 172.52, 169.77, 167.45, 166.92, 139.49, 134.67, 133.13, 131.49, 127.04, 121.78, 59.60, 48.84, 37.57, 35.02, 33.38, 30.91, 28.08, 24.83, 24.16, 21.96, 14.09; Anal. Calcd. For C$_{23}$H$_{27}$N$_3$O$_7$: C, 60.39; H, 5.95; N, 9.18. Found: C, 60.10; H, 5.82; N, 8.82.

3-[(tert-Butoxy)carbonylamino]-N-{[2-(2,6-dioxo(3-piperidyl))-1,3-dioxoisoindolin-4-yl]methyl}propanamide I-21

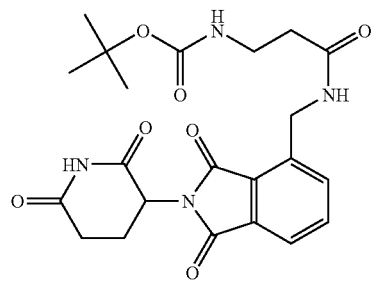

1,8-Diazabicyclo[5,4,0]undec-7-ene (0.7 g, 4.62 mmol) was added to a stirred suspension of 4-(aminomethyl)-2-(2,6-dioxo(3-piperidyl))isoindoline-1,3-dione hydrochloride (0.6 g, 1.85 mmol) in CH$_3$CN (50 ml). After stirring for 20 min, 1-hydroxybenzotriazole (0.3 g, 2.22 mmol), N—BOC-b-alanine (0.42 g, 2.22 mol) and 1-[3-(dimethylamino)propyl]-3-ethylcarbodimide hydrochloride 0.53 g, 2.78 mmol) were added. The mixture was stirred at room temperature for 17 hours. The solvent was removed in vacuo and the residue was dissolved in CH$_2$Cl$_2$ (70 ml). The CH$_2$Cl$_2$ solution was washed with 1N citric acid (30 ml), H$_2$O (2×30 ml), brine (30 ml) and dried (MgSO$_4$). The solvent was removed in vacuo and the residue was purified by chromatography (SiO$_2$, CH$_2$Cl$_2$: CH$_3$OH 100:2) to give 3-[(tert-butoxy)carbonylamino]-N-{[2-(2,6-dioxo(3-piperidyl))-1,3-dioxoisoindolin-4-yl]methyl}propanamide (0.57 g, 67%) as a white solid: mp 96-98° C.; $^1$H NMR (DMSO-d$_6$) δ d 11.14 (s, 1H), 8.50 (t, J=5.8 Hz, 1H), 7.82-7.67 (m, 3H), 6.81 (t, J=5.1 Hz, 1H), 5.19-5.11 (dd, J=5.4 and 12.4 Hz, 1H), 4.72 (d, J=5.7 Hz, 2H), 3.21-3.13 (dd, J=6.8 and 13.1 Hz, 2H), 2.92-2.85 (m, 1H), 2.64-2.33 (m, 4H), 2.08-2.04 (m, 1H), 1.37 (s, 9H); $^{13}$C NMR (DMSO-d$_6$) δ d 172.71, 170.87, 169.77, 167.46, 166.93, 155.45, 139.27, 134.67, 133.17, 131.47, 127.03, 121.80, 77.57, 48.84, 37.63, 36.69, 35.62, 30.91, 28.21, 21.96; Anal. Calcd. For C$_{22}$H$_{26}$N$_4$O$_7$+0.28H$_2$O: C, 57.01; H, 5.78; N, 12.09. Found: C, 56.99; H, 5.89; N, 11.79.

3-Amino-N-{[2-(2,6-dioxo(3-piperidyl))-1,3-dioxoisoindolin-4-yl]methyl}propanamide I-22, hydrochloride

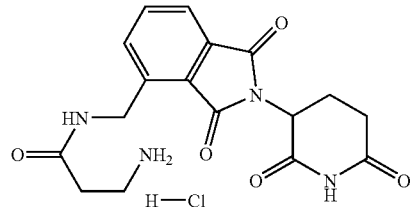

A 4N HCl solution in dioxane (1 ml) was added to a stirred solution of 3-[(tert-butoxy)carbonylamino]-N-{[2-(2,6-dioxo(3-piperidyl))-1,3-dioxoisoindolin-4-yl]methyl}propanamide (0.5 g, 1.09 mmol) in CH$_2$Cl$_2$ (15 ml) and stirred for 17 hours. The resulting suspension was filtered to give 3-amino-N-{[2-(2,6-dioxo(3-piperidyl))-1,3-dioxoisoindolin-4-yl]methyl}propanamide hydrochloride (0.34 g, 79%) as a white solid: mp 161-163° C.; $^1$H NMR (DMSO-d$_6$) δ d 11.15 (s, 1H), 8.88 (t, J=5.8, Hz, 1H), 8.06 (b, 3H), 7.87-7.79 (m, 3H), 5.19-5.12 (dd, J=5.3 and 12.6 Hz, 1H), 4.76 (d, J=5.8 Hz, 2H), 3.03-2.84 (m, 3H), 2.67-2.47 (m, 4H), 2.08-2.04 (m, 1H); $^{13}$C NMR (DMSO-d$_6$) δ d 172.74, 169.88, 169.80, 167.45, 166.92, 138.92, 134.74, 133.46, 131.48, 127.09, 121.92, 48.86, 37.69, 35.11, 32.03, 30.92, 21.97; Anal. Calcd. For C$_{17}$H$_{19}$N$_4$O$_5$Cl+0.13 CH$_2$Cl$_2$+0.57 H$_2$O: C, 49.44; H, 4.94; N, 13.46; Cl, 10.73. Found: C, 49.22; H, 4.88; N, 13.08; Cl, 10.95.

N-{[2-(2,6-Dioxo(3-piperidyl))-1,3-dioxoisoindolin-4-yl]methyl}2-thienylcarboxamide I-23

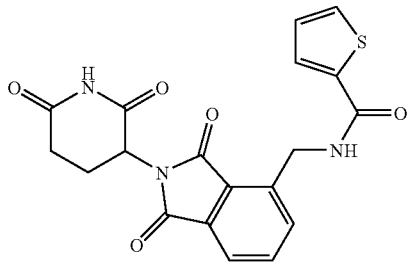

1,8-Diazabicyclo[5,4,0]undec-7-ene (0.620 g, 4.07 mmol) was added to a stirred suspension of 4-(aminomethyl)-2-(2,6-dioxo(3-piperidyl))-isoindoline-1,3-dione hydrochloride (0.600 g, 1.85 mmol) in $CH_3CN$ (50 ml). After stirring for 20 min, 2-thiophene-carbonyl chloride (0.3 g, 2.03 mmol) was added. The mixture was stirred at room temperature for 17 hours. The solvent was removed in vacuo and the residue was dissolved in $CH_2Cl_2$ (70 ml). The $CH_2Cl_2$ solution was washed with 1N HCl (30 ml), $H_2O$ (30 ml), brine (30 ml) and dried ($MgSO_4$). The solvent was removed in vacuo and the residue was purified by chromatography ($SiO_2$, $CH_2Cl_2$: EtOAc 6:4) to give N-{[2-(2,6-dioxo(3-piperidyl))-1,3-dioxoisoindolin-4-yl]methyl}-2-thienylcarboxamide (0.35 g, 47%) as a white solid: mp 192-194° C.; $^1$H NMR (DMSO-$d_6$) δ d 11.16 (s, 1H), 9.18 (t, J=5.8 Hz, 1H), 7.88-7.72 (m 5H), 7.20-7.17 (dd, J=3.9 and 4.7 Hz, 1H), 5.22-5.15 (dd, J=5.5 and 12.7 Hz, 1H), 4.94 (d, J=5.8 Hz, 2H), 2.98-2.85 (m, 1H), 2.66-2.50 (m, 2H), 2.11-2.06 (m, 1H); $^{13}$C NMR (DMSO-$d_6$) δ d 172.72, 169.80, 167.51, 166.93, 161.52, 139.26, 139.14, 134.83, 133.14, 131.53, 131.11, 128.51, 127.96, 127.12, 121.93, 48.89, 38.09, 30.93, 21.99; Anal. Calcd. For $C_{19}H_{15}N_3O_5S$: C, 57.42; H, 3.80; N, 10.57; S, 8.07. Found: C, 57.80; H, 3.93; N, 10.22; S, 7.99.

N-{[2-(2,6-Dioxo(3-piperidyl))-1,3-dioxoisoindolin-4-yl]methyl}-2-methoxyacetamide I-24

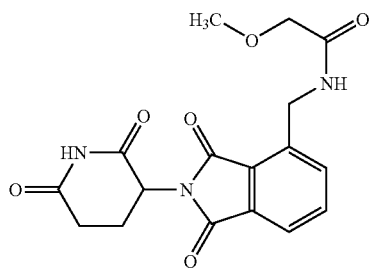

1,8-Diazabicyclo[5,4,0]undec-7-ene (0.62 g, 4.07 mmol) was added to a stirred suspension of 4-(aminomethyl)-2-(2,6-dioxo(3-piperidyl))isoindoline-1,3-dione hydrochloride (0.600 g, 1.85 mmol) in $CH_3CN$ (50 ml). After stirring for 20 min, methoxyacetyl chloride (0.22 g, 2.03 mmol) was added. The mixture was stirred at room temperature for 17 hours. The solvent was removed in vacuo and the residue was dissolved in $CH_2Cl_2$ (70 ml). The $CH_2Cl_2$ solution was washed with 1N HCl (30 ml), $H_2O$ (30 ml), brine (30 ml) and dried ($MgSO_4$). The solvent was removed in vacuo and the residue was purified by chromatography ($SiO_2$, $CH_2Cl_2$: $CH_3OH$ 100:2.5) to give N-{[2-(2,6-dioxo(3-piperidyl))-1,3-dioxoisoindolin-4-yl]methyl}-2-methoxyacetamide (0.44 g, 66%) as a white solid: mp 196-198° C.; $^1$H NMR (DMSO-$d_6$) δ d 11.14 (s, 1H), 8.49 (t, J=6.1 Hz, 1H), 7.86-7.79 (m, 2H), 7.68-7.65 (m, 1H), 5.19-5.12 (dd, J=5.3 and 12.5 Hz, 1H), 4.77 (d, J=6.1 Hz, 2H), 3.92 (s, 2H), 3.36 (s, 3H), 2.96-2.83 (m, 1H), 2.64-2.49 (m, 2H), 2.09-2.04 (m, 1H); $^{13}$C NMR (DMSO-$d_6$) δ d 172.71, 169.78, 169.58, 167.52, 166.94, 139.09, 134.70, 133.00, 131.51, 127.08, 121.82, 71.46, 58.70, 48.86, 37.47, 30.91, 21.95; Anal. Calcd. For $C_{17}H_{17}N_3O_6$: C, 56.82; H, 4.77; N, 11.69. Found: C, 57.02; H, 4.87; N. 11.36.

(N-{[2-(2,6-Dioxo(3-piperidyl))-1,3-dioxoisoindolin-4-yl]methyl}carbamoyl)methyl acetate I-25

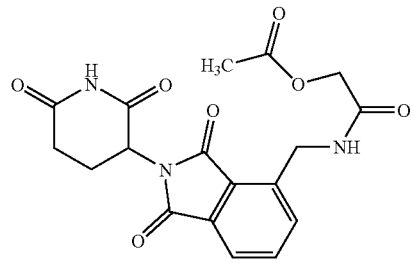

1,8-Diazabicyclo[5,4,0]undec-7-ene (0.62 g, 4.08 mmol) was added to a stirred suspension of 4-(aminomethyl)-2-(2,6-dioxo(3-piperidyl))isoindoline-1,3-dione hydrochloride (0.600 g, 1.85 mmol) in $CH_3CN$ (50 ml). After stirring for 20 min, acetoxyacetyl chloride (0.28 g, 2.03 mmol) was added. The mixture was stirred at room temperature for 17 hours. The solvent was removed in vacuo and the residue was dissolved in $CH_2Cl_2$ (70 ml). The $CH_2Cl_2$ solution was washed with 1N HCl (30 ml), $H_2O$ (30 ml), brine (30 ml) and dried ($MgSO_4$). The solvent was removed in vacuo and the residue was purified by chromatography ($SiO_2$, $CH_2Cl_2$: $CH_3OH$ 100:2.5) to give (N-{[2-(2,6-dioxo(3-piperidyl))-1,3-dioxoisoindolin-4-yl]methyl}carbamoyl)methyl acetate (0.54 g, 75%) as a white solid: mp 108-110° C.; $^1$H NMR (DMSO-$d_6$) δ d 11.14 (s, 1H), 8.68 (t, J=6.0 Hz, 1H), 7.87-7.79 (m, 2H), 7.71-7.65 (m, 1H), 5.19-5.12 (dd, J=5.3 and 12.4 Hz, 1H), 4.77 (d, J=5.9 Hz, 2H), 4.56 (s, 2H), 2.96-2.83 (m, 1H), 2.63-2.47 (m, 2H), 2.11 (s, 3H), 2.08-1.98 (m, 1H); $^{13}$C NMR (DMSO-$d_6$) δ d 172.66, 169.96, 169.72, 167.46, 167.37, 166.36, 138.80, 134.68, 133.01, 132.47, 127.04, 121.87, 62.36, 48.84, 37.46, 30.38, 21.93, 20.49; Anal. Calcd. For $C_{18}H_{17}N_3O_7$+0.15$H_2O$: C, 55.43; H, 4.47; N, 10.77. Found: C, 55.43; H, 4.54; N, 10.44.

Ethyl 2-[(N-{[2-(2,6-dioxo(3-piperidyl))-1,3-dioxoisoindolin-4-yl]-methyl}carbamoyl) amino]acetate I-26

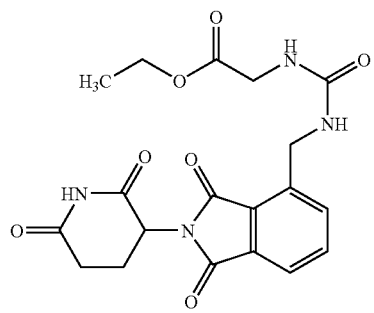

1,8-Diazabicyclo[5,4,0]undec-7-ene (0.29 g, 1.9 mmol) was added to a stirred suspension of 4-(aminomethyl)-2-(2,6-dioxo(3-piperidyl))isoindoline-1,3-dione hydrochloride (0.6 g, 1.85 mmol) in CH₃CN (50 ml). After stirring for 20 min, ethyl isocyanatacetate (0.29 g, 2.22 mmol) was added. The mixture was stirred at room temperature for 17 hours. The solvent was removed in vacuo and the residue was dissolved in CH₂Cl₂ (70 ml). The CH₂Cl₂ solution was washed with 1N HCl (30 ml), H₂O (30 ml), brine (30 ml) and dried (MgSO₄). The solvent was removed in vacuo and the residue was purified by chromatography (SiO₂, CH₂Cl₂: EtOAc 1:1) to give ethyl 2-[(N-{[2-(2,6-dioxo(3-piperidyl))-1,3-dioxoisoindolin-4-yl]methyl}carbamoyl)amino]acetate (0.30 g, 39%) as a white solid: mp 187-189° C.; $^1$H NMR (DMSO-$d_6$) δ d 11.14 (s, 1H), 7.86-7.70 (m, 3H), 6.83 (t, J=6.1 Hz, 1H), 6.53 (t, J=6.0 Hz, 1H), 5.18-5.11 (dd, J=5.4 and 12.5 Hz, 1H), 4.65 (d, J=6.0 Hz, 2H), 4.09 (q, J=7.2 Hz, 2H), 3.79 (d, J=6.0 Hz, 2H), 2.98-2.83 (m, 1H), 2.64-2.48 (m, 2H), 2.08-2.04 (m, 1H), 1.18 (t, J=7.2 Hz, 3H); $^{13}$C NMR (DMSO-$d_6$) δ d 172.72; 171.01, 169.78, 167.54, 167.00, 158.00, 140.78, 134.57, 133.25, 131.48, 126.95, 121.66, 60.17, 48.83, 41.58, 38.72, 30.91, 21.97, 14.06; Anal. Calcd. For $C_{19}H_{20}N_4O_7$: C, 54.81; H, 4.84; N, 13.46. Found: C, 54.73; H, 4.77; N, 13.35.

N-{[2-(2,6-Dioxo(3-piperidyl))-1,3-dioxoisoindolin-4-yl]methyl}(ethylamino)carboxamide I-27

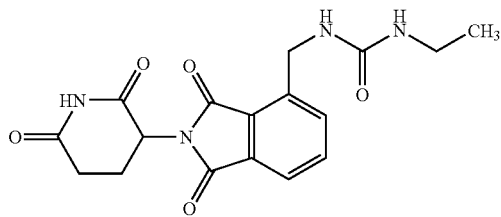

1,8-Diazabicyclo[5,4,0]undec-7-ene (0.29 g, 1.90 mmol) was added to a stirred suspension of 4-(aminomethyl)-2-(2,6-dioxo(3-piperidyl))isoindoline-1,3-dione hydrochloride (0.60 g, 1.85 mmol) in CH₃CN (50 ml). After stirring for 20 min, ethyl isocyanate (0.16 g, 2.22 mmol) was added. The mixture was stirred at room temperature for 17 hours. The solvent was removed in vacuo and the residue was dissolved in CH₂Cl₂ (70 ml). The CH₂Cl₂ solution was washed with 1N HCL (30 ml), H₂O (30 ml), brine (30 ml) and dried (MgSO₄). The solvent was removed in vacuo and the residue was purified by chromatography (SiO₂, CH₂Cl₂: CH₃CN 6:4) to give N-{[2-(2,6-dioxo(3-piperidyl))-1,3-dioxoisoindolin-4-yl]methyl}(ethylamino)carboxamide (0.2 g, 30%) as a white solid: mp 173-175° C.; $^1$H NMR (DMSO-$d_6$). δ d 11.13 (s, 1H), 7.86-7.69 (m, 3H), 6.44 (t, J=6.1 Hz, 1H), 6.11 (t, J=5.55 Hz, 1H), 5.18-5.11 (dd, J=5.4 and 12.6 Hz, 1H), 4.63 (d, J=6.1 Hz, 2H), 3.07-2.83 (m, 3H), 2.64-2.49 (m, 2H), 2.08-2.04 (m, 1H), 0.99 (t, J=7.1 Hz, 3H); $^{13}$C NMR (DMSO-$d_6$) δ d 172.73, 169.80, 167.58, 167.03, 157.93, 141.15, 134.61, 133.37, 131.49, 126.96, 121.61, 48.83, 38.71, 34.17, 30.92, 21.98, 15.58; Anal. Calcd. For $C_{17}H_{18}N_4O_5$+0.14$H_2O$: C, 56.58; H, 5.11; N, 15.53. Found: C, 56.56; H, 5.05; N, 15.28.

2-(2,6-Dioxo(3-piperidyl))-4-[(2-furylmethyl)amino]isoindoline-1,3-dione I-28

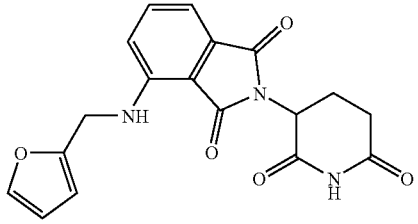

To a suspension of 4-amino-2-(2,6-dioxo(3-piperidyl))isoindoline-1,3-dione (0.55 g, 2 mmol) in acetic acid (20 ml) was added furan-2-carbaldehyde (0.20 g, 2.05 mmol). The mixture was heated to reflux for 5 hours and allowed to cool at room temperature. Sodium borohydride (80 mg, 2 mmol) was added to the reaction mixture. The reaction mixture was stirred for 24 hours. The solvent was evaporated in vacuo and the residue was dissolved in ethyl acetate (100 ml), washed with H₂O (3×100 ml), saturated aqueous NaHCO₃ (2×100 ml), brine (1×100 ml), and dried. The solvent was evaporated and the residue was purified by chromatography (ethyl acetate/hexane, 1:1) to give 0.25 g (35%) of product as a yellow solid: mp 171-173° C.; $^1$H NMR (DMSO-$d_6$) δ 11.10 (s, 1H), 7.58 (t, J=7.1 Hz, 2H), 7.18 (d, J=8.6 Hz, 1H), 7.08-6.97 (m, 2H), 6.39-6.36 (m, 2H), 5.06 (dd, J=5.2 and 12.4 Hz, 1H), 4.57 (d, J=6.0 Hz, 2H), 2.96-2.82 (m, 1H), 2.63-2.46 (m, 2H), 2.06-2.02 (m, 1H; $^{13}$C NMR (DMSO-$d_6$) δ 172.76, 170.01, 168.75, 167.21, 151.97, 145.81, 142.42, 136.05, 132.09, 117.60, 111.04, 110.42, 109.73, 107.38, 48.57, 30.95, 22.10; Anal. Calcd. For $C_{11}H_{15}N_3O$, C, 61.19; H, 4.28; N, 11.89. Found: C, 61.02; H, 4.24; N, 11.81.

N-[2-(2,6-dioxo(3-piperidyl))-1,3-dioxoisoindolin-4-yl]-2-methoxyacetamide I-29

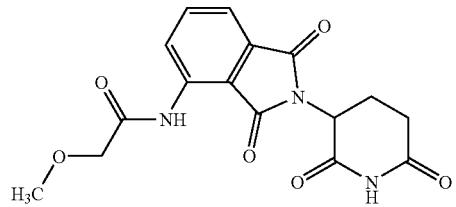

To a suspension of 4-amino-2-(2,6-dioxo(3-piperidyl))isoindoline-1,3-dione (0.55 g, 2.0 mmol) in THF (30 ml) was added 2-methoxyacetyl chloride (0.43 g, 4.0 mmol). The stirred mixture was heated to reflux for 18 hours. The solvent was evaporated in vacuo and the resulting solid was slurried in diethyl ether (20 ml) and filtered to give 0.69 g (100%) of product as an off-white solid: mp 246-248° C.; $^1$H NMR (DMSO-$d_6$) δ 11.15 (s, 1H), 10.30 (s, 1H), 8.70 (d, J=8.4 Hz, 1H), 7.86 (t, J=7.8 Hz, 1H), 7.63 (d, J=7.3 Hz, 1H), 5.17 (dd, J=5.2 and 12.7 Hz, 1H), 4.11 (s, 2H), 3.49 (s, 3H), 2.98-2.84 (m, 0,1H), 2.66-2.47 (m, 2H), 2.12-2.07 (m, 1H); $^{13}$C NMR (DMSO-$d_6$) δ 172.67, 169.66, 169.02, 168.25, 166.61, 136.48, 135.91, 131.24, 124.35, 118.31, 116.04, 71.40, 59.10, 48.96, 30.91, 21.94; Anal. Calcd. For $C_{16}H_{15}N_3O_6$: C, 55.65; H, 4.38; N, 12.17. Found: C, 55.58; H, 4.40; N, 12.08.

N-[2-(2,6-dioxo(3-piperidyl))-1,3-dioxoisoindolin-4-yl]heptanamide I-30

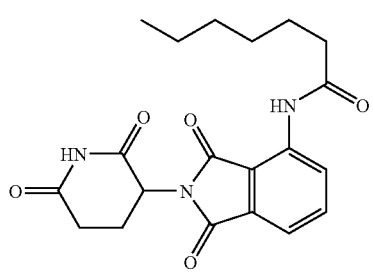

To a stirred suspension of 4-amino-2-(2,6-dioxo(3-piperidyl))isoindoline-1,3-dione (0.55 g, 2.0 mmol) in THF (30 ml) was added heptanoyl chloride (0.59 g, 4.0 mmol). The mixture was heated to reflux for 18 hours. The solvent was evaporated in vacuo and the resulting solid was slurried in diethyl ether (20 ml) and filtered to give 0.61 g (79%) of product as an off-white solid: mp 200-202° C.; $^1$H NMR (DMSO-$d_6$) δ 11.16 (s, 1H), 9.65 (s, 1H), 8.48 (d, J=8.3 Hz, 1H), 7.81 (t, J=7.7 Hz, 1H), 7.58 (d, J=7.2 Hz, 1H), 5.15 (dd, J=4.8 and 12.2 Hz, 1H), 2.97-2.87 (m, 1H), 2.65-2.43 (m, 4H), 2.10-2.06 (m, 1H), 1.61-1.58 (m, 2H), 1.28 (bs, 6H), 0.85 (bs, 3H); $^{13}$C NMR (DMSO-$d_6$) δ 172.67, 171.96, 169.69, 167.78, 166.61, 136.62, 136.04, 131.36, 125.97, 118.13, 116.67, 48.93, 36.56, 30.95, 28.16, 24.69, 21.94, 13.84; Anal. Calcd. For $C_{20}H_{23}N_3O_5$: C, 62.33; H, 6.02; N, 10.90. Found: C, 62.14; H, 6.05; N, 10.72.

{N-[2-(2,6-dioxo(3-piperidyl))-1,3-dioxoisoindolin-4-yl]carbamoyl}methyl acetate I-31

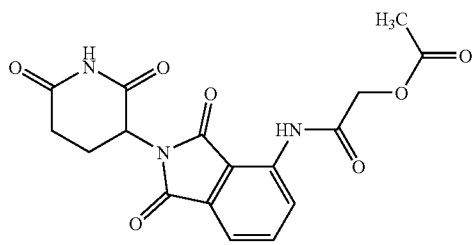

To a stirred suspension of 4-amino-2-(2,6-dioxo(3-piperidyl))isoindoline-1,3-dione (0.55 g, 2.0 mmol) in THF (30 ml) was added (chlorocarbonyl)methyl acetate (0.55 g, 4.0 mmol). The mixture was heated to reflux for 18 hours. The solvent was evaporated in vacuo and the resulting solid was slurried in diethyl ether (20 ml) and filtered to give 0.56 g (75%) of product as an off-white solid: mp 234-236° C.; $^1$H NMR (DMSO-$d_6$), 11.15 (s, 1H), 10.06 (s, 1H), 8.55 (d, J=8.3 Hz, 1H), 7.87 (t, J=8.0 Hz, 1H), 7.65 (d, J=7.2 Hz, 1H), 5.17 (dd, J=5.0 and 12.4 Hz, 1H), 4.78 (s, 2H), 2.99-2.85 (m, 1H), 2.65-2.52 (m, 2H), 2.22 (s, 2H), 2.11-2.07 (m, 1H); $^{13}$C NMR (DMSO-$d_6$) δ 172.70, 169.69, 169.50, 167.99, 166.57, 136.40, 135.59, 131.35, 125.34, 118.72, 116.96, 62.60, 48.98, 30.90, 21.91, 20.41; Anal. Calcd. For $C_{17}H_{15}N_3O_7$: C, 54.69; H, 4.05; N, 11.26. Found: C, 54.43; H, 4.05; N, 10.97.

N-[2-(2,6-dioxo(3-piperidyl))-1,3-dioxoisoindolin-4-yl]pentanamide I-32

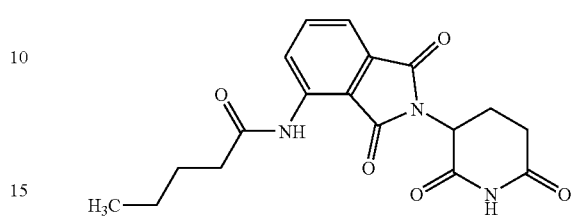

To a stirred suspension of 4-amino-2-(2,6-dioxo(3-piperidyl))isoindoline-1,3-dione (0.55 g, 2.0 mmol) in THF (30 ml) was added pentanoyl chloride (0.48 g, 4.0 mmol). The stirred mixture was heated to reflux for 18 hours. The solvent was evaporated in vacuo and the resulting solid was slurried in diethyl ether (20 ml) and filtered to give 0.61 g (85%) of product as an off-white solid: mp 178-179° C.; $^1$H NMR (DMSO-$d_6$) δ 11.17 (s, 1H), 9.65 (s, 1H), 8.50 (d, J=8.3 Hz, 1H), 7.82 (t, J=7.5 Hz, 1H), 7.59 (d, J=7.2 Hz, 1H), 5.18 (dd, J=5.0 and 12.4 Hz, 1H), 2.99-2.89 (m, 1H), 2.68-2.45 (m, 4H), 2.13-2.09 (m, 1H), 1.69-1.57 (m, 2H), 1.44-1.30 (m, 2H), 0.92 (t, J=7.2 Hz, 3H); $^{13}$C NMR (DMSO-$d_6$) δ 172.72, 171.99, 169.73, 167.83, 166.64, 136.64, 136.07, 131.36, 125.96, 118.15, 116.68, 48.97, 36.32, 30.97, 26.88, 22.03, 21.70, 13.64; Anal. Calcd. For $C_{18}H_{19}N_3O_5$: C, 60.50; H, 5.36; N, 11.76. Found: C, 60.10; H, 5.37; N, 11.58.

N-[2-(2,6-dioxo(3-piperidyl))-1,3-dioxoisoindolin-4-yl]-2-thienylcarboxamide I-33

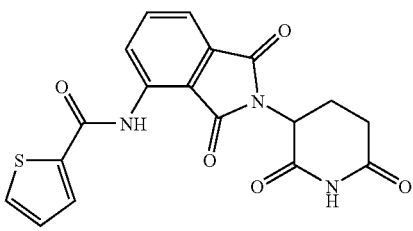

To a stirred suspension of 4-amino-2-(2,6-dioxo(3-piperidyl))isoindoline-1,3-dione (0.55 g, 2.0 mmol) in THF (30 ml) was added thiophene-2-carbonyl chloride (0.59 g, 4.0 mmol). The mixture was heated to reflux for 18 hours. To the reaction mixture was added additional thiophene-2-carbonyl chloride (0.30 g, 2 mmol). The mixture was heated to reflux for an additional 8 hours. The solvent was evaporated in vacuo and the resulting solid was slurried in diethyl ether (20 ml) and filtered to give an of off-white solid which was recrystallized from acetic acid to give 0.50 g (65%) of product: mp 284-286° C.; $^1$H NMR (DMSO-$d_6$) δ 11.19 (s, 1H), 10.34 (s, 1H), 8.47 (d, J=8.3 Hz, 1H), 7.98-7.86 (m, 3H), 7.68 (d, J=7.3 Hz, 1H), 7.29 (dd, J=4.0 and 4.8 Hz, 1H), 5.19 (dd, J=5.4 and 12.6 Hz, 1H), 2.99-2.85 (m, 1H), 2.67-2.49 (m, 2H), 2.12-2.08 (m, 1H); $^{13}$C NMR (DMSO-$d_6$) δ 172.72, 169.69, 167.96, 166.60, 159.67, 138.02, 136.26, 136.19, 133.26, 131.42, 129.91, 128.58, 126.42, 118.82, 117.94, 49.00, 30.93, 22.00; Anal. Calcd. For $C_{18}H_{13}N_3O_5S$: C, 55.77; H, 3.54; N, 10.60. Found: C, 55.67; H, 3.36; N, 10.42+ 0.2 AcOH+0.05H$_2$O.

Methyl{N-[2-(2,6-dioxo(3-piperidyl))-1,3-dioxoisoindolin-4-yl]carbamoyl}formate I-34

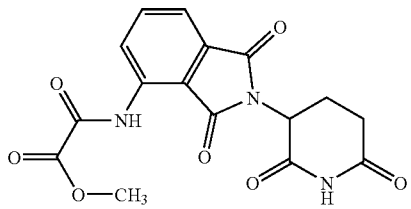

To a stirred suspension of 4-amino-2-(2,6-dioxo(3-piperidyl))isoindoline-1,3-dione (0.55 g, 2.0 mmol) in THF (30 ml) was added methyl (chlorocarbonyl)formate (0.49 g, 4.0 mmol). The mixture was heated to reflux for 18 hours. The solvent was evaporated in vacuo and the resulting solid was slurried in diethyl ether (20 ml) and filtered to give 0.55 g (76%) of product as an off-white solid: mp 247-249° C.; $^1$H NMR (DMSO-d$_6$) δ 11.17 (s, 1H), 10.81 (s, 1H), 8.59 (d, J=8.3 Hz, 1H), 7.92 (t, J=7.7 Hz, 1H), 7.70 (d, J=7.3 Hz, 1H), 5.19 (dd, J=5.0 and 12.5 Hz, 1H), 3.91 (s, 3H), 2.98-2.85 (m, 1H), 2.68-2.50 (m, 2H), 2.14-2.09 (m, 1H); $^{13}$C NMR (DMSO-d$_6$) δ 172.70, 169.63, 168.03, 166.45, 159.81, 154.57, 136.65, 134.93, 131.36, 124.67, 119.34, 117.17, 53.80, 49.06, 30.92, 21.94; Anal. Calcd. For $C_{16}H_{13}N_3O_7$: C, 53.49; H, 3.65; N, 11.70. Found: C, 53.53; H, 3.66; N, 11.52.

N-[2-(2,6-dioxo(3-piperidyl))-1,3-dioxoisoindolin-4-yl]-2-furylcarboxamide I-35

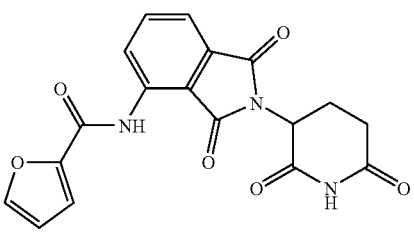

To a stirred suspension of 4-amino-2-(2,6-dioxo(3-piperidyl))isoindoline-1,3-dione (0.55 g, 2.0 mmol) in THF (30 ml) was added furan-2-carbonyl chloride (0.52 g, 4.0 mmol). The mixture was heated to reflux for 18 hours. To the reaction mixture was added additional furan-2-carbonyl chloride (0.26 g, 2 mmol). The mixture was heated to reflux for an additional 8 hours. The solvent was evaporated in vacuo and the resulting solid was slurried in diethyl ether (20 ml) and filtered to give 0.65 g (88%) of product as an off-white solid: mp 299-301° C.; $^1$H NMR (DMSO-d$_6$) δ 11.19 (s, 1H), 10.37 (s, 1H), 8.68 (dd, J=1.4 and 8.4 Hz, 1H), 8.06 (s, 1H), 7.90 (t, J=8.1 Hz, 1H), 7.65 (d, J=7.3 Hz, 1H), 7.39 (d, J=3.5 Hz, 1H), 6.79 (dd, J=1.5 and 3.2 Hz, 1H), 5.19 (dd, J=5.1 and 12.5 Hz, 1H), 2.98-2.84 (m, 1H), 2.67-2.49 (m, 2H), 2.13-2.08 (m, 1H); $^{13}$C NMR (DMSO-d$_6$) δ 172.66, 169.62, 168.44, 166.59, 155.71, 146.80, 146.34, 136.55, 136.23, 136.12, 131.30, 124.86, 118.54, 116.64, 113.06, 48.98, 30.90, 22.01; Anal. Calcd. For $C_{18}H_{13}N_3O_6$: C, 58.86; H, 3.57; N, 11.44. Found: C, 58.69; H, 3.54; N, 11.41.

N-[2-(2,6-dioxo(3-piperidyl))-1,3-dioxoisoindolin-4-yl]benzamide I-36

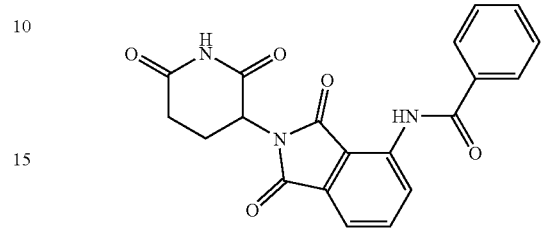

To a stirred suspension of 4-amino-2-(2,6-dioxo(3-piperidyl))isoindoline-1,3-dione (0.55 g, 2.0 mmol) in THF (30 ml) was added benzoyl chloride (0.56 g, 4.0 mmol). The mixture was heated to reflux for 18 hours. To the reaction mixture was added additional benzoyl chloride (0.28 g, 2.0 mmol). The mixture was heated at reflux for an additional 8 hours. The solvent was evaporated in vacuo and the resulting solid was slurried in diethyl ether (20 ml) and filtered to give an of off-white solid which was recrystallized from acetic acid to give 0.49 g (65%) of product: mp 268-270° C.; $^1$H NMR (DMSO-d$_6$) δ 11.18 (s, 1H), 10.43 (s, 1H), 8.64-8.59 (m, 1H), 8.00-7.89 (m, 3H), 7.72-7.60 (m, 4H), 5.19 (dd, J=5.2 and 12.5 Hz, 1H), 2.98-2.84 (m, 1H), 2.66-2.50 (m, 2H), 2.12-2.07 (m, 1H); $^{13}$C NMR (DMSO-d$_6$) δ 172.62, 169.59, 168.16, 166.64, 164.91, 136.50, 136.36, 133.23, 132.67, 131.36, 129.06, 127.24, 126.00, 118.74, 117.74, 48.98, 30.89, 21.98; Anal. Calcd. For $C_{20}H_{15}N_3O_5$: C, 63.02; H, 4.08; N, 10.90. Found: C, 63.05; H, 4.06; N, 10.69+0.11 AcOH+0.08H$_2$O.

N-[2-(2,6-dioxo(3-piperidyl))-1,3-dioxoisoindolin-4-yl]propanamide I-37

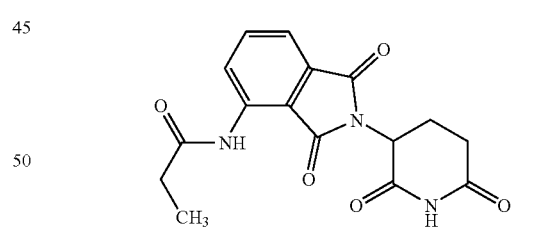

To a stirred suspension of 4-amino-2-(2,6-dioxo(3-piperidyl))isoindoline-1,3-dione (0.55 g, 2.0 mmol) in THF (30 ml) was added propanoyl chloride (0.37 g, 4.0 mmol). The mixture was heated to reflux for 18 hours. The solvent was evaporated in vacuo and the resulting solid was slurried in diethyl ether (20 ml) and filtered to give 0.58 g (88%) of product as an off-white solid: mp 221-223° C.; $^1$H NMR (DMSO-d$_6$) δ 11.15 (s, 1H), 9.65 (s, 1H), 8.50 (d, J=8.3 Hz, 1H), 7.83 (t, J=7.6 Hz, 1H), 7.60 (d, J=7.2 Hz, 1H), 5.16 (dd, J=5.2 and 12.6 Hz, 1H), 2.99-2.85 (m, 1H), 2.66-2.45 (m, 4H), 2.11-2.07 (m, 1H), 1.14 (t, J=7.5 Hz, 3H); $^{13}$C NMR (DMSO-d$_6$) δ 172.69, 172.65, 169.71, 167.79, 166.62, 136.65, 136.09, 131.35, 125.93, 118.12, 116.66, 48.91, 30.91, 29.73, 21.97, 9.13; Anal. Calcd. For $C_{16}H_{15}N_3O_5$: C, 58.36; H, 4.59; N, 12.76. Found: C, 58.01; H, 4.45; N, 12.61.

Methyl 3-{N-[2-(2,6-dioxo(3-piperidyl))-1,3-dioxoisoindolin-4-yl]carbamoyl}propanoate I-38

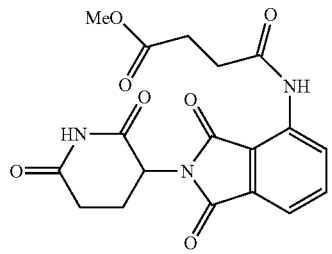

To a stirred suspension of 4-amino-2-(2,6-dioxo(3-piperidyl))isoindoline-1,3-dione (0.55 g, 2.0 mmol) in THF (30 ml) was added methyl 3-(chlorocarbonyl)propanoate (0.63 g, 4.0 mmol). The mixture was heated to reflux for 18 hours. The solvent was evaporated in vacuo and the resulting solid was slurried in diethyl ether (20 ml) and filtered to give 0.75 g (97%) of product as an off-white solid: mp 224-226° C.; $^1$H NMR (DMSO-$d_6$) δ 11.18 (s, 1H), 9.79 (s, 1H), 8.43 (d, J=8.4 Hz, 1H), 7.83 (t, J=7.8 Hz, 1H), 7.62 (d, J=7.3 Hz, 1H), 5.16 (dd, J=5.2 and 12.6 Hz, 1H), 3.61 (s, 3H), 2.99-2.48 (m, 7H), 2.11-2.06 (m, 1H); $^{13}$C NMR (DMSO-$d_6$) δ 172.84, 172.66, 170.94, 169.75, 167.61, 166.70, 136.39, 136.15, 131.52, 126.39, 118.43, 117.04, 51.51, 48.95, 31.22, 30.96, 28.39, 22.03; Anal. Calcd. For $C_{18}H_{17}N_3O_7$: C, 55.82; H, 4.42; N, 10.85. Found: C, 55.68; H, 4.41; N, 10.61.

N-[2-(2,6-dioxo(3-piperidyl))-1,3-dioxoisoindolin-4-yl]-2-phenylacetamide I-39

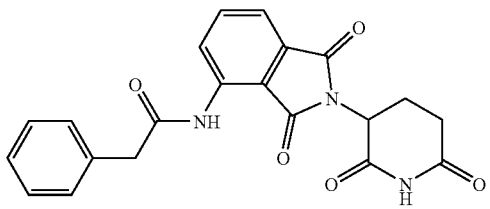

To a stirred suspension of 4-amino-2-(2,6-dioxo(3-piperidyl))isoindoline-1,3-dione (0.55 g, 2.0 mmol) in THF (30 ml) was added 2-phenylacetyl chloride (0.62 g, 4.0 mmol). The mixture was heated to reflux for 18 hours. The solvent was evaporated in vacuo and the resulting solid was slurried in diethyl ether (20 ml) and filtered to give 0.72 g (92%) of product as an off-white solid: mp 217-218° C.; $^1$H NMR (DMSO-$d_6$) δ 11.15 (s, 1H), 9.79 (s, 1H), 8.49 (d, J=8.4 Hz, 1H), 7.82 (t, J=7.9 Hz, 1H), 7.60 (t, J=7.3 Hz, 1H), 7.41-7.27 (m, 5H), 5.13 (dd, J=5.1 and 12.7 Hz, 1H), 3.85 (s, 2H), 2.98-2.83 (m, 1H), 2.64-2.44 (m, 2H), 2.08-2.04 (m, 1H); $^{13}$C NMR (DMSO-$d_6$) δ 172.71, 170.07, 169.74, 167.60, 166.61, 136.38, 136.10, 134.70, 131.41, 129.41, 128.58, 126.97, 125.96, 118.39, 116.90, 48.89, 43.47, 30.90, 21.91; Anal. Calcd. For $C_{21}H_{17}N_3O_5$: C, 64.45; H, 4.38; N, 10.74. Found: C, 64.23; H, 4.34; N, 10.53.

N-[2-(2,6-dioxo(3-piperidyl))-1,3-dioxoisoindolin-4-yl]-2-pyridylcarboxamide I-40

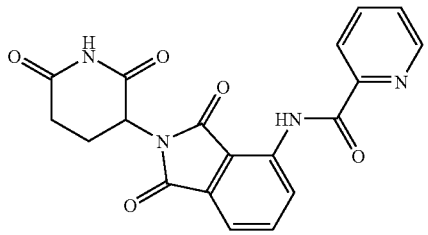

To a stirred suspension of 4-amino-2-(2,6-dioxo(3-piperidyl))isoindoline-1,3-dione (0.55 g, 2.0 mmol) in THF (30 ml) was added pyridine-2-carbonyl chloride hydrochloride (0.71 g, 4.0 mmol). The mixture was heated to reflux for 18 hours. The solvent was evaporated in vacuo and the resulting solid was slurried in a biphasic mixture of diethyl ether (20 ml)/20% $NH_4OH$ (20 ml) and filtered to give an off-white solid. The solid was re-slurried in methanol (20 ml) and filtered to give 0.30 g (40%) of product: mp 336-338° C.; $^1$H NMR (DMSO-$d_6$) δ 11.83 (s, 1H), 11.20 (s, 1H), 8.92 (d, J=8.4 Hz, 1H), 8.81 (d, J=3.6 Hz, 1H), 8.22 (d, J=7.7 Hz, 1H), 8.15 (t, J=7.4 Hz, 1H), 7.92 (t, J=7.7 Hz, 1H), 7.77-7.72 (m, 1H), 7.65 (d, J=7.2 Hz, 1H), 5.22 (dd, J=5.2 and 12.5 Hz, 1H), 3.00-2.86 (m, 1H), 2.69-2.52 (m, 2H), 2.15-2.11 (m, 1H); $^{13}$C NMR (DMSO-$d_6$) δ 172.67, 169.67, 168.20, 166.61, 162.69, 148.83, 148.19, 138.45, 136.50, 136.16, 131.39, 127.72, 124.23, 122.46, 118.29, 116.32, 48.96, 30.91, 21.98; Anal. Calcd. For $C_{19}H_{14}N_4O_5$: C, 60.32; H, 3.73; N, 14.81. Found: C, 60.05; H, 3.57; N, 14.45.

N-[2-(2,6-dioxo(3-piperidyl))-1,3-dioxoisoindolin-4-yl]-2-chloroacetamide I-41

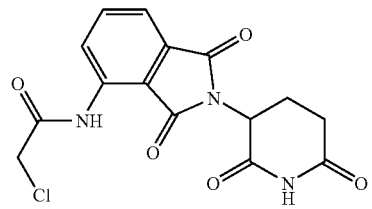

To a stirred suspension of 4-amino-2-(2,6-dioxo(3-piperidyl))isoindoline-1,3-dione (1.37 g, 5.00 mmol) in THF (30 ml) was added chloroacetyl chloride (0.62 g, 5.5 mmol). The mixture was heated to reflux for 30 minutes. The solvent was evaporated in vacuo and the resulting solid was slurried in diethyl ether (20 ml) and filtered to give 1.67 g (96%) of product as an off-white solid: $^1$H NMR (DMSO-$d_6$) δ 11.18 (s, 1H), 10.31 (s, 1H), 8.54 (d, J=8.4 Hz, 1H), 7.88 (t, J=7.7 Hz, 1H), 7.68 (d, J=7.3 Hz, 1H), 5.17 (dd, J=5.2 and 12.7 Hz, 1H), 4.54 (s, 2H), 2.90-2.85 (m, 1H), 2.65-2.51 (m, 2H), 2.10-2.06 (m, 1H).

2-azido-N-[2-(2,6-dioxo(3-piperidyl))-1,3-dioxoisoindolin-4-yl]acetamide I-42

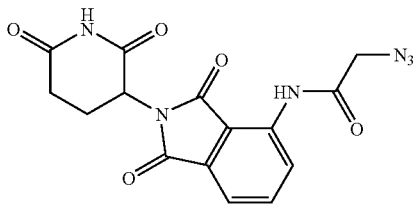

To a suspension of N-[2-(2,6-dioxo(3-piperidyl))-1,3-dioxoisoindolin-4-yl]-2-chloroacetamide (1.53 g, 4.4 mmol) in acetone (30 ml) was added sodium azide (0.43 g, 6.6 mmol). The mixture was heated to reflux for 18 hours. The solvent was evaporated in vacuo to give 1.49 g (96%) of product as an off-white solid: $^1$H NMR (DMSO-$d_6$) δ 11.19 (s, 1H), 10.20 (s, 1H), 8.49 (d, J=8.3 Hz, 1H), 7.88 (t, J=7.7 Hz, 1H), 7.68 (d, J=7.3 Hz, 1H), 5.17 (dd, J=5.1 and 12.7 Hz, 1H), 4.34 (s, 2H), 2.99-2.84 (m, 1H), 2.65-2.47 (m, 2H), 2.09-2.00 (m, 1H).

2-Amino-N-[2-(2,6-dioxo(3-piperidyl))-1,3-dioxoisoindolin-4-yl]acetamide I-43, hydrochloride

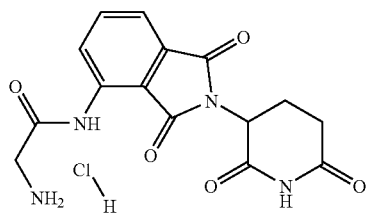

To a solution of 2-azido-N-[2-(2,6-dioxo(3-piperidyl))-1,3-dioxoisoindolin-4-yl]acetamide (1.49 g, 4.2 mmol) in methanol (50 ml) was added 10% Pd—C (0.1 g). Hydrogenation at 50 psi of hydrogen in a Parr Type shaker for 2 hours yielded a slurry. The mixture was filtered leaving a gray solid that was stirred in H$_2$O (50 ml). The pH of the aqueous mixture was adjusted to 4 by addition of 3N HCl. The aqueous mixture was filtered through celite to remove catalyst and the filtrate was stirred with 50 ml of ethyl acetate for 3 hours. The aqueous layer was separated and was evaporated in vacuo to give a solid which was slurried in ethyl acetate and filtered to give 0.72 g (45%) of product as an off-white solid: mp 305-307° C.; $^1$H NMR (DMSO-$d_6$) δ 11.17 (s, 1H), 10.35 (s, 1H), 8.44 (bs, 3H), 8.32 (d, J=8.2 Hz, 1H), 7.90 (t, J=8.0 Hz, 1H), 7.71 (d, J=7.2 Hz, 1H), 5.16 (dd, J=5.1 and 12.6 Hz, 1H), 3.97 (s, 2H), 2.99-2.84 (m, 1H), 2.65-2.46 (m, 2H), 2.10-2.06 (m, 1H); $^{13}$C NMR (DMSO-$d_6$) δ 172.81, 169.80, 166.75, 166.56, 166.19, 136.19, 134.91, 131,89, 127.62, 119.47, 118.68, 48.96, 41.13, 30.94, 22.00; Anal. Calcd. For C$_{15}$H$_{15}$ClN$_4$O$_5$: C, 48.62; H, 4.19; N, 15.12. Found: C, 48.68; H, 4.18; N, 15.05+0.21H$_2$O.

N-[2-(2,6-dioxo(3-piperidyl))-1-oxoisoindolin-4-yl]-2-chloroacetamide I-44

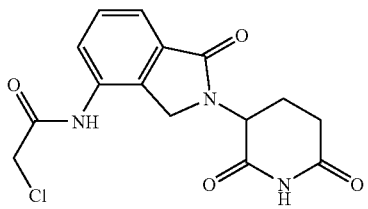

To a stirred suspension of 3-(4-amino-1-oxoisoindolin-2-yl)piperidine-2,6-dione (3.89 g, 15.0 mmol) in THF (50 ml) was added chloroacetyl chloride (1.86 g, 16.5 mmol). The mixture was heated to reflux for 45 minutes. To the reaction mixture was added additional chloroacetyl chloride (0.15 g, 0.13 mmol). The reaction mixture was heated at reflux for an additional 30 minutes. The solvent was evaporated in vacuo and the resulting solid was slurried in diethyl ether (20 ml) and filtered to give 4.64 g (92%) of product as an off-white solid: $^1$H NMR (DMSO-$d_6$) δ 11.04 (s, 1H), 10.22 (s, 1H), 7.82 (dd, J=1.6 and 7.2 Hz, 1H), 7.59-7.50 (m, 2H), 5.16 (dd, J=5.1 and 13.2 Hz, 1H), 4.46-4.30 (m, 4H), 3.00-2.85 (m, 1H), 2.65-2.58 (m, 1H), 2.44-2.28 (m, 1H), 2.06-2.01 (m, 1H).

2-azido-N-[2-(2,6-dioxo(3-piperidyl))-1-oxoisoindolin-4-yl]acetamide I-45

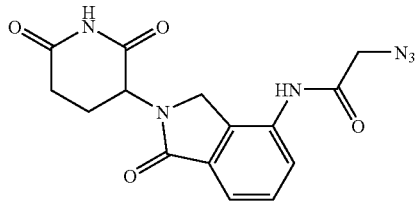

To a stirred suspension of N-[2-(2,6-dioxo(3-piperidyl))-1-oxoisoindolin-4-yl]-2-chloroacetamide (4.64 g, 13.8 mmol) in acetone (60 ml) was added sodium azide (1.35 g, 20.7 mmol). The mixture was heated to reflux for 18 hours. After 18 hours, to the reaction mixture was added NaI (2.05 g, 13.8 mmol) and additional sodium azide (0.90 g, 13.8 mmol). The mixture was heated at reflux for an additional 18 hours. The solvent was evaporated in vacuo to give an off-white solid which was slurried in a mixture of dichloromethane (50 ml) and H$_2$O (50 ml). This slurry was filtered to give 4.39 g (93%) of product: $^1$H NMR (DMSO-$d_6$) δ 11.50-9.52 (bs, 2H), 7.87-7.84 (m, 1H), 7.59-7.50 (m, 2H), 5.17 (dd, J=5.0 and 13.1 Hz, 1H), 4.44 (d, J=17.6 Hz, 1H), 4.34 (d, J=17.6 Hz, 1H), 4.13 (s, 2H), 3.00-2.86 (m, 1H), 2.65-2.59 (m, 1H), 2.44-2.29 (m, 1H), 2.07-2.02 (m, 1H).

2-Amino-N-[2-(2,6-dioxo(3-piperidyl))-1-oxoisoindolin-4-yl]acetamide 146, hydrochloride

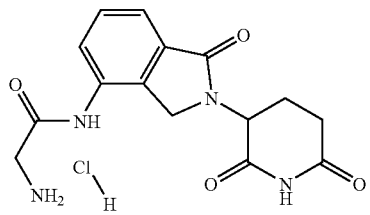

To a stirred suspension of 2-azido-N-[2-(2,6-dioxo(3-piperidyl))-1-oxoisoindolin-4-yl]acetamide (1.49 g, 4.20 mmol) in a mixture of methanol (50 ml) and 3N HCl (6 ml) was added 10% Pd—C (0.1 μg). Hydrogenation at 50 psi of hydrogen in a Parr Type shaker for 24 hours gave a slurry. The mixture was filtered leaving a gray solid that was stirred in H$_2$O (100 ml). The aqueous mixture was filtered through celite to remove catalyst. The aqueous and methanolic filtrates were combined and evaporated in vacuo to give a white solid. The solid was slurried in ethyl acetate (20 ml), filtered, re-slurried in methanol (20 ml), and filtered to give 2.35 g (48%) of product: mp 293-295° C.; $^1$H NMR (DMSO-d$_6$) δ 11.06 (s, 1H), 10.86 (s, 1H), 8.45 (bs, 2H), 7.90 (d, J=6.3 Hz, 1H), 7.59-7.51 (m, 2H), 5.17 (dd, J=4.9 and 13.0 Hz, 1H), 4.54 (d, J=17.8 Hz, 1H), 4.39 (d, J=17.8 Hz, 1H), 3.91 (s, 2H), 3.02-2.88 (m, 1H), 2.68-2.61 (m, 1H), 2.37-2.23 (m, 1H), 2.09-2.05 (m, 1H); $^{13}$C NMR (DMSO-d$_6$) δ 172.94, 171.07, 167.74, 165.24, 133.73, 132.86, 128.95, 125.01, 119.65, 51.59, 46.74, 40.90, 31.22, 22.82; Anal. Calcd. For C$_{15}$H$_{17}$ClN$_4$O$_4$: C, 50.43; H, 4.94; N, 15.68. Found: C, 50.08; H, 4.92; N, 15.53+0.25H$_2$O.

3-{4-[(2-Furylmethyl)amino]-1-oxoisoindolin-2-yl}piperidine-2,6-dione I-47

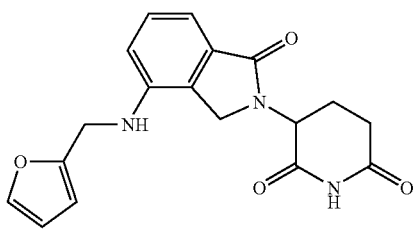

To a stirred suspension of 3-(4-amino-1-oxoisoindolin-2-yl)piperidine-2,6-dione (0.52 g, 2.0 mmol) in methanol (50 ml) was added furan-2-carbaldehyde (0.200 g, 2.05 mmol). The mixture was heated to reflux for 4 hours. The solvent was evaporated in vacuo and the residue was dissolved in acetic acid (20 ml). Sodium triacetoxyborohydride (0.450 g, 2.05 mmol) was added to the reaction mixture. The reaction mixture was stirred for 24 hours. The solvent was evaporated in vacuo and the residue was dissolved in ethyl acetate (100 ml), washed with H$_2$O (3×100 ml), saturated aqueous NaHCO$_3$ (2×100 ml), brine (1×100 ml), and dried over MgSO$_4$. The solvent was evaporated in vacuo and the residue was partially purified by chromatography (100% ethyl acetate) to give an off-white solid which was recrystallized from ethanol to give 0.20 g of product as a white solid: mp 248-250° C.; $^1$H NMR (DMSO-d$_6$) δ 11.02 (s, 1H), 7.57 (s, 1H), 7.27 (t, J=7.6 Hz, 1H), 6.96 (d, J=7.3 Hz, 1H), 6.85 (d, J=8.0 Hz, 1H), 6.36 (d, J=11.2 Hz, 2H), 6.22 (t, J=5.4 Hz, 1H), 5.12 (dd, J=4.9 and 13.1 Hz, 1H), 4.37 (d, J=5.5 Hz, 2H), 4.27 (d, J=17.2 Hz, 1H), 4.14 (d, J=17.2 Hz, 1H) 3.00-2.86 (m, 1H), 2.65-2.59 (m, 1H), 2.37-2.23 (m, 1H), 2.08-1.99 (m, 1H); $^{13}$C NMR (DMSO-d$_6$) δ 172.83, 171.16, 168.70, 152.82, 143.06, 142.00, 132.09, 129.02, 126.76, 112.35, 110.63, 110.33, 107.08, 51.50, 45.73, 31.20, 22.75; Anal. Calcd. For C$_{18}$H$_{17}$N$_3$O$_4$: C, 63.71; H, 5.05; N, 12.38. Found: C, 63.41; H, 5.03; N, 11.98.

3-[1-Oxo-4-(pentylamino)isoindolin-2-yl]piperidine-2,6-dione I-48

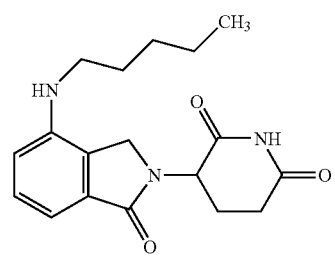

To a stirred solution of 3-(4-amino-1-oxoisoindolin-2-yl)piperidine-2,6-dione (0.52 g, 2.0 mmol) in DMF (10 ml) was added pentanal (0.26 g, 3.0 mmol), acetic acid (0.24 g, 4.0 mmol), and sodium triactoxyborohydride (0.85 g, 4.0 mmol). The reaction mixture was stirred at room temperature for 6 hours. The solvent was evaporated in vacuo and the residue was dissolved in ethyl acetate (100 ml), washed with H$_2$O (3×100 ml), brine (1×100 ml), and dried over MgSO$_4$. The solvent was evaporated and the residue was partially purified by chromatography (ethyl acetate/hexane, 75:25) to give an off-white solid which was slurried in ethyl acetate and filtered to give 0.14 g (21%) of product as a white solid: mp 244-246° C.; $^1$H NMR (DMSO-d$_6$) δ 11.00 (s, 1H), 7.28 (t, J=7.7 Hz, 1H), 6.92 (d, J=7.3 Hz, 1H), 6.73 (d, J=8.0 Hz, 1H), 5.54 (t, J=5.3 Hz, 1H), 5.12 (dd, J=5.1 and 13.2 Hz, 1H), 4.24 (d, J=17.2 Hz, 1H), 4.13 (d, J=17.2 Hz, 1H) 3.15-3.07 (m, 2H), 3.00-2.86 (m, 1H), 2.65-2.59 (m, 1H), 2.39-2.23 (m, 1H), 2.08-1.99 (m, 1H), 1.61-1.57 (m, 2H), 1.41-1.32 (m, 4H), 0.89 (t, J=6.8 Hz, 3H); $^{13}$C NMR (DMSO-d$_6$) δ 172.83, 171.19, 168.86, 143.74, 132.00, 129.15, 126.42, 111.66, 109.86, 51.46, 45.69, 42.68, 31.20, 28.80, 28.21, 22.79, 21.96, 13.89; Anal. Calcd. For C$_{18}$H$_{23}$N$_3$O$_3$: C, 65.63; H, 7.04; N, 12.76. Found: C, 65.69; H, 7.22; N, 12.55.

3-(2-Methoxy-ethylamino)-phthalic acid dimethyl ester

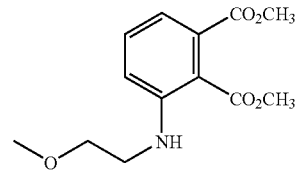

To a stirred solution of oxalyl chloride (1.75 ml, 20 mmol) in methylene chloride (20 ml) under a nitrogen atmosphere at −78° C. was added DMSO (1.42 ml, 20 mmol) in methylene chloride (10 ml) dropwise over 5 minutes. The mixture was stirred for 5 minutes followed by the dropwise addition of 2-methoxyethanol (1.58 ml, 20 mmol) in methylene chloride (10 ml) over 5 minutes. The mixture was stirred for 20 minutes followed by the dropwise addition of triethylamine (8.36 ml, 60 mmol) over 5 minutes. The resulting suspension was stirred for 30 minutes at −78° C. and then allowed to warm to room temperature. The reaction mixture was diluted with methylene chloride (20 ml). To this stirred mixture was added 3-amino-phthalic acid dimethyl ester (2.09 g, 10 mmol) and acetic acid (4.60 ml, 80 mmol). The mixture was stirred at room temperature under a nitrogen atmosphere for 5 minutes followed by the addition of sodium triacetoxyborohydride (4.24 g, 20 mmol). The mixture was stirred for 3 h. The reaction mixture was diluted with methylene chloride (50 ml) and washed with water (3×100 ml), saturated aqueous sodium bicarbonate (2×100 ml), brine (100 ml), and dried (MgSO$_4$). The solvent was evaporated in vacuo and the residue purified by chromatography (25% ethyl acetate/hexane) to give 2.24 g (84%) of product as an oil. $^1$H NMR (DMSO-d$_6$) d 732 (t, J=8.0 Hz, 1H), 6.88-6.79 (m, 3H), 3.85 (s, 3H), 3.83 (s, 3H), 3.62 (t, J=5.4 Hz, 2H), 3.41 (s, 3H), 3.35 (q, J=5.2 Hz, 2H).

3-(2-Methoxy-ethylamino)-phthalic acid

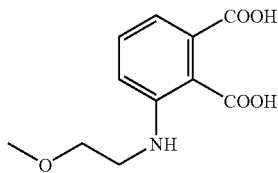

To a stirred solution of 3-(2-methoxy-ethylamino)-phthalic acid dimethyl ester (2.24 g, 8.38 mmol) in methanol (50 ml) was added 5N potassium hydroxide (10 ml). The mixture was stirred at room temperature overnight. The solvent was evaporated in vacuo and the residue dissolved in water (50 ml). The water was washed with diethyl ether (2×75 ml). The aqueous portion was cooled in an ice bath and the pH was adjusted to 2-3 by dropwise addition of concentrated hydrochloric acid. The aqueous solution was then extracted with ethyl acetate (3×75 ml). The combined ethyl acetate extracts were washed with brine (100 ml) and dried (MgSO$_4$). The solvent was evaporated in vacuo and the residue, which contained a mixture of diacid and monomethyl esters, was used without further purification.

2-(2,6-Dioxo-piperidin-3-yl)-4-(2-methoxy-ethylamino)-isoindole-1,3-dione I-49

To a stirred solution of 3-(2-methoxy-ethylamino)-phthalic acid (8.38 mmol) in pyridine (40 ml) was added 3-amino-piperidine-2,6-dione hydrochloride (1.39 g, 8.42 mmol). The reaction mixture was heated to reflux for 5 hours. The solvent was evaporated in vacuo and the residue dissolved in methylene chloride (125 ml). The methylene chloride mixture was treated with Norit (2 g), washed with water (2×100 ml), 0.1N HCl (1×100 ml), brine (1×100 ml), and dried (MgSO$_4$). The solvent was evaporated in vacuo and the residue (oil) crystallized from a minimal amount of ethanol to give a yellow solid that was purified by preparative HPLC to give 1.71 g (64%) of product as a yellow solid: mp 1.82-1,84° C.; $^1$H NMR (DMSO-d$_6$) d 11.12 (s, 1H), 7.58 (t, J=7.7 Hz, 1H), 7.12 (d, J=8.5 Hz, 1H), 7.04 (d, J=6.9 Hz, 1H), 6.59 (bs, 1H), 5.07 (dd, J=4.7 and 12.1 Hz, 1H), 3.54-3.30 (m, 7H), 2.95-2.85 (m, 1H), 2.64-2.52 (m, 2H), 2.07-2.02 (m, 1H); $^{13}$C NMR (DMSO-d$_6$) d 172.79, 170.06, 168.98, 167.27, 146.38, 136.21, 132.07, 117.33, 110.67, 109.24, 70.39, 58.12, 48.58, 41.50, 30.99, 22.15; Anal. Calcd. For C$_{16}$H$_{17}$N$_3$O$_5$: C, 58.00; H15.17; N, 12.68. Found: C, 58.06; H, 5.12; N, 12.76.

2-Benzyloxy-N-[2-(2,6-dioxo-piperidin-3-yl)-1,3-dioxo-2,3-dihydro-1H-isoindol-4-yl]-acetamide I-50

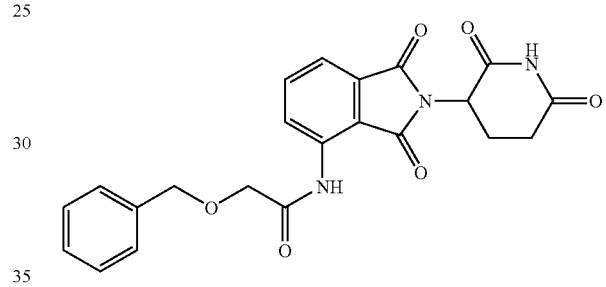

To a suspension of 4-amino-2-(2,6-dioxo(3-piperidyl))isoindoline-1,3-dione (1.10 g, 4 mmol) in THF (30 ml) was added benzyloxyacetyl chloride (1.26 ml, 8 mmol). The mixture was heated to reflux for 1.8 hours. The reaction was cooled to room temperature, methanol (2 ml) was added, and the mixture stirred for 1 hour. The solvent was evaporated in vacuo and the residue was slurried in diethyl ether (30 ml), filtered, recrystallized from a minimal amount of acetic acid, slurried in ethyl acetate (15 ml), and filtered to give 1.35 g (80%) of product: mp 204-206° C.; $^1$H NMR (DMSO-d$_6$) d 11.20 (s, 1H), 10.40 (s, 1H), 8.71 (d, J=8.4 Hz, 1H), 7.86 (t, J=7.9 Hz, 1H), 7.64 (d, J=7.2 Hz, 1H), 7.50-7.28 (m, 5H), 5.17 (dd, J=5.0 and 12.5 Hz, 1H), 4.72 (s, 2H), 4.21 (s, 2H), 2.99-2.85 (m, 1H), 2.67-2.51 (m, 2H), 2.12-2.08 (m, 1H); $^{13}$C NMR (DMSO-d$_6$) d 172.78, 169.78, 169.01, 168.27, 166.67, 137.04, 136.52, 135.93, 131.29, 128.36, 127.82, 124.40, 118.38, 116.08, 72.78, 69.23, 48.97, 30.92, 21.98; Anal. Calcd. For C$_{22}$H$_{19}$N$_3$O$_6$: C, 62.70; H, 4.54; N, 9.97. Found: C, 62.77; H, 4.54; N, 9.82.

3-Pentylamino-phthalic acid dimethyl ester

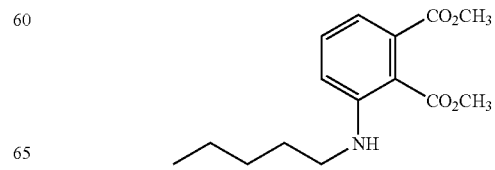

To a stirred solution of 3-amino-phthalic acid dimethyl ester (3.14 g, 15 mmol) in methylene chloride (50 ml) under a nitrogen atmosphere were added valeraldehyde (2.0 ml, 18.75 mmol) and acetic acid (5.18 ml, 90 mmol). The mixture was stirred for 5 minutes followed by addition of sodium triacetoxyborohydride (6.36 g, 30 mmol). The reaction was stirred for 30 minutes, diluted with methylene chloride (50 ml), washed with water (2×100 ml), saturated aqueous sodium bicarbonate (2×100 ml), brine (100 ml), and, dried (MgSO$_4$). The solvent was evaporated in vacuo to give 4.19 g of product (100%) that used without further purification. $^1$H NMR (DMSO-d$_6$) d 7.31 (t, J=7.9 Hz, 1H), 6.81-6.75 (m, 2H), 3.85 (s, 3H), 3.82 (s, 3H), 3.15 (bs, 2H), 1.68-1.60 (m, 2H), 1.45-1.32 (m, 4H), 0.89 (t, J=6.9 Hz, 3H).

3-Pentylamino-phthalic acid

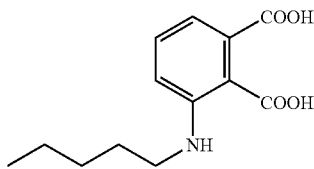

3-Pentylamino-phthalic acid dimethyl ester (4.19, 15 mmol) was treated in the same manner as described above for the synthesis of 3-(2-methoxy-ethylamino)-phthalic acid. The product of the reaction, which contained a mixture of diacid and monomethyl esters, was used without further purification.

2-(2,6-Dioxo-piperidin-3-yl)-4-pentylamino-isoindole-1,3-dione I-51

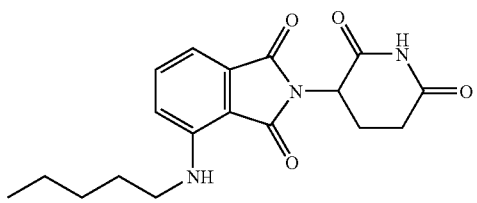

To a stirred solution of 3-pentylamino-phthalic acid (2.51 g, 10 mmol) in acetic acid (50 ml) was added 3-aminopiperidine-2,6-dione hydrochloride (1.81 g, 11 mmol). The reaction mixture was heated to reflux overnight. The solvent was evaporated in vacuo and the residue dissolved in ethyl acetate (100 ml). The ethyl acetate mixture was washed with water (2×100 ml), saturated aqueous sodium bicarbonate (2×100 ml), brine (1×100 ml), and dried (MgSO$_4$). The solvent was evaporated in vacuo and the solid residue was purified by chromatography (25% ethyl acetate/hexane) to give 1.82 g (53%) of product as a yellow solid: mp 141-143° C.; $^1$H NMR (DMSO-d$_6$) d 11.09 (s, 1H); 7.58 (t, J=8.3 Hz, 1H), 7.08 (d, J=8.6 Hz, 1H), 7.02 (d, J=7.0 Hz, 1H), 6.519 (t, J=5.7 Hz, 1H), 5.06 (dd, J=5.3 and 12.4 Hz, 1H), 3.32-3.25 (m, 2H), 2.97-2.82 (m, 1H), 2.62-2.46 (m, 2H), 2.06-2.01 (m, 1H), 1.61-1.55 (m, 2H), 1.35-1.32 (m, 4H), 0.88 (t, J=6.7 Hz, 3H); $^{13}$C NMR (DMSO-d$_6$) d 172.72, 170.01, 168.92, 167.25, 146.39, 136.21, 132.14, 117.08, 110.31, 108.99, 48.52, 41.77, 30.94, 28.46, 28.33, 22.12, 21.82, 13.85; Anal. Calcd. For C$_{18}$H$_{21}$N$_3$O$_4$: C, 62.96; H, 6.16; N, 12.24. Found: C, 62.92; H, 6.17; N, 12.15.

3-Chloro-N-[2-(2,6-dioxo-piperidin-3-yl)-1,3-dioxo-2,3-dihydro-1H-isoindol-4-yl]-benzamide I-52

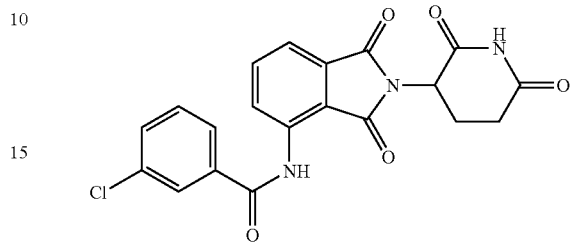

To a suspension of 4-amino-2-(2,6-dioxo(3-piperidyl)) isoindoline-1,3-dione (0.55 g, 2 mmol) in THF (30 ml) was added 3-chlorobenzoyl chloride (0.51 ml, 4 mmol). The mixture was heated to reflux for 18 hours. The reaction was cooled to room temperature, methanol (2 ml) was added, and the mixture stirred for 1 hour. The solvent was evaporated in vacuo leaving a solid which was slurried in diethyl ether (20 ml) and filtered to give 0.82 g (100%) of product as an off-white solid: mp 257-259° C.; $^1$H NMR (DMSO-d$_6$) d 11.06 (s, 1H), 10.43 (s, 1H), 8.50 (d, J=8.4 Hz, 1H), 7.99-7.88 (m, 3H), 7.75-7.61 (m, 3H), 5.17 (dd, J=5.5 and 12.7 Hz, 1H), 2.99-2.84 (m, 1H), 2.67-2.49 (m, 2H), 2.12-2.07 (m, 1H); $^{13}$C NMR (DMSO-d$_6$) d 172.36, 169.78, 169.36, 167.59, 166.39, 163.57, 135.99, 135.31, 133.59, 132.11, 131.33, 130.73, 127.07, 126.76, 125.78, 118.93, 118.55, 48.91, 30.77, 21.85; Anal. Calcd. For C$_{20}$H$_{14}$ClN$_3$O$_5$: C, 58.33; H, 3.43; N, 10.20. Found: C, 58.38; H, 3.23; N, 9.95.

N-[2-(2,6-Dioxo-piperidin-3-yl)-1,3-dioxo-2,3-dihydro-1H-isoindol-4-yl]-2-phenoxy-acetamide I-53

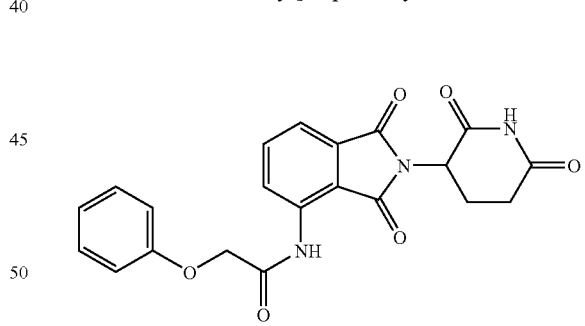

To a suspension of 4-amino-2-(2,6-dioxo(3-piperidyl)) isoindoline-1,3-dione (0.55 g, 2 mmol) in THF (30 ml) was added phenoxyacetyl chloride (0.55 ml, 4 mmol). The mixture was heated to reflux for 18 hours. The reaction was cooled to room temperature, methanol (2 ml) was added, and the mixture stirred for 1 hour. The solvent was evaporated in vacuo leaving a solid which was slurried in diethyl ether (20 ml) and filtered to give 0.76 g (93%) of product as an off-white solid: mp 236-238° C.; $^1$H NMR (DMSO-d$_6$) d 11.19 (s, 1H), 10.53 (s, 1H), 8.73 (d, J=8.4 Hz, 1H), 7.88 (t, J=7.6 Hz, 1H), 7.64 (d, J=7.3 Hz, 1H), 7.38 (t, J=7.6 Hz, 2H) 7.14-7.01 (m, 3H), 5.21 (dd, J=5.3 and 12.6 Hz, 1H), 4.81 (s, 2H), 3.00-2.86 (m, 1H), 2.67-20.51 (m, 2H), 2.13-2.09 (m, 1H); $^{13}$C NMR (DMSO-d$_6$) d 172.77, 169.77, 168.37, 167.59, 166.67, 156.85, 136.58, 135.84, 131.28, 129.74, 124.45, 121.91, 118.50, 116.28, 114.86, 67.03, 49.02, 30.96, 21.93; Anal. Calcd. For $C_{21}H_{17}N_3O_6$: C, 61.92; H, 4.21; N, 10.31. Found: C, 61.87; H, 4.27; N. 10.25.

3-(2-Benzyloxy-ethylamino)-phthalic acid dimethyl ester

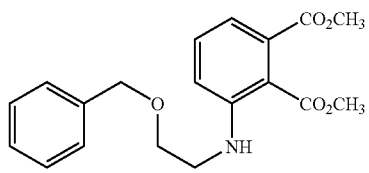

Benzyloxyacetaldehyde (5.27 ml, 37.5 mmol) was treated in the same manner as described above for the synthesis of 3-pentylamino-phthalic acid dimethyl ester. The residue (oil) was purified by chromatography (6:3:1 methylene chloride/hexane/ethyl acetate) to give 7.98 g (78%) of yellow oil: $^1$H NMR (DMSO-$d_6$) d 7.38-7.26 (m, 5H), 6.89-6.77 (m, 3H), 4.57 (s, 2H), 3.85 (s, 3H), 3.82 (s, 3H), 3.69 (t, J=5.5 Hz, 2H), 3.38 (q, J=5.4 Hz, 2H).

3-(2-Benzyloxy-ethylamino)-phthalic acid

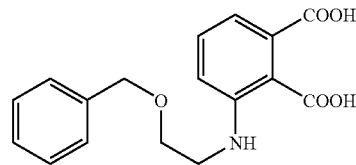

3-(2-Benzyloxy-ethylamino)-phthalic acid dimethyl ester (2.50 g, 7.28 mmol) was treated in the same manner as described above for the synthesis of 3-(2-methoxy-ethylamino)-phthalic acid. The product of the reaction, which contained a mixture of diacid and monomethyl esters, was used without further purification.

4-(2-Benzloxy-ethylamino)-2-(2,6-dioxo-piperidin-3-yl)-isoindole-1,3-dione I-54

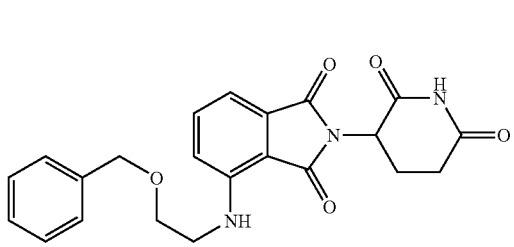

3-(2-Benzyloxy-ethylamino)-phthalic acid (1.78 g, 5.65 mmol) was treated in the same manner as described above for the synthesis of 2-(2,6-Dioxo-piperidin-3-yl)-4-(2-methoxy-ethylamino)-isoindole-1,3-dione. The solid yellow residue was recrystallized from a minimal amount of ethanol to give 1.32 g (57%) of product as a yellow solid: mp 158-160° C.; $^1$H NMR (DMSO-$d_6$) d 11.11 (s, 1H), 7.57 (t, J=7.3 Hz, 1H), 7.37-7.24 (m, 5H), 7.14 (d, J=8.6 Hz, 1H), 7.04 (d, J=7.0 Hz, 1H), 6.67 (t, J=5.7 Hz, 1H), 5.07 (dd, J=5.4 and 12.5 Hz, 1H), 4.54 (s, 2H), 3.66-3.62 (m, 2H), 3.55-3.49 (m, 2H), 2.97-2.82 (m, 1H), 2.63-2.45 (m, 2H), 2.06-2.02 (m, 1H); $^{13}$C NMR (DMSO-$d_6$) d 172.81, 170.08, 168.96, 167.28, 146.40, 138.23, 136.16, 132.06, 128.22, 127.42, 117.47, 110.69, 109.30, 71.90, 68.09, 48.54, 41.68, 30.97, 22.13; Anal. Calcd. For $C_{22}H_{21}N_3O_5$: C, 64.86; H, 5.20; N, 10.31. Found: C, 64.95; H, 5.03; N, 10.27.

N-[2-(2,6-Dioxo-piperidin-3-yl)-1,3-dioxo-2,3-dihydro-1H-isoindol-4-yl]-3-fluoro-benzamide I-55

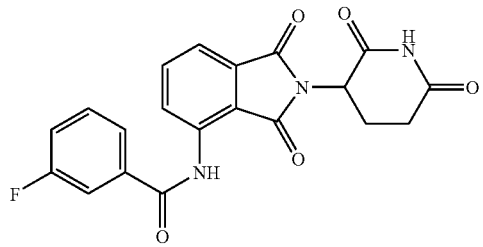

To a suspension of 4-amino-2-(2,6-dioxo(3-piperidyl))isoindoline-1,3-dione (0.55 g, 2 mmol) in THF (30 ml) was added 3-Fluorobenzoyl chloride (0.49 ml, 4 mmol). The mixture was heated to reflux for 18 hours. The reaction was cooled to room temperature, methanol (2 ml) was added, and the mixture stirred for 1 hour. The solvent was evaporated in vacuo leaving a solid which was slurried in diethyl ether (20 ml) and filtered to give 0.69 g (96%) of product as an off-white solid: mp 260-262° C.; $^1$H NMR (DMSO-$d_6$) d 11.00 (s, 1H), 10.39 (s, 1H), 8.53 (d, J=8.3 Hz, 1H), 7.94-7.50 (m, 6H), 5.15 (dd, J=5.6 and 12.7 Hz, 1H), 2.97-2.83 (m, 1H), 2.66-2.49 (m, 2H), 2.14-2.06 (m, 1H); $^{13}$C NMR (DMSO-$d_6$) d 172.36, 169.36, 167.66, 166.39, 163.62, 136.03, 131.31, 131.12, 130.99, 126.60, 123.19, 123.15, 119.44, 119.11, 118.89, 118.42, 114.31, 113.94, 48.91, 30.77, 21.83; Anal. Calcd. For $C_{20}H_{14}FN_3O_5$: C, 60.76; H, 3.57; N, 10.63. Found: C, 60.88; H, 3.38; N, 10.51.

N-[2-(2,6-Dioxo-piperidin-3-yl)-1,3-dioxo-2,3-dihydro-1H-isoindol-4-yl]-3-methyl-benzamide I-56

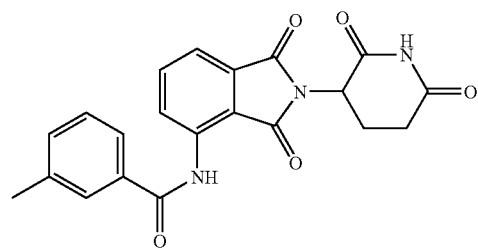

To a suspension of 4-amino-2-(2,6-dioxo(3-piperidyl))isoindoline-1,3-dione (0.55 g 2 mmol) in THF (30 ml) was added m-toluoyl chloride (0.53 ml, 4 mmol). The mixture was heated to reflux for 18 hours. The reaction was cooled to room temperature, methanol (2 ml) was added, and the mixture stirred for 1 hour. The solvent was evaporated in vacuo leaving a solid that was slurried in diethyl ether (20 ml), filtered, reslurried in ethyl acetate (20 ml), and filtered to give 0.69 g (88%) of product as an off-white solid: mp 234-236° C.; $^1$H NMR (DMSO-d$_6$) d 10.97 (s, 1H), 10.31 (s, 1H), 8.64 (d, J=8.4 Hz, 1H), 7.92-7.47 (m, 6H), 5.16 (dd, J=5.5 and 12.7 Hz, 1H), 2.97-2.84 (m, 1H), 2.68-2.43 (m, 5H), 2.14-2.09 (m, 1H); $^{13}$C NMR (DMSO-d$_6$) d 172.13, 169.15, 168.03, 166.30, 164.80, 138.18, 136.54, 135.95, 133.14, 132.87, 131.09, 128.57, 127.45, 126.64, 123.95, 118.23, 117.33, 48.88, 30.67, 21.76, 20.62; Anal. Calcd. For C$_{21}$H$_{17}$N$_3$O$_5$: C, 64.45; H, 4.38; N, 10.74. Found: C, 64.23; H, 4.18; N, 10.56.

N-[2-(2,6-Dioxo-piperidin-3-yl)-1,3-dioxo-2,3-dihydro-1H-isoindol-4-yl]-3-methoxy-benzamide I-57

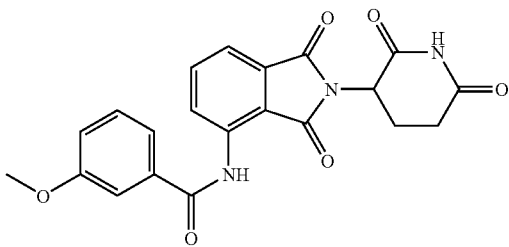

To a suspension of 4-amino-2-(2,6-dioxo(3-piperidyl))isoindoline-1,3-dione (0.55 g, 2 mmol) in THF (30 ml) was added m-anisoyl chloride (0.56 ml, 4 mmol). The mixture was heated to reflux for 18 hours. The reaction was cooled to room temperature, methanol (2 ml) was added, and the mixture stirred for 1 hour. The solvent was evaporated in vacuo leaving a solid that was slurried in diethyl ether (20 ml), filtered, reslurried in ethyl acetate (20 ml), filtered, and recrystallized from minimal acetic acid to give 0.51 g (63%) of product as an off-white solid: mp 240-242° C.; $^1$H NMR (DMSO-d$_6$) d 11.15 (s, 1H), 10.38 (s, 1H), 8.60 (d, J=8.3 Hz, 1H), 7.91 (t, J=7.5 Hz, 1H), 7.67 (d, J=7.2 Hz, 1H), 7.55-7.50 (m, 3H), 7.29-7.22 (m, 1H), 5.19 (dd, J=5.3 and 12.5 Hz, 1H), 3.86 (s, 3H), 2.99-2.84 (m, 1H), 2.66-2.50 (m, 2H), 2.12-2.07 (m, 1H); $^{13}$C NMR (DMSO-d$_6$) d 172.02, 169.71, 168.12, 166.64, 164.70, 159.56, 136.52, 136.31, 134.73, 131.36, 130.26, 126.18, 119.19, 118.78, 118.26, 117.92, 112.74, 55.41, 48,97, 30.93, 21.99; Anal. Calcd. For C$_{21}$H$_{17}$N$_3$O$_6$: C, 59.73; H, 4.46; N, 9.29. Found: C, 59.37; H, 4.34; N, 9.10+ 0.75 AcOH.

N-[2-(2,6-Dioxo-piperidin-3-yl)-1,3-dioxo-2,3-dihydro-1H-isoindol-4-yl]-3-trifluoromethyl-benzamide I-58

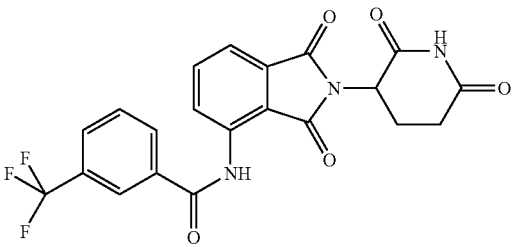

To a suspension of 4-amino-2-(2,6-dioxo(3-piperidyl))isoindoline-1,3-dione (0.55 g, 2 mmol) in THF (30 ml) was added 3-trifluoromethylbenzoyl chloride (0.60 ml, 4 mmol). The mixture was heated to reflux for 18 hours. The reaction was cooled to room temperature, methanol (2 ml) was added, and the mixture stirred for 1 hour. The solvent was evaporated in vacuo leaving a solid that was slurried in diethyl ether (20 ml) and filtered to give 0.41 g (46%) of product as an off-white solid: mp 257-259° C.; $^1$H NMR (DMSO-d$_6$) d 10.86 (s, 1H), 10.45 (s, 1H), 8.50 (d, J=8.5 Hz, 1H), 8.24-8.25 (m, 2H), 8.02-7.82 (m, 3H), 7.69 (d, J=7.3 Hz, 1H), 5.14 (dd, J=5.7 and 12.8 Hz, 1H), 2.95-2.82 (m, 1H), 2.67-2.48 (m, 2H), 2.14-2.07 (m, 1H); $^{13}$C NMR (DMSO-d$_6$) d 171.75, 168.80, 167.31, 166.06, 163.43, 135.80, 135.60, 134.28, 131.16, 130.71, 129.75, 128.35, 128.29, 126.63, 123.59, 123.52, 118.65, 118.55, 48.84, 30.51, 21.62; Anal. Calcd. For C$_{21}$H$_{14}$F$_3$N$_3$O$_5$: C, 56.64; H, 3.17; N, 9.44. Found: C, 56.48; H, 3.15; N, 9.41.

N-[2-(2,6-Dioxo-piperidin-3-yl)-1,3-dioxo-2,3-dihydro-1H-isoindol-4-yl]-3-nitro-benzamide I-59

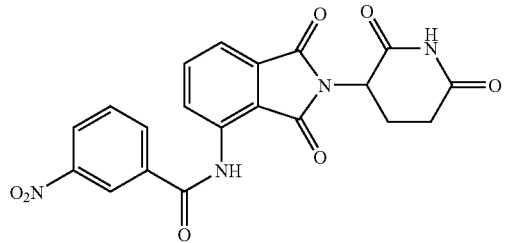

To a suspension of 4-amino-2-(2,6-dioxo(3-piperidyl))isoindoline-1,3-dione (1.10 g, 4 mmol) in THF (30 ml) was added 3-nitrobenzoyl chloride 1.48 g, 8 mmol). The mixture was heated to reflux for 18 hours. The reaction was cooled to room temperature, methanol (2 ml) was added, and the mixture stirred for 1 hour. The solvent was evaporated in vacuo leaving a solid that was slurried in diethyl ether (30 ml) and filtered to give 1.60 g (95%) of product as an off-white solid: mp 245-247° C.; $^1$H NMR (DMSO-d$_6$) d 10.85 (s, 1H), 10.53 (s, 1H), 8.76 (s, 1H), 8.50-8.37 (m, 3H), 7.95-7.87 (m, 2H), 7.70 (d, J=7.4 Hz, 1H), 5.14 (dd, J=5.7 and 12.7 Hz, 1H), 3.02-2.83 (m, 1H), 2.67-2.47 (m, 2H), 2.15-2.07 (m, 1H); $^{13}$C NMR (DMSO-d$_6$) d 171.73, 168.79, 167.19, 166.04, 162.85, 147.84, 135.60, 134.79, 132.92, 131.21, 130.19, 126.87, 126.20, 121.69, 118.83, 48.86, 30.51, 21.63; Anal. Calcd. For C$_{20}$H$_{14}$N$_4$O$_7$: C, 56.88; H, 3.34; N, 13.27. Found: C, 56.87; H, 3.33; N, 13.05.

N-[2-(2,6-Dioxo-piperidin-3-yl)-1,3-dioxo-2,3-dihydro-1H-isoindol-4-yl]-butyramide I-60

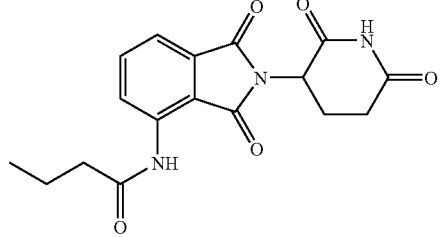

To a suspension of 4-amino-2-(2,6-dioxo(3-piperidyl))isoindoline-1,3-dione (0.55 g, 2 mmol) in THF (30 ml) was added butanoyl chloride (0.42 ml, 4 mmol). The mixture was heated to reflux for 18 hours. The reaction was cooled to room

2-(2,6-Dioxo-piperidin-3-yl)-4-heptylamino-isoindole-1,3-dione I-62

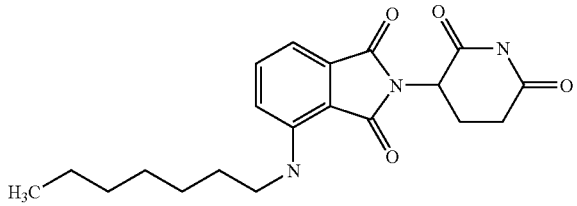

A mixture of 4-amino-2-(2,6-dioxo(3-piperidyl))isoindoline-1,3-dione (1.1 g, 4.0 mmol) and heptanal (3.4 mL, 24 mmol) and acetic acid (2 mL) in DMF (20 mL) was heated until all solid was dissolved. To the mixture was added sodium borohydride (605 mg, 16 mmol) and kept at room temperature for 18 h. To the mixture was added sodium borohydride (150 mg, 3.9 mmol) and kept at room temperature for 1 d. The mixture was extracted with ethyl acetate (200 mL) and water (100 mL). The organic layer was washed with water (100 mL). The solvent was removed in vacuo to give an oil. The oil was purified by column chromatography (Silca Gel, 33% EtOAc:$CH_2Cl_2$) to give 2-(2,6-Dioxo-piperidin-3-yl)-4-heptylamino-isoindole-1,3-dione as a yellow solid (610 mg, 41% yield): mp, 107-109° C.; $^1$H NMR (DMSO-$d_6$) δ 0.82-0.87 (m, 3H, $CH_3$), 1.24-1.29 (m, 8H, 4 $CH_2$), 2.00-2.04 (m, 1H, CHH), 2.43-2.62 (m, 2H, $CH_2$), 2.82-2.96 (m, 1H, CHH), 3.23-3.31 (m, 2H, $CH_2$), 5.06 (dd, J=5.3, 12.4 Hz, 1H, NCH), 6.51 (t, J=5.9 Hz, 1H, NH), 7.01 (d, J=7.0 Hz, 1H, Ar), 7.07 (d, J=8.6 Hz, 1H, Ar), 7.57 (dd, J=7.4, 8.4 Hz, 1H, Ar), 11.10 (s, 1H, NH); $^{13}$C NMR (DMSO-$d_6$) δ 13.91, 22.03, 22.17, 26.28, 28.42, 28.69, 30.98, 31.22, 34.84, 48.55, 109.03, 110.36, 117.13, 132.18, 136.24, 146.43, 167.29, 168.96, 170.05, 172.77; Anal Calcd for $C_{20}H_{25}N_3O_4$: C, 64.67; H, 6.78; N, 11.31. Found: C, 64.62; H, 6.76; N, 11.13.

4-Chloro-N-[2-(2,6-dioxo-piperidin-3-yl)-1,3-dioxo-2,3-dihydro-1H-isoindol-4-yl]-benzamide I-63

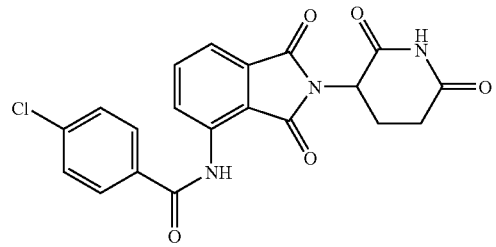

A mixture of 4-amino-2-(2,6-dioxo(3-piperidyl))isoindoline-1,3-dione (1.2 g, 4.5 mmol) and 4-chlorobenzoyl chloride (1.1 mL, 8.8 mmol) in THF (40 mL) was heated to reflux for 15 h. To the mixture was added methanol (5 mL) to give a suspension. The suspension was filtered and washed with ether (2×10 mL) then methanol (5 mL) to give 4-chloro-N-[2-(2,6-dioxo-piperidin-3-yl)-1,3-dioxo-2,3-dihydro-1H-isoindol-4-yl]-benzamide as a white solid (1.5 g, 81% yield): mp, 261-263° C.; $^1$H NMR (DMSO-$d_6$) δ 2.05-2.09 (m, 1H,

--- temperature, methanol (2 ml) was added, and the mixture stirred for 1 hour. The solvent was evaporated in vacuo leaving a solid that was slurried in diethyl ether (20 ml) and filtered to give 0.55 g (80%) of product as an off-white solid: mp 171-173° C.; $^1$H NMR (DMSO-$d_6$) d 11.14 (s, 1H), 9.68 (s, 1H), 8.48 (d, J=8.3 Hz, 1H), 7.83 (t, J=7.5 Hz, 1H), 7.61 (d, J=7.2 Hz, 1H), 5.15 (dd, J=5.2 and 12.6 Hz, 1H), 2.96-2.84 (m, 1H), 2.65-2.42 (m, 4H), 2.11-2.06 (m, 1H), 1.73-1.58 (m, 2H), 0.95 (t, J=7.4 Hz, 3H); $^{13}$C NMR (DMSO-$d_6$) d 172.70, 171.84, 169.72, 167.70, 166.63, 136.54, 136.07, 131.41, 126.17, 118.23, 116.89, 48.90, 30.91, 21.96, 18.25, 13.46; Anal. Calcd. For $C_{17}H_{17}N_3O_5$: C, 59.47; H, 4.99; N, 12.24. Found: C, 59.45; H, 4.82; N, 12.15.

N-[2-(2,6-Dioxo-piperidin-3-yl)-1,3-dioxo-2,3-dihydro-1H-isoindol-4-yl]-2-methylamino-acetamide hydrochloride I-61

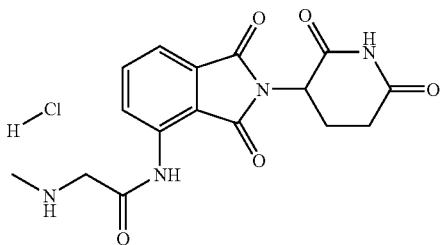

To a suspension of N-[2-(2,6-dioxo(3-piperidyl))-1,3-dioxoisoindolin-4-yl]-2-chloroacetamide (0.95 g, 2.72 mmol) in THF (30 ml) was added sodium iodide (0.41 g, 2.72 mmol) and 2M methyl amine in THF (4.08 ml, 8.15 mmol). The mixture was stirred at room temperature for 5 hours. The solvent was evaporated in vacuo leaving a white solid. The solid was slurried in ethyl acetate (200 ml) for 2 h. The suspension was then washed with water (3×100 ml), brine (100 ml), and dried (MgSO$_4$). The solvent was evaporated in vacuo leaving an off-white solid. The solid was dissolved in acetonitrile (20 ml) and to this solution was added 2M HCl in ether (2 ml). The mixture was stirred for 1 h and the solvent evaporated in vacuo. The residue was slurried in ethyl acetate for 3 h and filtered to give an off-white solid. The solid was dissolved in water (40 ml) and washed with ethyl acetate 2×50 ml). The pH of the aqueous portion was adjusted to 11-12 by dropwise addition of saturated aqueous sodium carbonate. The aqueous mixture was washed with ethyl acetate (3×100 ml). The combined ethyl acetate extracts were washed with brine (100 ml), and dried (MgSO$_4$). The solvent was evaporated in vacuo leaving a white solid. The solid was dissolved in acetonitrile (15 ml) and 2M HCl in ether (2 ml) was added to the solution. The mixture was stirred for 1 h and the solvent was evaporated in vacuo leaving a white solid. The solid was slurried in diethyl ether (20 ml) and filtered to give 0.18 g (17%) of product as a white solid: mp 228-230° C.; $^1$H NMR (DMSO-$d_6$) d 11.13 (s, 1H), 10.50 (s, 1H), 9.35 (bs, 2H), 8.28-8.21 (m, 1H), 7.93-7.63 (m, 2H), 5.15 (dd, J=5.1 and 12.6 Hz, 1H), 4.09 (s, 2H), 3.03-2.85 (m, 1H), 2.63-2.47 (m, 5H), 2.10-2.05 (m, 1H); $^{13}$C NMR (DMSO-$d_6$) d 171.99, 169.03, 166.35, 166.07, 164.75, 135.63, 134.46, 131.56, 127.45, 119.14, 118.85, 49.56, 48.82, 32.49, 30.59, 21.69; Anal. Calcd. For $C_{16}H_{17}ClN_4O_5$: C, 48.99; H, 4.70; N, 14.28. Found: C, 48.82; H, 4.72; N, 14.02+0.64H$_2$O.

CHH), 2.49-2.65 (m, 2H, CH$_2$), 2.83-2.98 (m, 1H, CHH), 5.18 (dd, J=5.5, 12.8 Hz, 1H, NCH), 7.68-7.72 (m, 3H, Ar), 7.89-8.01 (m, 3H, Ar), 8.52 (d, J=8.2, Hz, 1H, Ar), 10.47 (s, 1H, NH), 11.16 (s, 1H, NH); $^{13}$C NMR (DMSO-d$_6$) δ 21.99, 30.92, 48.98, 118.48, 119.06, 126.76, 129.10, 129.29, 131.46, 132.13, 136.28, 137.47, 164.08, 166.60, 167.86, 169.67, 172.72; Anal Calcd for C$_{21}$H$_{14}$N$_3$O$_5$Cl+0.2H$_2$O: C, 57.83; H, 3.49; N, 10.12; Cl, 8.53; H$_2$O, 0.87. Found: C, 57.88; H, 3.33; N, 9.93; Cl, 8.53; H$_2$O, 0.73.

Cyclopropanecarboxylic acid [2-(2,6-dioxo-piperidin-3-yl)-1,3-dioxo-2,3-dihydro-1H-isoindol-4-yl]-amide I-64

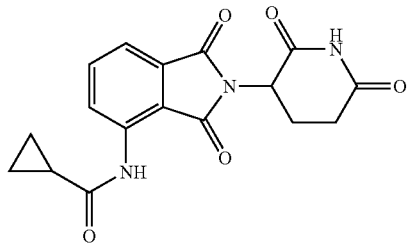

A mixture of 4-amino-2-(2,6-dioxo(3-piperidyl))isoindoline-1,3-dione (0.60 g, 2.2 mmol) and cyclopropanecarbonyl chloride (0.4 mL, 4.4 mmol) in THF (20 mL) was heated to reflux for 15 h. To the mixture was added methanol (5 mL). The solvent was removed in vacuo to give a solid. The solid was slurried in ether (30 mL) for 1 h. The suspension was filtered and washed with ether (30 mL) to give cyclopropanecarboxylic acid [2-(2,6-dioxo-piperidin-3-yl)-1,3-dioxo-2,3-dihydro-1H-isoindol-4-yl]-amide as a solid (630 mg, 84% yield): mp, 237-239° C.; $^1$H NMR (DMSO-d$_6$) δ 0.87-0.90 (m, 4H, 2CH$_2$), 1.93-2.09 (m, 2H, CH, CHH), 2.49-2.65 (m, 2H, CH$_2$), 2.64-2.96 (m, 1H, CHH), 5.15 (dd, J=5.2, 12.6 Hz, 1H, NCH), 7.61 (d, J=7.2 Hz, 1H, Ar), 7.82 (t, J=7.7 Hz, 1H, Ar), 8.41 (d, J=8.3 Hz, 1H, Ar), 9.99 (s, 1H, NH), 11.16 (s, 1H, NH); $^{13}$C NMR (DMSO-d$_6$) δ 8.10, 14.93, 22.00, 30.93, 48.92, 117.07, 118.30, 126.69, 131.49, 135.97, 136.43, 166.67, 167.57, 169.77, 172.55, 172.74; Anal Calcd for C$_{17}$H$_{15}$N$_3$O$_5$: C, 59.82; H. 4.43; N. 12.31. Found: C, 59.50; H, 4.39; N, 12.04.

N-[2-(2,6-Dioxo-piperidin-3-yl)-1,3-dioxo-2,3-dihydro-1H-isoindol-4-yl]-4-fluoro-benzamide I-65

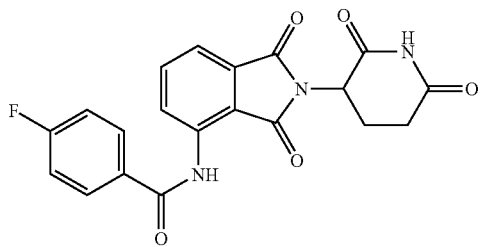

A mixture of 4-amino-2-(2,6-dioxo(3-piperidyl))isoindoline-1,3-dione (1.1 g, 4.0 mmol) and 4-fluorobenzoyl chloride (0.95 mL, 8.0 mmol) in THF (40 mL) was heated to reflux for 15 h. To the mixture was added methanol (5 mL) to give a suspension. The suspension was filtered and washed with ether (2×10 mL) then methanol (5 mL) to give N-[2-(2,6-dioxo-piperidin-3-yl)-1,3-dioxo-2,3-dihydro-1H-isoindol-4-yl]-4-fluoro-benzamide as a yellow solid (1.2 g, 77% yield): mp, 283-285° C.; $^1$H NMR (DMSO-d$_6$) δ 2.06-2.10 (m, 1H, CHH), 2.48-2.65 (m, 2H, CH$_2$), 2.83-2.97 (m, 1H, CHH), 5.18 (dd, J=5.4, 12.6 Hz, 1H, NCH), 7.42-7.49 (m, 2H, Ar), 7.69 (d, J=7.2, Hz, 1H, Ar), 7.91 (t, J=8.2 Hz, 1H, Ar), 8.03-8.08 (m, 2H, Ar), 8.54 (d, J=8.3 Hz, 1H, Ar), 10.41 (s, 1H, NH), 11.15 (s, 1H, NH); $^{13}$C NMR (DMSO-d$_6$) δ 22.10, 30.98, 49.29, 115.96 (d, J$_{C-F}$=22 Hz); 118.03, 118,67, 128.09 (d, J$_{C-F}$=235 Hz), 130.12, 131.49, 136.18, 136.75, 162.70, 164.08, 166.56, 168.22, 169.29, 172.27; Anal Calcd for C$_{20}$H$_{14}$N$_3$O$_5$F+0.2H$_2$O: C, 60.21; H, 3.64; N, 10.53; F, 4,76; H$_2$O, 0.90. Found: C, 60.17; H, 3.55; N, 10.47; F, 4.90; H$_2$O, 0.95.

N-[2-(2,6-Dioxo-piperidin-3-yl)-1,3-dioxo-2,3-dihydro-1H-isoindol-4-yl]-4-trifluoromethyl-benzamide I-66

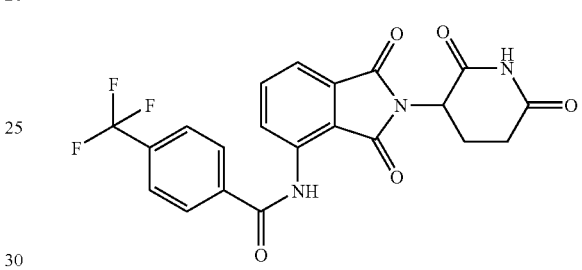

A mixture of 4-amino-2-(2,6-dioxo(3-piperidyl))isoindoline-1,3-dione (0.6 g, 2.2 mmol) and 4-(trifluoromethyl)benzoyl chloride (1 g, 4.8 mmol) in THF (20 mL) was heated to reflux for 15 h. The solvent was removed in vacuo to give a solid. The solid was slurried in methanol (20 mL) for 2 h. The suspension was filtered and washed with ether (15 mL) then methanol (15 mL) to give N-[2-(2,6-dioxo-piperidin-3-yl)-1,3-dioxo-2,3-dihydro-1H-isoindol-4-yl]-4-trifluoromethyl-benzamide as a white solid (750 mg, 77% yield): mp, 213-215° C.; $^1$H NMR (DMSO-d$_6$) δ 2.05-2.10 (m, 1H, CHH), 2.49-2.65 (m, 2H, CH$_2$), 2.83-2.98 (m, 1H, CHH), 5.18 (dd, J=5.2, 12.5 Hz, 1H, NCH), 7.72 (d, J=7.2 Hz, 1H, Ar), 7.90-8.02 (m, 3H, Ar), 8.16-8.19 (m, 2H, Ar), 8.49 (d, J=8.4 Hz, 1H, Ar), 10.58 (s, 1H, NH), 11.17 (s, 1H, NH); $^{13}$C NMR (DMSO-d$_6$) δ 21.99, 30.92, 48.99, 118.88, 119.36, 119.32, 123.76 (q, J$_{C-F}$=271 Hz); 125.99 (q, J$_{C-F}$=3.6 Hz), 127.10 128.37, 131.54, 132.16 (q, J$_{C-F}$=32 Hz), 136.00, 136.26, 13721, 164.05, 166.59, 167.65, 169.68, 172.73; Anal Calcd for C$_{21}$H$_{14}$N$_3$O$_5$F$_3$: C, 56.64; H. 3.17; N, 9.44; F, 12.80. Found: C, 56.25; H, 3.05; N, 9.32; F, 12.69.

N-[2-(2,6-Dioxo-piperidin-3-yl)-1,3-dioxo-2,3-dihydro-1H-isoindol-4-yl]-4-methyl-benzamide I-67

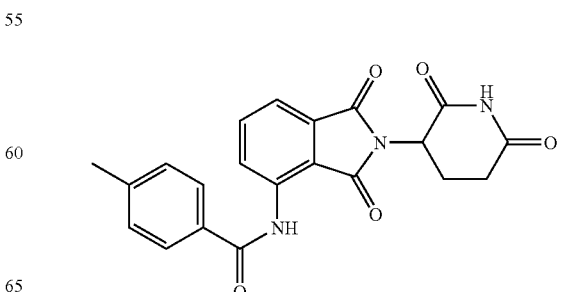

A mixture of 4-amino-2-(2,6-dioxo(3-piperidyl))isoindoline-1,3-dione (1.1 g, 4.0 mmol) and 4-methylbenzoyl chloride (1.1 g, 8.0 mmol) in THF (40 mL): was heated to reflux for 36 h. To the mixture was added methanol (5 mL) to give a suspension. The suspension was filtered and washed with methanol (15 mL) to give N-[2-(2,6-dioxo-piperidin-3-yl)-1,3-dioxo-2,3-dihydro-1H-isoindol-4-yl]-4-methyl-benzamide as a yellow solid (1.3 g, 83% yield): mp, 322-324° C.; $^1$H NMR (DMSO-$d_6$) δ 2.06-2.10 (m, 1H, CHH), 2.41 (s, 3H, $CH_3$), 2.50-2.65 (it, 2H, $CH_2$), 2.83-2.97 (m, 1H, CHH), 5.19 (dd, J=5.3, 12.6 Hz, 1H, NCH), 7.42 (d, J=8.1 Hz, 2H, Ar), 7.67 (d, J=7.2 Hz, 1H, Ar), 7.86-7.93 (m, 3H, Ar), 8.62 (d, J=8.4 Hz, 1H, Ar), 10.37 (s, 1H, NH), 11.18 (s, 1H, NH); $^{13}$C NMR (DMSO-$d_6$) δ 21.07, 21.99, 30.93, 48.99, 117.57, 118.58, 125.94, 127.28, 129.58, 130.44, 131.33, 136.34, 136.77, 142.96, 164.80, 166.65, 168.29, 169.69, 172.72; Anal Calcd for $C_{21}H_{17}N_3O_5$: C, 64.45; H, 4.38; N, 10.74. Found: C, 64.65; H, 4.17; N, 10.70.

N-[2-(2,6-Dioxo-piperidin-3-yl)-1,3-dioxo-2,3-dihydro-1H-isoindol-4-yl]-4-nitro-benzamide I-68

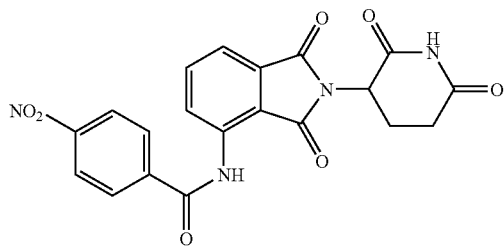

A mixture of 4-amino-2-(2,6-dioxo(3-piperidyl))isoindoline-1,3-dione (2.2 g, 8.0 mmol) and 4-nitrobenzoyl chloride (3.0 g, 16.0 mmol) in THF (80 mL) was heated to reflux for 15 h. To the mixture was added methanol (20 mL) to give a suspension. The suspension was filtered and washed with methanol (20 mL) to give N-[2-(2,6-Dioxo-piperidin-3-yl)-1,3-dioxo-2,3-dihydro-1H-isoindol-4-yl]-4-nitro-benzamide as a white solid (2.5 g, 73% yield): mp, 298-300° C.; $^1$H NMR (DMSO-$d_6$) δ 2.06-2.10 (m, 1H, CHH), 2.49-2.65 (m, 2H, $CH_2$), 2.83-2.98 (m, 1H, CHH), 5.18 (dd, J=5.2, 12.6 Hz, 1H, NCH), 7.73 (d, J=7.2 Hz, 1H, Ar), 7.93 (t, J=8.0 Hz, 1H, Ar), 8.19-8.22 (m, 2H, Ar), 8.42-8.47 (m, 3H, Ar), 10.65 (s, 1H, NH), 11.18 (s, 1H, NH); $^{13}$C NMR (DMSO-$d_6$) δ 21.99, 30.92, 48.99, 119.30, 119.56, 124.06, 127.49, 129.01, 131, 58, 135.77, 136.23, 138.96, 149.69, 163.65, 166.57, 167.48, 169.68, 172.72; Anal Calcd for $C_{21}H_{14}N_4O_7$: C, 56.88; H, 3.34; N, 13.27. Found: C, 57.15; H, 3.02; N, 13.22.

N-[2-(2,6-Dioxo-piperidin-3-yl)-1,3-dioxo-2,3-dihydro-1H-isoindol-4-yl]-2-ethoxy-acetamide I-69

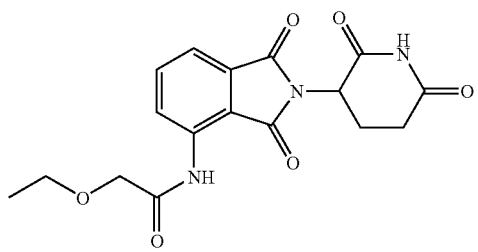

To a solution of ethoxyacetic acid (0.8 mL, 8.5 mmol) and oxalyl chloride (0.7 mL, 8.0 mmol) in ether (5 mL) was added DMF (0.03 mL) at room temperature. After 3 h, 4-amino-2-(2,6-dioxo(3-piperidyl))isoindoline-1,3-dione (1.1 g, 4.0 mmol) and THF (40 mL) was added to the mixture. Then the mixture was heated to reflux for 15 h. To the mixture was added methanol (10 mL) to give a suspension. The suspension was filtered and washed with methanol (10 mL) to give N-[2-(2,6-dioxo-piperidin-3-yl)-1,3-dioxo-2,3-dihydro-1H-isoindol-4-yl]-2-ethoxy-acetamide as a white solid (1.3 g, 87% yield): mp, 253-255° C.; $^1$H NMR (DMSO-$d_6$) δ 1.27 (t, J=7.0 Hz, 3H, $CH_3$), 2.06-2.10 (m, 1H, CHH), 2.46-2.64 (m, 2H, $CH_2$), 2.84-2.98 (m, 1H, CHH), 3.66 (q, J=7.0 Hz, 2H, $CH_2$), 4.14 (s, 2H, $CH_2$), 5.17 (dd, J=5.2, 12.7 Hz, 1H, NCH), 7.62 (d, J=7.2 Hz, 1H, Ar), 7.87 (t, J=8.2 Hz, 1H, Ar), 8.75 (d, J=8.4 Hz, 1H, Ar), 10.39 (s, 1H, NH), 11.16 (s, 1H, NH); $^{13}$C NMR (DMSO-d6) δ 14.88, 21.93, 30.92, 48.98, 66.89, 69.49, 116.00, 118.28, 124.25, 131.31, 135.99, 136.53, 166.69, 168.31, 169.49, 169.73, 174.71; Anal Calcd for $C_{17}H_{17}N_3O_6$: C, 56.82; H, 4.77; N, 11.69. Found: C, 56.82; H, 4.71; N, 11.60.

N-[2-(2,6-Dioxo-piperidin-3-yl)-1,3-dioxo-2,3-dihydro-1H-isoindol-4-yl]-2-methoxy-benzamide I-70

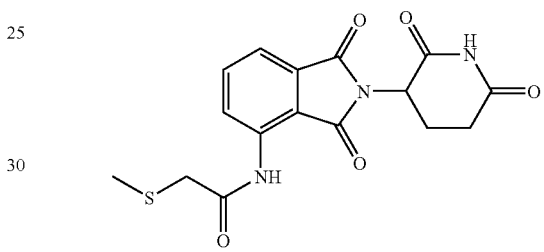

To a solution of (methylthio)acetic acid (0.77 mL, 8.9 mmol) and oxalyl chloride (0.7 mL, 8.0 mmol) in ether (5 mL) was added DMF (0.02 mL) at room temperature. After 3 h, 4-amino-2-(2,6-dioxo(3-piperidyl))isoindoline-1,3-dione (1.1 g, 4.0 mmol) and THF (40 mL) was added to the mixture. Then the mixture was heated to reflux for 15 h. To the mixture was added methanol (10 mL) to give a suspension. The suspension was filtered and washed with methanol (10 mL) to give N-[2-(2,6-dioxo-piperidin-3-yl)-1,3-dioxo-2,3-dihydro-1H-isoindol-4-yl]-2-methylsulfanyl-acetamide as a white solid (1.0 g, 69% yield): mp, 228-230° C.; $^1$H NMR (DMSO-$d_6$) δ 2.05-2.10 (m, 1H, CHH), 2.18 (s, 3H, $CH_3$), 2.46-2.65 (m, 2H, $CH_2$), 2.82-2.95 (m, 1H, CHH), 3.53 (s, 2H, $CH_2$), 5.17 (dd, J=5.2, 12.6 Hz, 1H, NCH), 7.63 (d, J=7.2 Hz, 1H, Ar), 7.86 (t, J=7.5 Hz, 1H, Ar), 8.61 (d, J=8.4 Hz, 1H, Ar), 10.39 (s, 1H, NH), 11.16 (s, 1H, NH); $^{13}$C NMR (DMSO-$d_6$) δ 15.62, 21.96, 30.93, 37.99, 48.94, 116.69, 118.46, 125.28, 131.44, 136.31, 166.67, 167.88, 168.63, 169.78, 172.75; Anal Calcd for $C_{16}H_{15}N_3O_5S$: C, 53.18; H, 4.18; N, 11.63. Found: C, 53.26; H, 4.17; N, 11.52.

N-[2-(2,6-Dioxo-piperidin-3-yl)-1,3-dioxo-2,3-dihydro-1H-isoindol-4-yl]-2-methoxy-benzamide I-71

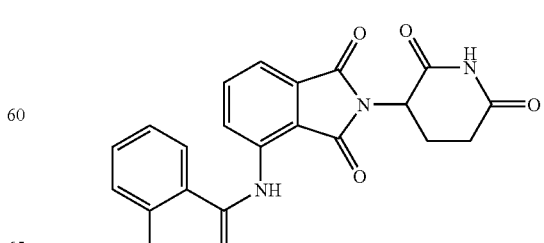

A mixture of 4-amino-2-(2,6-dioxo(3-piperidyl))isoindoline-1,3-dione (660 mg, 2.4 mmol) and 2-methoxybenzoyl chloride (0.7 mL, 4.7 mmol) in THF (20 mL) was heated to reflux for 15 h. To the mixture was added methanol (5 mL) to give a suspension. The suspension was filtered and washed with methanol (20 mL) to give N-[2-(2,6-dioxo-piperidin-3-yl)-1,3-dioxo-2,3-dihydro-1H-isoindol-4-yl]-2-methoxy-benzamide as a white solid (760 mg, 78% yield): mp, 286-287° C.; $^1$H NMR (DMSO-$d_6$) (at 340K) δ 2.09-2.14 (m, 1H, CHH), 2.55-2.66 (m, 2H, $CH_2$), 2.85-2.98 (m, 1H, CHH). 4.14 (s, 3H, $OCH_3$), 5.19 (dd, J=5.5, 12.9 Hz, 1H, NCH), 7.17 (t, J=7.2 Hz, 1H, Ar), 7.30 (d, J=8.3 Hz, 1H, Ar), 7.61-7.68 (m, 2H, Ar), 7.89 (t, J=. 7.7 Hz, 1H, Ar), 8.12 (dd, J=1.8, 7.9 Hz, 1H Ar), 9.03 (d, J=8.5 Hz, 1H, Ar), 11.17 (s, 1H, NH), 11.64 (s, 1H, NH); $^{13}$C NMR (DMSO-$d_6$) (at 340K) δ 22.09, 31.02, 49.29, 56.19, 112.65, 116.31, 117,93, 120.66, 121.14, 125.52, 131.59, 131.75, 134.34, 136.22, 137.00, 157.64, 163.82, 166.69, 168.15, 169.43, 172.32; Anal Calcd for $C_{21}H_{17}N_3O_6$: C, 61.92; H, 4.21; N, 10.31. Found: C, 62.05; H, 4.10; N, 10.38.

N-[2-(2,6-Dioxo-piperidin-3-yl)-1,3-dioxo-2,3-dihydro-1H-isoindol-4-yl]-2-fluoro-benzamide I-72

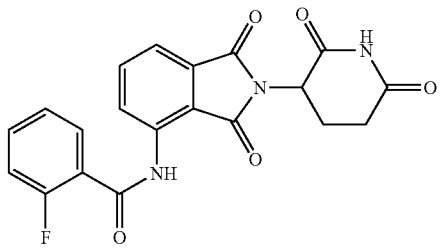

A mixture of 4-amino-2-(2,6-dioxo(3-piperidyl))isoindoline-1,3-dione (1.1 g, 4.0 mmol) and 2-fluorobenzoyl chloride (1.0 mL, 8.4 mmol) in THF (40 mL) was heated to reflux for 15 h. To the mixture was added methanol, (10 mL) to give a suspension. The suspension was filtered and washed with methanol (20 mL) to give N-[2-(2,6-dioxo-piperidin-3-yl)-1,3-dioxo-2,3-dihydro-1H-isoindol-4-yl]-2-fluoro-benzamide as a white solid (1.5 g, 93% yield): mp, 300-302° C.; $^1$H NMR (DMSO-$d_6$) δ 2.05-2.12 (m, 1H, CHH), 2.45-2.65 (m, 2H, $CH_2$), 2.83-2.97 (m, 1H, CHH), 5.18 (dd, J=5.5, 12.9 Hz, 1H, NCH), 7.40-7.49 (m, 2H, Ar), 7.67-7.76 (m, 2H, Ar), 7.88-7.98 (m, 1H, Ar), 8.01-8.05 (m, 1H, Ar), 8.76 (d, J=8.4 Hz, 1H Ar), 10.56 (d, $J_{N-F}$=10 Hz, 1H, NH), 11.17 (s, 1H, NH); $^{13}$C NMR (DMSO-$d_6$) δ 21.96, 30.92, 48.97, 116.48, 116.97 (d, $J_{C-F}$=14 Hz), 118.82, 120.87 (d, $J_{C-F}$=12 Hz), 125.32 (d, $J_{C-F}$=1.5 Hz), 125.74, 131.32, 131.39, 134.88 (d, $J_{C-F}$=9 Hz), 136.22, 136.48, 159.75 (d, $J_{C-F}$=252 Hz), 161.76 (d, $J_{C-F}$=7 Hz), 166.58, 168.04, 169.70, 172.71; Anal Calcd for $C_{20}H_{14}N_3O_5F$: C, 60.76; H, 3.57; N, 10.63; F, 4.81. Found: C, 60.70; H, 3.64; N, 10.64; F. 4.91.

7-Amino-N-{[2-(2,6-dioxo(3-piperidyl))-1,3-dioxoisoindolin-4-yl]methyl}heptanamide Hydrochloride I-73

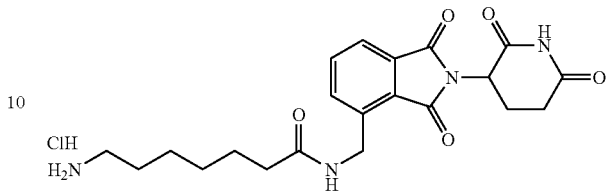

Step 1: 1,8-Diazabicyclo[5,4,0]undec-7-ene (0.7 g, 4.62 mmol) was added to a stirred suspension of 4-(aminomethyl)-2-(2,6-dioxo(3-piperidyl))isoindoline-1,3-dione hydrochloride (0.6 g, 1.85 mmol) in $CH_3CN$ (50 mL). After stirring for 20 min, 1-hydroxybenzotriazole (0.3 g, 2.22 mmol), N—BOC-7-aminoheptanoic acid (0.54 g, 2.22 mmol) and 1-[3-(dimethylamino)propyl]-3-ethylcarbodimide hydrochloride (0.53 g, 2.78 mmol) were added. The mixture was stirred at room temperature for 17 hours. The solvent was removed in vacuo and the residue was dissolved in $CH_2Cl_2$ (70 mL). The $CH_2Cl_2$ solution was washed with 1N citric acid (30 mL), $H_2O$ (2×30 mL), brine (30 mL) and dried ($MgSO_4$). The solvent was removed in vacuo and the residue was purified by chromatography ($SiO_2$, $CH_2Cl_2$: EtOAc 1:1) to give 7-[(tert-butoxy)carbonylamino]-N-{[2-(2,6-dioxo(3-piperidyl))-1,3-dioxoisoindolin-4-yl]methyl}heptanamide (0.74 g, 77%) as a white solid: $^1$H NMR ($CDCl_3$) δ 11.4 (s, 1H), 8.44 (t, J=5.7 Hz, 1H), 7.83-7.78 (m, 2H), 7.68-7.65 (m, 1H), 6.77 (t, J=5.1 Hz, 1H), 5.19-5.11 (dd, J=5.4 and 12.4 Hz, 1H), 4.71 (d, J=5.8 Hz, 2H), 2.93-2.84 (m, 3H), 2.63-2.49 (m, 2H), 2.21-2.05 (m, 1H), 1.55-1.49 (m, 2H), 1.36 (s, 9H), 1.36-1.20 (m, 6H).

Step 2: A 4N HCl solution in dioxane (1.5 mL) was added to a stirred solution of 7-[(tert-butoxy)carbonylamino]-N-{[2-(2,6-dioxo(3-piperidyl))-1,3-dioxoisoindolin-4-yl]methyl}heptanamide (0.72 g, 1.40 mmol) in $CH_2Cl_2$ (25 mL) and stirred for 17 hours. The resulting suspension was filtered to give 7-amino-N-{[2-(2,6-dioxo(3-piperidyl))-1,3-dioxoisoindolin-4-yl]methyl}heptanamide hydrochloride (0.26 g, 41%) as a white solid. mp 187-189° C.; $^1$H NMR (DMSO-$d_6$) δ 11.12 (s, 1H), 8.52 (t, J=5.7 Hz, 1H), 7.93 (b, 3H), 7.88-7.67 (m, 3H), 5.18-5.11 (dd, J=5.3 and 12.4 Hz, 1H), 4.72 (d, J=5.7 Hz, 2H), 2.91-2.50 (m, 5H), 2.21 (t, J=7.2 Hz, 2H), 2.08-2.04 (m, 1H), 1.57-1.52 (m, 4H), 1.31-1.29 (m, 4H), $^{13}$C NMR ($CDCl_3$) δ 172.70, 172.55, 169.77, 167.44, 166.90, 139.54, 134.68, 133.08, 131.47, 127.01, 121.77, 48.82, 38.64, 37.53, 35.00, 30.90, 28.05, 26.73, 25.50, 24.89, 21.95; Anal. Calcd. For $C_{21}H_{27}N_4O_5Cl$+0.64$H_2O$: C, 54.95; H, 6.13; N, 12.21; Cl, 7,72. Found: C, 54.56; H, 6.10; N, 11.96; Cl, 8.04.

N-{[2-(2,6-Dioxo(3-piperidyl))-1,3-dioxoisoindolin-4-yl]methyl}butanamide I-74

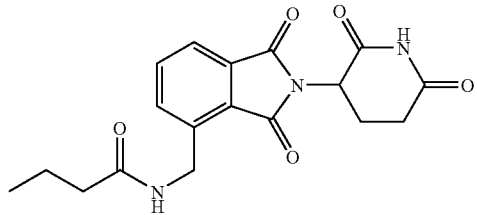

1,8-Diazabicyclo[5,4,0]undec-7-ene (0.62 g, 4.08 mmol) 2, 139.53, 134.68, 133.11, 131.49, 127.04, 12.1.77, 48.84, 37.55, 37.16, 30.91, 21,96, 18.60, 13.63; Anal. Calcd. For $C_{18}H_{19}N_3O_5$: C, 60.50; H, 5.36; N, 11.76. Found: C, 60.46; H, 5.36; N, 11.59.

N-{[2-(2,6-Dioxo(3-piperidyl))-1,3-dioxoisoindolin-4-yl]methyl}benzamide I-75

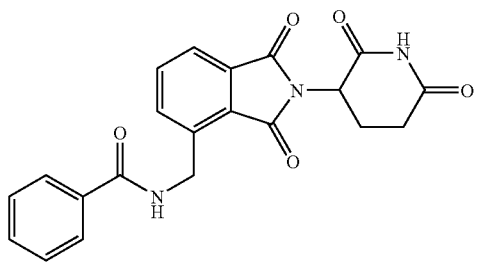

1,8-Diazabicyclo[5,4,0]undec-7-ene (0.62 g, 4.08 mmol) was added to a stirred suspension of 4-(aminomethyl)-2-(2,6-dioxo(3-piperidyl))isoindoline-1,3-dione hydrochloride (0.6 g, 1.85 mmol) in $CH_3CN$ (50 mL). After stirring for 20 min, benzoyl chloride (0.31 g, 2.22 mmol) was added. The mixture was stirred at room temperature for 17 hours. The solvent was removed in vacuo and the residue was dissolved in $CH_2Cl_2$ (70 mL). The $CH_2Cl_2$ solution was washed with $H_2O$ (30 mL), brine (30 mL) and dried ($MgSO_4$). The solvent was removed and the residue was purified by chromatography ($SiO_2$, $CH_2Cl_2$: EtOAC 6:4) to give N-{[2-(2,6-dioxo(3-piperidyl))-1,3-dioxoisoindolin-4-yl]methyl}benzamide (0.55 g, 76%) as a white solid: mp 227-229° C.; $^1$H NMR (DMSO-$d_6$) δ 11.16 (s, 1H), 9.16 (t, J=5.7 Hz, 1H), 7.95-7.72 (m, 5H), 7.60-7.46 (m, 3H), 5.22-5.12 (dd, J=5.4 and 12.8 Hz, 1H), 4.96 (d, J=5.7 Hz, 2H), 2.98-2.85 (m, 1H), 2.65-2.50 (m, 2H), 2.11-2.06 (m, 1H); $^{13}$C NMR (DMSO-$d_6$) δ 172.72, 169.80, 167.54, 166.96, 166.60, 139.34, 134.77, 133.92, 133.02, 131.52, 131.42, 128.34, 127.28, 127.12, 121.83, 48.88, 38.32, 30.93, 21.98; Anal. Calcd. For $C_{21}H_{17}N_3O_5$: C, 64.45; H, 4.38; N, 10.74. Found: C, 64.47; H, 4.50; N, 10.34.

N-{[2-(2,6-Dioxo(3-piperidyl))-1,3-dioxoisoindolin-4-yl]methyl}phenylacetamide I-76

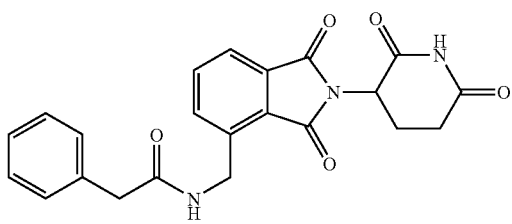

1,8-Diazabicyclo[5,4,0]undec-7-ene (0.65 g, 4.26 mmol) was added to a stirred suspension of 4-(aminomethyl)-2-(2,6-dioxo(3-piperidyl))isoindoline-1,3-dione hydrochloride (0.60 g, 1.85 mmol) in $CH_3CN$ (50 mL). After stirring for 20 min, phenylacetyl chloride (0.35 g, 2.22 mmol) was added. The mixture was stirred at room temperature for 17 hours. The solvent was removed in vacuo and the residue was dissolved in $CH_2Cl_2$ (70 mL). The $CH_2Cl_2$ solution was washed with 1N HCl (30 mL), $H_2O$ (30 mL), brine (30 mL) and dried ($MgSO_4$). The solvent was removed in vacuo and the residue was purified by chromatography ($SiO_2$, $CH_2Cl_2$: EtOAc 6:4) to give N-{[2-(2,6-dioxo(3-piperidyl))-1,3-dioxoisoindolin-4-yl]methyl}-2-phenylacetamide (0.41 g, 55%) as a white solid: mp 128-130° C.; $^1$H NMR (DMSO-$d_6$) δ 11.14 (s, 1H), 8.67 (t, J=5.5 Hz, 1H), 7.80-7.61 (m, 3H), 7.29 (s, 5H), 5.19-5.12 (dd, J=5.1 and 12.4 Hz, 1H), 4.71 (d, J=5.5 Hz, 2H), 3.53 (s, 2H), 2.96-2.83 (m, 1H), 2.63-2.50 (m, 2H), 2.08-2.03 (m, 1H); $^{13}$HNMR (DMSO-$d_6$) δ 172.77, 170.65, 169.82, 167.45, 166.93, 139.19, 136.15, 134.68, 133.18, 131.53, 129.05, 128.25, 127.13, 126.43, 121.90, 48.85, 42.24, 37.85, 30.93, 21.98; Anal. Calcd. For $C_{22}H_{19}N_3O_5$: C, 65.18; H, 4.72; N, 10.36. Found: C, 65.16; H, 4.75; N, 10.11.

N-{[2-(2,6-Dioxo(3-piperidyl))-1,3-dioxoisoindolin-4-yl]methyl}2pyridylcarboxamide I-77

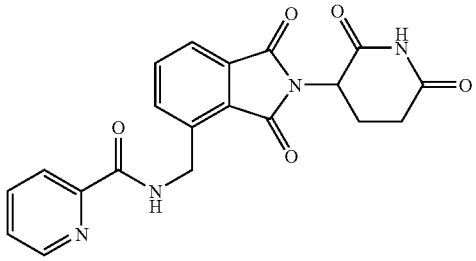

1,8-Diazabicyclo[5,4,0]undec-7-ene (0.98 g, 6.48 mmol) was added to a stirred suspension of 4-(aminomethyl)-2-(2,6-dioxo(3-piperidyl))isoindoline-1,3-dione hydrochloride (0.60 g, 1.85 mmol) in $CH_3CN$ (50 mL). After stirring for 20 min, picolinoyl chloride hydrochloride (0.41 g, 2.22 mmol) was added. The mixture was stirred at room temperature for 17 hours. The solvent was removed in vacuo and the residue was dissolved in $CH_2Cl_2$ (70 mL). The $CH_2Cl_2$ solution was washed with 1N HCL (30 mL), $H_2O$ (30 mL), brine (30 mL) and dried ($MgSO_4$). The solvent was removed in vacuo and the residue was purified by chromatography ($SiO_2$, $CH_2Cl_2$: $CH_3OH$ 97.5:2.5) to give N-{[2-(2,6-dioxo(3-piperidyl))-1,3-dioxoisoindolin-4-yl]methyl}-2-pyridylcarboxamide (0.40 g, 55%) as a white solid: mp 155-157° C.; $^1$H NMR (DMSO-$d_6$) δ 11.15 (s, 1H), 9.50 (t, J=6.2 Hz, 1H), 8.70 (d, J=4.6 Hz, 1H), 8.08-7.98 (m, 2H), 7.82-7.62 (m, 4H), 5.21-5.14 (dd, J=5.4 and 12.6 Hz, 1H), 4.97 (d, J=6.3 Hz, 2H), 2.99-2.84 (m, 1H), 2.65-2.50 (m, 2H), 2.10-2.06 (m, 1H); $^{13}$C NMR (DMSO-$d_6$) δ 172.77, 169.85, 167.59, 166.99, 164.38, 149.56, 148.56, 139.02, 137.87, 134.79, 132.95, 131.57, 127.16, 126.76, 122.05, 121.87, 48.87, 38.37, 30.94, 21.97; Anal. Calcd. For $C_{20}H_{16}N_4O_5$+0.08$H_2O$: C, 61.08; H, 4.13; N, 14.25. Found: C, 61.48; H, 4.22; N, 13.87.

N-{[2-(2,6-Dioxo(3-piperidyl))-1,3-dioxoisoindolin-4-yl]methyl}undecamide I-78

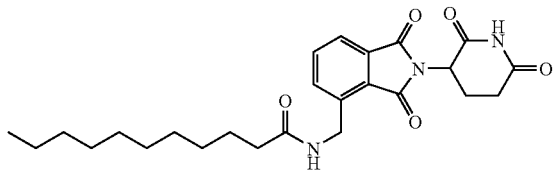

1,8-Diazabicyclo[5,4,0]undec-7-ene (0.62 g, 4.08 mmol) was added to a stirred suspension of 4-(aminomethyl)-2-(2,6-dioxo(3-piperidyl))isoindoline-1,3-dione hydrochloride (0.60 g, 1.85 mmol) in $CH_3CN$ (50 mL). After stirring for 20 min, undecanoyl chloride (0.45 g, 2.22 mmol) was added. The mixture was stirred at room temperature for 17 hours. The solvent was removed and the residue was dissolved in $CH_2Cl_2$ (70 mL). The $CH_2Cl_2$ solution was washed with 1N HCl (30 mL), $H_2O$ (30 mL), brine (30 mL) and dried ($MgSO_4$). The solvent was removed in vacuo and the residue was purified by chromatography ($SiO_2$, $CH_2Cl_2$: EtOAc 6:4) to give N-{[2-(2,6-dioxo(3-piperidyl))-1,3-dioxoisoindolin-4-yl]methyl}undecanamide (0.53 g, 63%) as a white solid: mp 138-139° C.; $^1$H NMR (DMSO-$d_6$) δ 11.12 (s, 1H), 8.42 (t, J=5.9 Hz, 1H), 7.85-7.78 (m, 2H), 7.71-7.65 (m, 1H), 5.18-5.11 (dd, J=5.4 and 12.5 Hz, 1H), 4.72 (d, J=5.9 Hz, 2H), 2.96-2.83 (m, 1H), 2.64-2.47 (m, 2H), 2.18 (t, J=7.3 Hz, 2H), 2.08-2.04 (m, 1H), 1.55-1.50 (m, 2H), 1.24 (s, 14H), 0.85 (t, J=6.1 Hz, 3H); $^{13}$C NMR (DMSO-$d_6$) δ 172.74, 172.63, 169.80, 167.47, 166.93, 139.55, 134.65, 133.10, 131.50, 127.04, 121.79, 48.83, 37.55, 35.21, 31,28, 30.92, 28.94, 28.74, 28.67, 25.20, 22.08, 21.97, 13.94; Anal. Calcd. For $C_{25}H_{33}N_3O_5$: C, 65.91; H, 7.30; N, 9.23. Found: C, 66.08; H, 7.13; N, 9.23.

N-{[2-(2,6-Dioxo(3-piperidyl))-1,3-dioxoisoindolin-4-yl]methyl}2-methylpropanamide I-79

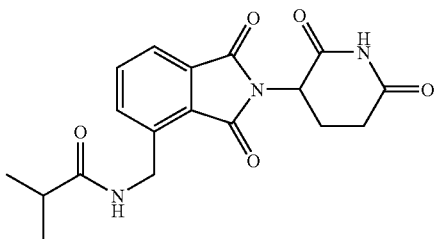

1,8-Diazabicyclo[5,4,0]undec-7-ene (0.62 g, 4.08 mmol) was added to a stirred suspension of 4-(aminomethyl)-2-(2,6-dioxo(3-piperidyl))i soindoline-1,3-dione hydrochloride (0.60 g, 1.85 mmol) in $CH_3CN$ (50 mL). After stirring for 20 min, isobutyryl chloride (0.24 g, 2.22 mmol) was added. The mixture was stirred at room temperature for 17 hours. The solvent was removed in vacuo and the residue was dissolved in $CH_2Cl_2$ (70 mL). The $CH_2Cl_2$ solution was washed with 1N HCl (30 mL), $H_2O$ (30 mL), brine (30 mL) and dried ($MgSO_4$). The solvent was removed in vacuo and the solid was purified from ether (10 mL) and hexane (10 mL) to give N-{[2-(2,6-dioxo(3-piperidyl))-1,3-dioxoisoindolin-4-yl]methyl}-2-methylpropanamide (0.48 g, 73%) as a white solid: mp 218-220° C.; $^1$H NMR (DMSO-$d_6$) δ 11.13 (s, 1H), 8.39 (t, J=5.8 Hz, 1H), 7.87-7.78 (m, 2H), 7.66-7.63 (m, 1H), 5.19-5.12 (dd, J=6.9 and 12.5 Hz, 1H), 4.71 (d, J=5.8 Hz, 2H), 2.97-2.83 (m, 1H), 2.63-2.43 (m, 3H), 2.08-2.04 (m, 1H), 1.07 (d, J=6.9 Hz, 6H); $^{13}$C NMR (DMSO-$d_6$) δ 176.52, 172.75, 169.82, 167.49, 166.95, 139.54, 134.77, 132.85, 131.50, 127.02, 121.77, 48.83, 37.48, 33.98, 30.92, 21.96, 19.53; Anal. Calcd. For $C_{18}H_{19}N_3O_5$: C, 60.50; H, 5.36; N, 11.76. Found: C, 60.48; H, 5.33; N, 11.64.

N-{[2-(2,6-Dioxo(3-piperidyl))-1,3-dioxoisoindolin-4-yl]methyl}cyclopentylcarboxamide I-80

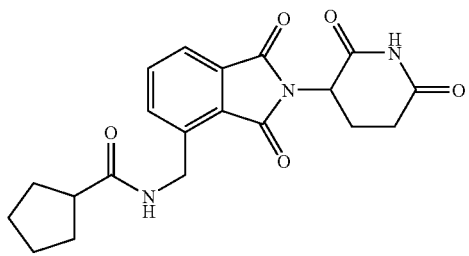

1,8-Diazabicyclo[5,4,0]undec-7-ene (0.62 g, 4.08 mmol) was added to a stirred suspension of 4-(aminomethyl)-2-(2,6-dioxo(3-piperidyl))isoindoline-1,3-dione hydrochloride (0.60 g, 1.85 mmol) in $CH_3CN$ (50 mL). After stirring for 20 min, cyclopentanecarbonyl chloride (0.29 g, 2.22 mmol) was added. The mixture was stirred at room temperature for 17 hours. The solvent was removed in vacuo and the residue was dissolved in $CH_2Cl_2$ (70 mL). The $CH_2Cl_2$ solution was washed with 1N HCl (30 mL), $H_2O$ (30 mL), brine (30 mL) and dried ($MgSO_4$). The solvent was removed in vacuo and the solid was stirred with ether (20 mL) to give N-{[2-(2,6-dioxo(3-piperidyl))-1,3-dioxoisoindolin-4-yl]methyl}cyclopentylcarboxamide (0.59 g, 83%) as a white solid: mp 175-177° C.; $^1$H NMR (DMSO-$d_6$) δ 11.13 (s, 1H), 8.41 (t, J=5.7 Hz, 1H), 7.87-7.78 (m, 2H), 7.66-7.63 (m, 1H), 5.19-5.12 (dd, J=5.3 and 12.5 Hz, 1H), 4.72 (d, J=5.8 Hz, 2H), 2.98-2.83 (m, 1H), 2.73-2.51 (m, 3H), 2.08-2.04 (m, 1H), 1.81-1.51 (m, 8H); $^{13}$C NMR (DMSO-$d_6$) δ 175.71, 172.75, 169.82, 167.49, 166.95, 139.68, 134.76, 132.91, 131.50, 127.01, 121.77, 48.84, 44.20, 37.60, 30.93, 29.96, 25.60, 21.97; Anal. Calcd. For $C_{20}H_{21}N_3O_5$: C, 62.65; H, 5.52; N, 10.96. Found: C, 62.52; H, 5.55; N, 10.81.

N-{[2-(2,6-Dioxo(3-piperidyl))-1,3-dioxoisoindolin-4-yl]methyl}cyclohexylcarboxamide I-81

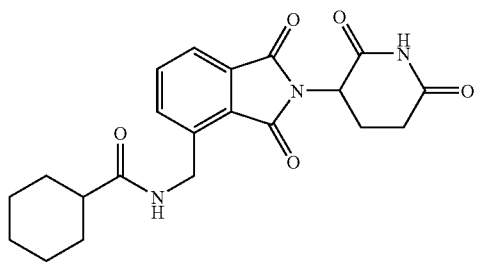

1,8-Diazabicyclo[5,4,0]undec-7-ene (0.62 g, 4.08 mmol) was added to a stirred suspension of 4-(aminomethyl)-2-(2, 6-dioxo(3-piperidyl))isoindoline-1,3-dione hydrochloride (0.60 g, 1.85 mmol) in CH₃CN (50 mL). After stirring for 20 min, cyclohexanecarbonyl chloride (0.33 g, 2.22 mmol) was added. The mixture was stirred at room temperature for 17 hours. The solvent was removed in vacuo and the residue was dissolved in CH₂Cl₂ (70 mL). The CH₂Cl₂ solution was washed with 1N HCL (30 mL), H₂O (30 mL), brine (30 mL) and dried (MgSO₄). The solvent was removed and the residue was purified by chromatography (SiO₂, CH₂Cl₂: EtOAc 6:4) to give N-{[2-(2,6-dioxo(3-piperidyl))-1,3-dioxoisoindolin-4-yl]methyl}cyclohexylcarboxamide (0.53 g, 72%) as a white solid: mp 142-144° C.; ¹H NMR (DMSO-d₆) δ 11.13 (s, 1H), 8.36 (t, J=5.8 Hz, 1H), 7.86-7.77 (m, 2H), 7.64-7.61 (m, 1H), 5.18-5.11 (dd, J=5.3 and 12.5 Hz, 1H), 4.70 (d, J=5.8 Hz, 2H), 2.97-2.83 (m, 1H), 2.63-2.47 (m, 2H), 2.26-2.17 (m, 1H), 2.08-2.03 (m, 1H), 1.79-1.61 (m, 5H), 1.43-1.12 (m, 5H); ¹³C NMR (DMSO-d₆) δ 175.58, 172.75, 169.82, 167.49, 166.96, 139.68, 134.75, 132.76, 131.49, 126.99, 121.73, 48.83, 43.90, 37.43, 30.92, 29.20, 25.43, 25.24, 21.96; Anal. Calcd. For C₂₁H₂₃N₃O₅: C, 63.47; H, 5.83; N, 10.57. Found: C, 63.12; H, 5.68; N, 10.41.

N-{[2-(2,6-Dioxo(3-piperidyl))-1,3-dioxoisoindolin-4-yl]methyl}-(phenylamino)-carboxamide I-82

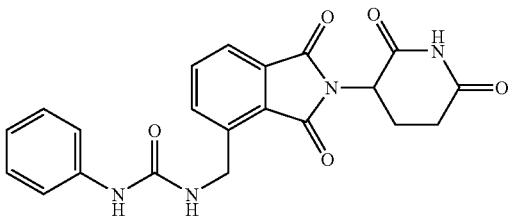

1,8-Diazabicyclo[5,4,0]undec-7-ene (0.29 g. 1.90 mmol) was added to a stirred suspension of 4-(aminomethyl)-2-(2,6-dioxo(3-piperidyl))isoindoline-1,3-dione hydrochloride (0.6 g, 1.85 mmol) in CH₃CN (50 mL). After stirring for 20 min, phenyl isocyanate (0.33 g, 2.77 mmol) was added. The mixture was stirred at room temperature for 17 hours. The solvent was removed in vacuo and the residue was dissolved in CH₂Cl₂ (70 mL). The CH₂Cl₂ solution was washed with 1N HCl (30 mL), H₂O (30 mL), brine (30 mL) and dried (MgSO₄). The solvent was removed in vacuo and the residue was purified by chromatography (SiO₂, CH₂Cl₂: EtOAc 7:3) to give N-{[2-(2,6-dioxo(3-piperidyl))-1,3-dioxoisoindolin-4-yl]methyl}(phenylamino)carboxamide (0.23 g, 31%) as a white solid: mp 212-214° C.; ¹H NMR (DMSO-d₆) δ 11.15 (s, 1H), 8.78 (s, 1H), 7.88-7.76 (m, 3H), 7.37 (d, J=7.7 Hz, 2H), 7.21 (t, J=7.7 Hz, 2H), 6.89 (t, J=7.3 Hz, 1H), 6.76 (t, J=5.9 Hz, 1H), 5.20-5.13 (dd, J=5.3 and 12.5 Hz, 1H), 4.72 (d, J=5.9 Hz, 2H), 2.97-2.84 (m, 1H), 2.65-2.49 (m, 2H), 2.09-2.05 (m, 1H); ¹³C NMR (DMSO-d₆) δ 172.72, 169.79, 167.58, 166.99, 155.22, 140.25, 134.69, 133.63, 131.59, 128.60, 127.18, 121.83, 121.18, 117.70, 48.86, 38.71, 30.92, 21.97; Anal. Calcd. For C₂₁H₁₈N₄O₅: C, 62.07; H, 4.46; N, 13.79. Found: C, 62.14; H, 4.49; N, 13.49.

N-{[2-(2,6-Dioxo(3-piperidyl))-1,3-dioxoisoindolin-4-yl]methyl}(butylamino)carboxamide I-83

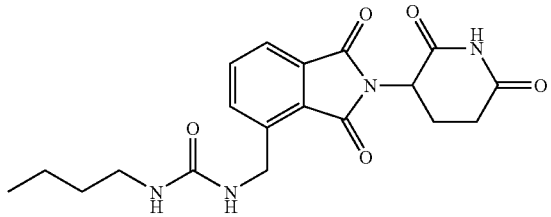

1,8-Diazabicyclo[5,4,0]undec-7-ene (0.29 g, 1.90 mmol) was added to a stirred suspension of 4-(aminomethyl)-2-(2,6-dioxo(3-piperidyl))isoindoline-1,3-dione hydrochloride (0.6 g, 1.85 mmol) in CH₃CN (50 mL). After stirring for 20 min n-butyl isocyanate (0.27 g, 2.77 mmol) was added. The mixture was stirred at room temperature for 17 hours. The solvent was removed in vacuo and the residue was dissolved in CH₂Cl₂ (70 mL). The CH₂Cl₂ solution was washed with 1N HCl (30 mL), H₂O (30 mL), brine (30 mL) and dried (MgSO₄). The solvent was removed in vacuo and the residue was purified by chromatography (SiO₂, CH₂Cl₂: EtOAc 1:1) to give N-{[2-(2,6-dioxo(3-piperidyl))1,3-dioxoisoindolin-4-yl]methyl}(butylamino)carboxamide (0.44 g, 61%) as a white solid: mp 172-174° C.; ¹H NMR (DMSO-d₆) δ 11.13 (s, 1H), 7.86-7.68 (m, 3H), 6.42 (t, J=5.9 Hz, 1H), 6.12 (t, J=5.4 Hz, 1H), 5.18-5.11 (dd, J=5.2 and 12.4 Hz, 1H), 4.63 (d, J=5.9 Hz, 1H), 3.03-2.83 (m, 3H), 2.64-2.51 (m, 2H), 2.08-2.04 (m, 1H), 1.37-1.22 (m, 4H), 0.86 (t, J=7.0 Hz, 3H); ¹³C NMR (DMSO-d₆) δ 172.70, 169.77, 167.54, 167.00, 157.98, 141.14, 134.56, 133.33, 131.47, 126.94, 121.58, 48.80, 38.98, 38.70, 32.01, 30.90, 21.95, 19.46, 13.64; Anal. Calcd. For C₁₉H₂₂N₄O₅: C, 59.06; H, 5.74; N, 14.50. Found: C, 59.24; H, 5.53; N, 14.37.

N-{[2-(2,6-Dioxo(3-piperidyl))-1,3-dioxoisoindolin-4-yl]methyl}(propylamino)-carboxamide I-84

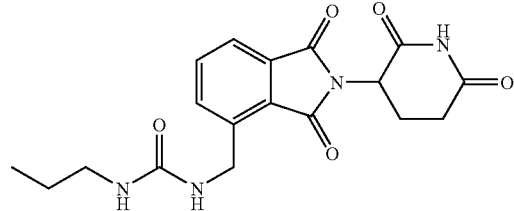

1,8-Diazabicyclo[5,4,0]undec-7-ene (0.29 g, 1.90 mmol) was added to a stirred suspension of 4-(aminomethyl)-2-(2,6-dioxo(3-piperidyl))isoindoline-1,3-dione hydrochloride (0.6 g, 1.85 mmol) in CH₃CN (50 mL). After stirring for 20 min, propyl isocyanate (0.24 g, 2.77 mmol) was added. The mixture was stirred at room temperature for 17 hours. The solvent was removed and the residue was dissolved in CH₂Cl₂ (70 mL). The CH₂Cl₂ solution was washed with 1N HCl (30 mL), H₂O (30 mL), brine (30 mL) and dried (MgSO₄). The solvent was removed in vacuo and the residue was purified by chromatography (SiO₂, CH₂Cl₂: CH₃OH 100:3) to give N-{[2-(2,6-dioxo(3-piperidyl))-1,3-dioxoisoindolin-4-yl]methyl}(propylamino)carboxamide (0.13 g, 20%) as a white solid: mp 160-162° C.; ¹H NMR (DMSO-d₆) δ 11.14 (s, 1H), 7.86-7.69 (m, 3H), 6.44 (t, J=5.9 Hz, 1H), 6.16 (t, J=1H), 5.18-5.11 (dd, J=5.3 and 12.4 Hz, 1H), 4.63 (d, J=5.9 Hz, 2H), 2.99-2.83 (m, 3H), 2.64-2.50 (m, 2H), 2.08-2.04 (m, 1H), 1.42-1.32 (m, 2H), 0.83 (t, J=7.3 Hz, 3H); $^{13}$C NMR (DMSO-$d_6$) δ 172.78, 169.84, 167.59, 167.05, 158.03, 141.16, 134.62, 133.34, 131.51, 126.96, 121.63, 48.82, 41.18, 30.94, 23.15, 21.99, 11.33; Anal. Calcd. For $C_{18}H_{20}N_4O_5$: C, 58.06; H, 5.41; N, 15.05. Found: C, 57.94; H, 5.31; N, 14.90.

N-{[2-(2,6-Dioxo(3-piperidyl))-1,3-dioxoisoindolin-4-yl]methyl}(cyclohexylamino)-carboxamide I-85

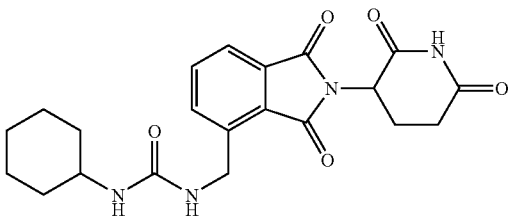

1,8-Diazabicyclo[5,4,0]undec-7-ene (0.29 g, 1.90 mmol) was added to a stirred suspension of 4-(aminomethyl)-2-(2,6-dioxo(3-piperidyl))isoindoline-1,3-dione hydrochloride (0.6 g, 1.85 mmol) in $CH_3CN$ (50 mL). After stirring for 20 min, cyclohexyl isocyanate (0.35 g, 2.77 mmol) was added. The mixture was stirred at room temperature for 17 hours. The solvent was removed in vacuo and the residue was dissolved in $CH_2Cl_2$ (70 mL). The $CH_2Cl_2$ solution was washed with 1N HCl (30 mL), $H_2O$ (30 mL), brine (30 mL) and dried ($MgSO_4$). The solvent was removed in vacuo and the residue was purified by chromatography ($SiO_2$, $CH_2Cl_2$: EtOAc 1:1) to give N-{[2-(2,6-dioxo(3-piperidyl))-1,3-dioxoisoindolin-4-yl]methyl}(cyclohexylamino)carboxamide (0.37 g, 49%) as a white solid: mp 208-210° C.; $^1$H NMR (DMSO-$d_6$) δ 11.13 (s, 1H), 7.86-7.68 (m. 3H), 6.34 (t, J=5.8 Hz, 1H), 6.04 (d, J=7.9 Hz, 1H), 5.18-5.11 (dd, J=5.3 and 12.4 Hz, 1H), 4.62 (d, J=5.8 Hz, 2H), 3.37 (m, 1H), 2.96-2.83 (m, 1H), 2.63-2.50 (m, 2H), 2.08-2.04 (m, 1H), 1.76-1.02 (m, 10H); $^{13}$C NMR (DMSO-$d_6$) δ 172.78, 169.84, 167.59, 167.04, 157.28, 141.13, 134.64, 133.42, 131.51, 126.98, 121.64, 48.82, 47.91, 38.66, 33.23, 30.94, 25.27, 24.47, 21.99; Anal. Calcd. For $C_{21}H_{24}N_4O_5$: C, 61.16; H, 5.87; N, 13.58. Found: C, 61.21; H, 5.79; N, 13.63.

N-{[2-(2,6-Dioxo(3-piperidyl))-1,3-dioxoisoindolin-4-yl]methyl}[(methylethylamino)]-carboxamide I-86

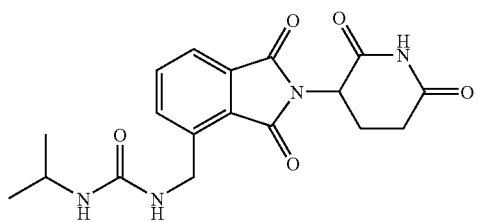

1,8-Diazabicyclo[5,4,0]undec-7-ene (0.29 g, 1.90 mmol) was added to a stirred suspension of 4-(aminomethyl)-2-(2,6-dioxo(3-piperidyl))isoindoline-1,3-dione hydrochloride (0.6 g, 1.85 mmol) in $CH_3CN$ (50 mL). After stirring for 20 min, isopropyl isocyanate (0.24 g, 2.77 mmol) was added. The mixture was stirred at room temperature for 17 hours. The solvent was removed in vacuo and the residue was dissolved in $CH_2Cl_2$ (70 mL). The $CH_2Cl_2$ solution was washed with 1N HCl (30 mL), $H_2O$ (30 mL), brine (30 mL) and dried ($MgSO_4$). The solvent was removed in vacuo and the residue was purified by chromatography ($SiO_2$, $CH_2Cl_2$: $CH_3OH$ 97.5:2.5) to give N-{[2-(2,6-dioxo(3-piperidyl))-1,3-dioxoisoindolin-4-yl]methyl}[(methylethylamino)]carboxamide (0.25 g, 36%) as a white solid: mp 180-182° C.; $^1$H NMR (DMSO-$d_6$) δ 11.19 (s, 1H), 7.87-7.68 (m, 3H), 6.33 (t, J=5.9 Hz, 1H), 6.02 (d, J=7.5 Hz, 1H), 5.18-5.11 (dd, J=5.2 and 12.4 Hz, 1H), 4.62 (d, J=5.9 Hz, 2H), 3.73-3.35 (m, 1H), 2.98-2.83 (m, 1H), 2.63-2.50 (m, 2H), 2.08-2.04 (m, 1H), 1.04 (d, J=6.5 Hz, 6H); $^{13}$C NMR (DMSO-$d_6$) δ 172.78, 169.85, 167.59, 167.05, 157.36, 141.16, 134.65, 133.39, 131.52, 126.98, 121.64, 48.82, 41.03, 38.64, 30.94, 23.18, 21.99; Anal. Calcd. For $C_{18}H_{20}N_4O_5$: C, 58.06; H, 5.41; N, 15.05. Found: C, 58.20; H. 5.44; N, 14.95.

N-{[2-(2,6-Dioxo(3-piperidyl))-1,3-dioxoisoindolin-4-yl]methyl}(octylamino)carboxamide I-87

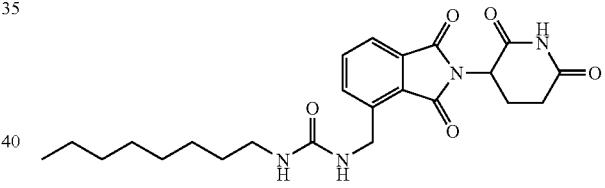

1,8-Diazabicyclo[5,4,0]undec-7-ene (0.29 g, 1.90 mmol) was added to a stirred suspension of 4-(aminomethyl)-2-(2,6-dioxo(3-piperidyl))isoindoline-1,3-dione hydrochloride (0.6 g, 1.85 mmol) in $CH_3CN$ (50 mL). After stirring for 20 min, octyl isocyanate (0.44 g, 2.77 mmol) was added. The mixture was stirred at room temperature for 17 hours. The slurry mixture was filtered and the solid was recrystallized from methanol to give N-{[2-(2,6-dioxo(3-piperidyl))-1,3-dioxoisoindolin-4-yl]methyl}(octylamino)carboxamide (0.46 g, 56%) as a white solid: mp 160-162° C.; $^1$H NMR (DMSO-$d_6$) δ 11.14 (s, 1H), 7.85-7.68 (m, 3H), 6.43 (t, J=6.0 Hz, 1H), 6.13 (t, J=5.6 Hz, 1H), 5.18-5.11 (dd, J=5.3 and 12.5 Hz, 1H), 4.62 (d, J=6.0 Hz, 2H), 3.02-2.83 (m, 3H), 2.64-2.50 (m, 2H), 2.08-2.04 (m, 1H), 1.36-1.24 (m 12H), 0.85 (t, J=6.2 Hz, 3H); $^{13}$C NMR (DMSO-$d_6$) δ 172.75, 169.82, 167.57, 167.03, 157.99, 141.19, 134.57, 133.33, 131.50, 126.95, 121.61, 48.82, 39.32, 38.83, 31.21, 30.93, 29.92, 28.73, 28.69, 26.37, 22.07, 21.98, 13.93; Anal. Calcd. For $C_{23}H_{30}N_4O_5$: C, 62.43; H, 6.83; N, 12.66. Found: C, 62.27; H, 6.94; N, 12.54.

N-{[2-(2,6-Dioxo(3-piperidyl))-1,3-dioxoisoindolin-4-yl]methyl}(benzylamino)-carboxamide I-88

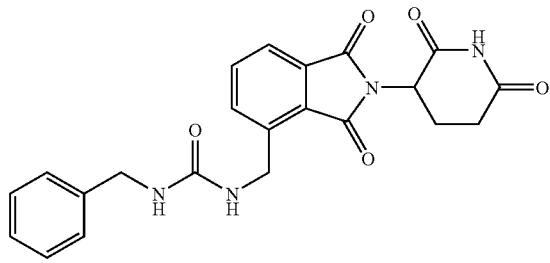

1,8-Diazabicyclo[5,4,0]undec-7-ene (0.29 g, 1.90 mmol) was added to a stirred suspension of 4-(aminomethyl)-2-(2,6-dioxo(3-piperidyl))isoindoline-1,3-dione hydrochloride (0.6 g, 1.85 mmol) in CH$_3$CN (50 mL). After stirring for 20 min, benzyl isocyanate (0.32 g, 2.41 mmol) was added. The mixture was stirred at room temperature for 17 hours. The solvent was removed in vacuo and the residue was dissolved in CH$_2$Cl$_2$ (70 mL). The CH$_2$Cl$_2$ solution was washed with 1N HCl (30 mL), H$_2$O (30 mL), brine (30 mL) and dried (MgSO$_4$). The solvent was removed in vacuo and the residue was purified by chromatography (SiO$_2$, CH$_2$Cl$_2$: CH$_3$OH 96:4) to give N-{[2-(2,6-dioxo(3-piperidyl))-1,3-dioxoisoindolin-4-yl]methyl}(benzylamino)carboxamide (0.42 g, 54%) as a white solid: mp 192-194° C.; $^1$H NMR (DMSO-d$_6$) δ 11.13 (s, 1H), 7.86-7.69 (m, 3H), 7.34-7.19 (m, 5H), 6.67 (t, J=5.8 Hz, 1H), 6.60 (t, J=5.9 Hz, 1H) 5.18-5.11 (dd, J=5.3 and 12.5 Hz, 1H), 4.67 (d, J=5.9 Hz, 2H), 4.23 (d, J=5.8 Hz, 2H), 2.97-2.83 (m, 1H), 2.63-2.50 (m, 2H), 2.07-2.03 (m, 1H); $^{13}$C NMR (DMSO-d$_6$) δ 175.63, 172.75, 167.56, 167.03, 158.05, 141.01, 140.70, 134.61, 133.31, 131.52, 128.19, 126.98, 126.55, 121.66, 48.83, 42.99, 30.93, 21.98; Anal. Calcd. For C$_{22}$H$_{20}$N$_4$O$_5$: C, 62.85; H. 4.79; N, 13.33. Found: C, 62.78; H, 4.53; N, 13.18.

N-{[2-(2,6-Dioxo(3-piperidyl))-1,3-dioxoisoindolin-4-yl]methyl}(cyclopropylamino)-carboxamide I-89

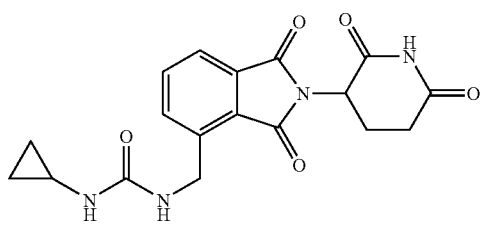

1,8-Diazabicyclo[5,4,0]undec-7-ene (0.58 g, 3.81 mmol) was added to a stirred suspension of 4-(aminomethyl)-2-(2,6-dioxo(3-piperidyl))isoindoline-1,3-dione hydrochloride (0.6 g, 1.85 mmol) in CH$_3$CN (50 mL). After stirring for 20 min, 4-nitrophenyl-N-cyclopropylcarbamate (0.41 g, 1.85 mmol) was added. The mixture was stirred at room temperature for 17 hours. The mixture was filtered and the solid was recrystallized from methanol to give N-{[2-(2,6-dioxo(3-piperidyl))-1,3-dioxoisoindolin-4-yl]methyl}(cyclopropylamino)carboxamide (0.53 g, 77%) as a white solid: mp 245-247° C.; $^1$H NMR (DMSO-d$_6$) δ 11.14 (s, 1H), 7.87-7.69 (m, 3H), 6.58 (t, J=5.7 Hz, 1H), 6.45 (d, J=2.2 Hz, 1H) 5.19-5.11 (dd, J=5.4 and 12.5 Hz, 1H), 4.65 (d, J=6.1 Hz. 2H), 2.96-2.83 (m, 1H), 2.64-2.40 (m, 3H), 2.08-2.04 (m, 1H), 0.62-0.55 (m, 2H), 0.40-0.34 (m, 2H); $^{13}$C NMR (DMSO-d$_6$) δ 172.75, 169.82, 167.63, 167.04, 158.69, 141.11, 134.61, 133.26, 131.49, 126.94, 121.60, 48.83, 30.93, 22.37, 21.97, 6.59; Anal. Calcd. For C$_{18}$H$_{18}$N$_4$O$_5$: C, 58.37; H, 4.90; N, 15.13. Found: C, 58.26; H, 4.82; N, 14.85.

2-(2,6-Dioxo(3-piperidyl))-4-({[(ethylamino)thioxomethyl]amino}methyl)isoindoline-1,3-dione I-114

1,8-Diazabicyclo[5,4,0]undec-7-ene (0.29 g, 1.90 mmol) was added to a stirred suspension of 4-(aminomethyl)-2-(2,6-dioxo(3-piperidyl))isoindoline-1,3-dione hydrochloride (0.6 g, 1.85 mmol) in CH$_3$CN (50 mL). After stirring for 20 min, ethyl idothiocyanate (0.2 g, 2.22 mmol) was added. The mixture was stirred at room temperature for 17 hours. The solvent was removed in vacuo and the residue was dissolved in CH$_2$Cl$_2$ (70 mL). The CH$_2$Cl$_2$ solution was washed with 2N HCl (30 mL), H$_2$O (30 mL), brine (30 mL) and dried (MgSO$_4$). The solvent was removed and the residue was purified by chromatography (SiO$_2$, CH$_2$Cl$_2$:EtOAc 6:4) to give 2-(2,6-dioxo(3-piperidyl))-4-({[(ethylamino)thioxomethyl]amino}methyl)isoindoline-1,3-dione (0.33 g, 48%) as a white solid: mp 154-156° C.; $^1$H NMR (DMSO-d$_6$) d 11.14 (s, 1H), 7.86-7.66 (m, 5H), 5.19-5.09 (m, 3H), 3.38 (m, 2H), 2.98-2.83 (m, 1H), 2.64-2.50 (m, 2H), 2.08-2.04 (m, 1H), 1.09 (t, J=7.1 Hz, 3H); $^{13}$C NMR (DMSO-d$_6$) d 172.78, 169.85, 167.56, 167.02, 139.64, 134.53, 133.22, 131.54, 127.06, 121.76, 48.85, 42.74, 30.84, 22.80, 21.99, 14.32; Anal. Calcd. For C$_{17}$H$_{18}$N$_4$O$_4$S: C, 54.53; H, 4.85; N, 14.96; S, 8.56. Found: C, 54.89; H, 4.82; N, 14.72; S, 8.51.

{5-[2-(2,6-Dioxo-piperidin-3-yl)-1,3-dioxo-2,3-dihydro-1H-isoindol-4-ylcarbamoyl]-pentyl}-carbamic acid benzyl ester I-117

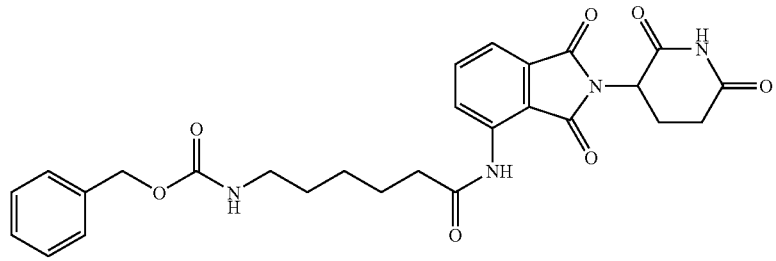

A solution of 6-benzyloxycarbonylamino-hexanoic acid (2.65 g, 10 mmol) in thionyl chloride (15 ml) was heated to reflux 1 h. The reaction mixture was allowed to cool to room temperature and the solvent was evaporated in vacuo to give (5-chlorocarbonyl-pentyl)-carbamic acid benzyl ester as tan oil. The oil was used without further purification. (5-Chlorocarbonyl-pentyl)-carbamic acid benzyl ester was dissolved in THF (50 ml). To this solution was added 4-amino-2-(2,6-dioxo(3-piperidyl))isoindoline-1,3-dione (1.37 g, 5 mmol). The resulting suspension was to reflux for 4 hours. The solvent was evaporated in vacuo and the resulting solid was partially purified by flash chromatography (60/40 ethyl acetate/hexane) to give a light yellow solid. The solid was recrystallized from minimal ethyl acetate to give 1.24 g (48%) of product as an off-white solid: mp 122-125° C.; $^1$H NMR (DMSO-$d_6$) 11.18 (s, 1H), 9.70 (s, 1H), 8.49 (d, J=8.4 Hz, 1H), 7.83 (t, J=7.7 Hz, 1H), 7.61 (d, J=7.2 Hz, 1H), 7.34-7.24 (m, 6H), 5.16 (dd, J=5.1 and 12.6 Hz, 1H), 5.00 (s, 2H), 3.02-2.84 (m, 3H), 2.65-2.43 (m, 4H), 2.12-2.05 (m, 1H), 1.65-1.15 (m, 6H; $^{13}$C NMR (DMSO-$d_6$) 172.75, 171.95, 169.77, 167.72, 166.67, 156.08, 137.29, 136.57, 136.09, 131.43, 128.32, 127.70, 126.21, 118.25, 116.90, 65.08, 48.92, 36.47, 30.94, 30.67, 29.14, 25.77, 24.47, 21.99; Anal. Calcd. For $C_{27}H_{28}N_4O_7$: C, 62.30; H, 5.42; N, 10.76. Found: C, 62.40; H, 5.31; N, 10.48.

2-Methoxy-N-[2-(3-methyl-2,6-dioxo-piperidin-3-yl)-1,3-dioxo-2,3-dihydro-1H-isoindol-4-yl]-acetamide I-118

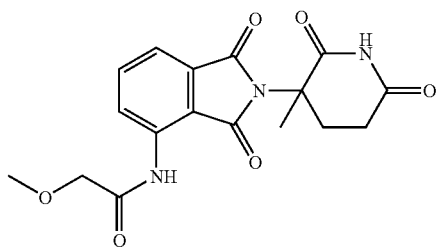

To a suspension of 4-amino-2-(3-methyl-2,6-dioxo-piperidin-3-yl)-isoindole-1,3-dione (0.10 g, 0.35 mmol) in THF (1-5 ml) was added methoxyacetyl chloride (0.08 g, 0.70 mmol). The mixture was heated to reflux for 6 hours. The reaction mixture was allowed to cool and to the solution was added methanol (2 ml). The reaction mixture was stirred for an additional 15 minutes followed by solvent evaporation in vacuo. The resulting solid was slurried in diethyl ether (20 ml) and filtered to give 0.11 g (87%) of product as an off-white solid: mp 244-246° C.; $^1$H NMR (DMSO-$d_6$) 11.07 (s, 1H), 10.26 (s, 1H), 8.68 (d, J=8.3 Hz, 1H), 7.82 (t, J=7.7 Hz, 1H), 7.55 (d, J=7.2 Hz, 1H), 4.10 (s, 2H), 3.47 (s; 3H), 2.77-2.51 (m, 3H), 2.09-2.04 (m, 1H), 1.90 (s, 3H); $^{13}$C NMR (DMSO-$d_6$) 172.12, 171.99, 169.15, 168.99, 167.38, 136.22, 135.68, 131.06, 124.25, 117.90, 115.91, 71.43, 59.06, 58.88, 29.01, 28.53, 20.92; Anal. Calcd. For $C_{17}H_{17}N_3O_6$: C, 56.48; H, 4.81; N. 11.62. Found: C, 56.10; H, 4.55; N, 11.39+0.12H$_2$O.

Pentanoic acid [2-(3-methyl-2,6-dioxo-piperidin-3-yl)-1,3-dioxo-2,3-dihydro-1H-isoindol-4-yl]-amide I-119

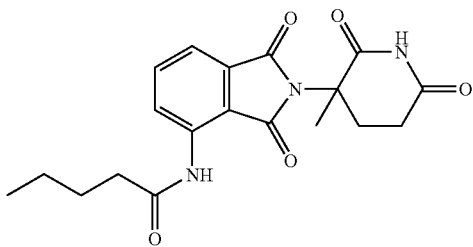

To a suspension of 4-amino-2-(3-methyl-2,6-dioxo-piperidin-3-yl)-isoindole-1,3-dione (0.10 g, 0.35 mmol) in THF (15 ml) was added valeryl chloride (0.08 g, 0.70 mmol). The mixture was heated to reflux for 18 h. The reaction mixture was allowed to cool and to the solution was added methanol (2 ml). The reaction mixture was stirred for an additional 15 minutes followed by solvent evaporation in vacuo. The resulting solid was slurried in diethyl ether (20 ml) and filtered to give 0.11 g (81%) of product as an off-white solid: mp 190-192° C.; $^1$H NMR (DMSO-$d_6$) 11.04 (s, 1H), 9.65 (s, 1H), 8.50 (d, J=8.4 Hz, 1H), 7.79 (t, J=7.8 Hz, 1H), 7.52 (d, J=7.2 Hz, 1H), 2.74-2.44 (m, 5H), 2.10-2.03 (m, 1H), 1.90 (s, 3H), 1.66-1.54 (m, 2H), 1.42-1.27 (m, 2H), 0.91 (t, J=7.3 Hz, 3H); $^{13}$C NMR (DMSO-$d_6$) 172.13, 172.03, 168.75, 167.36, 136.42, 135.91, 131.20, 125.68, 117.71, 116.29, 58.81, 36.25, 29.07, 28.54, 26.83, 21.65, 20.98, 13.64; Anal. Calcd. For $C_{19}H_{21}N_3O_5$: C, 61.39; H, 5.70; N, 11.30. Found: C, 61.03; H, 5.51; N, 11.13+0.02H$_2$O.

Heptanoic acid [2-(3-methyl-2,6-dioxo-piperidin-3-yl)-1,3-dioxo-2,3-dihydro-1H-isoindol-4-yl]-amide I-120

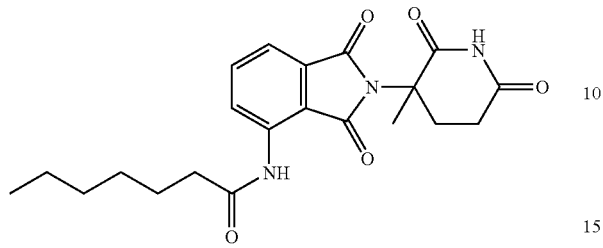

To a suspension of 4-amino-2-(3-methyl-2,6-dioxo-piperidin-3-yl)-isoindole-1,3-dione (0.10 g, 0.35 mmol) in THF (15 ml) was added heptanoyl chloride (0.10 g, 0.70 mmol). The mixture was heated to reflux for 18 h. The reaction mixture was allowed to cool and to the solution was added methanol (2 ml). The reaction mixture was stirred for an additional 15 minutes followed by solvent evaporation in vacuo. The resulting solid was slurried in diethyl ether (20 ml) and filtered to give 0.10 g (74%) of product as an off-white solid: mp 172-174° C.; $^1$H NMR (DMSO-$d_6$) 11.05 (s, 1H), 9.65 (s, 1H), 8.50 (d, J=8.3 Hz, 1H), 7.79 (t, J=7.6 Hz, 1H), 7.52 (d, J=7.2 Hz, 1H), 2.77-2.43 (m, 5H), 2.08-2.03 (m, 1H), 1.90 (s, 3H), 1.61 (t, J=6.4 Hz, 2H), 1.29 (bs, 6H), 0.87 (t, J=6.3 Hz, 3H); $^{13}$C NMR (DMSO-$d_6$) 172.12, 172.02, 168.74, 167.36, 136.41, 135.90, 131.20, 125.70, 117.71, 116.31, 58.81, 36.51, 30.93, 29.07, 28.54, 28.12, 24.69, 21.94, 20.98, 13.86; Anal. Calcd. For $C_{21}H_{21}N_3O_5$: C, 62.83; H, 6.33; N, 10.47 Found: C, 62.45; H, 6.18; N, 10.24+0.50$H_2O$.

3-Chloro-N-[2-(3-methyl-2,6-dioxo-piperidin-3-yl)-1,3-dioxo-2,3-dihydro-1H-isoindol-4-yl]-benzamide I-121

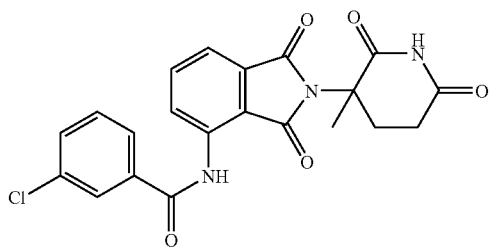

To a suspension of 4-amino-2-(3-methyl-2,6-dioxo-piperidin-3-yl)-isoindole-1,3-dione (0.10 g, 0.35 mmol) in THF (15 ml) was added 3-chlorobenzoyl chloride (0.12 g, 0.70 mmol) The mixture was heated to reflux for 18 h. The reaction mixture was allowed to cool and to the solution was added methanol (2 ml). The reaction mixture was stirred for an additional 15 minutes followed by solvent evaporation in vacuo. The resulting solid was slurried in diethyl ether (20 ml) and filtered to give 0.11 g (73%) of product as an off-white solid: mp 283-285° C.; $^1$H NMR (DMSO-$d_6$) 11.06 (s, 1H), 10.43 (s, 1H), 8.48 (d, J=8.3 Hz, 1H), 7.98-7.61 (m, 6H), 2.80-2.51 (m, 3H), 2.11-2.01 (m, 1H), 1.92 (s, 3H), 1.61 (t, J=6.4 Hz, 2H), 1.29 (bs, 6H), 0.87 (t, J=6.3 Hz, 3H); $^{13}$C NMR (DMSO-$d_6$) 171.72, 171.64, 168.53; 167.11, 163.55, 135.81, 135.75, 135.35, 133.59, 132.07, 131.03, 130.73, 127.03, 126.37, 125.58, 118.43, 118.06, 58.80, 28.90, 28.37, 20.84; Anal. Calcd. For $C_{21}H_{16}ClN_3O_5$: C, 59.23; H, 3.79; N, 9.87 Found: C, 59.00; H, 3.80; N, 9.70.

N-[2-(3-Methyl-2,6-dioxo-piperidin-3-yl)-1,3-dioxo-2,3-dihydro-1H-isoindol-4-yl]-propionamide I-122

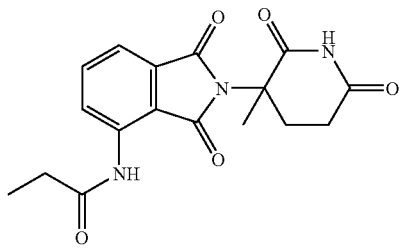

To a suspension of 4-amino-2-(3-methyl-2,6-dioxo-piperidin-3-yl)-isoindole-1,3-dione (0.10 g, 0.35 mmol) in THF (15 ml) was added propionyl chloride (0.07 g, 0.70 mmol). The mixture was heated to reflux for 18 h. The reaction mixture was allowed to cool and to the solution was added methanol (2 ml). The reaction mixture was stirred for an additional 15 minutes followed by solvent evaporation in vacuo. The resulting solid was slurried in diethyl ether (20 ml) and filtered to give 0.07 g (63%) of product as an off-white solid: mp 222-224° C.; $^1$H NMR (DMSO-$d_6$) 11.03 (s, 1H), 9.63 (s, 1H), 8.51 (d, J=8.3 Hz, 1H), 7.79 (t, J=7.6 Hz, 1H), 7.51 (d, J=7.3 Hz, 1H), 2.76-2.45 (m, 5H), 2.10-2.03 (m, 1H), 1.90 (s, 3H), 1.12 (t, J=7.5 Hz, 3H); $^{13}$C NMR (DMSO-$d_6$) 172.70, 172.14, 172.03, 168.80, 167.37, 136.48, 135.94, 131.20, 125.59, 117.67, 116.21, 58.81, 29.71, 29.07, 28.53, 20.97, 14.74, 9.18; Anal. Calcd. For $C_{17}H_{17}N_3O_5$: C, 59.47; H, 4.99; N, 12.24 Found: C, 59.24; H, 5.06; N, 11.97.

Thiophene-2-carboxylic acid [2-(3-methyl-2,6-dioxo-piperidin-3-yl)-1,3-dioxo-2,3-dihydro-1H-isoindol-4-yl]-amide I-123

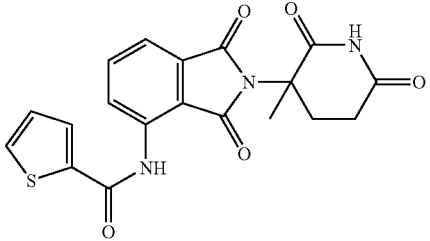

To a suspension of 4-amino-2-(3-methyl-2,6-dioxo-piperidin-3-yl)-isoindole-1,3-dione (0.10 g, 0.35 mmol) in THF (15 ml) was added 2-thiophenecarbonyl chloride (0.10 g, 0.70 mmol). The mixture was heated to reflux for 18 h. The reaction mixture was allowed to cool and to the solution was added methanol (2 ml). The reaction mixture was stirred for an additional 15 minutes followed by solvent evaporation in vacuo. The resulting solid was slurried in ethyl acetate (10 ml) and filtered to give 0.13 g of light yellow solid. The solid was recrystallized from acetonitrile to give 0.10 g of product (72%) as a off-white solid: mp 288-290° C.; ¹H NMR (DMSO-d₆) 11.07 (s, 1H), 10.32 (s, 1H), 8.49 (d, J=8.4 Hz, 1H), 7.98 (d, J=4.8 Hz, 1H), 7.8977.83 (m, 2H), 7.59 (d, J=7.0 Hz, 1H), 7.31 (t, J=4.1 Hz, 1H), 2.80-2.51 (m, 3H), 2.12-2.01 (m, 1H), 1.92 (s, 3H); ¹³C NMR (DMSO-d₆) 172.10, 171.99, 169.00, 167.33, 159.60, 137.99, 136.05, 136.03, 133.26, 131.13, 129.82, 128.60, 125.91, 118.29, 117.43, 58.93, 29.04, 28.55, 20.96; Anal. Calcd. For $C_{19}H_{15}N_3O_5S$: C, 57.17; H, 3.84; N, 10.53 Found: C, 56.91; H, 3.48; N, 10.55+ $0.1H_2O$.

3-[(5-Methyl-furan-2-ylmethyl)-amino]-phthalic acid dimethyl ester

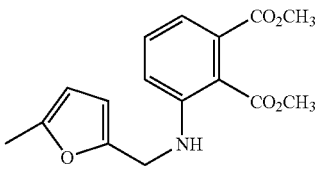

3-Amino-phthalic acid dimethyl ester (1.05 µg, 5 mmol) was treated in the same manner as described above for the synthesis of 3-pentylamino-phthalic acid dimethyl ester. The product of the reaction was used without further purification.

3-[(5-Methyl-furan-2-ylmethyl)-amino]-phthalic acid

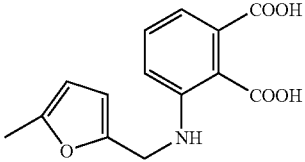

3-[(5-Methyl-furan-2-ylmethyl)-amino]-phthalic acid dimethyl ester (5 mmol) was treated in the same manner as described above for the synthesis of 3-(2-methoxy-ethylamino)-phthalic acid. The product of the reaction, which contained a mixture of diacid and monomethyl esters, was used without further purification.

2-(2,6-Dioxo-piperidin-3-yl)-4-[(5-methyl-furan-2-ylmethyl)-amino]-isoindole-1,3-dione I-124

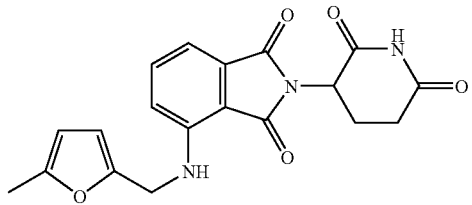

3-[(5-Methyl-furan-2-ylmethyl)-amino]-phthalic acid (5 mmol) was treated in the same manner as described above for the synthesis of 2-(2,6-dioxo-piperidin-3-yl)-4-(2-methoxy-ethylamino)-isoindole-1,3-dione. The residue was purified by preparative HPLC (Symmetry $C_{18}$, isocratic, 35/65 acetonitrile/water) to give 0.31 g (20%) of product as a yellow solid: mp 305-307° C.; ¹H NMR (DMSO-d₆) δ 11.10 (s, 1H), 7.58 (t, J=7.7 Hz, 1H), 7.18 (d, J=8.6 Hz, 1H), 7.06 (d, J=7.1 Hz, 1H), 6.93 (t, J=6.0 Hz, 1H), 6.22 (d, J=2.9 Hz, 1H), 5.98 (d, J=1.9 Hz, 1H), 5.07 (dd, J=5.3 and 12.5 Hz, 1H), 4.49 (d, J=6.0 Hz, 2H), 2.97-2.82 (m, 1H), 2.62-2.44 (m, 2H), 2.22 (s, 3H), 2.06-1.99 (m, 1H); ¹³C NMR (DMSO-d₆) δ 172.77, 170.02, 168.77, 167.21, 151,04, 150.02, 145.80, 136.04, 132.08, 117.57, 110.96, 109.63, 108.27, 106.34, 48.55, 38.94, 30.95, 22.10, 13.24; Anal. Calcd. For $C_{19}H_{17}N_3O_5$: C, 62.12; H, 4.66; N, 11.44. Found: C, 61.75; H, 4.71; N, 11.15.

3-[(5-Hydroxymethyl-furan-2-ylmethyl)-amino]-phthalic acid dimethyl ester

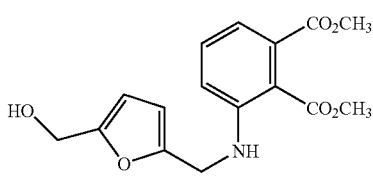

5-Hydroxymethyl-furan-2-carbaldehyde (0.95 ml, 7.5 mmol) was treated in the same manner as described above for the synthesis of 3-pentylamino-phthalic acid dimethyl ester. The residue (oil) was purified by chromatography ($SiO_2$, 40/60 ethyl acetate/hexanes) to give 0.97 g (76%) of yellow oil: ¹H NMR (CDCl₃) δ 7.35-7.27 (m, 1H), 7.05 (bs, 1H), 6.87-6.83 (m, 2H), 6.21 (d, J=3.1 Hz, 1H), 6.17 (d, J=3.2 Hz, 1H), 4-57 (s, 2H), 4.38 (bs, 2H) 3.86 (s, 3H), 3.83 (s, 3H), 1.98 (bs, 1H).

3-[(5-Hydroxymethyl-furan-2-ylmethyl)-amino]-phthalic acid

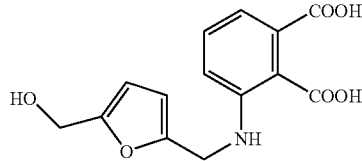

3-[(5-Hydroxymethyl-furan-2-ylmethyl)-amino]-phthalic acid dimethyl ester (0.97 g, 3.04 mmol) was treated in the same manner as described above for the synthesis of 3-(2-methoxy-ethylamino)-phthalic acid. The product of the reaction, which contained a mixture of diacid and monomethyl esters, was used without further purification.

2-(2,6-Dioxo-piperidin-3-yl)-4-[(5-hydroxymethyl-furan-2-ylmethyl)-amino]-isoindole-1,3-dione I-125

3-[(5-Hydroxymethyl-furan-2-ylmethyl)-amino]-phthalic acid (3.04 mmol) was treated in the same manner as described above for the synthesis of 2-(2,6-Dioxo-piperidin-3-yl)-4-(2-methoxy-ethylamino)-isoindole-1,3-dione. The solid yellow residue was purified by chromatography (SiO$_2$, 60% ethyl acetate/hexanes) to give 0.40 g of solid which was dissolved in methylene chloride (70 ml) and washed with saturated NaHCO$_3$ (2×100 ml), brine (1×100 ml), dried (magnesium sulfate), and filtered. The solvent was evaporated leaving 0.32 g (27%) of product as a yellow solid: mp 172-174° C.; $^1$H NMR (DMSO-d$_6$) δ 11.11 (s, 1H), 7.58 (t, J=7.9 Hz, 1H), 7.18 (d, J=8.6 Hz, 1H), 7.06 (d, J=7.0 Hz, 1H), 6.99 (t, J=6.0 Hz. 1H), 6.27 (d, J=2.9 Hz, 1H), 6.20 (d, J=2.9 Hz, 1H), 5.18 (t, J=5.7 Hz, 1H), 5.07 (dd, J=5.2 and 12.5 Hz, 1H), 4.54 (d, J=5.9 Hz, 2H), 4.33 (d, J=5.7 Hz, 2H), 2.96-2.82 (m, 1H), 2.63-2.46 (m, 2H), 2.06-1.99 (m, 1H); $^{13}$C NMR (DMSO-d$_6$) δ 172.80, 170.07, 168.80, 167.24, 155.00, 151.10, 145.79, 136.08, 132.12, 117.57, 111.04, 109.71, 108.06, 107.60, 55.63, 48.60, 39.05, 30.98, 22.13; Anal. Calcd. For C$_{19}$H$_{17}$N$_3$O$_6$: C, 59.53; H, 4.47; N, 10.96. Found: C, 59.30; H, 4.54; N, 10.70.

3-[(Thiophen-2-ylmethyl)-amino]-phthalic acid dimethyl ester

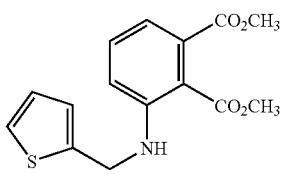

2-Thiophenecarboxaldehyde (1.12 g, 10 mmol) was treated in the same manner as described above for the synthesis of 3-pentylamino-phthalic acid dimethyl ester. The residue (oil) was purified by preparative HPLC (Symmetry C$_{18}$, isocratic, 45% acetonitrile/water) to give 0.88 g (58%) of yellow oil: $^1$H NMR (CDCl$_3$) δ 7.38-7.15 (m, 3H), 7.00-6.93 (m, 2H), 6.87-6.82 (m, 2H), 4.58 (d, J=5.3 Hz, 2H), 3.86 (s, 3H), 3.83 (s, 3H).

3-[(Thiophen-2-ylmethyl)-amino]-phthalic acid

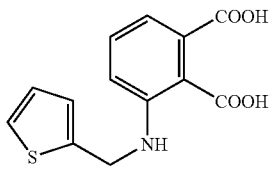

3-[(Thiophen-2-ylmethyl)-amino]-phthalic acid dimethyl ester (0.88 g, 2.88 mmol) was treated in the same manner as described above for the synthesis 3-(2-methoxy-ethylamino)-phthalic acid. The product of the reaction, which contained a mixture of diacid and monomethyl esters, was used without further purification.

2-(2,6-Dioxo-piperidin-3-yl)-4-[(thiophen-2-ylmethyl)-amino]-isoindole-1,3-dione I-126

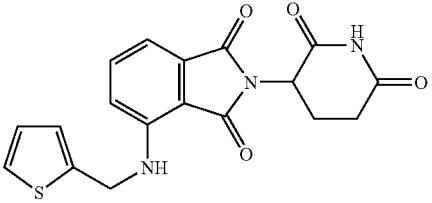

3-[(Thiophen-2-ylmethyl)-amino]-phthalic acid (2.88 mmol) was treated in the same manner as described above for the synthesis of 2-(2,6-dioxo-piperidin-3-yl)-4-(2-methoxy-ethylamino)-isoindole-1,3-dione. The solid yellow residue was purified by preparative HPLC (Symmetry C$_{18}$, isocratic, 35% acetonitrile/water) to give 0.31 g (29%) of product as a yellow solid: mp 223-225° C.; $^1$H NMR (DMSO-d$_6$) δ 11.12 (s, 1H), 7.56 (t, J=7.8 Hz, 1H), 7.39 (d, J=4.8 Hz, 1H), 7.23-6.96 (m, 5H), 5.07 (dd, J=5.3 and 12.4 Hz, 1H), 4.75 (d, J=6.0 Hz, 2H), 2.97-2.83 (m, 1H), 2.63-2.46 (m, 2H), 2.09-1.99 (m, 1H); $^{13}$C NMR (DMSO-d$_6$) δ 172.77, 170.03, 168.67, 167.20, 145.60, 142.51, 136.04, 132.15, 126.88, 125.40, 125.00, 117.67, 111.05, 109.80, 48.56, 40.88, 30.96, 22.10; Anal. Calcd. For C$_{18}$H$_{15}$N$_3$O$_4$S: C, 58.53; H, 4.09; N, 11.38. Found: C, 58.20; H, 3.96; N, 10.99.

3-(3-Chloro-benzylamino)-phthalic acid dimethyl ester

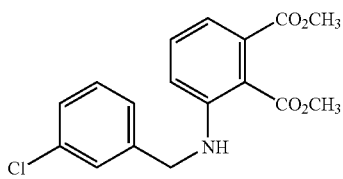

3-Chlorobenzacetaldehyde (11.14 ml, 10 mmol) was treated in the same manner as described above for the synthesis of 3-pentylamino-phthalic acid dimethyl ester. The residue (oil) was purified by chromatography (SiO$_2$, 15% ethyl acetate/hexanes) to give 1.61 g (96%) of yellow oil: $^1$H NMR (CDCl$_3$) δ 7.35-7.18 (m, 6), 6.83 (d, J=7.4 Hz, 1H), 6.65 (d, J=8.5 Hz, 1H), 4.39 (d, J=5.8 Hz, 2H), 3.86 (s, 3H), 3.84 (s, 3H).

3-(3-Chloro-benzylamino)-phthalic acid

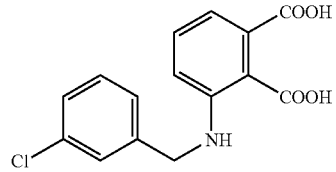

3-(3-Chloro-benzylamino)-phthalic acid dimethyl ester (1.61 g, 4.8 mmol) was treated in the same manner as described above for the synthesis of 3-(2-methoxy-ethylamino)-phthalic acid. The product of the reaction, which contained a mixture of diacid and monomethyl esters, was used without further purification.

4-(3-Chloro-benzylamino)-2-(2,6-dioxo-piperidin-3-yl)-isoindole-1,3-dione I-127

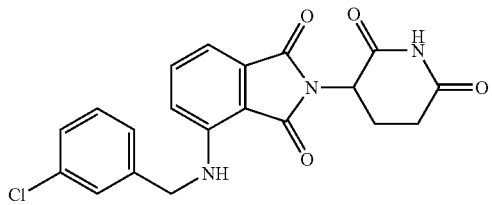

3-(3-Chloro-benzylamino)-phthalic acid (4.8 mmol) was treated in the same manner as described above for the synthesis of 2-(2,6-dioxo-piperidin-3-yl)-4-(2-methoxy-ethylamino)-isoindole-1,3-dione. The solid yellow residue was slurried in diethyl ether (30 ml) for 18 h and filtered to give 1.42 g (89%) of product as a yellow solid: mp 207-209° C.; $^1$H NMR (DMSO-$d_6$) δ 11.11 (s, 1H), 7.55-7.28 (m, 6H), 7.03 (d, J=7.0 Hz, 1H), 6.95 (d, J=8.6 Hz, 1H), 5.08 (dd, J=5.4 and 12.4 Hz, 1H), 4.58 (d, J=6.3 Hz, 2H), 2.98-2.83 (m, 1H), 2.64-2.46 (m, 2H), 2.08-2.04 (m, 1H); $^{13}$C NMR (DMSO-$d_6$) δ 172.56, 169.84, 168.59, 167.11, 145.76, 141.68, 136.01, 133.10, 132.16, 130.25, 126.83, 126.68, 125.48, 117.40, 110.81, 109.74, 48.54, 41.54, 44.80, 30.87, 22.05; Anal. Calcd. For $C_{20}H_{16}ClN_3O_4$: C, 60.38; H, 4.05; N, 10.56. Found: C, 60.22; H, 4.05; N, 10.38.

3-[(Pyridin-3-ylmethyl)-amino]-phthalic acid dimethyl ester

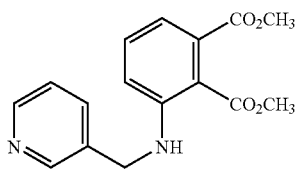

3-Pyridinecarboxaldehyde (0.94 ml, 10 mmol) was treated in the same manner as described above for the synthesis of 3-pentylamino-phthalic acid dimethyl ester. After removal of pyridine the residue was dissolved in methylene chloride (100 ml) and washed with water (2×100 ml), saturated NaHCO$_3$ (2×100 ml), brine (1×100 ml), dried (magnesium sulfate), and filtered. The solvent was evaporated in vacuo to give an oil. The oil was dissolved in diethyl ether (100 ml) and extracted with 0.1 N HCl (2×100 ml). The combined aqueous HCl extracts were washed with diethyl ether (2×100 ml) and the pH adjusted to 10 by dropwise addition of saturated Na$_2$CO$_3$. The product was extracted with diethyl ether (3×100 ml). The combined ether extracts were washed with brine (1×100 ml), dried (magnesium sulfate), and filtered. The solvent was evaporated in vacuo to give 0.91 g (61%) of product as a light yellow oil which was used without further purification: $^1$H NMR (CDCl$_3$) δ 8.61 (d, J=2.0 Hz, 1H), 8.53 (dd, J=1.1 Hz and 4.8 Hz, 1H), 7.65 (d, J=7.9 Hz, 1H), 7.31-7.21 (m, 3H), 6.85 (d, J=7.3 Hz, 1H), 6.69 (d, J=8.5 Hz, 1H), 4.45 (d, J=5.7 Hz, 2H), 3.87 (s, 3H), 3.85 (s, 3H).

3-[(Pyridin-3-ylmethyl)-amino]-phthalic acid

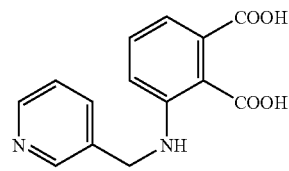

3-[(Pyridin-3-ylmethyl)-amino]-phthalic acid dimethyl ester (0.91 g, 3.03 mmol) was treated in the same manner as described above for the synthesis of 3-(2-methoxy-ethylamino)-phthalic acid except the pH of crude reaction mixture was adjusted to 2-3 by dropwise addition of concentrated HCl. The solvent was then evaporated in vacuo leaving a dry salt mixture that was used without further purification.

2-(2,6-Dioxo-piperidin-3-yl)-4-[(pyridin-3-ylmethyl)-amino]-isoindole-1,3-dione I-128

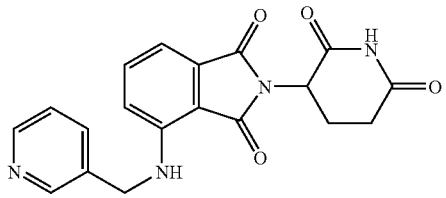

3-[(Pyridin-3-ylmethyl)-amino]-phthalic acid (3.03 mmol) was treated in the same manner as described above for the synthesis of 2-(2,6-dioxo-piperidin-3-yl)-4-(2-methoxy-ethylamino)-isoindole-1,3-dione. The solid yellow residue was slurried in 50% methanol/ethyl acetate (20 ml) for 18 h to give 0.50 g (46%) of product as a yellow solid: mp 231-233° C.; $^1$H NMR (DMSO-$d_6$) δ 11.14 (s, 1H), 8.63 (s, 1H), 8.47 (s, 1H), 7.78 (d, J=7.7 Hz, 1H), 7.53 (t, J=7.8 Hz, 1H), 7.39-7.30 (m, 2H), 7.03 (t, J=6.6 Hz, 2H), 5.09 (dd, J=5.2 and 12.4 Hz, 1H), 4.61 (d, J=6.0 Hz, 2H), 2.97-2.84 (m, 1H), 2.64-2.48 (m, 2H), 2.08-2.04 (m, 1H); $^{13}$C NMR (DMSO-$d_6$) δ 172.78, 170.05, 168.65, 167.22, 148.66, 148.27, 145.75, 136.14, 134.79, 134.54, 132.25, 123.58, 117.50, 110.92, 109.82, 48.57, 42.99, 30.96, 22.12; Anal. Calcd. For $C_{19}H_{16}N_4O_4$: C, 62.63; H, 4.43; N, 15.38. Found: C, 62.30; H, 4.27; N, 15.30.

3-[(5-Carboxy-furan-2-ylmethyl)-amino]-phthalic acid dimethyl ester

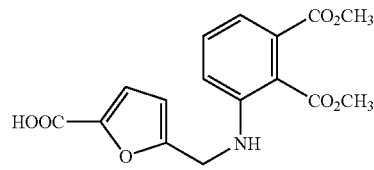

5-Formyl-furan-2-carboxylic acid (1 g, 7.14 mmol) was treated in the same manner as described above for the synthesis of 3-pentylamino-phthalic acid dimethyl ester except the combined aqueous NaHCO$_3$ extracts were washed with methylene chloride (1×70 ml) and the pH adjusted to 2-3 by dropwise addition of concentrated HCl. The mixture was then extracted with ethyl acetate (3×75 ml). The combined ethyl acetate extracts were washed with brine (1×100 ml), dried (magnesium sulfate), and filtered. The solvent was evaporated in vacuo to give 0.90 g product as an off-white solid: $^1$H NMR (CDCl$_3$) δ 7.42-7.36 (m, 1H), 7.16 (d, J=3.5 Hz, 1H), 7.03-6.97 (m, 2H), 6.90 (dd, J=1.0 Hz and 7.3 Hz, 1H), 6.48 (d, J=3.5 Hz, 1H), 4.60 (d, J=5.2 Hz, 2H), 3.82 (s, 3H), 3.81 (s, 3H).

3-[(5-Carboxy-furan-2-ylmethyl)-amino]-phthalic acid

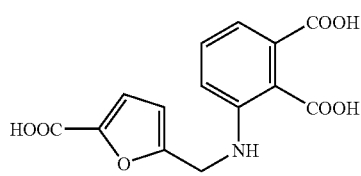

3-[(5-Carboxy-furan-2-ylmethyl)-amino]-phthalic acid dimethyl ester (0.90 g, 2.70 mmol) was treated in the same manner as described above for the synthesis of 3-(2-methoxy-ethylamino)-phthalic acid. The product of the reaction, which contained a mixture of diacid and monomethyl esters, was used without further purification.

5-{[2-(2,6-Dioxo-piperidin-3-yl)-1,3-dioxo-2,3-dihydro-1H-isoindol-4-ylamino]-methyl}-furan-2-carboxylic acid I-129

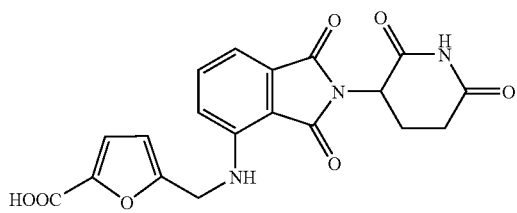

3-[(5-Carboxy-furan-2-ylmethyl)-amino]-phthalic acid (1.78 g, 5.65 mmol) was treated in the same manner as described above for the synthesis of 2-(2,6-dioxo-piperidin-3-yl)-4-(2-methoxy-ethylamino)-isoindole-1,3-dione. The solid yellow residue was purified by preparative HPLC (Symmetry, C$_{18}$, isocratic, 30% acetonitrile/water) to give 0.39 g (36%) of product as a yellow solid: mp 202-204° C.; $^1$H NMR (DMSO-d$_6$) δ 13.01 (bs, 1H), 11.11 (s, 1H), 7.58 (t, J=7.8 Hz, 1H), 7.17-7.07 (m, 4H), 6.51 (d, J=3.2 Hz, 1H), 5.08 (dd, J=5.2 Hz and 12.4 Hz, 1H), 4.65 (d, J=5.9 Hz, 2H), 2.97-2.83 (m, 1H), 2.63-2.47 (m, 2H), 2.07-2.03 (m, 1H); $^{13}$C NMR (DMSO-d$_6$) δ 172.78, 170.02, 168.65, 167.20, 159.13, 156.61, 145.58, 144.19, 136.13, 132.17, 118.59, 117.52, 111.24, 109.97, 109.55, 48.59, 30.96, 22.11; Anal. Calcd. For C$_{19}$H$_{15}$N$_3$O$_7$: C, 56.76; H, 3.89; N, 10.45. Found: C, 56.53; H, 4.16; N, 10.24+1.18% H$_2$O.

3-[(4,5-Dimethyl-furan-2-ylmethyl)-amino]-phthalic acid dimethyl ester

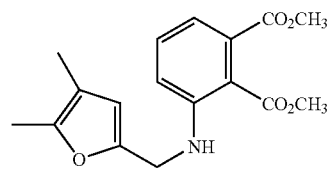

4,5-Dimethyl-furan-2-carbaldehyde (0.98 ml, 8 mmol) was treated in the same manner as described above for the synthesis of 3-pentylamino-phthalic acid dimethyl ester. The residue (oil) was purified by chromatography (SiO$_2$, 10% ethyl acetate/hexanes) to give 0.95 g (75%) of product as a yellow oil: $^1$H NMR (CDCl$_3$) δ 7.32 (t, J=8.2 Hz, 1H), 6.97 (bs, 1H), 6.88-6.83 (m, 2H), 5.99 (s, 1H), 4.28 (d, J=5.5 Hz, 2H), 3.86 (s, 3H), 3.83 (s, 3H), 2.17 (s, 3H), 1.87 (s, 3H).

3-[(4,5-Dimethyl-furan-2-ylmethyl)-amino]-phthalic acid

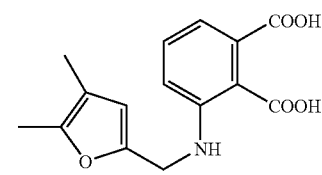

3-[(4,5-Dimethyl-furan-2-ylmethyl)-amino]-phthalic acid dimethyl ester (0.95 g, 3 mmol) was treated in the same manner as described above for the synthesis of 3-(2-methoxy-ethylamino)-phthalic acid. The product of the reaction, which contained a mixture of diacid and monomethyl esters, was used without further purification.

4-[(4,5-Dimethyl-furan-2-ylmethyl)-amino]-2-(2,6-dioxo-piperidin-3-yl)-isoindole-1,3-dione I-130

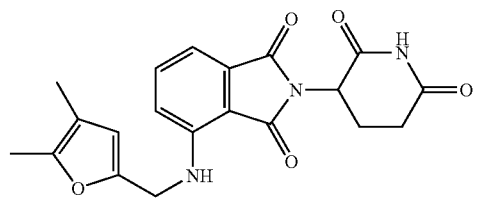

3-[(4,5-Dimethyl-furan-2-ylmethyl)-amino]-phthalic acid (3 mmol) was treated in the same manner as described above for the synthesis of 2-(2,6-dioxo-piperidin-3-yl)-4-(2-methoxy-ethylamino)-isoindole-1,3-dione. The solid yellow residue was purified by preparative HPLC (Symmetry C$_{18}$, isocratic, 40% acetonitrile/water) to give 0.25 g (22%) of product as a yellow solid: mp 127-129° C.; $^1$H NMR (DMSO-d$_6$) δ 11.10 (s, 1H), 7.58 (dd, J=7.4 Hz and 8.4 Hz, 1H), 7.17 (d, J=8.6 Hz, 1H), 7.06 (d, J=7.1 Hz, 1H), 6.91 (t, J=6.1 Hz, 1H), 5.11 (s, 1H), 5.06 (dd, J=5.4 and 12.5 Hz, 1H), 4.45 (d, J=6.0 Hz, 2H), 2.97-2.82 (m, 1H), 2.63-2.44 (m, 2H), 2.13 (s, 3H), 2.08-1.99 (m, 1H), 1.85 (s, 3H); $^{13}$C NMR (DMSO-$d_6$) δ 172.75, 170.02, 168.77, 167.21, 148.75, 146.18, 145.82, 136.05, 132.07, 117.57, 114.16, 110.94, 110.55, 109.61, 48.56, 38.94, 30.95, 22.10, 11.08, 9.50; Anal. Calcd. For $C_{20}H_{19}N_3O_5$: C, 62.99; H, 5.02; N, 11.02. Found: C, 62.75; H, 4.97; N, 10.72.

3-[(Benzofuran-2-ylmethyl)-amino]-phthalic acid dimethyl ester

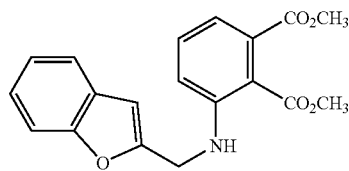

Benzofuran-2-carbaldehyde (1.17 ml, 8 mmol) was treated in the same manner as described above for the synthesis of 3-pentylamino-phthalic acid dimethyl ester. The residue (oil) was purified by chromatography ($SiO_2$, 50% methylene chloride/hexane) to give 1.12 g (83%) of product as a yellow oil: $^1$H NMR ($CDCl_3$) δ 7.50-7.43 (m, 2H), 7.33-7.16 (m, 3H), 6.88-6.84 (m, 2H), 6.58 (s, 1H), 4.54 (d, J=6.1 Hz, 2H), 3.86 (s, 3H), 3.85 (s, 3H).

3-[(Benzofuran-2-ylmethyl)-amino]-phthalic acid

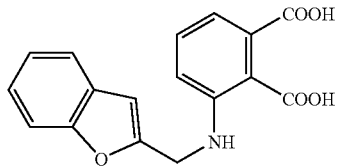

3-[(Benzofuran-2-ylmethyl)-amino]-phthalic acid dimethyl ester (1.12 g, 3.3 mmol) was treated in the same manner as described above for the synthesis of 3-(2-methoxy-ethylamino)-phthalic acid. The product of the reaction, which contained a mixture of diacid and monomethyl esters, was used without further purification.

4-[(Benzofuran-2-ylmethyl)-amino]-2-(2,6-dioxo-piperidin-3-yl)-isoindole-1,3-dione I-131

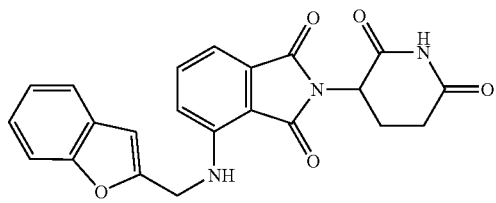

3-[(Benzofuran-2-ylmethyl)-amino]-phthalic acid (3.3 mmol) was treated in the same manner as described above for the synthesis of 2-(2,6-dioxo-piperidin-3-yl)-4-(2-methoxy-ethylamino)-isoindole-1,3-dione. The solid yellow residue was slurried in methylene chloride (20 ml) for 18 h and filtered to give 0.59 g (37%) of product as a yellow solid: mp 199-201° C.; $^1$H NMR (DMSO-$d_6$) δ 11.14 (s, 1H), 7.61-7.52 (m, 3H), 7.29-7.18 (m, 4H), 7.08 (d, J=7.0 Hz, 1H), 6.80 (s, 1H), 5.10 (dd, J=5.4 and 12.5 Hz, 1H), 4.77 (d, J=6.1 Hz, 2H), 2.98-2.83 (m, 1H), 2.64-2.46 (m, 2H), 2.07-2.03 (m, 1H); $^{13}$C NMR (DMSO-$d_6$) δ 172.76, 170.02, 168.71, 167.20, 155.33, 154.33, 154.22, 145.71, 136.09, 132.15, 127.93, 123.96, 122.81, 120.88, 117.64, 111.19, 110.93, 109.96, 103.85, 48.59, 30.96, 22.12; Anal. Calcd. For $C_{22}H_{17}N_3O_5$: C, 65.50; H, 4.25; N, 10.42. Found: C, 65.35; H, 4.12; N, 10.34.

4-(3-Chloro-benzylamino)-2-(3-methyl-2,6-dioxo-piperidin-3-yl)-isoindole-1,3-dione I-132

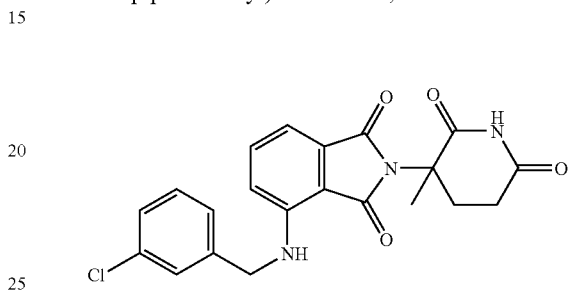

To a stirred solution of 3-(3-Chloro-benzylamino)-phthalic acid (4 mmol) in pyridine (50 ml) was added 3-amino-3-methyl-piperidine-2,6-dione hydrochloride (0.71 g, 4 mmol). The reaction mixture was heated to reflux for 18 h. The solvent was evaporated in vacuo and the residue dissolved in methylene chloride (150 ml). The methylene chloride mixture was washed with water (2×100 ml), 0.1N HCl (2×100 ml), brine (1×100 ml), dried (magnesium sulfate), and filtered. The solvent was evaporated in vacuo to give a yellow semi-solid. The residue was purified by preparative HPLC (Symmetry $C_8$, isocratic, 50% acetonitrile/water) to give 0.67 g (41%) of product as a yellow solid: mp 199-201° C.; $^1$H NMR (DMSO-$d_6$) δ 10.99 (s, 1H), 7.52-7.28 (m, 6H), 6.97-6.89 (m, 2H), 4.54 (d, J=6.1 Hz, 1H), 2.78-2.50 (m, 3H), 2.08-1.98 (m, 1H), 1.89 (s, 3H); $^{13}$C NMR (DMSO-$d_6$) δ 172.42, 172.19, 169.62, 167.92, 145.59, 141.82, 136.02, 133.14, 132.06, 130.35, 126.91, 126.78, 125.60, 117.23, 110.42, 109.49, 58.37, 44.74, 29.27, 28.62, 21.02; Anal. Calcd. For $C_{21}H_{18}ClN_3O_4$: C, 61.24; H, 4.41; N, 10.20. Found: C, 61.30; H, 4.28; N, 9.97.

3-[4-(3-Chloro-benzylamino)-1-oxo-1,3-dihydro-isoindol-2-yl]-piperidine-2,6-dione I-133

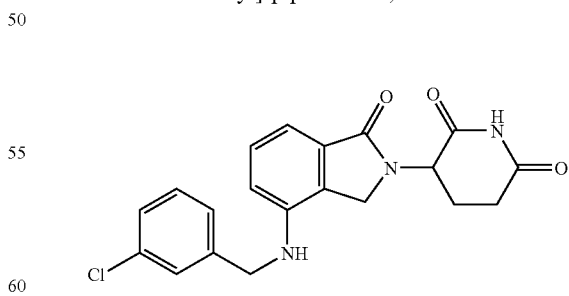

3-(4-Amino-1-oxo-1,3-dihydro-isoindol-2-yl)-piperidine-2,6-dione (1.04 g, 4 mmol) was dissolved in acetic acid (7 ml) with heat. The mixture was cooled slightly and methylene chloride (50 ml) was added slowly followed by 3-chlorobenzaldehyde (0.91 ml, 8 mmol) and sodium triacetoxyborohydride. (2.54 g, 12 mmol). The reaction mixture was stirred at room temperature under a nitrogen atmosphere for 2 h, diluted with methylene chloride (100 ml), washed with water (2×100 ml), saturated aqueous sodium bicarbonate (2×100 ml), brine (100 ml), dried (magnesium sulfate), and filtered. The solvent was evaporated in vacuo to give a white solid. The solid was recrystallized from methylene chloride/methanol to give 0.48 g (31%) of product as a white solid: mp 253-255° C.; $^1$H NMR (DMSO-d$_6$) δ 11.05 (s, 1H), 7.45 (s, 1H), 7.37-7.19 (m, 4H), 6.95 (d, J=7.4 Hz, 1H), 6.63 (d, J=8.0 Hz, 1H), 6.45 (t, J=5.9 Hz, 1H), 5.14 (dd, J=5.1 and 13.1 Hz, 1H), 4.41 (d, J=5.8 Hz, 2H), 4.34 (d, J=17.3 Hz, 1H), 4.20 (d, J=17.2 Hz, 1H) 3.01-2.87 (m, 1H), 2.66-2.60 (m, 1H), 2.42-2.25 (m, 1H), 2.08-2.04 (m, 1H); $^{13}$C NMR (DMSO-d$_6$) δ 172.90, 171.24, 168.74, 143.03, 142.59, 133.08, 132.16, 130.19, 129.12, 126.80, 126.70, 125.73, 112.27, 110.55, 51.54, 45.73, 45.47, 31.25, 22.79; Anal. Calcd. For C$_{20}$H$_{18}$ClN$_3$O$_3$: C, 62.58, H, 4.73; N, 10.95. Found: C, 62.32; H, 4.61; N, 10.80.

N-{[2-(2,6-Dioxo(3-piperidyl))-1,3-dioxoisoindolin-4-yl]methyl}(cyclopentylamino)carboxamide I-134

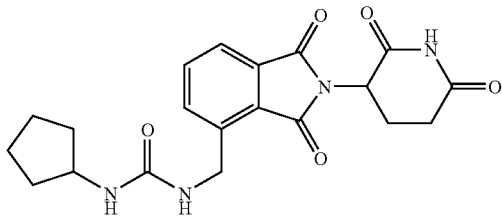

1,8-Diazabicyclo[5,4,0]undec-7-ene (0.29 g, 1.9 mmol) was added to a stirred suspension of 4-(aminomethyl)-2-(2,6-dioxo(3-piperidyl))isoindoline-1,3-dione hydrochloride (0.6 g, 1.85 mmol) in acetonitrile (50 mL). After stirring for 20 min, 4-nitrophenyl-N-cyclopentylcarbamate (0.44 g, 1.85 mmol) was added. The mixture was stirred at room temperature for 17 hours. The mixture was filtered to afford N-{[2-(2,6-dioxo(3-piperidyl))-1,3-dioxoisoindolin-4-yl]methyl}(cyclopentylamino)carboxamide (0.2 g, 27%) as a white solid: mp 151-153° C.; $^1$H NMR (DMSO-d$_6$) δ 11.13 (s, 1H), 7.86-7.68 (m, 3H), 6.31 (t, 1H), 6.17 (d, J=6.9 Hz, 1H), 5.18-5.11 (dd, J=4.6 and 12.3 Hz, 1H), 4.62 (d, J=5.4 Hz, 2H), 3.83 (q, J=6.4 Hz, 2H), 2.96-2.85 (m, 1H), 2.64-2.50 (m, 2H), 2.07-2.04 (m, 1H), 1.70-1.29 (m, 8H); $^{13}$C NMR (DMSO-d$_6$) δ 172.77, 169.83, 167.59, 167.04, 157.63, 141.12, 134.64, 133.43, 131.52, 128.99, 121.64, 51.09, 48.83, 38.70, 32.91, 30.94, 23.16, 21.99; Anal. Calcd. For C$_{20}$H$_{22}$N$_4$O$_5$: C, 60.29; H, 5.57; N, 14.06. Found: C, 60.09; H, 5.66; N; 14.15.

N-{[2-(2,6-Dioxo(3-piperidyl))-1,3-dioxoisoindolin-4-yl]methyl}(3-pyridylamino)carboxamide Hydrochloride I-135

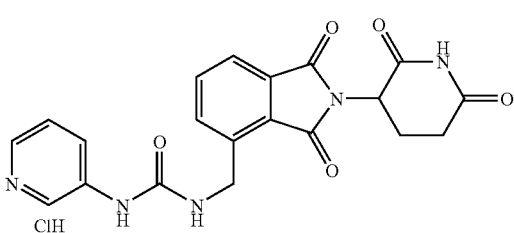

1,8-Diazabicyclo[5,4,0]undec-7-ene (0.29 g, 1.9 mmol) was added to a stirred suspension of 4-(aminomethyl)-2-(2,6-dioxo(3-piperidyl))isoindoline-1,3-dione hydrochloride (0.6 g, 1.85 mmol) in acetonitrile (50 mL). After stirring for 20 min, (2,5-dioxopyrrolidinyloxy)-N-(3-pyridyl)carboxamide (0.44 g, 1.85 mmol) was added. The mixture was stirred at room temperature for 17 hours. The mixture was filtered and the solid was recrystallized from methanol (25 mL) to give N-{[2-(2,6-dioxo(3-piperidyl))-1,3-dioxoisoindolin-4-yl]methyl}(3-pyridylamino)carboxamide (0.23 g. 30%). 2N HCl/ether was added to a stirred solution of N-{[2-(2,6-dioxo(3-piperidyl))-1,3-dioxoisoindolin-4-yl]methyl}(3-pyridylamino)carboxamide (0.23 g) in methanol (5 mL) and ethyl acetate (10 mL). The mixture was stirred for 2 hours and filtered to give N-{[2-(2,6-dioxo(3-piperidyl))-1,3-dioxoisoindolin-4-yl]methyl}(3-pyridylamino)carboxamide hydrochloride (0.2 g) as a white solid: mp 263-265° C.; $^1$H NMR (DMSO-d$_6$) δ 11.17 (s, 1H), 10.43 (s, 1H), 9.08 (d, J=1.7 Hz, 1H), 8.44 (d, J=5.4 Hz, 1H), 8.33-8.29 (dd, J=1.2 and 8.5 Hz, 1H), 7.93-7.78 (m, 4H), 7.55 (t, J=6.0 Hz, 1H), 5.21-5.14 (dd, J=5.a and 12.5 Hz, 1H), 4.80 (d, J=5.9 Hz, 2H), 2.97-2.84 (m, 1H), 2.65-2.50 (m, 2H), 2.10-2.06 (m, 1H); $^{13}$C NMR (DMSO-d$_6$) δ 172.78, 169.83, 167.54, 166.96, 154.78, 139.97, 139.51, 134.80, 134.37, 133,35, 132.34, 131.60, 130.43, 127.17, 127.10, 121.99, 48.88, 38.68, 30.94, 21.99; Anal. Calcd. For C$_{20}$H$_{18}$N$_5$O$_5$Cl: C, 54.12; H, 4.09; N, 15.78; Cl, 7.99. Found: C, 54.11; H, 4.10; N, 15.44; Cl, 7.81.

N-{[2,(2,6-dioxo(3-piperidyl))-1,3-dioxoisoindolin-4-yl]methyl}piperidylcarboxamide I-136

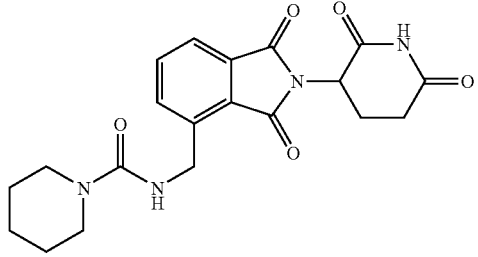

Diisopropylethylamine (0.88 g, 6.79 mmol) was added to a stirred suspension of 4-(aminomethyl)-2-(2,6-dioxo(3-piperidyl))isoindoline-1,3-dione hydrochloride (1.0 g, 3.09 mmol) in acetonitrile (50 mL). After stirring for 20 min, the mixture was slowly added to a stirred solution of triphosgene (0.34 g, 1.14 mmol) in acetonitrile (15 mL) over 30 min. After a further 10 min of stirring, a solution of piperidine (0.26 g, 3.09 mmol) and diisopropylethylamine (0.48 g, 3.71 mmol) in acetonitrile (10 mL) was added in one portion. The mixture was stirred at room temperature for 17 hours. The mixture was concentrated and the residue was dissolved in methylene chloride (80 mL). The methylene chloride solution was washed with 10% KHSO$_4$ (30 mL), H$_2$O (2×30 mL), brine (30 mL) and dried (MgSO$_4$). Solvent was removed and the residue was purified by chromatography (CH$_2$Cl$_2$: CH$_3$OH 97.5:2.5) to give N-{[2-(2,6-dioxo(3-piperidyl))-1,3-dioxoisoindolin-4-yl]methyl}piperidylcarboxamide (0.66 g, 53%) as a white solid: mp 156-158° C.; $^1$H NMR (DMSO-d$_6$) δ 11.14 (s, 1H), 7.86-7.75 (m, 2H), 7.69 (d, J=7.4 Hz, 1H), 7.12 (t, J=5.6 Hz, 1H), 5.18-5.11 (dd, J=5.3 and 12.5 Hz, 1H), 4.69 (d, J=5.5 Hz, 2H), 3.42-3.32 (m, 4H), 2.96-2.83 (m, 1H), 2.63-2.50 (m, 2H), 2.08-2.03 (m, 1H), 1.54-1.44 (m, 6H); $^{13}$C NMR (DMSO-d$_6$) δ 172.74, 169.83, 167.60, 157.26, 141.46, 134.58, 132.82, 131.38, 126.74, 121.43, 48.82, 44.37, 30.93, 25.37, 24.12, 21.98; Anal. Calcd. For $C_{20}H_{22}N_4O_5$+ 0.22$H_2O$: C, 59.70; H, 5.62; N, 13.92. Found: C, 60.14; H, 5.59; N, 13.47.

Tert-Butyl 4-(N-{[2-(2,6-dioxo(3-piperidyl))-1,3-dioxoisoindolin-4-yl]methyl}(carbamoyl)piperazinecarboxylate I-137

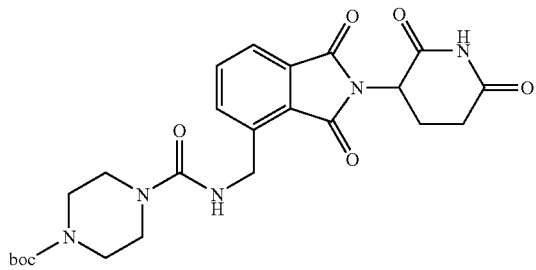

Diisopropylethylamine (1.05 g, 8.16 mmol) was added to a stirred suspension of 4-(aminomethyl)-2-(2,6-dioxo(3-piperidyl))isoindoline-1,3-dione hydrochloride (1.2 g, 3.71 mmol). After stirring for 20 min, the mixture was added slowly to a stirred solution of triphosgene (0.41 g, 1.37 mmol) in acetonitrile (20 mL) over 30 min. After a further 10 min of stirring, a solution of t-BOC-1-piperazine carboxylate (0.69 g, 3.71 mmol) and diisopropylethylamine (0.58 g, 4.45 mmol) in acetonitrile (10 mL) was added in one portion. The mixture was stirred at room temperature for 17 hours. The mixture was concentrated and the residue was dissolved in methylene chloride (100 mL). The methylene chloride solution was washed with water (2×40 mL), brine (40 mL) and dried (MgSO$_4$). Solvent was removed and the residue was purified by chromatography (CH$_2$CL$_2$: CH$_3$OH 97.5:2.5) to give tert-butyl 4-(N-{[2-(2,6-dioxo(3-piperidyl))-1,3-dioxoisoindolin-4-yl]methyl}(carbamoyl)piperazinecarboxylate (0.98 g, 52%) as a white solid: mp 158-160° C.; $^1$H NMR (DMSO-d$_6$) δ 11.14 (s, 1H), 7.86-7.69 (m, 3H), 7.27 (t, J=5.5 Hz, 1H), 5.18-5.11 (dd, J=5.4 and 12.5 Hz, 1H), 4.71 (d, J=5.4 Hz, 2H), 3.33 (s, 8H), 2.98-2.83 (m, 1H), 2.63-2.49 (m, 2H), 2.08-2.04 (m, 1H), 1.41 (s, 9H); $^{13}$C NMR DMSO-d$_6$) δ 172.74, 170.04, 169.83, 167.58, 167.03, 157.30, 153.86, 140.99, 136.52, 134.64, 132.94, 131.39, 126.80, 121.53, 111.33, 79.03, 74.43, 48.82, 43.22, 30.92, 28.03, 21.98; Anal. Calcd. For $C_{24}H_{29}N_5O_7$+0.13$H_2O$: C, 57.44; H, 5.88; N, 13.95. Found: C, 57.83; H, 6.09; N, 13.45.

N-{[2-(2,6-Dioxo(3-piperidyl))-1,3-dioxoisoindolin-4-yl]methyl}(diethylamino)carboxamide I-138

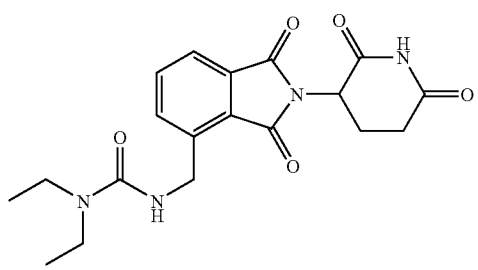

Diisopropylethylamine (0.88 g, 6.80 mmol) was added to a stirred suspension of 4-(aminomethyl)-2-(2,6-dioxo(3-piperidyl))isoindoline-1,3-dione hydrochloride (1.0 g, 3.09 mmol) in acetonitrile (50 mL). After stirring for 20 min, the mixture was slowly added to a stirred solution of triphosgene (0.34 g, 1.14 mmol) in acetonitrile (20 mL) over 20 min. After a further 10 min of stirring, a solution of diethylamine (0.23 g, 3.09 mmol) and diisopropylethylamine (0.48 g, 3.71 mmol) in acetonitrile (10 mL) was added in one portion. The mixture was stirred at room temperature for 17 hours. The mixture was concentrated and the residue was dissolved in methylene chloride (80 mL). The methylene chloride solution was washed with 1N HCl (40 mL), H$_2$O (2×40 mL), brine (40 mL) and dried (MgSO$_4$). Solvent was removed and the residue was purified by chromatography (CH$_2$Cl$_2$: CH$_3$OH 97.5:2.5) to afford N-{[2-(2,6-dioxo(3-piperidyl))-1,3-dioxisoindolin-4-yl]methyl}(diethylamino)carboxamide (0.8 g, 67%) as a white solid: mp 142-144° C.; $^1$H NMR (DMSO-d$_6$) δ 11.14 (s, 1H), 7.86-7.66 (m, 3H), 6.91 (t, J=5.7 Hz, 1H), 5.19-5.12 (dd, J=5.4 and 12.6 Hz, 1H), 4.70 (d, J=5.6 Hz, 2H), 3.26 (q, J=6.9 Hz, 4H), 2.98-2.83 (m, 1H), 2.64-2.49 (m, 2H), 2.08-2.04 (m, 1H), 1.06 (t, J=7.0 Hz, 6H); $^{13}$C NMR (DMSO-d$_6$) δ 172.73, 169.81, 167,63, 167.04, 156.74, 134.54, 132.80, 131.38, 126.72, 121.38, 48.82, 40.24, 30.92, 21.97, 13,90; Anal. Calcd. For $C_{19}H_{22}N_4O_5$: C, 59.06; H, 5.74; N, 14.50. Found: C, 58.71; H, 5.76; N, 14.10.

Cyclopropyl-N-{[2-(3-methyl-2,6-dioxo(3-piperidyl))-1,3-dioxoisoindolin-4-yl]methyl}carboxamide I-139

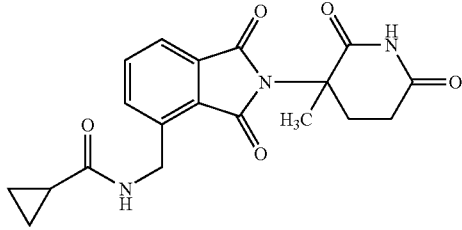

1,8-Diazabicyclo[5,4,0]undec-7-ene (0.68 g, 4.44 mmol) was added to a stirred suspension of 4-(aminomethyl)-2-(3-methyl-2,6-dioxo(3-piperidyl))isoindoline-1,3-dione hydrochloride (0.6 g, 1.78 mmol) in acetonitrile (50 mL). After stirring for 20 min, cyclopropanecarbonyl chloride (0.22 g, 2.14 mmol) was added. The mixture was stirred at room temperature for 17 hours. The mixture was filtered and the solid was washed with acetonitrile (10 mL) to give cyclopropyl-N-{[2-(3-methyl-2,6-dioco(3-piperidyl))-1,3-dioxoisoindolin-4-yl]methyl}carboxamide (0.49 g, 74%) as a white solid: mp 243-245° C.; $^1$H NMR (DMSO-d$_6$) δ 11.04 (s, 1H), 8.68 (t, J=5.8 Hz, 1H), 7.84-7.63 (m, 3H), 5.76 (s, 1H), 4.70 (d, J=5.8 Hz, 2H), 2.71-2.54 (m, 2H), 2.10-2.02 (m, 1H), 1.90 (s, 3H), 1.68-1.63 (m, 1H), 0.71-0.68 (m, 4H); $^{13}$C NMR (DMSO-d$_6$) δ 173.07, 172.20, 172.15, 168.29, 167.68, 139.01, 134.61, 133.19, 131.40, 126.78, 121.50, 58.71, 54.88, 37.72, 29.09, 28.57, 21.00, 13.51, 6.42; Anal. Calcd. For $C_{19}H_{19}N_3O_5$: C, 61.78; H, 5.18; N, 11.38. Found: C, 61.53; H, 5.20; N, 11.39.

Methyl 3-bromo-2-methylbenzoate

A mixture of 3-bromo-2-methylbenzoic acid (16 g, 74.4 mmol), sodium bicarbonate (12.5 g, 148.8 mmol) and iodomethane (21.2 g, 148.8 mmol) in DMF (160 mL) was heated at 60° C. for 2 hours. The mixture was cooled to room temperature and poured into ice water (400 mL). The mixture was extracted with ethyl acetate (4×100 mL). The EtOAc solution was washed with water (3×10 mL), brine (100 mL) and dried (MgSO$_4$). Solvent was removed to give methyl 3-bromo-2-methylbenzoate (17.6 g, 100%) as an oil: $^1$H NMR (CDCl$_3$) δ 7.70 (t, J=7.6 Hz, 2H), 7.08 (t, J=7.9 Hz, 1H), 3.90 (s, 3H), 2.67 (s, 3H).

Methyl 3-bromo-2-bromomethylbenzoate

A mixture of methyl 3-bromo-2-methylbenzoate (17.0 g, 74.22 mmol) and N-bromosuccinimide (15.85 g, 89.06 mmol) in acetonitrile (200 mL) was heated under gently refluxing for 17 hours while a 200 W bulb situated 2 cm away was shining on the reaction flask. The mixture was cooled to room temperature and solvent was removed. The residue was dissolved in ethyl acetate (200 mL) and washed with water (3×80 mL), brine (80 mL) and dried (MgSO$_4$). Solvent was removed to give methyl 3-bromo-2-bromomethylbenzoate (24.5 g, 97% by HPLC): $^1$H NMR (CDCl$_3$) δ 7.90-7.86 (dd, J=1.0 and 7.9 Hz, 1H), 7.78-7.74 (dd, J=1.2 and 8.2 Hz, 1H), 7.22 (t, J=7.9 Hz, 1H), 5.12 (s, 2H), 3.95 (s, 3H).

Tert-Butyl 2-(4-bromo-1-oxoisoindolin-2-yl)-4-carbamoylbutanoate

Triethylamine (4.66 g, 46.09 mmol) was added to a stirred suspension of methyl 3-bromo-2-bromomethylbenzoate (6.45 g, 20.95 mmol) and L-glutamine t-butyl ester hydrochloride (5.0 g, 20.95 mmol) in THF (100 mL). The mixture was heated to reflux for 18 hours. The mixture was cooled to room temperature and solvent was removed. The residue was dissolved in methylene chloride (100 mL) and washed with water (2×80 mL), brine (80 mL) and dried (MgSO$_4$). Solvent was removed and the residue was purified by chromatography (CH$_2$Cl$_2$: CH$_3$OH 97.5:2.5) to afford tert-butyl 2-(4-bromo-1-oxoisoindolin-2-yl)-4-carbamoylbutanoate 3.97 g, 48%): $^1$H NMR (CDCl$_3$) δ 7.74 (d, J=7.1 Hz, 1H), 7.65 (d, J=7.9 Hz, 1H), 7.35 (t, J=7.8 Hz, 1H), 6.15 (s, 1H), 5.77 (s, 1H), 5.02-4.96 (m, 1H), 4.58 (d, J=17.4 Hz, 1H), 4.34 (d, J=17.4 Hz, 1H), 2.45-2.10 (m, 4H), 1.46 (s, 9H); $^{13}$C NMR (CDCl$_3$) δ 173.83, 169.42, 168.74, 142.28, 134.70, 133.65, 129.80, 122.70, 117.75, 82.66, 54.29, 47.80, 32.27, 27.95, 25.54.

Tert-Butyl 2-(4-cyano-1-oxoisoindolin-2-yl)-4-carbamoylbutanoate

A mixture of tert-butyl 2-(4-bromo-1-oxoisoindolin-2-yl)-4-carbamoylbutanoate (1.2 g, 3.02 mmol), zinc cyamide (0.21 g, 1.81 mmol), tris(dibenzylideneacetone)dipalladium (0.06 g, 0.06 mmol), 1,1'-bis(diphenylphosphino)ferrocene (0.067 g, 0.12 mmol) in deoxygenated DMF (15 mL) was heated to 120° C. under N$_2$ for 6 hours. The mixture was cooled to room temperature and poured into EtOAc (100 mL) and sat. NaHCO$_3$ (40 mL). The EtOAc solution was washed with water (2×40 mL), brine (40 mL), and dried (MgSO$_4$). Solvent was removed and the residue was purified by chromatography (CH$_2$Cl$_2$: CH$_3$OH 97.5:2.5) to afford tert-butyl 2-(4-cyano-1-oxoisoindolin-2-yl)-4-carbamoylbutanoate (0.77 g, 74%): $^1$H NMR (CDCl$_3$) δ 8.07-8.03 (dd, J=0.7 and 7.4 Hz, 1H), 7.86-7.83 (dd, J=1.0 and 7.9 Hz, 1H), 7.61 (t, J=7.6 Hz, 1H), 5.91 (s, 1H), 5.68 (s, 1H), 5.03-4.98 (m, 1H), 4.85 (d, J=17.9 Hz, 1H), 4.62 (d, J=17.9 Hz, 1H), 2.48-2.41 (m, 4H), 1.46 (s, 9H); $^{13}$C NMR (CDCl$_3$) δ 173.56, 169.21, 167.70, 145.23, 134.94, 133.11, 128.93, 128.21, 115,65, 107.86, 82.98, 63.68, 54.47, 46.55, 32.34, 27.95, 25.46.

2-(4-Cyano-1-oxoisoindolin-2-yl)-4-carbamoylbutanoic acid

A mixture of tert-butyl 2-(4-cyano-1-oxoisoindolin-2-yl)-4-carbamoylbutanoate (1.0 g, 2.91 mmol) and trifluoroacetic acid (5 mL) was stirred for 2 hours. The mixture was concentrated and the residue was crystallized from ether (15 mL) to give 2-(4-cyano-1-oxoisoindolin-2-yl)-4-carbamoylbutanoic acid (0.74 g, 89%) as a white solid: $^1$H NMR (DMSO-d$_6$) δ 13.12 (b, 1H), 8.12 (d, J=7.6 Hz, 1H). 8.03 (d, J=7.6 Hz, 1H), 7.73 (t, J=7.6 Hz, 1H), 7.23 (s, 1H), 6.76 (s, 1H), 4.80-4.62 (m, 3H), 2.32-2.09 (m, 4H).

2-(2,6-Dioxo(3-piperidyl))-1-oxoisoindoline-4-carbontrile

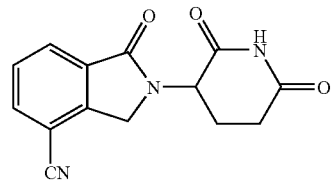

A mixture of 2-(4-cyano-1-oxoisoindolin-2-yl)-4-carbamoylbutanoic acid (0.6 g, 2.09 mmol) and 1,1-carbonyldiimidazole (0.44 g, 2.72 mmol) in acetonitrile (20 mL) was heated to reflux for 2 hours. The mixture was cooled to room temperature and filtered to give 2-(2,6-dioxo(3-piperidyl))-1-oxoisoindoline-4-carbonitrile (0.44 g, 83%) as a white solid: mp 312-314° C.; $^1$H NMR (DMSO-d$_6$) δ 11.04 (s, 1H), 8.16 (d, J=7.0 Hz, 1H), 8.06 (d, J=7.1 Hz, 1H), 7.74 (t, J=7.7 Hz, 1H), 5.20-5.13 (dd, J=5.2 and 13.2 Hz, 1H), 4.69 (d, J=18.1 Hz, 1H), 4.57 (d, J=18.1 Hz, 1H), 2.97-2.85 (m, 1H), 2.64-2.45 (m, 2H), 2.05-1.97 (m, 1H); $^{13}$C NMR (DMSO-d$_6$) δ 172.81, 170.69, 166.49, 145.36, 135.37, 132.85, 129.36, 127.91, 116.01, 107.09, 51.77, 46.72, 31.14, 22.22; Anal. Calcd. For C$_{14}$H$_$N$_3$O$_3$: C, 62.45; H, 4.12; N, 15.61. Found: C, 62.26; H, 4.10; N, 15.51.

3-[4-(Aminomethyl)-1-oxoisoindolin-2-yl]piperidine-2,6-dione Hydrochloride

A mixture of 2-(2,6-dioxo(3-piperidyl))-1-oxoisoindoline-4-carbonitrile (1.0 g, 3.71 mmol) and 10% Pd/C (0.2 g) in 4N HCl (20 mL) and methanol (600 mL) was hydrogenated at 50 psi for 17 hours. The mixture was filtered through celite and the filtrate was concentrated. The residue was stirred with ether (30 mL) to give 3-[4-(aminomethyl)-1-oxoisoindolin-2-yl]piperidine-2,6-dione hydrochloride (1.1 g, 99%) as a white solid: $^1$H NMR (DMSO-d$_6$) δ 11.06 (s, 1H), 8.64 (s, 3H), 7.79 (d, J=7.5 Hz, 1H), 7.74 (d, J=7.4 Hz, 1H), 7.59 (t, J=7.5 Hz, 1H), 5.21-5.14 (dd, J=5.0 and 13.2 Hz, 1H), 4.69 (d, J=17.4 Hz, 1H), 4.51 (d, J=17.4 Hz, 1H), 4.09 (d, J=4.9 Hz, 2H), 3.00-2.87 (m, 1H), 2.66-2.35 (m, 2H), 2.03-1.98 (m, 1H); $^{13}$C NMR (DMSO-d$_6$) δ 172.87, 170.92, 167.77, 141.58, 132.50, 131.88, 129.39, 128.48, 123.25, 51.52, 46.19, 38.39, 31.17, 22.69.

N-{[2-(2,6-Dioxo(3-piperidyl))-1-oxoisoindolin-4-yl]methyl}cyclopropylcarboxamide I-140

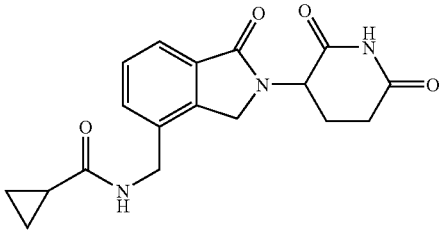

1,8-Diazabicyclo[5,4,0]undec-7-ene (0.7 g, 4.62 mmol) was added to a stirred suspension of 3-[4-(aminomethyl)-1-oxoisoindolin-2-yl]piperidine-2,6-dione hydrochloride (0.65 g, 2.10 mmol) in acetonitrile (50 mL). After stirring for 30 min, cyclopropanecarbonyl chloride (0.24 g, 2.31 mmol) was added. The mixture was stirred at room temperature for 17 hours. The mixture was filtered and the solid was recrystallized from methanol (100 mL) to afford N-{[2-(2,6-dioxo(3-piperidyl))-1-oxoisoindolin-4-yl]methyl}cyclopropylcarboxamide (0.36 g, 50%) as a white solid: mp 262-264° C.; $^1$H NMR (DMSO-d$_6$) δ 11.02 (s, 1H), 8.63 (t, J=5.7 Hz, 1H), 7.65-7.47 (m, 3H), 5.18-5.11 (dd, J=5.0 and 13.2 Hz, 1H), 4.46 (d, J=17.3 Hz, 1H), 4.38-4.31 (m, 3H), 3.00-2.85 (m, 1H), 2.65-2.30 (m, 2H), 2.04-1.99 (m, 1H), 1.64-1.54 (m, 1H), 0.69-0.65 (m, 4H); $^{13}$C NMR (DMSO-d$_6$) δ 172.82, 172.69, 170.96, 168.03, 140.08, 134.76, 131.66, 130.70, 128.30, 121.64, 51.54, 46.15, 31.16, 22.59, 13.47, 6.27; Anal. Calcd. For C$_{18}$H$_{19}$N$_3$O$_4$: C, 63.33; H, 5.61; N, 12.31. Found: C, 62.97; H, 5.55; N, 12.33.

N-{[2-(2,6-Dioxo(3-piperidyl))-1-oxoisoindolin-4-yl]methyl}(ethylamino)carboxamide I-141

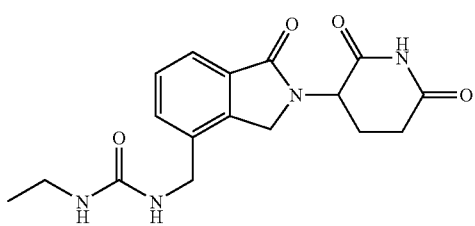

1,8-Diazabicyclo[5,4,0]undec-7-ene (0.44 g, 2.91 mmol) was added to a stirred suspension of 3-[4-(aminomethyl)-1-oxoisoindolin-2-yl]piperidine-2,6-dione hydrochloride (0.6 g, 1.94 mmol) in acetonitrile (50 mL). After stirring for 30 min, ethyl isocyanate (0.21 g, 2.91 mmol) was added. The mixture was stirred at room temperature for 17 hours. Solvent was removed and the residue was stirred with methylene chloride (70 mL) to give N-{[2-(2,6-dioxo(3-piperidyl))-1-oxoisoindolin-4-yl]methyl}(ethylamino)carboxamide (0.28 g, 42%) as a white solid: mp 341-343° C.; $^1$H NMR DMSO-d$_6$) δ 11.02 (s, 1H), 7.62-7.47 (m, 3H), 6.40 (t, J=5.9 Hz, 1H), 5.95 (t, J=5.6 Hz, 1H), 5.18-5.10 (dd, J=5.3 and 13.3 Hz, 1H), 4.52-4.30 (dd, J=17.3 and 37.7 Hz, 2H), 4.28 (d, J=5.9 Hz, 2H), 3.04 (q, J=7.2 Hz, 2H), 3.01-2.86 (m, 1H), 2.65-2.34 (m, 2H0, 2.04-1.99 (m, 1H), 0.98 (t, J=7.2 Ha, 3H), $^{13}$C NMR (DMSO-d$_6$) δ 172.82, 170.97, 168.10, 157.86, 139.78, 136.24, 131.55, 130.25, 128.16, 121.32, 51.51, 46.13, 34.14, 31.16, 22.59, 15.67; Anal. Calcd for C$_{17}$H$_{20}$N$_4$O$_4$: C, 59.29; H, 5.85; N, 16.27. Found: C, 58.98; H, 5.85; N, 16.89.

The present invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the appended claims.

What is claimed is:

1. A compound of the formula:

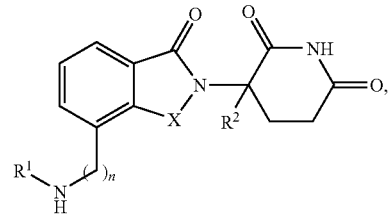

or a pharmaceutically acceptable salt or stereoisomer thereof, wherein:

X is CH$_2$ or C=O;

n is 0 or 1;

R$^1$ is C(O)R$^3$;

R$^2$ is H or methyl; and

R$^3$ is: (C$_1$-C$_8$)alkyl, optionally substituted with one or more substituents selected from a group consisting of halogen, N$_3$, —S—(C$_1$-C$_8$)alkyl, aryl and OH; or aryl, optionally substituted with one or more substituents selected from a group consisting of (C$_1$-C$_8$)alkyl, —O—(C$_1$-C$_8$)alkyl, halogen, CF$_3$ and NO$_2$.

2. The compound of claim 1, wherein X is CH$_2$.

3. The compound of claim 1, wherein R$^3$ is (C$_1$-C$_8$)alkyl, optionally substituted with one or more substituents selected from a group consisting of halogen, N$_3$, —S—(C$_1$-C$_8$)alkyl, aryl and OH.

4. The compound of claim 3, wherein the compound is:

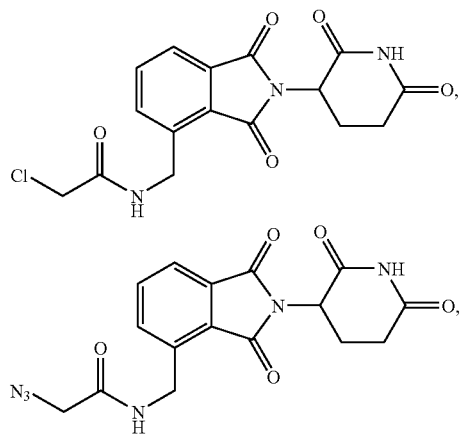

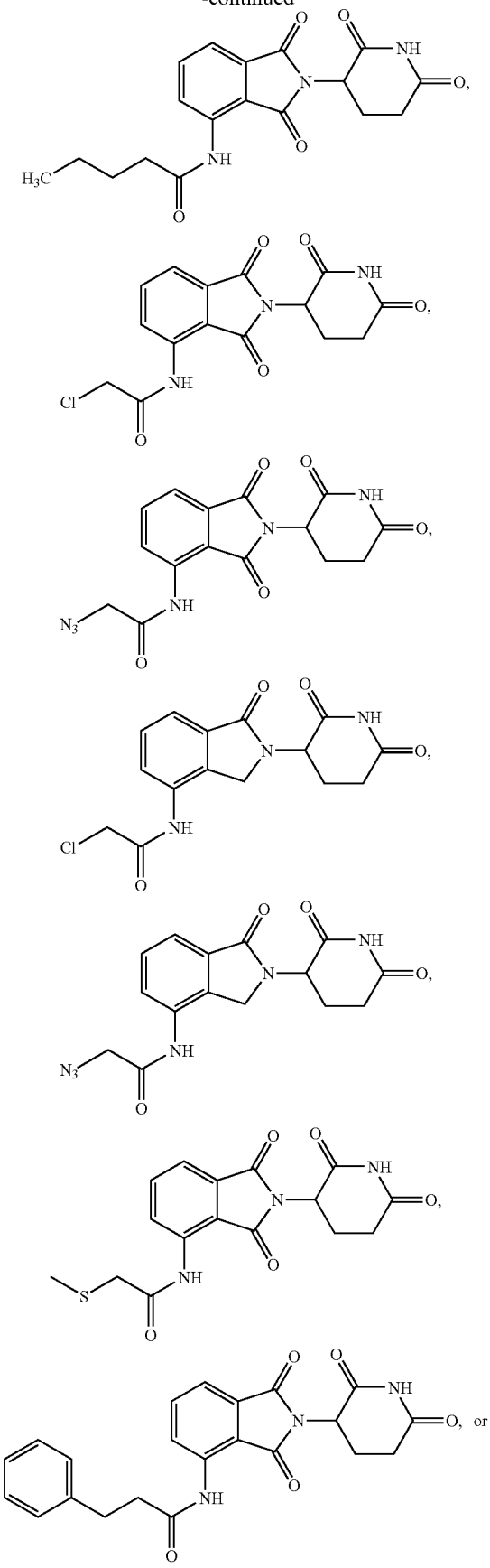

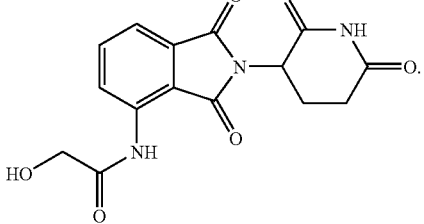

5. The compound of claim 1, wherein $R^3$ is aryl, optionally substituted with one or more substituents selected from a group consisting of $(C_1\text{-}C_8)$alkyl, —O—$(C_1\text{-}C_8)$alkyl, halogen, $CF_3$ and $NO_2$.

6. The compound of claim 5, wherein $R^3$ is phenyl, optionally substituted with one or more substituents selected from a group consisting of $(C_1\text{-}C_8)$alkyl, —O—$(C_1\text{-}C_8)$alkyl, halogen, $CF_3$ and $NO_2$.

7. The compound of claim 6, wherein the compound is:

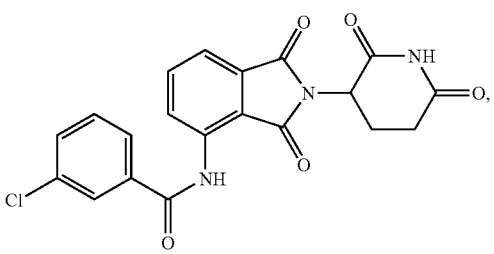

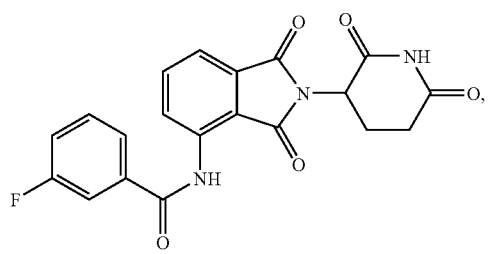

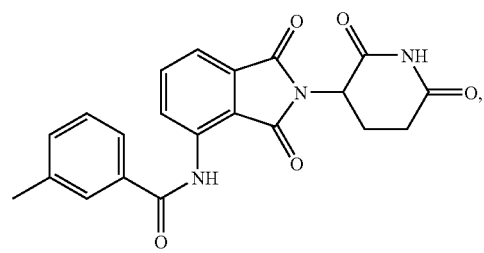

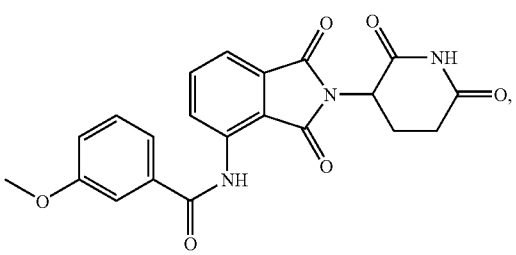

179
-continued
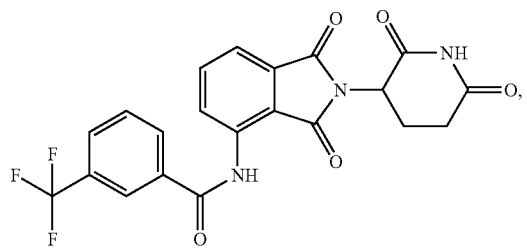
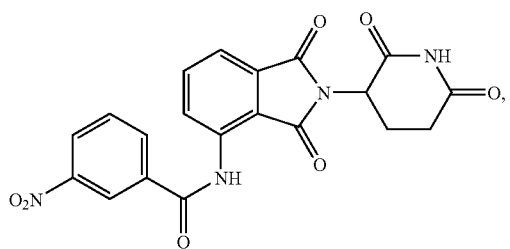
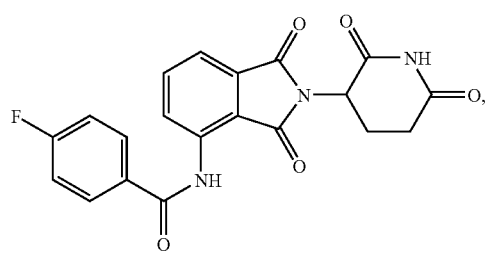
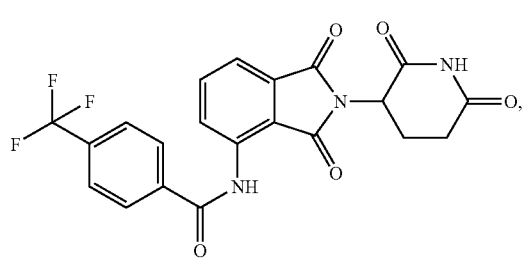
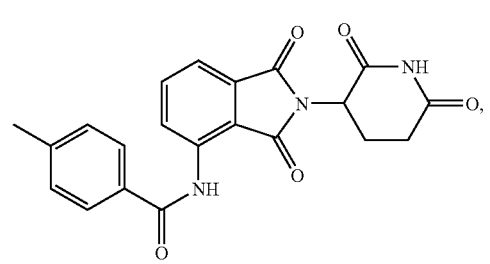
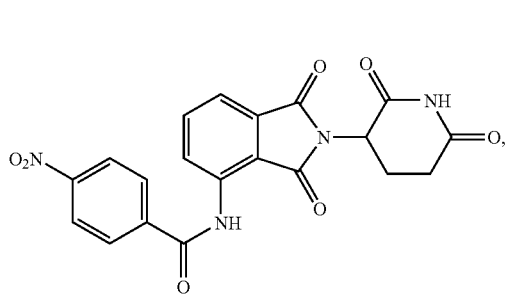
180
-continued
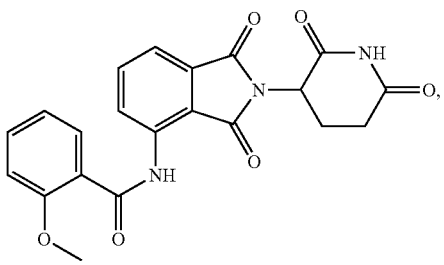
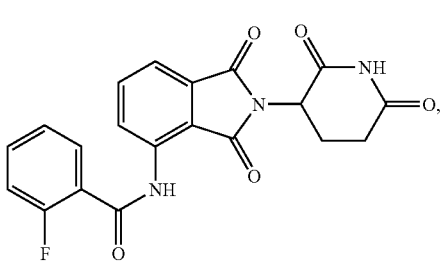
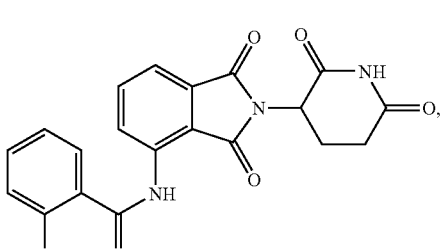
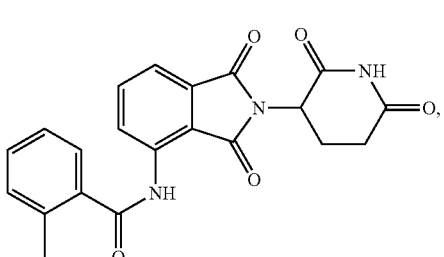
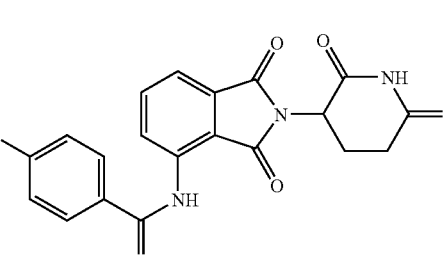
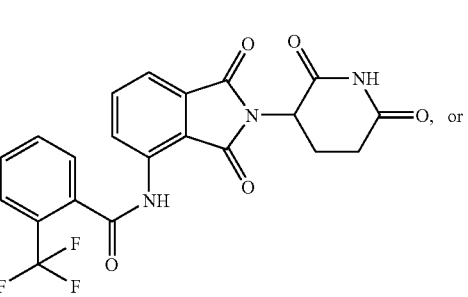

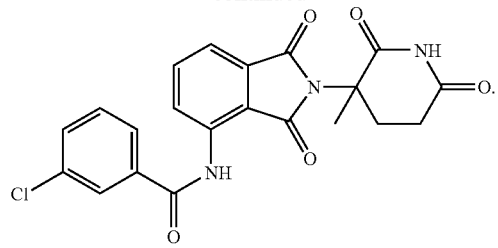
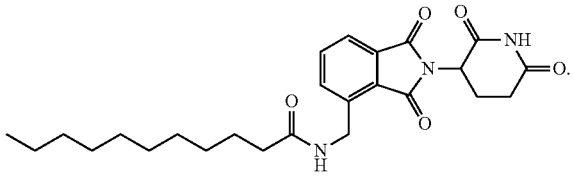
8. A compound, or a pharmaceutically acceptable salt or stereoisomer thereof, wherein the compound is: